(12) United States Patent
Derouazi et al.

(10) Patent No.: US 12,214,048 B2
(45) Date of Patent: *Feb. 4, 2025

(54) COMBINATION OF AN IMMUNE CHECKPOINT MODULATOR AND A COMPLEX COMPRISING A CELL PENETRATING PEPTIDE, A CARGO AND A TLR PEPTIDE AGONIST FOR USE IN MEDICINE

(71) Applicant: AMAL THERAPEUTICS SA, Geneva (CH)

(72) Inventors: Madiha Derouazi, Grand-Saconnex (CH); Elodie Belnoue, Geneva (CH)

(73) Assignee: AMAL THERAPEUTICS SA, Geneva (CH)

( * ) Notice: Subject to any disclaimer, the term of this patent is extended or adjusted under 35 U.S.C. 154(b) by 47 days.

This patent is subject to a terminal disclaimer.

(21) Appl. No.: 17/569,261

(22) Filed: Jan. 5, 2022

(65) Prior Publication Data

US 2022/0118102 A1 Apr. 21, 2022

Related U.S. Application Data

(63) Continuation of application No. 16/084,170, filed as application No. PCT/EP2017/056034 on Mar. 14, 2017, now abandoned.

(30) Foreign Application Priority Data

Mar. 16, 2016 (WO) ............... PCT/EP2016/000472
Aug. 26, 2016 (WO) ............... PCT/EP2016/070264

(51) Int. Cl.
| | | |
|---|---|---|
| C07K 7/06 | (2006.01) |
| A61K 38/10 | (2006.01) |
| A61K 38/17 | (2006.01) |
| A61K 38/18 | (2006.01) |
| A61K 39/00 | (2006.01) |
| A61K 39/395 | (2006.01) |
| A61K 47/42 | (2017.01) |
| A61K 47/64 | (2017.01) |
| A61K 47/66 | (2017.01) |
| A61P 35/00 | (2006.01) |
| C07K 2/00 | (2006.01) |
| C07K 7/08 | (2006.01) |
| C07K 14/47 | (2006.01) |
| C07K 14/475 | (2006.01) |
| C07K 16/22 | (2006.01) |

(Continued)

(52) U.S. Cl.
CPC ............. *A61K 47/66* (2017.08); *A61K 38/17* (2013.01); *A61K 38/18* (2013.01); *A61K 39/00* (2013.01); *A61K 39/0011* (2013.01); *A61K 39/3955* (2013.01); *A61K 39/464416* (2023.05); *A61K 47/42* (2013.01); *A61K 47/64* (2017.08); *A61K 47/642* (2017.08); *A61K 47/6425* (2017.08); *A61P 35/00* (2018.01); *C07K 2/00* (2013.01); *C07K 7/06* (2013.01); *C07K 7/08* (2013.01); *C07K 14/475* (2013.01); *C07K 16/2818* (2013.01); *C07K 16/2863* (2013.01); *C07K 16/2878* (2013.01); *C07K 19/00* (2013.01); *C12N 15/625* (2013.01); *A61K 2039/505* (2013.01); *A61K 2039/507* (2013.01); *A61K 2039/545* (2013.01); *A61K 2039/55516* (2013.01); *A61K 2039/55572* (2013.01); *C07K 2317/75* (2013.01); *C07K 2317/76* (2013.01); *C07K 2319/10* (2013.01); *C07K 2319/40* (2013.01)

(58) Field of Classification Search
CPC ........ A61K 38/18; A61K 38/10; A61K 38/17; A61K 38/1709; A61K 47/64; A61K 39/00; A61K 39/35; A61K 47/42; A61K 47/642; A61K 47/6425; A61K 47/55; A61K 39/3955; A61K 2039/505; A61K 2039/555; A61K 2039/55516; A61K 2039/55572; C07K 7/06; C07K 7/08; C07K 19/00; C07K 14/47; C07K 14/475; C07K 2319/01; C07K 16/2863; C07K 16/2878

See application file for complete search history.

(56) References Cited

U.S. PATENT DOCUMENTS 5,811,097 A 9/1998 Allison et al.
5,855,887 A 1/1999 Allison et al.
(Continued)

FOREIGN PATENT DOCUMENTS

EP 1212422 A2 6/2002
EP 2320940 A2 5/2011
(Continued)

OTHER PUBLICATIONS

Buhl, T., et al. (2013), Internalization routes of cell-penetrating melanoma antigen peptides into human dendritic cells, *Experimental Dermatology*, 23: 20-26.
(Continued)

*Primary Examiner* — Bridget E Bunner
(74) *Attorney, Agent, or Firm* — Harness Dickey & Pierce P.L.C.

(57) ABSTRACT

The present invention provides a combination of an immune checkpoint modulator and a complex comprising a cell penetrating peptide, at least one antigen or antigenic epitope, and a TLR peptide agonist for use in medicine, in particular in the prevention and/or treatment of cancer. Moreover, the present invention also provides compositions, such as a pharmaceutical compositions and vaccines, which are useful in medicine, for example in the prevention and/or treatment of cancer.

32 Claims, 40 Drawing Sheets

Specification includes a Sequence Listing.

(51) Int. Cl.
 C07K 16/28 (2006.01)
 C07K 19/00 (2006.01)
 C12N 15/62 (2006.01)

(56) References Cited

U.S. PATENT DOCUMENTS

| | | |
|---|---|---|
| 5,977,318 A | 11/1999 | Linsley et al. |
| 6,051,227 A | 4/2000 | Allison et al. |
| 6,093,794 A | 7/2000 | Barney et al. |
| 6,207,156 B1 | 3/2001 | Kuchroo et al. |
| 6,337,180 B1 | 1/2002 | Drouet et al. |
| 6,682,736 B1 | 1/2004 | Hanson et al. |
| 6,984,720 B1 | 1/2006 | Korman et al. |
| 7,109,003 B2 | 9/2006 | Hanson et al. |
| 7,132,281 B2 | 11/2006 | Hanson et al. |
| 8,119,775 B2 | 2/2012 | Moretta et al. |
| 8,217,149 B2 | 7/2012 | Irving et al. |
| 8,795,678 B2 | 8/2014 | Liang et al. |
| 9,187,534 B2 | 11/2015 | Derouazi et al. |
| 9,657,064 B2 | 5/2017 | Derouazi et al. |
| 10,206,986 B2 | 2/2019 | Ohlfest et al. |
| 11,338,027 B2 | 5/2022 | Derouazi et al. |
| 2002/0039581 A1 | 4/2002 | Carreno et al. |
| 2002/0086014 A1 | 7/2002 | Korman et al. |
| 2003/0105000 A1 | 6/2003 | Pero et al. |
| 2005/0019344 A1 | 1/2005 | Khanna et al. |
| 2005/0201994 A1 | 9/2005 | Korman et al. |
| 2006/0051372 A1 | 3/2006 | Vande Velde |
| 2007/0148184 A1 | 6/2007 | Straten et al. |
| 2008/0044407 A1 | 2/2008 | Strome et al. |
| 2009/0220532 A1 | 9/2009 | Leclerc et al. |
| 2009/0297552 A1 | 12/2009 | Aderem et al. |
| 2010/0029571 A1 | 2/2010 | Rammensee et al. |
| 2010/0133338 A1 | 6/2010 | Brown et al. |
| 2011/0236406 A1 | 9/2011 | Messmer et al. |
| 2012/0052080 A1 | 3/2012 | Okada |
| 2012/0070491 A1 | 3/2012 | Blais et al. |
| 2012/0177645 A1 | 7/2012 | Langermann et al. |
| 2012/0214744 A1 | 8/2012 | Bourdoulous et al. |
| 2012/0231030 A1 | 9/2012 | Derouazi et al. |
| 2012/0294796 A1 | 11/2012 | Johnson et al. |
| 2013/0116201 A1 | 5/2013 | Lenormand et al. |
| 2013/0183377 A1 | 7/2013 | Agrewala et al. |
| 2013/0331546 A1 | 12/2013 | Ohlfest et al. |
| 2016/0279212 A1 | 9/2016 | Ohlfest et al. |
| 2017/0313775 A1 | 11/2017 | Diaz et al. |
| 2018/0133205 A1 | 5/2018 | Gelormini |
| 2018/0133295 A1 | 5/2018 | Derouazi et al. |
| 2018/0133327 A1 | 5/2018 | Derouazi |
| 2018/0133338 A1 | 5/2018 | Derouazi et al. |
| 2018/0133339 A1 | 5/2018 | Derouazi et al. |
| 2019/0022203 A1 | 1/2019 | Lichty et al. |
| 2019/0175748 A1 | 6/2019 | Derouazi et al. |
| 2019/0255165 A1 | 8/2019 | Derouazi et al. |
| 2020/0000898 A1 | 1/2020 | Yee et al. |
| 2020/0031825 A1 | 1/2020 | Slassi et al. |
| 2020/0061097 A1 | 2/2020 | Iwasaki et al. |
| 2021/0085768 A1 | 3/2021 | Derouazi et al. |
| 2022/0031850 A1 | 2/2022 | Derouazi et al. |
| 2022/0040314 A1 | 2/2022 | Derouazi et al. |
| 2022/0088162 A1 | 3/2022 | Wollmann et al. |
| 2022/0111028 A1 | 4/2022 | Rossi et al. |
| 2022/0118102 A1 | 4/2022 | Derouazi et al. |
| 2022/0175933 A1 | 6/2022 | Derouazi et al. |

FOREIGN PATENT DOCUMENTS

| | | |
|---|---|---|
| EP | 2476440 A1 | 7/2012 |
| EP | 1 913 954 B1 | 8/2012 |
| EP | 3270955 A1 | 1/2018 |
| JP | 2006500358 A | 1/2006 |
| JP | 2007519612 A | 7/2007 |
| JP | 2008528643 A | 7/2008 |
| JP | 2011519834 A | 7/2011 |
| JP | 2015527313 A | 9/2015 |
| KR | 1020020079887 | 10/2002 |
| KR | 101040281 B1 | 6/2011 |
| WO | WO-1998/042752 A1 | 10/1998 |
| WO | WO-1999/059615 A1 | 11/1999 |
| WO | WO-2000/037504 A2 | 6/2000 |
| WO | WO-2001/014424 A2 | 3/2001 |
| WO | WO-2001/051673 A1 | 7/2001 |
| WO | WO-2004016241 A1 | 2/2004 |
| WO | WO-2004/035607 A2 | 4/2004 |
| WO | WO-2005/039632 A1 | 5/2005 |
| WO | WO-2006/081826 A2 | 8/2006 |
| WO | WO-2008083174 A2 | 7/2008 |
| WO | WO-2008/132601 A1 | 11/2008 |
| WO | WO-2008/156712 A1 | 12/2008 |
| WO | WO-2009/015843 A1 | 2/2009 |
| WO | WO-2009018500 A1 | 2/2009 |
| WO | WO-2009/044273 A2 | 4/2009 |
| WO | WO-2009155535 A2 | 12/2009 |
| WO | WO-2010105347 A1 | 9/2010 |
| WO | WO-2011/014438 A1 | 2/2011 |
| WO | WO-2011/036211 A1 | 3/2011 |
| WO | WO-2011/066389 A1 | 6/2011 |
| WO | WO-2011/101332 A1 | 8/2011 |
| WO | WO-2011/135222 A2 | 11/2011 |
| WO | 2012/013326 A1 | 2/2012 |
| WO | WO-2012/048190 A1 | 4/2012 |
| WO | WO-2012/050365 A2 | 4/2012 |
| WO | WO-2012097012 A1 | 7/2012 |
| WO | WO-2013/006490 A2 | 1/2013 |
| WO | WO-2013/025779 A1 | 2/2013 |
| WO | WO-2013/067492 A1 | 5/2013 |
| WO | WO-2013/075048 A1 | 5/2013 |
| WO | 2013/113501 A1 | 8/2013 |
| WO | WO-2013/120073 A1 | 8/2013 |
| WO | WO-2014009209 A2 | 1/2014 |
| WO | WO-2014/041505 A1 | 3/2014 |
| WO | WO-2014046983 A1 | 3/2014 |
| WO | WO-2014/070663 A1 | 5/2014 |
| WO | WO-2014/165101 A1 | 10/2014 |
| WO | WO-2015/069932 A1 | 5/2015 |
| WO | WO-2015/103037 A2 | 7/2015 |
| WO | WO-2015/188197 A2 | 12/2015 |
| WO | WO-2016070136 A1 | 5/2016 |
| WO | WO-2016146143 A1 | 9/2016 |
| WO | WO-2016146260 A1 | 9/2016 |
| WO | WO-2016146261 A1 | 9/2016 |
| WO | WO-201702345 A1 | 1/2017 |
| WO | WO-2017089779 A1 | 6/2017 |
| WO | WO-2017118864 A1 | 7/2017 |
| WO | WO-2017195032 A1 | 11/2017 |
| WO | WO-201815845 A1 | 1/2018 |
| WO | WO-2018053508 A1 | 3/2018 |
| WO | WO-2018055060 A1 | 3/2018 |
| WO | WO-2018187356 A2 | 10/2018 |
| WO | WO-2019150310 A1 | 8/2019 |

OTHER PUBLICATIONS

Pardoll, D. (2012), "The blockade of immune checkpoints in cancer immunotherapy", *Nature Reviews Cancer*, 12(4): 252-264.
Zhang, T., et al. (2012), "LAH4 enhances CD8+ T cell immunity of protein/peptide-based vaccines", *Vaccine*, 30: 784-793.
Walker, P, et al. (2016), "Cell-penetrating peptides—the Swiss Army knife of cancer vaccines", *Oncoimmunology*, 5(3): p. e1095435 (3 pages).
Aranda, F., et al. (2013), "Trial Watch: peptide vaccines in cancer therapy", *OncoImmunology*, 2(12): e26621.
International Search Report issued in PCT/EP2017/056034 dated May 24, 2017.
Written Opinion issued in PCT/EP2017/056034 dated May 24, 2017.
International Search Report issued in International Patent Application No. PCT/EP2016/000471 mailed Mar. 16, 2017.
Written Opinion issued in International Patent Application No. PCT/EP2016/000471, mailed Mar. 16, 2016.
Derouazi M. et al., (2015) "Novel cell-penetrating peptide-based vaccine induces robust CD4+ and CD8+ T cell-mediated antitumor immunity" Cancer Research, 75:15 3020-3031.

(56) References Cited

OTHER PUBLICATIONS

Minsig C. et al., (2014) "Identifying Appropriate Colorectal Cancer-Associated Antigens for the Clinical Trials" Current Colorectal Cancer Reports, 11:1 29-36.
Novellino L. et al., (2005) "A listing of human tumor antigens recognizes by T-cells: Mar. 2004 update" Cancer Immunology, 54:3 187-207.
Vigneron N. et al., (2013) "Database of T cell-defined human tumor antigens: the 2013 update" Cancer Immunity. 13:15.
International Search Report issued in International Patent Application No. PCT/EP2016/000473 mailed Jun. 17, 2016.
Reardon D. et al., (2013)"An update on vaccine therapy and other immunotherapeutic approaches for glioblastoma" Expert Review of Vaccines 12:6 597-615.
International Search Report issued in International Patent Application No. PCT/EP2016/000470, mailed Jun. 17, 2016.
Written Opinion issued in International Patent Application No. PCT/EP2016/000470, mailed Jun. 17, 2016.
International Search Report issued in PCT/EP2015/002598, mailed Mar. 16, 2016.
Written Opinion issued in PCT/EP2015/002598, mailed Mar. 16, 2016.
Written Opinion issued in International Patent Application No. PCT/EP2016/00473, mailed Jun. 17, 2016.
Office Action dated Oct. 5, 2018 as issued in U.S. Appl. No. 15/557,651.
International Search Report and Written Opinion dated Jan. 8, 2014 issued in PCT Patent Application No. PCT/IB2013/058497.
Anton, L., et al. (1997), "MHC Class-I-Associated Peptides Produced from Endogenous Gene Products with Vastly Different Efficiencies", *The Journal of Immunology*, 158: 2535-2542.
Brooks, N. et al. (2010), "Cell-penetrating peptides: Application in vaccine delivery", *Biochimica et Biophysica Acta*, 1805: 25-34.
Derouazi, M., et al. (2010), "Towards an Efficient DC Vaccine by Antigenic Protein Loading Using a Novel Protein Transduction Domain", *Poster at 11th International Sumposium on Dendritic Cells in Fundamental and Clinical Immunology—DC 2010, Palazzo dei Congressi, Lungano*.
Durántez, M., et al. (2008), "Induction of Multiepitopic and Long-Lasting Immune Responses Against Tumour Antigens by Immunization with Peptides, DNA and Recombinant Adenoviruses Expressing Minigenes", *Scandinavian Journal of Immunology*, 69: 80-89.
Ishioka G., et al. (1999), "Utilization of MHC Class I Transgenic Mic for Development of MINIgene DNA Vaccines Encoding Multiple HLAK-Restricted CTL Epitopes", *The Journal of Immunology*, 162: 3915-3925.
Mateo, L., et al. (1999), "An HLA-A2 Polyepitope Vaccine for Melanoma Immunotherapy", *The American Association of Immunologist*, 163: 4058-4063.
McPherson, S., et al. (2003), Resting CD8 T cells recognize β-galactosidase expressed in the immune-privileged retina and mediate autoimmune disease when activated, *Immunology*, 110: 386-396.
NCBI Reference YP01673.1—BZLF1 [Human herpesvirus 4]—Protein—www.ncbi.nlm.nih.gov/protein/YP_401673—3 pages, 2012.
Rosenzweig, M., et al. (2001), "Induction of cytotoxic T lymphocyte and antibody responses to enhanced green fluorescent protein following transplantation of transduced CD 34+ hematopoietic cells", *Blood*, 97(7): 1951-1959.
Rothe, R., et al. (2008), "Expression and Purification of ZEBRA Fusion Proteins and Applications for the Delivery of Macromolecules into Mammalian Cells", *Current Protocols in Protein Science*, Supplemental 54(18): 11.1-11.29.
Rothe, R., et al. (2010), "Characterization of the Cell-penetrating Properties of the Epstein-Barr Virus ZEBRA trans-Activator", *The Journal of Biological Chemistry*, 285(26): 20224-20233.
Rothe, R., et al. (2010), "PHD Thesis—Caractérisation de la propriété de la Protéine ZEBRA du virus Epstein-Barr á pénétrer dans les cellules", *Universite De Grenoble*, 156 pages.
Scardino, A., et al. (2007), "A Polyepitope DNA Vaccine Targeted to Her-2/ErbB-2 Elicits a Broad Range of Human and Murine CTL Effectors to Protect against Tumor Challenge", *Cancer Research*, 64(14): 7028-7036.
Stubbs, A., et al. (2001), "Whole recombinant yeast vaccine activates dendritic cells and elicits protective cell-mediated immunity", *Nature Medicine*, 7(5): 625-629.
Thomson, S., et al. (1995), "Minimal epitopes expressed in a recombinant polyepitope protein are processed and presented to CD8+ cytotoxic T cells: Implications for vaccine design", *Proc. Natl. Acad. Sci. USA.*, 92: 5845-5849.
Thomson, S., et al. (1996), "Recombinant Polyepitope Vaccines for the Delivery of Multiple CD8 Cytotoxic T Cell Epitopes", *The Journal of Immunology*, 157: 822-826.
Tine, J., et al. (2005), "Enhanced multiepitope-based vaccines elicit CD8+ cytotoxic T cells against both immunodominant and cryptic epitopes", *Vaccine*, 23: 1085-1091.
Tünnemann, G., et al. (2006), "Cargo-dependent mode of uptake and bioavailability of TAT-Containing proteins and peptides in living cells", *The FASEB Journal*, 1775-1784.
Van Montfoort, N., et al. (2009), "Antigen storage compartments in mature dendritic cells facilitate prolonged cytotoxic T lymphocyte cross-priming capacity", *PNAS*, 106(16): 6730-6735.
Waeckerle-Men Y., et al. (2005), "Dendritic cell-based multiepitope immunotherapy of hormone-refractory prostate carcinoma", *Cancer Immunol Immunother*, 55: 1524-1533.
International Search Report and Written Opinion for PCT Application No. PCT/EP2017/073954 dated Dec. 22, 2017.
International Search Report issued in International Patent Application No. PCT/EP2016/000471, mailed Jun. 17, 2016.
Written Opinion issued in International Patent Application No. PCT/EP2016/000473, mailed Jun. 17, 2016.
Written Opinion issued in International Patent Application No. PCT/EP2016/000471. mailed Jun. 17, 2016.
Office Action dated Jul. 11, 2019 from U.S. Appl. No. 15/557,653.
Restriction Requirement from U.S. Appl. No. 15/557,649 dated Sep. 26, 2019.
Final Office Action from U.S. Appl. No. 15/557,651 dated Oct. 25, 2019.
Tacken, P.J., et al., "No Advantage of Cell-Penetrating Peptides over Receptor-Specific Antibodies in Targeting Antigen to Human Dendritic Cells for Cross-Presentation," The Journal of Immunology 180: 7687-7696 (2008).
Yadav, M., et al., "Predicting immunogenic tumor mutations by combining mass spectrometry and exome sequencing," Nature 515: 572-576 (2014).
Gnjatic, S., et al., "Toll-Like Receptor Agonists; Are They Good Adjuvants?," The Cancer Journal 16(4): 382-391 (2010).
Restriction Requirement from U.S. Appl. No. 15/557,647 dated Aug. 22, 2019.
Schmitz, M., et al., "Generation of Survivin-specific CD8[+] T Effector Cells by Dendritic Cells Pulsed with Protein or Selected Peptides[1]," Cancer Research, 60: 4845-4849 (2000).
Hidekazu, K., et al., "Immunogenic enhancement and clinical effect by Type-I interferon of anti-apoptotic protein, survivin-derived peptide vaccine, in advanced colorectal cancer in patients," Cancer Science, 102(6): 1181-1187 (2011).
Friedrichs, B., et al., "Survivin-derived peptide epitopes and their role for induction of antitumor immunity in hematological malignancies," Leukemia & Lymphoma, 47(6): 978-985 (2006).
Non-final Office Action from U.S. Appl. No. 15/557,649 dated Feb. 3, 2020.
Office Action from U.S. Appl. No. 15/557,653 dated Apr. 13, 2020.
Oh, T., et al., "Immunocompetent murine models for the study of glioblastoma immunotherapy," Journal of Translational Medicine, 12(107): 1-10 (2014).
Office Action issued in U.S. Appl. No. 15/557,651 dated Apr. 22, 2020.
Office Action from U.S. Appl. No. 15/557,647 dated Jun. 22, 2020.
Office Action from U.S. Appl. No. 15/557,649 dated Jul. 7, 2020.
Houot, R., and Levy, R., "T-cell modulation combined with intratumoral CpG cures lymphoma in a mouse model without the need for chemotherapy," Blood, 113(15): 3546-3552 (2009).

(56) References Cited

OTHER PUBLICATIONS

Office Action issued in corresponding RU Application No. 2018135097 dated Jul. 30, 2020.
Muller, S., et al., "Nucleic Acids From A to Z," Moscow: BINOM. Knowledge laboratory, p. 216 (2013).
Office Action from corresponding U.S. Appl. No. 15/557,653 dated Dec. 14, 2020.
Office Action from corresponding U.S. Appl. No. 16/084,170 dated Nov. 10, 2020.
Zamarin, D., and Postow, M.A., "Immune checkpoint modulation: Rational design of combination strategies," Pharmacology & Therapeutics, 150: 23-32 (2015).
Stewart, B. and C. Wild, *World Cancer Report* 2014, B. Stewart and C. Wild, Editors. 2014, International Agency for Research on Cancer: Geneva.
Burt, R.W., J.A. DiSario, and L. Cannon-Albright, *Genetics of colon cancer: impact of inheritance on colon cancer risk*. Annu Rev Med, 1995. 46: p. 371-9.
Sieber, O.M., et al., *Multiple colorectal adenomas, classic adenomatous polyposis, and germ-line mutations in MYH*. N Engl J Med, 2003. 348(9): p. 791-9.
Lynch, H.T., et al., *Genetics, natural history, tumor spectrum, and pathology of hereditary nonpolyposis colorectal cancer: an updated review*. Gastroenterology, 1993. 104(5): p. 1535-49.
Ekbom, A., et al., *Ulcerative colitis and colorectal cancer. A population-based study*. N Engl J Med, 1990. 323(18): p. 1228-33.
Jemal, A., et al., *Global cancer statistics*. CA Cancer J Clin, 2011. 61(2): p. 69-90.
Moertel, C.G., *Chemotherapy for colorectal cancer*. N Engl J Med, 1994. 330(16): p. 1136-42.
Meyerhardt, J.A. and R.J. Mayer, *Systemic therapy for colorectal cancer*. N Engl J Med, 2005. 352(5): p. 476-87.
Gallagher, D.J. and N. Kemeny, *Metastatic colorectal cancer: from improved survival to potential cure*. Oncology, 2010. 78(3-4): p. 237-48.
Smith, C.L., et al., *Immunotherapy of colorectal cancer*. Br Med Bull, 2002. 64: p. 181-200.
Koido, S., et al., *Immunotherapy for colorectal cancer*. World J Gastroenterol, 2013. 19(46): p. 8531-42.
Xiang, B., et al., *Colorectal cancer immunotherapy*. Discov Med, 2013. 15(84): p. 301-8.
Clarke, J.M. and H.I. Hurwitz, *Ziv-aflibercept: binding to more than VEGF-A—does more matter?* Nat Rev Clin Oncol, 2013. 10(1): p. 10-1.
Siegel, R., C. Desantis, and A. Jemal, *Colorectal cancer statistics*, 2014. CA Cancer J Clin, 2014. 64(2): p. 104-17.
Slingluff CL, Jr. The present and future of peptide vaccines for cancer: single or multiple, long or short, alone or in combination? Cancer journal 2011; 17(5):343-50.
Melief CJ, van der Burg SH. Immunotherapy of established (pre-)malignant disease by synthetic long peptide vaccines. Nature reviews Cancer 2008;8(5):351-60.
Kruit WH, Suciu S, Dreno B, Mortier L, Robert C, Chiarion-Sileni V, et al. Selection of immunostimulant AS15 for active immunization with MAGE-A3 protein: results of a randomized phase II study of the European Organisation for Research and Treatment of Cancer Melanoma Group in Metastatic Melanoma. Journal of clinical oncology : official journal of the American Society of Clinical Oncology 2013;31(19):2413-20.
Vansteenkiste J, Zielinski M, Linder A, Dahabreh J, Gonzalez EE, Malinowski W, et al. Adjuvant MAGE-A3 immunotherapy in resected non-small-cell lung cancer: phase II randomized study results. Journal of clinical oncology : official journal of the American Society of Clinical Oncology 2013;31(19):2396-403.
Toes RE, Offringa R, Blom RJ, Melief CJ, Kast WM. Peptide vaccination can lead to enhanced tumor growth through specific T-cell tolerance induction. Proceedings of the National Academy of Sciences of the United States of America 1996;93(15):7855-60.
Rosalia RA, Quakkelaar ED, Redeker A, Khan S, Camps M, Drijfhout JW, et al. Dendritic cells process synthetic long peptides better than whole protein, improving antigen presentation and T-cell activation. European journal of immunology 2013;43(10):2554-65.
Apetoh L, Locher C, Ghiringhelli F, Kroemer G, Zitvogel L. Harnessing dendritic cells in cancer. Semin Immunol. 2011; 23:42-49.
Banchereau J, Steinman RM. Dendritic cells and the control of immunity. Nature. 1998; 392:245-252.
Wang RF, Wang HY. Enhancement of antitumor immunity by prolonging antigen presentation on dendritic cells. Nat Biotechnol. 2002; 20:149-156.
Copolovici DM, Langel K, Eriste E, Langel U. Cell-penetrating peptides: design, synthesis, and applications. ACS nano 2014;8(3):1972-94.
Milletti, F., Cell-penetrating peptides: classes, origin, and current landscape. Drug Discov Today 17 (15-16): 850-60, 2012.
Berry CC. Intracellular delivery of nanoparticles via the HIV-1 tat peptide. Nanomedicine. 2008, 3:357-365.
Deshayes S, Morris MC, Divita G, Heitz F. Cell-penetrating peptides: Tools for intracellular delivery of therapeutics. Cell Mol Life Sci. 2005; 62:1839-1849.
Edenhofer F. Protein transduction revisited: Novel insights into the mechanism underlying intracellular delivery of proteins. Curr Pharm Des. 2008; 14:3628-3636.
Gupta B, Levchenko TS, Torchilin VP. Intracellular delivery of large molecules and small particles by cell-penetrating proteins and peptides. Adv Drug Deliv Rev. 2005; 57:637-651.
Torchilin VP. Recent approaches to intracellular delivery of drugs and DNA and organelle targeting. Annu Rev Biomed Eng. 2006; 8:343-375.
Wang HY, Fu T, Wang G, Gang Z, Donna MPL, Yang JC, Restifo NP, Hwu P, Wang RF. Induction of CD4+ T cell-dependent antitumor immunity by TAT-mediated tumor antigen delivery into dendritic cells. J Clin Invest. 2002a; 109:1463-1470.
Frankel, A.D. and C.O. Pabo, Cellular uptake of the tat protein from human immunodeficiency virus. Cell, 1988. 55(6): p. 1189-93.
Joliot, A., et al., Antennapedia homeobox peptide regulates neural morphogenesis. Proc Natl Acad Sci U S A, 1991. 88(5): p. 1864-8.
Derossi, D., et al., The third helix of the Antennapedia homeodomain translocates through biological membranes. J Biol Chem, 1994. 269(14): p. 10444-50.
Vives, E., P. Brodin, and B. Lebleu, A truncated HIV-1 Tat protein basic domain rapidly translocates through the plasma membrane and accumulates in the cell nucleus. J Biol Chem, 1997. 272(25): p. 16010-7.
Elliott, G. and P. O'Hare, Intercellular trafficking and protein delivery by a herpesvirus structural protein. Cell, 1997. 88(2): p. 223-33.
Dempsey, C.E., The actions of melittin on membranes. Biochim Biophys Acta, 1990. 1031 (2): p. 143-61.
Konno, K., et al., Structure and biological activities of eumenine mastoparan-AF (EMP-AF), a new mast cell degranulating peptide in the venom of the solitary wasp (*Anterhynchium flavomarginatum micado*). Toxicon, 2000. 38(11): p. 1505-15.
Esteve, E., et al., Transduction of the scorpion toxin maurocalcine into cells. Evidence that the toxin crosses the plasma membrane. J Biol Chem, 2005. 280(13): p. 12833-9.
Nascimento, F.D., et al., Crotamine mediates gene delivery into cells through the binding to heparan sulfate proteoglycans. J Biol Chem, 2007. 282(29): p. 21349-60.
Kobayashi, S., et al., Membrane translocation mechanism of the antimicrobial peptide buforin 2. Biochemistry, 2004. 43(49): p. 15610-6.
Futaki, S., et al., Arginine-rich peptides. An abundant source of membrane-permeable peptides having potential as carriers for intracellular protein delivery. J Biol Chem, 2001. 276(8): p. 5836-40.
Pooga, M., et al., Cell penetration by transportion. FASEB J, 1998. 12(1): p. 67-77.
Nair et al. (2003, Nucleic Acids Res. 31(1): 397-399.
Kapoor et al. (2012, PLoS ONE 7(4): e35187.
Lim, Y.T., Vaccine adjuvant materials for cancer immunotherapy and control of infectious disease. Clin Exp Vaccine Res, 2015. 4(1): p. 54-8.

(56) References Cited

OTHER PUBLICATIONS

Baxevanis, C.N., I.F. Voutsas, and O.E. Tsitsilonis, Toll-like receptor agonists: current status and future perspective on their utility as adjuvants in improving anticancer vaccination strategies. Immunotherapy, 2013. 5(5): p. 497-511.
Duthie MS, Windish HP, Fox CB, Reed SG. Use of defined TLR ligands as adjuvants within human vaccines. Immunol Rev. 2011; 239:178-196.
Manicassamy S, Pulendran B. Modulation of adaptive immunity with Toll-like receptors. Semin Immunol. 2009; 21:185-193.
Zom GG, Khan S, Filippov DV, Ossendorp F. TLR ligand-peptide conjugate vaccines: toward clinical application. Adv Immunol. 2012;114:177-201.
Fujita, Y. and H. Taguchi, *Overview and outlook of Toll-like receptor ligand-antigen conjugate vaccines*. Ther Deliv, 2012. 3(6): p. 749-60.
Monie, T. P., Bryant, C. E., et al. 2009: Activating immunity: Lessons from the TLRs and NLRs. Trends Biochem. Sci. 34(11), 553-561.
Gay, N. J., and Gangloff, M. (2007): Structure and function of Toll receptors and their ligands. Annu. Rev. Biochem. 76, 141-165.
Spohn, R., Buwitt-Beckmann, U., et al. (2004): Synthetic lipopeptide adjuvants and Toll-like receptor 2-Structure-activity relationships. Vaccine 22(19), 2494-2499.
Bryant, C. E., Spring, D. R., et al. (2010). The molecular basis of the host response to lipopolysaccharide. Nat. Rev. Microbiol. 8(1), 8-14.
Barbalat R, Lau L, Locksley RM, Barton GM. Toll-like receptor 2 on inflammatory monocytes induces type I interferon in response to viral but not bacterial ligands. Nat Immunol. 2009: 10(11):1200-7.
Akira S, Uematsu S, Takeuchi O. Pathogen recognition and innate immunity. Cell. Feb. 24; 2006: 124(4):783-801.
Kumar H, Kawai T, Akira S. Toll-like receptors and innate immunity. Biochem Biophys Res Commun. Oct. 30; 2009 388(4):621-5.
Lasarte, J.J., et al., The extra domain A from fibronectin targets antigens to TLR4-expressing cells and induces cytotoxic T cell responses in vivo. J Immunol, 2007. 178(2): p. 748-56.
Applequist, S.E., R.P. Wallin, and H.G. Ljunggren, Variable expression of Toll-like receptor in murine innate and adaptive immune cell lines. Int Immunol, 2002. 14(9): p. 1065-74.
Okamura, Y., et al., The extra domain A of fibronectin activates Toll-like receptor 4. J Biol Chem, 2001. 276(13): p. 10229-33.
Jameson et al., Nature, 368,744-746 (1994).
Brady et al., Nature, 368,692-693 (1994).
Seifter et al. (1990) Analysis for protein modifications and nonprotein cofactors, Meth. Enzymol. 182: 626-646.
Rattan et al., (1992) Protein Synthesis: Post-translational Modifications and Aging, Ann NY Acad Sci, 663: 48-62.
Karlin et al. (1993), PNAS USA, 90:5873-5877.
Altschul et al., 1990, J. Mol. Biol. 215, 403-410.
Altschul et al. (1997), Nucleic Acids Res, 25:3389-3402.
Pearson (1990), Methods Enzymol. 183, 63-98.
Pearson and Lipman (1988), Proc. Natl. Acad. Sci. U. S. A 85, 2444-2448.
Devereux et al., 1984, Nucleic Acids Res., 387-395.
Smith and Waterman (1981), J. Mol. Biol. 147, 195-197.
Apostolopoulos et al., 1996 Immunol. Cell. Biol. 74: 457-464.
Pandey et al., 1995, Cancer Res. 55: 4000-4003.
Kierkegaard et al., 1995, Gynecol. Oncol. 59: 251-254.
Kievit et al., 1997, Int. J. Cancer 71: 237-245.
Lozza et al., 1997 Anticancer Res. 17: 525-529.
Mota et al., 1997, Am. J Pathol. 150: 1223-1229.
Fishman et al., 1997 Cancer 79: 1461-1464.
Notelet et al., 1997 Surg. Neurol. 47: 364-370.
Lucas et al., 1996 Anticancer Res. 16: 2493-2496.
Macs et al., 1996, J. Cancer Res. Clin. Oncol. 122: 296-300.
Tolliver and O'Brien, 1997, South Med. J. 90: 89-90.
Tsuruta at al., 1997 Urol. Int. 58: 20-24.
Huang et al., Exper Rev. Vaccines (2002)1:49-63.
Zantek et al., Cell Growth Differ. (1999) 10:629-38.
Carles-Kinch et al., Cancer Res. (2002) 62:2840-7.
Cheng at al., 2002, Cytokine Growth Factor Rev. 13:75-85.
Dahlenborg et al., 1997, Int. J Cancer 70: 63-71.
Zajac et al., 1997, Int. J Cancer 71: 491-496.
Deshpande and Danishefsky, 1997, Nature 387: 164-166.
Kawakami and Rosenberg, 1997, Int. Rev. Immunol. 14: 173-192.
Molldrem et al., Blood (1996) 88:2450-7.
Molldrem et al., Blood (1997) 90:2529-34.
De wit Amer 2010, Neuro Oncol, 12(3):304-16.
Maccalli, C., et al., *Identification of a colorectal tumor-associated antigen (COA-1) recognized by CD4(+)T lymphocytes*. Cancer Res, 2003. 63(20): p. 6735-43.
Derouazi M, Wang Y, Marlu R, et al. Optimal epitope composition after antigen screening using a live bacterial delivery vector: Application to TRP-2. Bioengineered Bugs. 2010;1 (1):51-60. doi:10.4161/bbug.1.1.9482.
Lu et al., Multiepitope trojan antigen peptide vaccines for the induction of antitumor CTL and Th immune responses J. Immunol., 172 (2004), pp. 4575-4582.
Rose et al. (1994), JACS 116, 30.
Means and Feeney, Chemical Modification of Proteins, Holden-Day, 1974, pp. 39-43.
Chen X. et al., 2013: Fusion Protein Linkers: Property, Design and Functionality. Adv Drug Deliv Rev. 65(10): 1357-1369.
Response Evaluation Criteria in Solid Tumors (RECIST) and World Health Organization (WHO) criteria; J. Natl. Cancer Inst. 2010, 102(18): 1388-1397.
Jewell, C.M., S.C. Lopez, and D.J. Irvine, *In situ engineering of the lymph node microenvironment via intranodal injection of adjuvant-releasing polymer particles*. Proc Natl Acad Sci US A, 2011. 108(38): p. 15745-50.
Newcomb, E. and D. Zagzag, The murine GL261 glioma experimental model to assess novel brain tumor treatments, in CNS Cancer Models, Markers, Prognostic, Factors, Targets, and Therapeutic Approaches, E.G. Van Meir, Editor. 2009, Humana Press: Atlanta. p. 227-241.
Jacobs, V.L., et al., Current review of in vivo GBM rodent models: emphasis on the CNS-1 tumour model. ASN Neuro, 2011. 3(3): p. e00063.
Zhu, X., et al., *Poly-/CLC promotes the infiltration of effector T cells into intracranial gliomas via induction of CXCL10 in IFN-alpha and IFN-gamma dependent manners*. Cancer Immunol Immunother, 2010. 59(9): p. 1401-9.
Zhu, X., et al., *Toll like receptor-3 ligand poly-/CLC promotes the efficacy of peripheral vaccinations with tumor antigen-derived peptide epitopes in murine CNS tumor models*. J Transl Med, 2007. 5: p. 10.
Ohlfest, J.R., et al., *Vaccine injection site matters: qualitative and quantitative defects in CDB T cells primed as a function of proximity to the tumor in a murine glioma model*. J Immunol, 2013. 190(2): p. 613-20.
Käll L, Canterbury JD, Weston J, Noble WS, MacCoss MJ (2007) Semi-supervised learning for peptide identification from shotgun proteomics datasets. Nat Methods 4(11):923-925.
Susumu Suzuki et al., 2016: Current status of immunotherapy. Japanese Journal of Clinical Oncology, 2016: doi: 10.1093/jjco/hyv201 [Epub ahead of print].
Hamid et al., 2013; N. Engl. J. Med. 369: 134-144.
Brignone et al., 2009, Clin. Cancer Res. 15: 6225-6231.
Keir, M.E., et al., PD-1 and its ligands in tolerance and immunity. Annu Rev Immunol, 2008. 26: p. 677-704.
Semakova, A.P., et al., "Adjuvant Technologies in the Construction of Advanced Vaccines", Problems of Particularly Dangerous Infections, 2: p. 28-35 (2016).
*Cancer Statistic 2015*. Americain Cancer Society.
Stupp, R., et al., *Radiotherapy plus concomitant and adjuvant temozolomide for glioblastoma*. N Engl J Med, 2005. 352(10): p. 987-96.
Hegi, M.E., et al., *MGMT gene silencing and benefit from temozolomide in glioblastoma*. N Engl J Med, 2005. 352(10): p. 997-1003.
Bechmann, I., I. Galea, and V.H. Perry, *What is the blood-brain barrier (not)?* Trends Immunol, 2007. 28(1): p. 5-11.

(56) References Cited

OTHER PUBLICATIONS

Walker, P.R., et al., *T-cell immune responses in the brain and their relevance for cerebral malignancies*. Brain Res Brain Res Rev, 2003. 42(2): p. 97-122.
Hickey, W.F., B.L. Hsu, and H. Kimura, *T-lymphocyte entry into the central nervous system*. J Neurosci Res, 1991. 28(2): p. 254-60).
Abou-Ghazal, M., et al., *The incidence, correlation with tumor-infiltrating inflammation, and prognosis of phosphorylated STAT3 expression in human gliomas*. Clin Cancer Res, 2008. 14(24): p. 8228-35.
Buckanovich, R.J., et al., *Endothelin B receptor mediates the endothelial barrier to T cell homing to tumors and disables immune therapy*. Nat Med, 2008. 14(1): p. 28-36.
Mittelbronn, M., et al., *Elevated HLA-E levels in human glioblastomas but not in grade I to III astrocytomas correlate with infiltrating CD8+ cells*. J Neuroimmunol, 2007. 189(1-2): p. 50-8.
Perrin, G., et al., *Astrocytoma infiltrating lymphocytes include major T cell clonal expansions confined to the CD8 subset*. Int Immunol, 1999. 11(8): p. 1337-50.
Bucciero, A., et al., *Prognostic significance of lymphoid infiltration in cerebral malignant gliomas*. J Neurosurg Sci, 1990. 34(2): p. 145-8.
Tang, J., et al., *Glioblastoma patients exhibit circulating tumor-specific CD8+ T cells*. Clin Cancer Res, 2005. 11(14): p. 5292-9.
Maus, M.V., et al., *Antibody-modified T cells: CARs take the front seat for hematologic malignancies*. Blood, 2014. 123(17): p. 2625-35.
Saikali, S., et al., *Expression of nine tumour antigens in a series of human glioblastoma multiforme: interest of EGFRvIII, IL-13Ralpha2, gp100 and TRP-2 for immunotherapy*. J Neurooncol, 2007. 81(2): p. 139-48.
Schuster, J., et al., *A phase II, multicenter trial of rindopepimut (CDX-110) in newly diagnosed glioblastoma: the Act III study*. Neuro Oncol, 2015. 17(6): p. 854-61.
Nakada, M., Y. Hayashi, and J. Hamada, *Role of Eph/ephrin tyrosine kinase in malignant glioma*. Neuro Oncol, 2011. 13(11): p. 1163-70.
Phuphanich, S., et al., *Phase I trial of a multi-epitope-pulsed dendritic cell vaccine for patients with newly diagnosed glioblastoma*. Cancer Immunol Immunother, 2013. 62(1): p. 125-35.
Kyte and Doolittle, 1982, J. Mol. Biol. 157(1):105-132.
Cobbs CS, Harkins L, Samanta M, et al. Human cytomegalovirus infection and expression human malignant glioma. Cancer Res. 2002;62:3347-3350.
Trivedi et al., Blood, 105:2793 (2005).
Shaw, E.G., et al., *Recurrence following neurosurgeon-determined gross-total resection of adult supratentorial low-grade glioma: results of a prospective clinical trial*. J Neurosurg, 2008. 109(5): p. 835-41.
Greenspan, N.S., & Cera, E.D., "Defining epitopes: It's not as easy as it seems," Nature Biotechnology, 17: 936-937 (1999).
Rudikoff, S., et al., "Single amino acid substitution altering antigen-binding specificity," Proc. Natl. Acad. Sci. USA, 79: 1979-1983 (1982).
Colman, P.M., "Effects of amino acid sequence changes on antibody-antigen interactions," Research in Immunology, 145(1): 33-36 (1994).
Wang, C.Y., et al., "Systematic analysis of the achaete-scute complex-like gene signature in clinical cancer patients". Mol Clin Oncol., 6(1):7-18 (2017).
Zhao, M., and Weissleder, R., "Intracellular Cargo Delivery Using Tat Peptide and Derivatives," Medicinal Research Reviews, 24(1): 1-12 (2004).
Heitz, F., et al., "Twenty years of cell-penetrating peptides: from molecular mechanisms to therapeutics," British Journal of Pharmacology, 157(2): 195-206 (2009).
Spencer, A.J., et al., "Fusion of the *Mycobacterium tuberculosis* Antigen 85A to an Oligomerization Domain Enhances Its Immunogenicity in Both Mice and Non-Human Primates," PLOS One, 7(3): p. e33555, (2012).
Shen, J., et al., "Single Variable Domain-IgG Fusion: A Novel Recombinant Approach to Fc Domain-Containing Bispecific Antibodies", The Journal of Biological Chemistry, 281(16), 10706-10714 (2006).
Swiech, K., et al., "Human cells: New platform for recombinant therapeutic protein production," Protein Expression and Purification, 84(1): 147-153 (2012).
Welniak, L.A., et al., "Immunobiology of Allogeneic Hematopoietic stem cell transplantation," Annu. Rev. Immunol., 25: 139-170 (2007).
Grupp, S.A., et al., "Chimeric Antigen Receptor-Modified T Cells for Acute Lymphoid Leukemia," New England Journal of Medicine, 368(16): 1509-1518 (2013).
Jones, H.L., et al., "Luminal Epithelial Antigen (LEA. 135) Expression Correlates with Tumor Progression for Transitional Carcinoma of the Bladder," AntiCancer Research, 17: 685-688 (1997).
Beckett, M.L., and Wright Jr., G.L., "Characterization of a Prostate Carcinoma Mucin-Like Antigen (PMA)," Int. J. Cancer, 62: 703-710 (1995).
Antonia, Scott et al., 2016, Safety and antitumour activity of durvalumab plus tremelimumab in non-small cell lung cancer: a multicentre, phase 1b study; Lancet Oncol. Feb. 5, 2016. pii: S1470-2045(15)00544-6. doi: 10.1016/S1470-2045(15)00544-6.
Greenwald, R.J., G.J. Freeman, and A.H. Sharpe, *The B7 family revisited*. Annu Rev Immunol, 2005. 23: p. 515-48.
Zou, W. and L. Chen, Inhibitory B7-family molecules in the tumour microenvironment. Nat Rev Immunol, 2008. 8(6): p. 467-77.
Chapoval, A.I., et al., *B7-H3: a costimulatory molecule for T cell activation and IFN-gamma production*. Nat Immunol, 2001. 2(3): p. 269-74.
Sica, G.L., et al., *B7-H4, a molecule of the B7 family, negatively regulates T cell immunity*. Immunity, 2003. 18(6): p. 849-61.
Loos, M., et al., *B7-h3 and its role in antitumor immunity*. Clin Dev Immunol, 2010. 2010: p. 683875.
Hofmeyer, K.A., A. Ray, and X. Zang, *The contrasting role of B7-H3*. Proc Natl Acad Sci US A, 2008.105(30): p. 10277-8.
Sun, J., et al., *Clinical significance and regulation of the costimulatory molecule B7-H3 in human colorectal carcinoma*. Cancer Immunol Immunother, 2010. 59(8): p. 1163-71.
Dangaj, D. and N. Scholler, *Blocking the B7-H4 pathway with novel recombinant antibodies enhances T cell-mediated antitumor responses*. Oncoimmunology, 2013. 2(8): p. e25913.
Dangaj, D., et al., *Novel recombinant human b7-h4 antibodies overcome tumoral immune escape to potentiate T-cell antitumor responses*. Cancer Res, 2013. 73(15): p. 4820-9.
Wang, X., et al., *B7-H4 Treatment o/T Cells Inhibits ERK,]NK, p38, and AKT Activation*. PLoS One, 2012. 7(1): p. e28232.
Leong, S.R., et al., *An anti-b7-h4 antibody-drug conjugate for the treatment of breast cancer*. Mol Pharm, 2015.12(6): p. 1717-29.
Buchbinder E. I. and Desai A., 2016: CTLA-4 and PD-1 Pathways—Similarities, Differences and Implications of Their Inhibition; American Journal of Clinical Oncology, 39(1): 98-106.
Hurwitz et al., Proc. Natl. Acad. Sci. USA, 95(17):10067-10071 (1998).
Camacho et al., J. Clin. Oncology, 22(14):Abstract No. 2505 (2004).
Mokyr et al., Cancer Res., 58:5301-5304 (1998).
Jenessa B. Smith et al., 2014: B7-H4 as a potential target for immunotherapy for gynecologic cancers: A closer look. Gynecol Oncol 134(1): 181-189.
Croft, M., C.A. Benedict, and C.F. Ware, *Clinical targeting of the TNF and TNER superfamilies*. Nat Rev Drug Discov, 2013.12(2): p. 147-68.
Aggarwal, B.B., *Signalling pathways of the TNF superfamily: a double-edged sword*. Nat Rev Immunol, 2003. 3(9): p. 745-56.
Avogadri, F., et al., *Modulation of CTLA-4 and GITR/or cancer immunotherapy*. Curr Top Microbiol Immunol, 2011. 344: p. 211-44.
Naidoo, J., D.B. Page, and J.D. Wolchok, *Immune modulation for cancer therapy*. Br J Cancer, 2014.111(12): p. 2214-9.
Bremer, E., *Targeting of the tum or necrosis factor receptor superfamily for cancer immunotherapy*. ISRN Oncol, 2013. 2013: p. 371854.
Sufia Butt Hassan, Jesper Freddie Sørensen, Barbara Nicola Olsen and Anders Elm Pedersen, 2014: Anti-CD40-mediated cancer

(56) References Cited

OTHER PUBLICATIONS immunotherapy: an update of recent and ongoing clinical trials, Immunopharmacology and Immunotoxicology, 36:2, 96-104.
Alison Crawford and E. John Wherry, 2009: Editorial: Therapeutic potential of targeting BTLA. Journal of Leukocyte Biology 86: 5-8.
Hemon, P., et al., *MHC class II engagement by its ligand LAG-3 (CD223) contributes to melanoma resistance to apoptosis*. J Immunol, 2011. 186(9): p. 5173-83.
Thielens, A., E. Vivier, and F. Romagne, *NK cell MHC class I specific receptors (KIR): from biology to clinical intervention*. Curr Opin Immunol, 2012. 24(2): p. 239-45.
Benson et al., 2012, Blood 120:4324-4333.
Ngiow, S.F., et al., *Anti-TIM3 antibody promotes T cell IFN-gammamediated antitumor immunity and suppresses established tumors*. Cancer Res, 2011. 71(10): p. 3540-51.
Jones et al., 2008, J Exp Med. 205 (12): 2763-79.
Huang, Y.H., et al., *CEACAM1 regulates TIM-3-mediated tolerance and exhaustion*. Nature, 2015. 517(7534): p. 386-90.
Gray-Owen, S.D. and R.S. Blumberg, *CEACAM1: contact-dependent control of immunity*. Nat Rev Immunol, 2006. 6(6): p. 433-46.
Creelan, B.C., *Update on immune checkpoint inhibitors in lung cancer*. Cancer Control, 2014. 21(1): p. 80-9.
Yin, Y., et al., *Phosphatidylserine-targeting antibody induces M1 macrophage polarization and promotes myeloid-derived suppressor cell differentiation*. Cancer Immunol Res, 2013. 1(4): p. 256-68.
Zhu, Y., et al., *CSF1/CSF1R Blockade Reprograms Tumor-Infiltrating Macrophages and Improves Response to T-cell Checkpoint Immunotherapy in Pancreatic Cancer Models*. Cancer Research, 2014. 74(18): p. 5057-5069.
Sheu, B.C., et al., *Up-regulation of inhibitory natural killer receptors CD94/NKG2A with suppressed intracellular perforin expression of tumor infiltrating CD8+ T lymphocytes in human cervical carcinoma*. Cancer Res, 2005. 65(7): p. 2921-9.
Tanaka, J., et al., *Cytolytic activity against primary leukemic cells by inhibitory NK cell receptor (CD94/NKG2A)-expressing T cells expanded from various sources of blood mononuclear cells*. Leukemia, 2005. 19(3): p. 486-9.
Ball, H.J., et al., *Indoleamine 2,3-dioxygenase-2; a new enzyme in the kynurenine pathway*. Int J Biochem Cell Biol, 2009. 41(3): p. 467-71.
Liu, X., et al., *Selective inhibition of IDO1 effectively regulates mediators of antitumor immunity*. Blood, 2010. 115(17): p. 3520-30.
Ino, K., et al., *Inverse correlation between tumoral indoleamine 2,3-dioxygenase expression and tumor-infiltrating lymphocytes in endometrial cancer: its association with disease progression and survival*. Clin Cancer Res, 2008. 14(8): p. 2310-7.
Muller, A.J., et al., *Chronic inflammation that facilitates tumor progression creates local immune suppression by inducing indoleamine 2,3 dioxygenase*. Proc Natl Acad Sci US A, 2008. 105( 44): p. 17073-8.
Sheridan C., *2015: IDO inhibitors move center stage in immune-oncology*; Nature Biotechnology 33: 321-322.
Garber, K., *Evading immunity: new enzyme implicated in cancer*. J Natl Cancer Inst, 2012. 104(5): p. 349-52.
Platten, M., W. Wick, and B.J. Van den Eynde, *Tryptophan catabolism in cancer: beyond !DO and tryptophan depletion*. Cancer Res, 2012. 72(21): p. 5435-40.
Platten, M., et al., *Cancer Immunotherapy by Targeting IDO1/TDO and Their Downstream Effectors*. Front Immunol, 2014. 5: p. 673.
Robert D. Leone et al., 2015: A2aR antagonists: Next generation checkpoint blockade for cancer immunotherapy. Computational and Structural Biotechnology Journal 13: 265-272.
Woo et al., 2012, Cancer Res. 72: 917-27.
Butler N. S. et al., 2011, Nat Immunol. 13: 188-95.
Fu et al., 2011, Cancer Res. 71: 5445-54.
Curran et al., 2011, PLoS One 6(4): el 9499.
Kryczek I, Zou L, Rodriguez P, Zhu G, Wei S, Mottram P, et al. B7-H4 expression identifies a novel suppressive macrophage population in human ovarian carcinoma. J Exp Med. 2006; 203:871-81.

Van Dijk, M. A., and van de Winkel, J. G., *Curr. Opin. Chem. Biol.* 5 (2001) 368-374.
Jakobovits, A., et al., *Proc. Natl. Acad. Sci. USA* 90 (1993) 2551-2555.
Jakobovits, A., et al., *Nature* 362 (1993) 255-258.
Bruggemann, M., et al., *Year Immunol.* 7 (1993) 3340).
Hoogenboom, H. R., and Winter, G., *J. Mol. Biol.* 227 (1992) 381-388.
Marks, J. D., et al., *J. Mol. Biol.* 222 (1991) 581-597.
Cole et al., *Monoclonal Antibodies and Cancer Therapy*, Alan R. Liss, p. 77 (1985).
Boerner, P., et al., *J. Immunol.* 147 (1991) 86-95.
Holliger and Hudson, 2005, *Nature Biotechnology* 9: 1126-1136.
Sayegh, E.T., et al., "Vaccine therapies for patients with glioblastoma," J Neurooncol, 119: 531-546 (2014).
Black, M., et al., "Advances in the design and delivery of peptide subunit vaccines with a focus on Toll-like receptor agonists," Expert Review of Vaccines, 9(2): 157-173 (2010).
Schirmbeck, R., et al., "Antigenic Epitopes Fused to Cationic Peptide Bound to Oligonucleotides Facilitate Toll-Like Receptor 9-Dependent, but CD4+ T Cell Help-Independent, Priming of CD8+ T Cells," Journal of Immunology, 171: 5198-5207 (2003).
National Cancer Institute, NCI Drug Dictionary, "glioblastoma multiforme multipeptide vaccine IMA950," (2019).
Woo, S.J., et al., "Co-administration of carcinoembryonic antigen and HIV TAT fusion protein with CpG-oligodeoxynucleotide induces potent antitumor immunity," Cancer Sci, 99(5): 1034-1039 (2008).
Office Action from corresponding U.S. Appl. No. 15/557,651 dated May 10, 2019.
Rini, B., "Future Approaches in Immunotherapy," Seminars in Oncology, 41(5): S30-S40 (2014).
Mangsbo, S.M., et al., "Enhanced Tumor Eradication by Combining CTLA-4 or PD-1 Blockade With CpG Therapy," J. Immunother., 33(3): 225-235 (2010).
Deres, K., et al., "In vivo priming of virus-specific cytotoxic T lymphocytes with synthetic lipopeptide vaccine," Nature, 342: 561-564 (1989).
Fujita, Y., & Taguchi, H., "Current status of multiple antigen-presenting peptide vaccine systems: Application of organic and inorganic nanoparticles," Chemistry Central Journal, 5(48): 1-5 (2011).
Garaude, J., et al., "Simultaneous Targeting of Toll- and Nod-Like Receptors Induces Effective Tumor-Specific Immune Responses," Science Translational Medicine, 4(120): 1-13 (2012).
Khan, S., et al., "Chirality of TLR-2 ligand $Pam_3CysSK_4$ in fully synthetic peptide conjugates critically influences the induction of specific $CD8^+$ T-cells," Molecular Immunology, 46: 1084-1091 (2009).
Li, Q., & Guo, Z., "Recent Advances in Toll Like Receptor-Targeting Glycoconjugate Vaccines," Molecules, 23: 1-24 (2018).
Wilkinson, B.L., et al., "Self-Adjuvanting Multicomponent Cancer Vaccine Candidates Combining Per-Glycosylates MUC1 Glycopeptides and the Toll-like Receptor 2 Agonist $Pam_3CysSer$**," Angew. Chem. Int. Ed., 50: 1635-1639 (2011).
Zhang, X., et al., "A Comparative Study of the Antigen-Specific Immune Response Induced by Co-Delivery of CpG ODN and Antigen Using Fusion Molecules or Biodegradable Microparticles," Journal of Pharmaceutical Sciences, 96(12): 3283-3292 (2007).
Aitken et al., "Taking a Stab at Cancer; Oncolytic Virus-Mediated Anti-Cancer Vaccination Strategies", Biomedicines, vol. 5, No. 1, 3, Jan. 4, 2017 (Jan. 4, 2017), XP055419683.
Belnoue et al., "Targeting self- and neoepitopes with a modular self-adjuvanting cancer vaccine", JCI Insight, vol. 4, No. 11, E127305, Jun. 6, 2019 (Jun. 6, 2019), XP055749546.
Das et al., "A modular self-adjuvanting cancer vaccine combined with an oncolytic vaccine induces potent antitumor immunity", Nature Communications, vol. 12, No. 1, 5195, Aug. 31, 2021 (Aug. 31, 2021), XP055879106.
Das et al., "Supplementary Materials: A modular self-adjuvanting cancer vaccine combined with an oncolytic vaccine induces potent antitumor immunity", Nature Communications, vol. 12, No. 1, 5195, Aug. 31, 2021 (Aug. 31, 2021), XP055879706.

(56) References Cited

OTHER PUBLICATIONS

Haq et al., "Evaluation of recombinant adenovirus vectors and adjuvanted protein as a heterologous prime-boost strategy using HER2 as a model antigen", Vaccine, vol. 37, No. 47, Sep. 7, 2019 (Sep. 7, 2019), pp. 7029-7040, XP085880235.
Hofer et al., "Heterologous Prime-Boost Vaccination with a Peptide-Based Vaccine and Viral Vector Reshapes Dendritic Cell, CD4+ and CDS+ T Cell Phenotypes to Improve the Antitumor Therapeutic Effect", Cancers, vol. 13, No. 23, Dec. 3, 2021 (Dec. 3, 2021), p. 6107, XP055879764.
Jung et al., "Heterologous prime-boost vaccination with adenoviral vector and protein nanoparticles induces both Th1 and Th2 responses against Middle East respiratory syndrome coronavirus", Vaccine, vol. 36, No. 24, Jun. 2018 (Jun. 2018), pp. 3468-3476, XP055879799.
Kim S-B et al., "A phase 1 study of a heterologous prime-boost vaccination involving a truncated HER2 sequence in patients with HER2-expressing breast cancer", Molecular Therapy, vol. 2, 15031, 2015, XP055879077.
Kim S-Y et al., "Prime-boost immunization by both DNA vaccine and oncolytic adenovirus expressing GM-CSF and shRNA of TGF-[beta]2 induces anti-tumor immune activation" , Oncotarget, vol. 8, No. 9, Feb. 28, 2017 (Feb. 28, 2017), pp. 15858-15877, XP055879746.
Ortiz et al., "Immunization of cattle against Babesia bovis combining a multi-epitope modified vaccinia Ankara virus and a recombinant protein induce strong Th1 cell responses but fails to trigger neutralizing antibodies required for protection", Ticks and Ticks-Borne Diseases, vol. 10, 10270, Aug. 16, 2019 (Aug. 16, 2019), XP085809964.
Tober et al., "VSV-GP: a Potent Viral Vaccine Vector That Boosts the Immune Response upon Repeated Applications", Journal of Virology, vol. 88, No. 9, May 2014 (May 2014), pp. 4897-4907, XP055879082.
Rossi et al., "Combination treatment using KISIMA TM protein-based cancer vaccine and systemic STING agonist results in profound modulation of tumor microenvironment and improved tumor control", Journal for Immunotherapy of Cancer, vol. 8, No. Suppl 3, 452, Dec. 10, 2020 (Dec. 10, 2020), pp. A479-A479, XP055882322.
Rossi et al., "STING Agonist Combined to a Protein-Based Cancer Vaccine Potentiates Peripheral and Intra-Tumoral T Cell Immunity", Frontiers in Immunology, vol. 12, Jul. 1, 2021 (Jul. 1, 2021), XP55882273.
Sallets et al., "Enhancing immunotherapy of STING agonist for lymphoma in preclinical models", Blood Advances, vol. 2, No. 17, Sep. 11, 2018 (Sep. 11, 2018) f pp. 2230-2241, XP055764731.
Non-Final Office Action issued in U.S. Appl. No. 17/558,906 dated Dec. 28, 2023.
Schutze-Redelmeier et al. (2003). Antennapedia transduction sequence promotes anti tumor immunity to epicutaneously administered CTL epitopes. Vaccine, 22:1985-1991.
Witkowski et al. (1999). Conversion of B-Ketoacyl Synthase to a Malonyl Decarboxylase by Replacement of the Active-Site Cysteine with Glutamine. Biochemistry, 38:11643-11650.
Seffernick et al. (2001). Melamine Deaminase and Atrazine Chlorohydrolase: 98 Percent Identical but Functionally Different. Bacterial. 183(8): 2405-2410.
Non-Final Office Action from U.S. Appl. No. 17/501,155 dated Mar. 1, 2024.
Sahdev et al. (2014). Biomaterials for nanoparticle vaccine delivery systems, 31(10): 2563-82.
Final Office Action from U.S. Appl. No. 17/397,447 dated Mar. 18, 2024.
Non-Final Office Action from U.S. Appl. No. 17/718,975 dated Apr. 10, 2024.
Wikipedia Webpage (2015). Toll-like receptor. Retrieved from https://en.wikipedia.org/w/index.php?title=Toll-like_receptor&oldid=649029932.

A

B

A

B

A

B

A

B

A

B

A

B

A

B

C

A

B

A

B

A

B

A

B

A

B

A

B

A

B

A

B

COMBINATION OF AN IMMUNE CHECKPOINT MODULATOR AND A COMPLEX COMPRISING A CELL PENETRATING PEPTIDE, A CARGO AND A TLR PEPTIDE AGONIST FOR USE IN MEDICINE

CROSS-REFERENCE TO RELATED PATENT APPLICATIONS

The present application is a continuation of U.S. patent application Ser. No. 16/084,170 filed on 11 Sep. 2018, which is a U.S. national stage of PCT/EP2017/056034 filed on 14 Mar. 2017, which claims foreign priority to both PCT/EP2016/070264 filed on 26 Aug. 2016 and PCT/EP2016/000472 filed on 16 Mar. 2016. Each of the patent applications recited above are hereby incorporated by reference in their entirety.

REFERENCE TO AN ELECTRONIC SEQUENCE LISTING

This application contains references to amino acid sequences and/or nucleic acid sequences which have been submitted concurrently herewith as the sequence listing.txt file entitled "Sequence_Listing.txt", file size 32,000 bytes, created on 3 Jul. 2018. The aforementioned sequence listing is hereby incorporated by reference in its entirety.

FIELD

The present invention relates to the field of vaccination, in particular to cancer vaccines.

BACKGROUND

The immune system can recognize and to some extent eliminate tumor cells, however, this anti-tumor response is often of low amplitude and inefficient. Boosting this weak anti-tumor response with therapeutic vaccination has been a long sought goal for cancer therapy. Modulating the immune system to enhance immune responses has thus become a promising therapeutic approach in oncology as it can be combined with standard of care treatments.

Promising preclinical data and advances in clinical trials, show that active immunization is a safe and feasible treatment modality for certain cancer types. Induction of tumor-specific cytotoxic T lymphocytes (CTLs) mediated immune responses has been reported using different approaches including modified tumor cell vaccines, peptide vaccines, recombinant viral vectors, DNA, protein, or dendritic cell vaccines. However, the anti-tumoral immunity mediated by CTLs only occasionally correlates with tumor regression and only a few projects have reached the phase III clinical stage.

Overall, cancer vaccines showed very limited clinical efficacy so far. Indeed, at the end of 2011, amongst the 300 hundred ongoing cancer vaccine clinical trials, only 19 phase III trials were reported (globaldata, 2012). Amongst them, there are NeuVax, a peptide vaccine for breast cancer, Stimuvax, a liposome based vaccine for Non-Small Cell Lung Carcinoma (NSCLC) and breast cancer, TG4010, a vaccinia-based vaccine for NSCLC and GSK1572932A, an adjuvanted liposome for NSCLC. These four cancer vaccines are based on different technologies and have in common that they are targeting one single antigen.

Therapeutic cancer vaccines can be divided into two principal categories: personalized (autologous) and standardized vaccines, and further classified depending on the technology platform. Current personalized vaccines include tumor lysate vaccines as well as dendritic cells based vaccine (hereinafter cell based). For the latter, antigen loading can occur either with a pulse using tumor lysates, or transfection with RNA extracted from the tumors. In this case, the antigens are tumor specific or associated, but are not clearly defined. Dendritic cells can also be loaded with defined antigens either with peptide pulse or using a protein such as the Prostatic Acid Phosphatase (PAP) used to engineer the Provenge® vaccine. However, the manufacturing process of these cell-based therapies is time-consuming and labor-intensive while quality standards are difficult to reach and maintain. Immunomonitoring creates further complications. Moreover, the majority of the autologous cancer vaccines do not allow the identities or quantities of antigens used to be controlled, unlike defined and standardized vaccines.

In contrast to cell-based therapy (APCs, T cells, CARs, lysates), subunits vaccines (protein or peptides) allow the development of a standardized vaccine with an easier production and significantly better batch to batch reproducibility that can be administrated to a broad range of patients. Furthermore, the antigens are fully defined allowing for better immune-monitoring and reducing the risk of unwanted effects of vaccine component.

The different approaches which were evaluated in pre-clinical and clinical development include short peptide vaccines (Slingluff C L, Jr. The present and future of peptide vaccines for cancer: single or multiple, long or short, alone or in combination? Cancer journal 2011; 17 (5): 343-50), long-peptide vaccines (Melief C J, van der Burg S H. Immunotherapy of established (pre) malignant disease by synthetic long peptide vaccines. Nature reviews Cancer 2008;8 (5): 351-60) and proteins. In contrast to long peptide and protein vaccines, short peptide vaccines have a very short half-life and can have negative consequences on the immune response.

A therapeutic cancer vaccine is administrated to cancer patients to strengthen the capability of their immune system to recognize and kill the tumor cells. The main goal of a therapeutic cancer vaccine is to generate killer T cells (also called cytotoxic T lymphocytes) specific for the tumor cells. To this end and to achieve a potent immune response, the vaccine must contain an antigen or an antigenic epitope that is also present in the tumor and that needs to be delivered to Antigen Presenting Cells (APCs), in particular dendritic cells (DCs), to initiate cancer immunity. The DCs process these tumor antigens into small peptides that are presented on cell surface expressed MHC class I or MHC class II molecules to T cells. Peptides that are then recognized by T cells and thereby induce their stimulation are called epitopes. Presentation by MHC class I and MHC class II molecules allows activation of two classes of T cells, $CD8^+$ cytotoxic T lymphocytes (CTLs) and $CD4^+$ helper T ($T_h$) cells, respectively. In addition, to become fully activated, beside antigen recognition T cells require a second signal, the co-stimulatory signal, which is antigen non-specific and is provided by the interaction between co-stimulatory molecules expressed on the surface of APCs and the T cell. Therefore two major requirements for an efficient therapeutic cancer vaccine are (i) the specificity of the tumor antigens and (ii) the ability to deliver them efficiently to DCs.

Taken together, induction of a tumor specific immune response thus requires three main steps: (i) an antigen must be delivered to dendritic cells, which will process it into epitopes, (ii) dendritic cells should receive a suitable activation signal, and (iii) activated tumor antigen-loaded dendritic cells must generate T-cell mediated immune responses in the lymphoid organs.

Since tumor cells can escape the immune system by down-regulating expression of individual antigens (passive immune escape), multi-epitopic antigen delivery provides an advantage. Indeed, protein based vaccines allow multi-epitopic antigen delivery to antigen presenting cells (APCs) such as dendritic cells (DCs) without the limitation of restriction to a single MHC allele. Another strength is long-lasting epitope presentation recently described in dendritic cells loaded with proteins (van Montfoort N, Camps M G, Khan S, Filippov D V, Weterings J J, Griffith J M, et al. Antigen storage compartments in mature dendritic cells facilitate prolonged cytotoxic T lymphocyte cross-priming capacity. Proceedings of the National Academy of Sciences of the United States of America 2009; 106 (16): 6730-5). Furthermore, proteins require uptake and processing by DCs to achieve MHC restricted presentation of their constituent epitopes. This reduces the risk of inducing peripheral tolerance as shown after vaccination with short peptides that do not have such stringent processing requirements (Toes R E, Offringa R, Blom R J, Melief C J, Kast W M. Peptide vaccination can lead to enhanced tumor growth through specific T-cell tolerance induction. Proceedings of the National Academy of Sciences of the United States of America 1996; 93 (15): 7855-60).

However, most soluble proteins are generally degraded in endolysosomes and are poorly cross-presented on MHC class I molecules and are therefore poorly immunogenic for $CD8^+$ T cell responses (Rosalia R A, Quakkelaar E D, Redeker A, Khan S, Camps M, Drijfhout J W, et al. Dendritic cells process synthetic long peptides better than whole protein, improving antigen presentation and T-cell activation. European journal of immunology 2013; 43 (10): 2554-65). Moreover, although mature DCs are more potent than immature DCs in priming and eliciting T-cell responses (Apetoh L, Locher C, Ghiringhelli F, Kroemer G, Zitvogel L. Harnessing dendritic cells in cancer. Semin Immunol. 2011; 23:42-49), they lose the ability to efficiently take up exogenous antigens, particularly for MHC class II restricted antigens (Banchereau J, Steinman R M. Dendritic cells and the control of immunity. Nature. 1998; 392:245-252). As a result, peptide-pulsed DCs as vaccines have several limitations. For example, peptide degradation, rapid MHC class I turnover, and the disassociation of peptide from MHC class I molecules during the preparation and injection of DC/peptides may result in short half-lives of MHC class I/peptide complexes on the DC surface, leading to weak T-cell responses.

To improve the efficacy of protein-based vaccine delivery, the use of cell penetrating peptides for intracellular delivery of cancer peptides into DCs was proposed (Wang R F, Wang H Y. Enhancement of antitumor immunity by prolonging antigen presentation on dendritic cells. Nat Biotechnol. 2002; 20:149-156). Cell penetrating peptides (CPPs) are peptides of typically 8 to 40 residues that have the ability to cross the cell membrane and enter into most cell types (Copolovici D M, Langel K, Eriste E, Langel U. Cell-penetrating peptides: design, synthesis, and applications. ACS nano 2014; 8 (3): 1972-94, Milletti F. Cell-penetrating peptides: classes, origin, and current landscape. Drug Discov Today 2012). Alternatively, they are also called protein transduction domain (PTDs) reflecting their origin as occurring in natural proteins. Several potent CPPs have been identified from proteins, including the Tat protein of human immunodeficiency virus, the VP22 protein of herpes simplex virus, and fibroblast growth factor (Berry C C. Intracellular delivery of nanoparticles via the HIV-1 tat peptide. Nanomedicine. 2008; 3:357-365; Deshayes S, Morris M C, Divita G, Heitz F. Cell-penetrating peptides: Tools for intracellular delivery of therapeutics. Cell Mol Life Sci. 2005; 62:1839-1849; Edenhofer F. Protein transduction revisited: Novel insights into the mechanism underlying intracellular delivery of proteins. Curr Pharm Des. 2008; 14:3628-3636; Gupta B, Levchenko T S, Torchilin V P. Intracellular delivery of large molecules and small particles by cell-penetrating proteins and peptides. Adv Drug Deliv Rev. 2005; 57:637-651; Torchilin V P. Recent approaches to intracellular delivery of drugs and DNA and organelle targeting. Annu Rev Biomed Eng. 2006; 8:343-375). It was found that T-cell activity elicited by DC/TAT-TRP2 was 3- to 10-fold higher than that induced by DC/TRP2 (Wang H Y, Fu T, Wang G, Gang Z, Donna M P L, Yang J C, Restifo N P, Hwu P, Wang R F. Induction of CD4+ T cell-dependent antitumor immunity by TAT-mediated tumor antigen delivery into dendritic cells. J Clin Invest. 2002a; 109:1463-1470).

In order to increase the level of co-stimulatory molecules on DCs and to augment the immune system's response to the target antigens, adjuvants may be used. Adjuvants may accomplish this task by mimicking conserved microbial components that are naturally recognized by the immune system. They include, for example, lipopolysaccharide (LPS), components of bacterial cell walls, and nucleic acids such as double-stranded RNA (dsRNA), single-stranded DNA (ssDNA), and unmethylated CpG dinucleotide-containing DNA. Their presence can increase the innate immune response to the antigen. Furthermore, this adjuvant should promote an adaptive immune response with CTLs and type polarized $T_h1$ rather than a humoral immune response resulting in antibody production. Different adjuvants have been evaluated, with a limited number having gained regulatory approval for human use. These include Alum, MPL (monophosphoryl lipid A) and ASO4 (Alum and MPL) in the US, and MF59 (oil-in-water emulsion), ASO4, liposomes in Europe (Lim, Y. T., Vaccine adjuvant materials for cancer immunotherapy and control of infectious disease. Clin Exp Vaccine Res, 2015. 4 (1): p. 54-8).

Recently, Toll Like Receptor (TLR) ligands are emerging as promising class of adjuvants (Baxevanis, C. N., I. F. Voutsas, and O. E. Tsitsilonis, Toll-like receptor agonists: current status and future perspective on their utility as adjuvants in improving anticancer vaccination strategies. Immunotherapy, 2013. 5 (5): p. 497-511). A significant development of cancer vaccine studies was thus to include various TLR agonists to vaccine formulations, including TLR-3 (poly I:C), TLR-4 (monophosphoryl lipid A; MPL), TLR-5 (flagellin), TLR-7 (imiquimod), and TLR-9 (CpG) (Duthie M S, Windish H P, Fox C B, Reed S G. Use of defined TLR ligands as adjuvants within human vaccines. Immunol Rev. 2011; 239:178-196). The types of signaling and cytokines by immune cells after TLR stimulation control CD4+ T-cell differentiation into Th1, Th2, Th17, and Treg cells. Stimulation of immune cells such as DCs and T cells by most TLR-based adjuvants produces proinflammatory cytokines and promotes Th1 and CD8+ T responses (Manicassamy S, Pulendran B. Modulation of adaptive immunity with Toll-like receptors. Semin Immunol. 2009; 21:185-193).

Conjugating the vaccine to a TLR ligand is an attractive approach that offers several advantages over non-conjugated vaccines including (i) preferential uptake by the immune cells expressing the TLR, (ii) higher immune response and (iii) reduced risk of inducing peripheral tolerance. Indeed, all the antigen presenting cells loaded with the antigen will be simultaneously activated. Different groups explored this approach with various TLR ligands being mainly linked chemically to the peptide or protein vaccine (Zom G G, Khan S, Filippov D V, Ossendorp F. TLR ligand-peptide conjugate vaccines: toward clinical application. Adv Immunol. 2012; 114:177-201). As the chemical linkage to peptide is easily performed, the most highly investigated TLR ligands for conjugate vaccine are the TLR2 agonist Pam2Cys and Pam3Cys (Fujita, Y. and H. Taguchi, Overview and outlook of Toll-like receptor ligand-antigen conjugate vaccines. Ther Deliv, 2012. 3 (6): p. 749-60).

Moreover, recently immune checkpoint modulators emerged as new targets for cancer immunotherapy, as shown by recent marketing approvals for Yervoy® (Ipilimumab; Bristol Myers Squibb), Opdivo® (Nivolumab; Bristol Myers Squibb) and Keytruda® (Pembrolizumab; Merck). Immune checkpoints are molecules in the immune system, in particular on certain immune cells, that need to be activated (stimulatory or costimulatory checkpoint molecules) or inactivated (inhibitory checkpoint molecules) to start an immune response. Many of the immune checkpoints are regulated by interactions between specific receptor and ligand pairs. Often cancers protect themselves from the immune system by using these checkpoints to avoid being attacked by the immune system.

In particular, the two checkpoint receptors CTLA-4 and PD-1 received a lot of attention. CTLA-4, PD-1 and their ligands are members of the CD28-B7 family of co-signaling checkpoint molecules that play important roles throughout all stages of T-cell function and other cell functions.

The PD-1 receptor is expressed on the surface of activated T cells and other immune cells, such as B cells. Its ligands (PD-L1 and PD-L2) are expressed on the surface of antigen-presenting cells, such as dendritic cells or macrophages, and other immune cells. Binding of PD-L1 or PD-L2 to PD1 triggers a signal in the T cell, which essentially switches the T cell off or inhibits it. Under non-pathological conditions, this interaction prevents T cells from attacking other cells in the body. However, cancer cells often take advantage of this system and express high levels of PD-L1 on their surface. Thereby, cancer cells are able to switch off T cells expressing PD-1 and, thus, to suppress the anticancer immune response. Inhibitors of PD1 and/or its ligands, such as inhibitory/antagonistic monoclonal antibodies directed to PD1 or to its ligands, can boost the immune response against cancer cells and are, thus, promising in treating cancers. Examples of inhibitory/antagonistic monoclonal antibodies against PD1, which are currently approved, include Opdivo® (Nivolumab; Bristol Myers Squibb) and Keytruda® (Pembrolizumab; Merck). Other inhibitors of the PD1 pathway, which are currently in clinical phase II and/or III include Pidilizumab (mAb inhibiting PD1; CureTech/Medivation), Durvalumab (mAb inhibiting PD-L1; MedImmune/AstraZeneca) and Atezolimab (mAb inhibiting PD-L1; Roche).

Yervoy® (Ipilimumab; Bristol Myers Squibb), another approved immune checkpoint modulator, is an inhibitory/antagonistic monoclonal antibody against cytotoxic T-lymphocyte-associated antigen 4 (CTLA-4). CTLA4 is also expressed on the surface of activated T cells and its ligands are expressed on the surface of professional antigen-presenting cells. CTLA-4 is thought to regulate T-cell proliferation early in an immune response, primarily in lymph nodes and affects the functioning of regulatory T cells. Another inhibitor of CTLA-4, which is currently in clinical phase II, is, for example, Tremelimumab (MedImmune/AstraZeneca).

Cancer immunotherapies with checkpoint modulators, in particular with checkpoint inhibitors, were shown to be very effective at least in a subgroup of subjects ("responders"). However, many patients do not respond to checkpoint modulators and even in the responding population the response is not always complete or optimal.

Combination of inhibition of PD1- and CTLA4-pathways with the aim of increasing efficacy is thus desirable. Accordingly, combination therapy with Nivolumab and Ipilimumab was approved by the FDA in 2015 for the treatment of patients with BRAF V600 wild-type, unresectable or metastatic melanoma. In addition, a successful phase 1b study on the combination of Durvalumab and Tremelimumab in non-small cell lung cancer was recently reported (Antonia, Scott et al., 2016, Safety and antitumour activity of durvalumab plus tremelimumab in non-small cell lung cancer: a multicentre, phase 1b study; Lancet Oncol. 2016 Feb. 5. pii: S1470-2045 (15) 00544-6. doi: 10.1016/S1470-2045 (15) 00544-6. [Epub ahead of print]).

However, the combination of checkpoint modulators which each other only targets endogenous tumor-specific immunity, in particular since no tumor-specific antigens are provided. Another strategy for the treatment of cancer is to combine a checkpoint modulator with a vaccine containing an antigen or an antigenic epitope as described above, which provides specificity against a certain tumor. The combination of a checkpoint modulator and a vaccine containing an antigen or an antigenic epitope may enhance or prolong an anti-tumor response in a subject. Further, the combination of a vaccine containing an antigen or an antigenic epitope with a checkpoint modulator may enhance or prolong the effects of the checkpoint modulator, enable a subject to respond to a checkpoint modulator, or enable the reduction of the toxicity or the dose of a checkpoint modulator. For example, the checkpoint modulator may remove the "immune brake" before pressing the "treatment gas pedal" by vaccine administration.

Accordingly, there is a need to develop combination therapies to initiate or enhance the efficacy of checkpoint modulators in both, responders and non-responders. To this end, a combination of a checkpoint modulator with a potent vaccine is desired. However, to date the majority of cancer vaccines trials have shown only limited efficacy. One explanation is the lack of a therapy that can simultaneously (i) stimulate multi-epitopic cytotoxic T cell-mediated immunity, (ii) induce $T_h$ cells and (iii) promote immunological memory. These three parameters are essential to generate potent, long lasting anti-tumor immunity. Indeed, CTLs specific for different epitopes will allow destruction of more cancer cells within a heterogeneous tumor mass and avoid the outgrowth of antigen-loss variants (tumor immune escape). $T_h$ cells are involved in the maintenance of long-lasting cellular immunity and tumor infiltration by $T_h$ cells is also an essential step for the recruitment and function of $CD8^+$ CTLs. Immunological memory is essential to protect against tumor relapse.

SUMMARY

In view of the above, it is the object of the present invention to overcome the drawbacks of current cancer vaccines outlined above and to provide a combination of an immune checkpoint modulator and a complex comprising a cell penetrating peptide, a cargo and a TLR agonist for cancer immunotherapy applications representing a more potent vaccine, in particular cancer vaccine, having improved anti-tumor activity. The present invention thus relates to a combination therapy to initiate, enable, enhance or improve an anti-tumor immune response, in particular which enables, enhances or improves the subject's or tumor response to checkpoint modulators.

This object is achieved by means of the subject-matter set out below and in the appended claims.

BRIEF DESCRIPTION OF THE FIGURES

In the following a brief description of the appended figures will be given. The figures are intended to illustrate the present invention in more detail. However, they are not intended to limit the subject matter of the invention in any way.

FIG. 7C shows a summary of the percentage of SIINFEKL-specific CD8 T cells in blood and BILs. C57BL/6 mice were implanted intracranially with $5 \times 10^5$ G1261-Quad tumor cells at day 0. After tumor implantation, mice of the groups "Z13Mad5Anaxa+Isotype" and "Z13Mad5Anaxa+anti-PD1" were vaccinated at days 7 and 21 by subcutaneous injection of 2 nmol of Z13Mad5Anaxa in the right flank. 200 μg of anti-PD1 antibody were administered i.p. on each of days 7, 10, 14, 17 and 21 to mice of groups "anti-PD1" and "Z13Mad5Anaxa +anti-PD1". For control, 200 μg of isotype mAB 2A3 were administered i.p. on each of days 7, 10, 14, 17 and 21 to mice of groups "isotype" and "Z13Mad5Anaxa+isotype". SIINFEKL-specific CD8 T cells were quantified in blood and in brain infiltrating leukocytes (BILs) at day 28 by multimer staining (5-8 mice per group). *, $p<0.05$.

DETAILED DESCRIPTION

Figure 1:
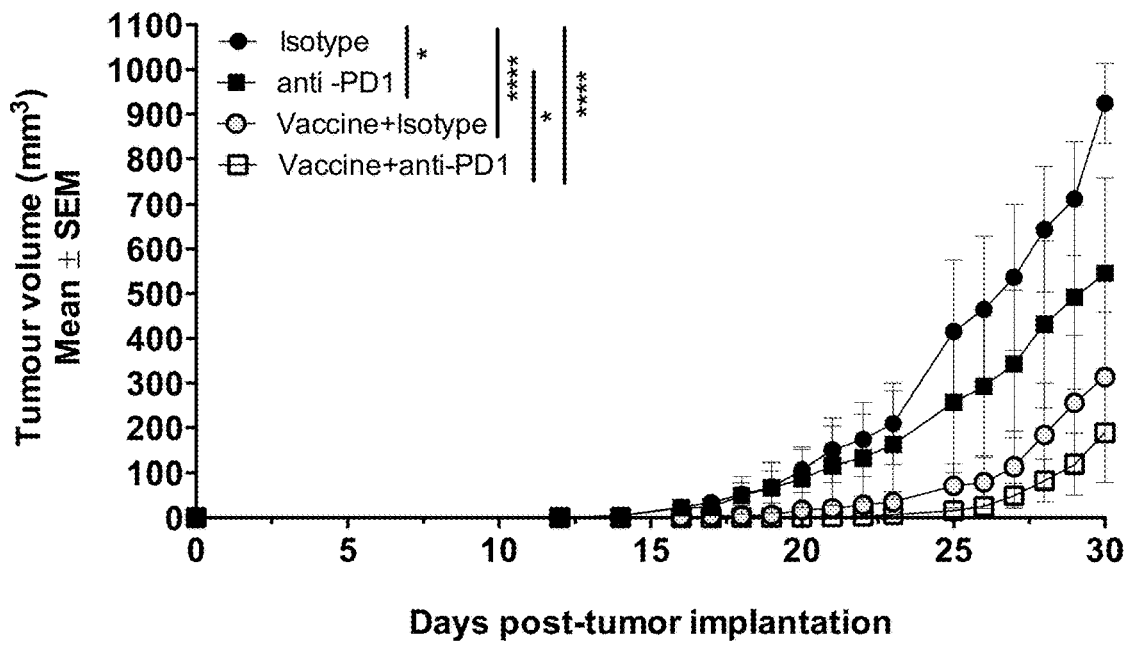
FIG. 1 shows for Example 1 the tumor growth (A) and the survival rate (B) of 7 mice per group (mean±SEM). C57BL/6 mice were implanted s.c. with $3 \times 10^5$ EG7-OVA tumor cells in the left flank. Mice of the groups "Z13Mad5Anaxa+Isotype" and "Z13Mad5Anaxa+anti-PD1" were vaccinated twice (d5 and d13) by subcutaneous injection of 2 nmol of Z13Mad5Anaxa in the right flank. 200 μg of anti-PD1 antibody were administered i.p. on each of days 5, 9 and 13 to mice of groups "anti-PD1" and "Z13Mad5Anaxa+anti-PD1". For control, 200 μg of isotype 2A3 were administered i.p. on each of days 5, 9 and 13 to mice of groups "isotype" and "Z13Mad5Anaxa+isotype". Tumor size was measured with a caliper. *, $p<0.05$; , $p<0.01$; *, $p<0.001$, ****, $p<0.0001$.
Figure 1:
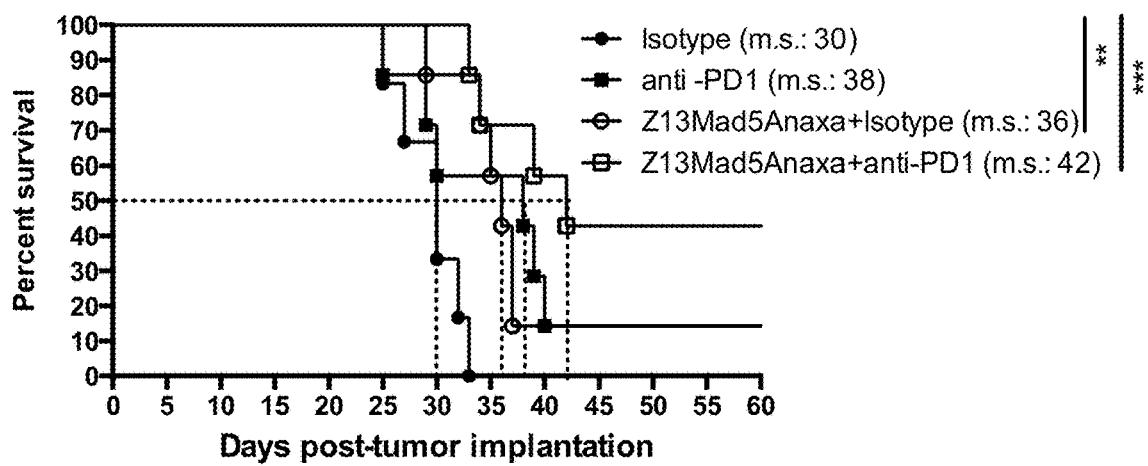

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

Combination of a Checkpoint Modulator and a Complex Comprising a Cell Penetrating Peptide, at Least One Antigen or Antigenic Epitope and a TLR Peptide Agonist for Use in Medicine In a first aspect the present invention provides a combination of
(i) an immune checkpoint modulator and
(ii) a complex comprising:
   a) a cell penetrating peptide;
   b) at least one antigen or antigenic epitope; and
   c) at least one TLR peptide agonist,
      wherein the components a)-c) comprised by the complex (i.e. the cell penetrating peptide, the at least one antigen or antigenic epitope and the at least one TLR peptide agonist) are covalently linked
for use in medicine.

In the following, the components of the combination for use according to the present invention, i.e. the immune checkpoint modulator and the complex comprising cell penetrating peptide, the at least one antigen or antigenic epitope and the at least one TLR peptide agonist, and preferred embodiments thereof, are described in detail. It is understood that (i) a preferred embodiment of the combination for use according to the present invention comprises a preferred embodiment of the immune checkpoint modulator; (ii) a preferred embodiment of the combination for use according to the present invention comprises a preferred embodiment of the complex comprising cell penetrating peptide, the at least one antigen or antigenic epitope and the at least one TLR peptide agonist; and (iii) a more preferred embodiment of the combination for use according to the present invention comprises a preferred embodiment of the immune checkpoint modulator and a preferred embodiment of the complex comprising cell penetrating peptide, the at least one antigen or antigenic epitope and the at least one TLR peptide agonist.

Immune Checkpoint Modulator

As used herein (i.e. throughout the present specification), the term "immune checkpoint modulator" (also referred to as "checkpoint modulator") refers to a molecule or to a compound that modulates (e.g., totally or partially reduces, inhibits, interferes with, activates, stimulates, increases, reinforces or supports) the function of one or more checkpoint molecules. Thus, an immune checkpoint modulator may be an "immune checkpoint inhibitor" (also referred to as "checkpoint inhibitor" or "inhibitor") or an "immune checkpoint activator" (also referred to as "checkpoint activator" or "activator"). An "immune checkpoint inhibitor" (also referred to as "checkpoint inhibitor" or "inhibitor") totally or partially reduces, inhibits, interferes with, or negatively modulates the function of one or more checkpoint molecules. An "immune checkpoint activator" (also referred to as "checkpoint activator" or "activator") totally or partially activates, stimulates, increases, reinforces, supports or positively modulates the function of one or more checkpoint molecules. Immune checkpoint modulators are typically able to modulate (i) self-tolerance and/or (ii) the amplitude and/or the duration of the immune response. Preferably, the immune checkpoint modulator used according to the present invention modulates the function of one or more human checkpoint molecules and is, thus, a "human checkpoint modulator". Preferably, the immune checkpoint modulator is an activator or an inhibitor of one or more immune checkpoint point molecule(s) selected from CD27, CD28, CD40, CD122, CD137, OX40, GITR, ICOS, A2AR, B7-H3, B7-H4, BTLA, CD40, CTLA-4, IDO, KIR, LAG3, PD-1, TIM-3, VISTA, CEACAM1, GARP, PS, CSF1R, CD94/ NKG2A, TDO, GITR, TNFR and/or FasR/DcR3; or an activator or an inhibitor of one or more ligands thereof.

Checkpoint molecules are molecules, such as proteins, are typically involved in immune pathways and, for example, regulate T-cell activation, T-cell proliferation and/or T-cell function. Accordingly, the function of checkpoint molecules, which is modulated (e.g., totally or partially reduced, inhibited, interfered with, activated, stimulated, increased, reinforced or supported) by checkpoint modulators, is typically the (regulation of) T-cell activation, T-cell proliferation and/or T cell function. Immune checkpoint molecules thus regulate and maintain self-tolerance and the duration and amplitude of physiological immune responses. Many of the immune checkpoint molecules belong to the B7: CD28 family or to the tumor necrosis factor receptor (TNFR) super family and, by the binding of specific ligands, activate signaling molecules that are recruited to the cytoplasmic domain (cf. Susumu Suzuki et al., 2016: Current status of immunotherapy. Japanese Journal of Clinical Oncology, 2016: doi: 10.1093/jjco/hyv201 [Epub ahead of print]; in particular Table 1).

Since a decade, the role of the B7 family was analyzed and new members and new functions of these important T cell regulator molecules were identified (Greenwald, R. J., G. J. Freeman, and A. H. Sharpe, *The B7 family revisited*. Annu Rev Immunol, 2005. 23: p. 515-48). Today, the B7: CD28 family comprises the most frequently used pathways in immune checkpoint research. The initial and complex mechanisms of CTLA-4-B7-1/B7-2 were progressively seconded by the highly interesting PD-1-B7-H1 (PDL1)/B7-DC (PD-L2) couple that was shown to have an association with many immunological and clinical tumor microenvironments (Zou, W. and L. Chen, *Inhibitory B7-family molecules in the tumour microenvironment*. Nat Rev Immunol, 2008. 8 (6): p. 467-77). Another member of this family is ICOS-ICOSL/B7-H2, which was identified at the same period. Other members of that family include B7-H3 (Chapoval, A. I., et al., *B7-H3: a costimulatory molecule for T cell activation and IFN-gamma production*. Nat Immunol, 2001. 2 (3): p. 269-74) and B7-H4 (Sica, G. L., et al., *B7-H4, a molecule of the B7 family, negatively regulates T cell immunity*. Immunity, 2003. 18 (6): p. 849-61), however, both ligands receptors' haven't yet been identified. However the role of B7-H3 in antitumor immunity (Loos, M., et al., *B7-h3 and its role in antitumor immunity*. Clin Dev Immunol, 2010. 2010: p. 683875) and its role in immune tumor evasion (Hofmeyer, K. A., A. Ray, and X. Zang, *The contrasting role of B7-H3*. Proc Natl Acad Sci US A, 2008.105 (30): p. 10277-8) as well as its overexpression many advanced stage cancers (Zou, W. and L. Chen, *Inhibitory B7-family molecules in the tumour microenvironment*. Nat Rev Immunol, 2008. 8 (6): p. 467-77), namely in colorectal cancer (Sun, J., et al., *Clinical significance and regulation of the costimulatory molecule B7-H3 in human colorectal carcinoma*. Cancer Immunol Immunother, 2010. 59 (8): p. 1163-71), suggest that research will be pursued in that direction. Similarly, B7-H4 recently entered in evaluation loop as possible agent acting on tumoral immune escape and antitumor response (Dangaj, D. and N. Scholler, *Blocking the B7-H4 pathway with novel recombinant antibodies enhances T cell-mediated antitumor responses*. Oncoimmunology, 2013. 2 (8): p. e25913; Dangaj, D., et al., *Novel recombinant human b7-h4 antibodies overcome tumoral immune escape to potentiate T-cell antitumor responses*. Cancer Res, 2013. 73 (15): p. 4820-9) or interacting with many kinase pathways (Wang, X., et al., *B7-H4 Treatment o/T Cells Inhibits ERK, JNK, p38, and AKT Activation*. PLOS One, 2012. 7 (1): p. e28232). The results of this interest is underlined by a publication on an anti-B7-H4 antibody-drug conjugate for the treatment of breast cancer (Leong, S. R., et al., *An anti-b7-h4 antibody-drug conjugate for the treatment of breast cancer*. Mol Pharm, 2015.12 (6): p.1717-29).

CD28 is constitutively expressed on almost all human CD4+ T cells and on around half of all CD8 T cells. Binding with its two ligands are CD80 (B7-1) and CD86 (B7-2), expressed on dendritic cells, prompts T cell expansion. The co-stimulatory checkpoint molecule CD28 competes with the inhibitory checkpoint molecule CTLA4 for the same ligands, CD80 and CD86 (cf. Buchbinder E. I. and Desai A., 2016: CTLA-4 and PD-1 Pathways-Similarities, Differences and Implications of Their Inhibition; American Journal of Clinical Oncology, 39 (1): 98-106).

Cytotoxic T-Lymphocyte-Associated protein 4 (CTLA4; also known as CD152) is a CD28 homolog with much higher binding affinity for B7. The ligands of CTLA-4 are CD80 (B7-1) and CD86 (B7-2), similarly to CD28. However, unlike CD28, binding of CTLA4 to B7 does not produce a stimulatory signal, but prevents the co-stimulatory signal normally provided by CD28. Moreover, CTLA4 binding to B7 is assumed to even produce an inhibitory signal counteracting the stimulatory signals of CD28:B7 and TCR: MHC binding. CTLA-4 is considered the "leader" of the inhibitory immune checkpoints, as it stops potentially autoreactive T cells at the initial stage of naïve T-cell activation, typically in lymph nodes (Buchbinder E. I. and Desai A., 2016: CTLA-4 and PD-1 Pathways: Similarities, Differences and Implications of Their Inhibition; American Journal of Clinical Oncology, 39 (1): 98-106). Preferred checkpoint inhibitors of CTLA4 include the monoclonal antibodies Yervoy® (Ipilimumab; Bristol Myers Squibb) and Tremelimumab (Pfizer/MedImmune). Further preferred CTLA-4 inhibitors include the anti-CTLA4 antibodies disclosed in WO 2001/014424, in WO 2004/035607, in US 2005/0201994, and in EP 1212422 B1. Additional preferred CTLA-4 antibodies are described in U.S. Pat. No. 5,811,097, in U.S. Pat. No. 5,855,887, in U.S. Pat. No. 6,051,227, in U.S. Pat. No. 6,984,720, in WO 01/14424 in WO 00/37504, in US 2002/0039581 and in US 2002/086014. Other preferred anti-CTLA-4 antibodies that can be used in the context of the present invention include, for example, those disclosed in WO 98/42752; U.S. Pat. Nos. 6,682,736 and 6,207,156; Hurwitz et al., Proc. Natl. Acad. Sci. USA, 95 (17): 10067-10071 (1998); Camacho et al., J. Clin. Oncology, 22 (145): Abstract No. 2505 (2004) (antibody CP-675206); Mokyr et al., Cancer Res., 58:5301-5304

(1998), in U.S. Pat. Nos. 5,977,318, 6,682,736, 7,109,003, and in U.S. Pat. No. 7,132,281.

Programmed Death 1 receptor (PD1) has two ligands, PD-L1 (also known as B7-H1 and CD274) and PD-L2 (also known as B7-DC and CD273). The PD1 pathway regulates previously activated T cells at the later stages of an immune response, primarily in peripheral tissues. An advantage of targeting PD1 is thus that it can restore immune function in the tumor microenvironment. Preferred inhibitors of the PD1 pathway include Opdivo® (Nivolumab; Bristol Myers Squibb), Keytruda® (Pembrolizumab; Merck), Durvalumab (MedImmune/AstraZeneca), MEDI4736 (AstraZeneca; cf. WO 2011/066389 A1), Atezolizumab (MPDL3280A, Roche/Genentech; cf. U.S. Pat. No. 8,217,149 B2), Pidilizumab (CT-011; CureTech), MEDI0680 (AMP-514; AstraZeneca), Avelumab (Merck), MSB-0010718C (Merck), PDR001 (Novartis), BMS-936559 (Bristol Myers Squibb), REGN2810 (Regeneron Pharmaceuticals), MIH1 (Affymetrix), AMP-224 (Amplimmune, GSK), BGB-A317 (BeiGene) and Lambrolizumab (e.g. disclosed as hPD109A and its humanized derivatives h409AII, h409A16 and h409A17 in WO2008/156712; Hamid et al., 2013; N. Engl. J. Med. 369:134-144).

Inducible T-cell costimulator (ICOS; also known as CD278) is expressed on activated T cells. Its ligand is ICOSL (B7-H2; CD275), expressed mainly on B cells and dendritic cells. The molecule seems to be important in T cell effector function.

B7-H3 (also known as CD276) was originally understood to be a co-stimulatory molecule but is now regarded as co-inhibitory. A preferred checkpoint inhibitor of B7-H3 is the Fc-optimized monoclonal antibody Enoblituzumab (MGA271; MacroGenics; cf. US 2012/0294796 A1).

B7-H4 (also known as VTCN1), is expressed by tumor cells and tumor-associated macrophages and plays a role in tumor escape. Preferred B7-H4 inhibitors are the antibodies described in Dangaj, D. et al., 2013; Cancer Research 73 (15): 4820-9 and in Table 1 and the respective description of Jenessa B. Smith et al., 2014: B7-H4 as a potential target for immunotherapy for gynecologic cancers: A closer look. Gynecol Oncol 134 (1): 181-189. Other preferred examples of B7-H4 inhibitors include antibodies to human B7-H4 as disclosed, e.g., in WO 2013/025779 A1 and in WO 2013/067492 A1 or soluble recombinant forms of B7-H4, such as disclosed in US 2012/0177645 A1.

The TNF superfamily comprises in particular 19 protein-ligands binding to 29 cytokine receptors. They are involved in many physiological responses such as apoptosis, inflammation or cell survival (Croft, M., C. A. Benedict, and C. F. Ware, *Clinical targeting of the TNF and TNFR superfamilies*. Nat Rev Drug Discov, 2013.12 (2): p. 147-68). These commonly encountered effects make the TNF superfamily members highly attractive for drug development (more than 60 TNF family drugs in development in 2013 (Croft, M., C. A. Benedict, and C. F. Ware, *Clinical targeting of the TNF and TNFR superfamilies*. Nat Rev Drug Discov, 2013.12 (2): p. 147-68)) but as well difficult to manage due to possible balancing counter-effects (Aggarwal, B. B., *Signalling pathways of the TNF superfamily: a double-edged sword*. Nat Rev Immunol, 2003. 3 (9): p. 745-56). Croft, M., C. A. Benedict, and C. F. Ware, *Clinical targeting of the TNF and TNFR superfamilies*. Nat Rev Drug Discov, 2013.12 (2): p. 147-68 suggest to prioritize nine receptors for cancer indications: TNFRSF4 (OX40/OX40L), TNFRSF5 (CD40L/CD40), TNFRSF7 (CD27/CD70), TNFRSF8 (CD30/CD30L), TNFRSF9 (4-1BB/4-1BBL), TNFRSF10 (TRAILR/TRAIL)), TNFRSF12 (FN14/TWEAK), TNFRSF13 (BAFFRTACI/APRIL-BAFF) and TNFRSF18 (GITR/GITRL) (Avogadri, F., et al., *Modulation of CTLA-4 and GITR/or cancer immunotherapy*. Curr Top Microbiol Immunol, 2011. 344: p. 211-44; Naidoo, J., D. B. Page, and J. D. Wolchok, *Immune modulation for cancer therapy*. Br J Cancer, 2014.111 (12): p. 2214-9). This list is complemented for immuno-therapies by Bremer, E., *Targeting of the turn or necrosis factor receptor superfamily for cancer immunotherapy*. ISRN Oncol, 2013. 2013: p. 371854), adding Fas-Ligand and TNFRSF1 (TNFα/TNFR). Moreover, the B- and T-lymphocyte attenuator (BTLA)/herpes virus entry mediator (HVEM) pathway should be considered as target for enhancing immune responses, just like the CTLA-4 blockade (Croft, M., C. A. Benedict, and C. F. Ware, *Clinical targeting of the TNF and TNFR superfamilies*. Nat Rev Drug Discov, 2013.12 (2): p. 147-68). Accordingly, in the context of the present invention such checkpoint modulators are preferred for the use in the treatment and/or prevention in cancer, which modulate one or more checkpoint molecules selected from TNFRSF4 (OX40/OX40L), TNFRSF5 (CD40L/CD40), TNFRSF7 (CD27/CD70), TNFRSF9 (4-1BB/4-1BBL), TNFRSF18 (GITR/GITRL), FasR/DcR3/Fas ligand, TNFRSF1 (TNFα/TNFR), BTLA/HVEM and CTLA4.

OX40 (also known as CD134 or TNFRSF4) promotes the expansion of effector and memory T cells, but it is also able to suppress the differentiation and activity of T-regulatory cells and to regulate cytokine production. The ligand of OX40 is OX40L (also known as TNFSF4 or CD252). OX40 is transiently expressed after T-cell receptor engagement and is only upregulated on the most recently antigen-activated T cells within inflammatory lesions. Preferred checkpoint modulators of OX40 include MEDI6469 (MedImmune/AstraZeneca), MEDI6383 (MedImmune/AstraZeneca), MEDI0562 (MedImmune/AstraZeneca), MOXR0916 (RG7888; Roche/Genentech) and GSK3174998 (GSK).

CD40 (also known as TNFRSF5) is expressed by a variety of immune system cells including antigen presenting cells. Its ligand is CD40L, also known as CD154 or TNFSF5, is transiently expressed on the surface of activated CD4+ T cells. CD40 signaling "licenses" dendritic cells to mature and thereby trigger T-cell activation and differentiation. However, CD40 can also be expressed by tumor cells. Thus, stimulation/activation of CD40 in cancer patients can be beneficial or deleterious. Accordingly, stimulatory and inhibitory modulators of this immune checkpoint were developed (Sufia Butt Hassan, Jesper Freddie Sørensen, Barbara Nicola Olsen and Anders Elm Pedersen, 2014: Anti-CD40-mediated cancer immunotherapy: an update of recent and ongoing clinical trials, Immunopharmacology and Immunotoxicology, 36:2, 96-104). Preferred examples of CD40 checkpoint modulators include (i) agonistic anti-CD antibodies as described in Sufia Butt Hassan, Jesper Freddie Sørensen, Barbara Nicola Olsen and Anders Elm Pedersen, 2014: Anti-CD40-mediated cancer immunotherapy: an update of recent and ongoing clinical trials, Immunopharmacology and Immunotoxicology, 36:2, 96-104, such as Dacetuzumab (SGN-40), CP-870893, FGK 4.5/FGK 45 and FGK115, preferably Dacetuzumab, and (ii) antagonistic anti-CD antibodies as described in Sufia Butt Hassan, Jesper Freddie Sørensen, Barbara Nicola Olsen and Anders Elm Pedersen, 2014: Anti-CD40-mediated cancer immunotherapy: an update of recent and ongoing clinical trials, Immunopharmacology and Immunotoxicology, 36:2, 96-104, such as Lucatumumab (HCD122, CHIR-12.12). Further preferred immune checkpoint modulators of CD40 include SEA-CD40 (Seattle Genetics), ADC-1013 (Alligator Biosciences), APX005M (Apexigen Inc) and RO7009789 (Roche).

CD27 (also known as TNFRSF7) supports antigen-specific expansion of naïve T cells and plays an important role in the generation of T cell memory. CD27 is also a memory marker of B cells. The transient availability of its ligand, CD70 (also known as TNFSF7 or CD27L), on lymphocytes and dendritic cells regulates the activity of CD27. Moreover, CD27 co-stimulation is known to suppress Th17 effector cell function. A preferred immune checkpoint modulator of CD27 is Varlilumab (Celldex). Preferred immune checkpoint modulators of CD70 include ARGX-110 (arGEN-X) and SGN-CD70A (Seattle Genetics).

CD137 (also known as 4-1BB or TNFRSF9) is a member of the tumor necrosis factor (TNF) receptor family and is increasingly associated with costimulatory activity for activated T cells. In particular, CD137 signaling (via its ligand CD137L, also known as TNFSF9 or 4-1BBL) results in T-cell proliferation and protects T cells, in particular, CD8+ T cells, from activation-induced cell death. Preferred checkpoint modulators of CD137 include PF-05082566 (Pfizer) and Urelumab (BMS).

Glucocorticoid-Induced TNFR family Related gene (GITR, also known as TNFRSF18), prompts T cell expansion, including Treg expansion. The ligand for GITR (GITRL, TNFSF18) is mainly expressed on antigen presenting cells. Antibodies to GITR have been shown to promote an anti-tumor response through loss of Treg lineage stability. Preferred checkpoint modulators of GITR include BMS-986156 (Bristol Myers Squibb), TRX518 (GITR Inc) and MK-4166 (Merck).

Another preferred checkpoint molecule to be modulated is BTLA. B and T Lymphocyte Attenuator (BTLA; also known as CD272) is in particular expressed by CD8+ T cells, wherein surface expression of BTLA is gradually downregulated during differentiation of human CD8+ T cells from the naive to effector cell phenotype. However, tumor-specific human CD8+ T cells express high levels of BTLA. BTLA expression is induced during activation of T cells, and BTLA remains expressed on Th1 cells but not Th2 cells. Like PD1 and CTLA4, BTLA interacts with a B7 homolog, B7H4. However, unlike PD-1 and CTLA-4, BTLA displays T-Cell inhibition via interaction with tumor necrosis family receptors (TNF-R), not just the B7 family of cell surface receptors. BTLA is a ligand for tumor necrosis factor (receptor) superfamily, member 14 (TNFRSF14), also known as herpes virus entry mediator (HVEM; Herpesvirus Entry Mediator, also known as CD270). BTLA-HVEM complexes negatively regulate T-cell immune responses.

Preferred BTLA inhibitors are the antibodies described in Table 1 of Alison Crawford and E. John Wherry, 2009: Editorial: Therapeutic potential of targeting BTLA. Journal of Leukocyte Biology 86:5-8, in particular the human antibodies thereof. Other preferred antibodies in this context, which block human BTLA interaction with its ligand are disclosed in WO 2011/014438, such as "4C7" as described in WO 2011/014438.

Another checkpoint molecule family includes checkpoint molecules related to the two primary class of major histocompatibility complex (MHC) molecules (MHC class I and class II). Their function to trigger a response from the immune system through their respective pathways; killer Ig-like Receptor (KIR) for class I and lymphocyte activation gene-3 (LAG-3) for class II, seems opening novel immunotherapeutic strategies for cancer patients treatment (Hemon, P., et al., *MHC class II engagement by its ligand LAG-3 (CD223) contributes to melanoma resistance to apoptosis.* J Immunol, 2011. 186 (9): p. 5173-83; Thielens, A., E. Vivier, and F. Romagne, *NK cell MHC class I specific receptors (KIR): from biology to clinical intervention.* Curr Opin Immunol, 2012. 24 (2): p. 239-45).

Killer-cell Immunoglobulin-like Receptor (KIR) is a receptor for MHC Class I molecules on Natural Killer cells. An exemplary inhibitor of KIR is the monoclonal antibody Lirilumab (IPH 2102; Innate Pharma/BMS; cf. U.S. Pat. No. 8,119,775 B2 and Benson et al., 2012, Blood 120:4324-4333).

Lymphocyte Activation Gene-3 (LAG3, also known as CD223) signaling leads to suppression of an immune response by action to Tregs as well as direct effects on CD8+ T cells. A preferred example of a LAG3 inhibitor is the anti-LAG3 monoclonal antibody BMS-986016 (Bristol-Myers Squibb). Other preferred examples of a LAG3 inhibitor include LAG525 (Novartis), IMP321 (Immutep) and LAG3-Ig as disclosed in WO 2009/044273 A2 and in Brignon et al., 2009, Clin. Cancer Res. 15:6225-6231 as well as mouse or humanized antibodies blocking human LAG3 (e.g., IMP701 as described in WO 2008/132601 A1), or fully human antibodies blocking human LAG3 (such as disclosed in EP 2320940 A2).

Another checkpoint molecule pathway is the TIM-3/GAL9 pathway). T-cell Immunoglobulin domain and Mucin domain 3 (TIM-3, also known as HAVcr-2) is expressed on activated human CD4+ T cells and regulates Th1 and Th17 cytokines. TIM-3 acts as a negative regulator of Th1/Tc1 function by triggering cell death upon interaction with its ligand, galectin-9 (GAL9). TIM-3 is a T helper type 1 specific cell surface molecule that is regulating the induction of peripheral tolerance. A recent study has indeed demonstrated that TIM-3 antibodies could significantly enhance antitumor immunity (Ngiow, S. F., et al., *Anti-TIM3 antibody promotes T cell IFN-gammamediated antitumor immunity and suppresses established tumors.* Cancer Res, 2011. 71 (10): p. 3540-51). Preferred examples of TIM-3 inhibitors include antibodies targeting human TIM3 (e.g. as disclosed in WO 2013/006490 A2) or, in particular, the anti-human TIM3 blocking antibody F38-2E2 as disclosed by Jones et al., 2008, J Exp Med. 205 (12): 2763-79.

More recently a novel target named CEACAM1 (Carcinoembryonic antigen-related cell adhesion molecule 1) was suggested, as recent studies showed the role for members of the CEA CAM family in modulating the immune responses associated with cancer (Huang, Y. H., et al., *CEACAM1 regulates TIM-3-mediated tolerance and exhaustion.* Nature, 2015. 517 (7534): p. 386-90; Gray-Owen, S. D. and R. S. Blumberg, *CEACAM1: contact-dependent control of immunity.* Nat Rev Immunol, 2006. 6 (6): p. 433-46). A preferred checkpoint modulator of CEACAM1 is CM-24 (cCAM Biotherapeutics).

Another novel immune checkpoint molecule is GARP, which plays a role in the ability of tumors to escape the patient's immune system. Presently in clinical trials, the candidate (ARGX-115) seems demonstrating interesting effect. Accordingly, ARGX-115 is a preferred GARP checkpoint modulator.

Moreover, various research groups have demonstrated that another checkpoint molecule is phosphatidylserine (also referred to as "PS") may be targeted for cancer treatment (Creelan, B. C., Update on immune checkpoint inhibitors in lung cancer. Cancer Control, 2014. 21 (1): p. 80-9; Yin, Y., et al., *Phosphatidylserine-targeting antibody induces MI macrophage polarization and promotes myeloid-derived suppressor cell differentiation.* Cancer Immunol Res, 2013.

1 (4): p. 256-68). A preferred checkpoint modulator of phosphatidylserine (PS) is Bavituximab (Peregrine).

Another checkpoint pathway is CSF1/CSF1R (Zhu, Y., et al., *CSF1/CSF1R Blockade Reprograms Tumor-Infiltrating Macrophages and Improves Response to T-cell Checkpoint Immunotherapy in Pancreatic Cancer Models*. Cancer Research, 2014. 74 (18): p. 5057-5069). Preferred checkpoint modulators of CSF1R include FPA008 (FivePrime), IMC-CS4 (Eli-Lilly), PLX3397 (Plexxicon) and RO5509554 (Roche). Furthermore, the CD94/NKG2A natural killer cell receptor is evaluated for its role in cervical carcinoma (Sheu, B. C., et al., *Up-regulation of inhibitory natural killer receptors CD94/NKG2A with suppressed intracellular perforin expression of tumor infiltrating CD8+ T lymphocytes in human cervical carcinoma*. Cancer Res, 2005. 65 (7): p. 2921-9) and in leukemia (Tanaka, J., et al., *Cytolytic activity against primary leukemic cells by inhibitory NK cell receptor (CD94/NKG2A)-expressing T cells expanded from various sources of blood mononuclear cells*. Leukemia, 2005. 19 (3): p. 486-9). A preferred checkpoint modulator of NKG2A is IPH2201 (Innate Pharma).

Another preferred checkpoint molecule is IDO, the indoleamine 2,3-dioxygenase enzyme from the kynurenine pathway (Ball, H. J., et al., *Indoleamine 2,3-dioxygenase-2; a new enzyme in the kynurenine pathway*. Int J Biochem Cell Biol, 2009. 41 (3): p. 467-71). Indoleamine 2,3-dioxygenase (IDO) is a tryptophan catabolic enzyme with immune-inhibitory properties. IDO is known to suppress T and NK cells, generate and activate Tregs and myeloid-derived suppressor cells, and promote tumour angiogenesis. IDO1 is overexpressed in many cancer and was shown to allow tumor cells escaping from the immune system (Liu, X., et al., *Selective inhibition of IDO1 effectively regulates mediators of antitumor immunity*. Blood, 2010. 115 (17): p. 3520-30; Ino, K., et al., *Inverse correlation between tumoral indoleamine 2,3-dioxygenase expression and tumor-infiltrating lymphocytes in endometrial cancer: its association with disease progression and survival*. Clin Cancer Res, 2008. 14 (8): p. 2310-7) and to facilitate chronic tumor progression when induced by local inflammation (Muller, A. J., et al., *Chronic inflammation that facilitates tumor progression creates local immune suppression by inducing indoleamine 2,3 dioxygenase*. Proc Natl Acad Sci US A, 2008. 105 (44): p. 17073-8). Preferred IDO inhibitors include Exiguamine A, epacadostat (INCB024360; InCyte), Indoximod (NewLink Genetics), NLG919 (NewLink Genetics/Genentech), GDC-0919 (NewLink Genetics/Genentech), F001287 (*Flexus* Biosciences/BMS) and small molecules such as 1-methyl-tryptophan, in particular 1-methyl-[D]-tryptophan and the IDO inhibitors listed in Table 1 of Sheridan C., 2015: IDO inhibitors move center stage in immune-oncology; Nature Biotechnology 33:321-322.

Another preferred immune checkpoint molecule to be modulated is also a member of the kynurenine metabolic pathway: TDO (tryptophan-2,3-dioxygenase). Several studies already demonstrated the interest of TDO in cancer immunity and autoimmunity (Garber, K., Evading immunity: new enzyme implicated in cancer. J Natl Cancer Inst, 2012. 104 (5): p. 349-52; Platten, M., W. Wick, and B. J. Van den Eynde, *Tryptophan catabolismin cancer: beyond IDO and tryptophan depletion*. Cancer Res, 2012. 72 (21): p. 5435-40; Platten, M., et al., *Cancer Immunotherapy by Targeting IDO1/TDO and Their Downstream Effectors*. Front Immunol, 2014. 5: p. 673).

Another preferred immune checkpoint molecule to be modulated is A2AR. The Adenosine A2A receptor (A2AR) is regarded as an important checkpoint in cancer therapy because the tumor microenvironment has typically relatively high concentrations of adenosine, which is activating A2AR. Such signaling provides a negative immune feedback loop in the immune microenvironment (for review see Robert D. Leone et al., 2015: A2aR antagonists: Next generation checkpoint blockade for cancer immunotherapy. Computational and Structural Biotechnology Journal 13:265-272). Preferred A2AR inhibitors include Istradefylline, PBS-509, ST1535, ST4206, Tozadenant, V81444, Preladenant, Vipadenant, SCH58261, SYN115, ZM241365 and FSPTP.

Another preferred immune checkpoint molecule to be modulated is VISTA. V-domain Ig suppressor of T cell activation (VISTA; also known as C10orf54) is primarily expressed on hematopoietic cells so that consistent expression of VISTA on leukocytes within tumors may allow VISTA blockade to be effective across a broad range of solid tumors. A preferred VISTA inhibitor is JNJ-61610588 (ImmuNext), an anti-VISTA antibody, which recently entered a phase 1 clinical trial.

Another immune checkpoint molecule is CD122. CD122 is the Interleukin-2 receptor beta sub-unit. CD122 increases proliferation of CD8+ effector T cells.

The most preferred examples of checkpoint molecules include the "CTLA4-pathway" and the "PD1-pathway" with CTLA4 and its ligands CD80 and CD86 as well as PD1 with its ligands PD-L1 and PD-L2 (more details on CTLA4 and PD-1 pathways as well as further participants are described in Buchbinder E. I. and Desai A., 2016: CTLA-4 and PD-1 Pathways-Similarities, Differences and Implications of Their Inhibition; American Journal of Clinical Oncology, 39 (1): 98-106). In more general, preferred examples of checkpoint molecules include CD27, CD28, CD40, CD122, CD137, OX40, GITR, ICOS, A2AR, B7-H3, B7-H4, BTLA, CD40, CTLA-4, IDO, KIR, LAG3, PD-1, TIM-3, VISTA, CEACAM1, GARP, PS, CSF1R, CD94/NKG2A, TDO, GITR, TNFR and/or FasR/DcR3 as well as, in particular, their ligands.

Immune checkpoint molecules are responsible for co-stimulatory or inhibitory interactions of T-cell responses. Accordingly, checkpoint molecules can be divided into (i) (co-)stimulatory checkpoint molecules and (ii) inhibitory checkpoint molecules. Typically, (co-)stimulatory checkpoint molecules act positively in concert with T-cell receptor (TCR) signaling induced by antigen stimulation and inhibitory checkpoint molecules negatively regulate TCR signaling. Examples of (co-)stimulatory checkpoint molecules include CD27, CD28, CD40, CD122, CD137, OX40, GITR and ICOS. Examples of inhibitory checkpoint molecules include CTLA4 as well as PD1 with its ligands PD-L1 and PD-L2; and A2AR, B7-H3, B7-H4, BTLA, IDO, KIR, LAG3, TIM-3, VISTA, CEACAM1, GARP, PS, CSF1R, CD94/NKG2A, TDO, TNFR and FasR/DcR3.

Preferably, the immune checkpoint modulator is an activator of a (co-)stimulatory checkpoint molecule or an inhibitor of an inhibitory checkpoint molecule or a combination thereof. Accordingly, the immune checkpoint modulator is more preferably (i) an activator of CD27, CD28, CD40, CD122, CD137, OX40, GITR and/or ICOS or (ii) an inhibitor of A2AR, B7-H3, B7-H4, BTLA, CD40, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or FasR/DcR3.

As described above, a number of CD27, CD28, CD40, CD122, CD137, OX40, GITR, ICOS, A2AR, B7-H3, B7-H4, CTLA-4, PD1, PDL-1, PD-L2, IDO, LAG-3, BTLA, TIM3, VISTA, KIR, CEACAM1, GARP, PS, CSF1R, CD94/NKG2A, TDO, TNFR and/or FasR/DcR3 modulators (inhibitors/activators) are known and some of them are already in clinical trials or even approved. Based on these known immune checkpoint modulators, alternative immune checkpoint modulators may be developed in the (near) future. In particular, known modulators of the preferred immune checkpoint molecules may be used as such or analogues thereof may be used, in particular chimerized, humanized or human forms of antibodies.

More preferably, the immune checkpoint modulator is an inhibitor of an inhibitory checkpoint molecule (but preferably no inhibitor of a stimulatory checkpoint molecule). Accordingly, the immune checkpoint modulator is even more preferably an inhibitor of A2AR, B7-H3, B7-H4, BTLA, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or DcR3 or of a ligand thereof.

It is also preferred that the immune checkpoint modulator is an activator of a stimulatory or costimulatory checkpoint molecule (but preferably no activator of an inhibitory checkpoint molecule). Accordingly, the immune checkpoint modulator is more preferably an activator of CD27, CD28, CD40, CD122, CD137, OX40, GITR and/or ICOS or of a ligand thereof.

It is even more preferred that the immune checkpoint modulator is a modulator of the CD40 pathway, of the IDO pathway, of the CTLA-4 pathway and/or of the PD-1 pathway. In particular, the immune checkpoint modulator is preferably a modulator of CD40, CTLA-4, PD-L1, PD-L2, PD-1 and/or IDO, more preferably the immune checkpoint modulator is an inhibitor of CTLA-4, PD-L1, PD-L2, PD-1 and/or IDO or an activator of CD40, even more preferably the immune checkpoint modulator is an inhibitor of CTLA-4, PD-L1, PD-1 and/or IDO and most preferably the immune checkpoint modulator is an inhibitor of CTLA-4 and/or PD-1.

It is even more preferred that the immune checkpoint modulator is a modulator of the CD40 pathway, of the IDO pathway, of the LAG3 pathway, of the CTLA-4 pathway and/or of the PD-1 pathway. In particular, the immune checkpoint modulator is preferably a modulator of CD40, LAG3, CTLA-4, PD-L1, PD-L2, PD-1 and/or IDO, more preferably the immune checkpoint modulator is an inhibitor of CTLA-4, PD-L1, PD-L2, PD-1, LAG3, and/or IDO or an activator of CD40, even more preferably the immune checkpoint modulator is an inhibitor of CTLA-4, PD-L1, PD-1, LAG3 and/or IDO, even more preferably the immune checkpoint modulator is an inhibitor of LAG3, CTLA-4 and/or PD-1, and most preferably the immune checkpoint modulator is an inhibitor of CTLA-4 and/or PD-1.

Accordingly, the checkpoint modulator may be selected from known modulators of the CD40 pathway, the CTLA-4 pathway or the PD-1 pathway. Preferably, the checkpoint modulator may be selected from known modulators of the CD40 pathway, the LAG3 pathway, the CTLA-4 pathway or the PD-1 pathway. Preferred inhibitors of the CTLA-4 pathway and of the PD-1 pathway include the monoclonal antibodies Yervoy® (Ipilimumab; Bristol Myers Squibb) and Tremelimumab (Pfizer/MedImmune) as well as Opdivo® (Nivolumab; Bristol Myers Squibb), Keytruda® (Pembrolizumab; Merck), Durvalumab (MedImmune/AstraZeneca), MEDI4736 (AstraZeneca; cf. WO 2011/066389 A1), MPDL3280A (Roche/Genentech; cf. U.S. Pat. No. 8,217,149 B2), Pidilizumab (CT-011; CureTech), MEDI0680 (AMP-514; AstraZeneca), MSB-0010718C (Merck), MIH1 (Affymetrix) and Lambrolizumab (e.g. disclosed as hPD109A and its humanized derivatives h409AII, h409A16 and h409A17 in WO2008/156712; Hamid et al., 2013; N. Engl. J. Med. 369:134-144). More preferred checkpoint inhibitors include the CTLA-4 inhibitors Yervoy® (Ipilimumab; Bristol Myers Squibb) and Tremelimumab (Pfizer/MedImmune) as well as the PD-1 inhibitors Opdivo® (Nivolumab; Bristol Myers Squibb), Keytruda® (Pembrolizumab; Merck), Pidilizumab (CT-011; CureTech), MEDI0680 (AMP-514; AstraZeneca), AMP-224 and Lambrolizumab (e.g. disclosed as hPD109A and its humanized derivatives h409AII, h409A16 and h409A17 in WO2008/156712; Hamid O. et al., 2013; N. Engl. J. Med. 369:134-144). As described above, a preferred example of a LAG3 inhibitor is the anti-LAG3 monoclonal antibody BMS-986016 (Bristol-Myers Squibb). Other preferred examples of a LAG3 inhibitor include LAG525 (Novartis), IMP321 (Immutep) and LAG3-Ig as disclosed in WO 2009/044273 A2 and in Brignon et al., 2009, Clin. Cancer Res. 15:6225-6231 as well as mouse or humanized antibodies blocking human LAG3 (e.g., IMP701 as described in WO 2008/132601 A1), or fully human antibodies blocking human LAG3 (such as disclosed in EP 2320940 A2).

Preferably, the immune checkpoint modulator is not a modulator of CD40. In particular it is preferred that the immune checkpoint modulator is not a CD40 ligand. It is also preferred that the immune checkpoint modulator is not an anti-CD40 antibody.

In the context of the present invention it is preferred if more than one immune checkpoint modulator (e.g., checkpoint inhibitor) is used, in particular at least 2, 3, 4, 5, 6, 7, 8, 9 or 10 distinct immune checkpoint modulators (e.g., checkpoint inhibitors) are used, preferably 2, 3, 4 or 5 distinct immune checkpoint modulators (e.g., checkpoint inhibitors) are used, more preferably 2, 3 or 4 distinct immune checkpoint modulators (e.g., checkpoint inhibitors) are used, even more preferably 2 or 3 distinct immune checkpoint modulators (e.g., checkpoint inhibitors) are used and most preferably 2 distinct immune checkpoint modulators (e.g., checkpoint inhibitors) are used. Thereby, "distinct" immune checkpoint modulators (e.g., checkpoint inhibitors) means in particular that they modulate (e.g., inhibit) different checkpoint molecule pathways.

Preferably, an inhibitor of the PD-1 pathway is combined with an inhibitor of the CTLA-4 pathway. For example, as described above a combination therapy with Nivolumab (anti-PD1) and Ipilimumab (anti-CTLA4) was approved by the FDA in 2015 for the treatment of patients with BRAF V600 wild-type, unresectable or metastatic melanoma. In addition, a successful phase 1b study on the combination of Durvalumab (anti-PD-L1) and Tremelimumab (anti-CTLA4) in non-small cell lung cancer was recently reported (Antonia, Scott et al., 2016, Safety and antitumour activity of durvalumab plus tremelimumab in non-small cell lung cancer: a multicentre, phase 1b study; Lancet Oncol. 2016 Feb. 5. pii: S1470-2045 (15) 00544-6. doi: 10.1016/S1470-2045 (15) 00544-6. [Epub ahead of print]). Accordingly, preferred combinations of immune checkpoint modulators of the PD-1 pathway and of the CTLA-4 pathway are (i) Nivolumab (anti-PD1) and Ipilimumab (anti-CTLA4) or (ii) Durvalumab (MEDI4736; anti-PD-L1) and Tremelimumab (anti-CTLA4). Combinations thereof, e.g. Nivolumab (anti-PD1) and Tremelimumab (anti-CTLA4) or Durvalumab (MEDI4736; anti-PD-L1) and Ipilimumab (anti-CTLA4) are also preferred.

Other preferred combinations of at least two distinct immune checkpoint modulators in the context of the present invention may comprise a combination selected from (i) a combination of a KIR inhibitor and a CTLA-4 inhibitor, such as Lirilumab/Ipilimumab; (ii) a combination of a KIR inhibitor and an inhibitor of the PD-1 pathway, such as a PD-1 inhibitor, for example Lirilumab/Nivolumab; (iii) a combination of a LAG3 inhibitor and an inhibitor of the PD-1 pathway, such as a PD-1 inhibitor or a PD-L1 inhibitor, for example as described in Woo et al., 2012, Cancer Res. 72:917-27 or in Butler N. S. et al., 2011, Nat Immunol. 13:188-95) and preferred examples of such a combination include Novilumab/BMS-986016 and PDR001/LAG525; (iv) a combination of checkpoint modulators targeting ICOS and an inhibitor of the CTLA-4, for example as described in Fu et al., 2011, Cancer Res. 71:5445-54; (v) a combination of checkpoint modulators modulating 4-1BB and inhibitors of CTLA-4, such as described in Curran et al., 2011, PLOS One 6 (4): el 9499); (vi) a combination of checkpoint modulators targeting PD1 and CD27, such as Novilumab/Varlilumab and Atezolizumab/Varlilumab; (vii) a combination of checkpoint modulators targeting OX40 and CTLA-4, such as MEDI6469/Tremelimumab; (viii) a combination of checkpoint modulators targeting OX40 and PD-1, such as MEDI6469/MEDI4736, MOXR0916/MPDL3280A, MEDI6383/MEDI4736 and GSK3174998/Pembrolizumab; (ix) a combination of checkpoint modulators targeting PD-1 and 4-1BB, such as Novilumab/Urelumab, Pembrolizumab/PF-05082566 and Avelumab/PF-05082566; (x) a combination of checkpoint modulators targeting PD-1 and IDO, such as Ipilimumab/Indoximod, Pembrolizumab/INCB024360, MEDI4736/INCB024360, MPDL3280A/GDC-0919 and Atezolizumab/INCB024360; (xi) a combination of checkpoint modulators targeting PD-1 and CSF1R, such as Pembrolizumab/PLX3397, Novilumab/FPA008 and MPDL3280A/RO5509554; (xii) a combination of checkpoint modulators targeting PD-1 and GITR, such as Novilumab/BMS-986156 and Pembrolizumab/MK-4166; (xiii) a combination of checkpoint modulators targeting PD-1 and CD40, such as MPDL3280A/RO7009789; (xiv) a combination of checkpoint modulators targeting PD-1 and B7-H3, such as Pembrolizumab/MGA271; (xv) a combination of checkpoint modulators targeting CTLA-4 and B7-H3, such as Ipilimumab/MGA271 and (xvi) a combination of checkpoint modulators targeting KIR and 4-1BB, such as Lirilumab/Urelumab.

Most preferably, the combination of the immune checkpoint modulator and the complex comprising a cell penetrating peptide, at least one antigen or antigenic epitope and at least one TLR peptide agonist for use according to the present invention comprises at least (i) an inhibitor of CTLA-4 and (ii) an inhibitor of PD-1, PD-L1 or PD-L2, preferably at least (i) an inhibitor of CTLA-4 and (ii) an inhibitor of PD-1. Examples of such a preferred combination include a combination of Yervoy® (Ipilimumab; Bristol Myers Squibb) and Opdivo® (Nivolumab; Bristol Myers Squibb), a combination of Yervoy® (Ipilimumab; Bristol Myers Squibb) and Keytruda® (Pembrolizumab; Merck), a combination of Yervoy® (Ipilimumab; Bristol Myers Squibb) and Durvalumab (MedImmune/AstraZeneca), a combination of Yervoy® (Ipilimumab; Bristol Myers Squibb) and MEDI4736 (AstraZeneca; cf. WO 2011/066389 A1), a combination of Yervoy® (Ipilimumab; Bristol Myers Squibb) and MPDL3280A (Roche/Genentech; cf. U.S. Pat. No. 8,217,149 B2), a combination of Yervoy® (Ipilimumab; Bristol Myers Squibb) and Pidilizumab (CT-011; CureTech), a combination of Yervoy® (Ipilimumab; Bristol Myers Squibb) and MEDI0680 (AMP-514; AstraZeneca), a combination of Yervoy® (Ipilimumab; Bristol Myers Squibb) and MSB-0010718C (Merck), a combination of Yervoy® (Ipilimumab; Bristol Myers Squibb) and MIH1 (Affymetrix), a combination of Yervoy® (Ipilimumab; Bristol Myers Squibb) and AMP-224, a combination of Yervoy® (Ipilimumab; Bristol Myers Squibb) and Lambrolizumab, a combination of Tremelimumab (Pfizer/MedImmune) and Opdivo® (Nivolumab; Bristol Myers Squibb), a combination of Tremelimumab (Pfizer/MedImmune) and Keytruda® (Pembrolizumab; Merck), a combination of Tremelimumab (Pfizer/MedImmune) and Durvalumab (MedImmune/AstraZeneca), a combination of Tremelimumab (Pfizer/MedImmune) and MEDI4736 (AstraZeneca; cf. WO 2011/066389 A1), a combination of Tremelimumab (Pfizer/MedImmune) and MPDL3280A (Roche/Genentech; cf. U.S. Pat. No. 8,217,149 B2), a combination of Tremelimumab (Pfizer/MedImmune) and Pidilizumab (CT-011; CureTech), a combination of Tremelimumab (Pfizer/MedImmune) and MEDI0680 (AMP-514; AstraZeneca), a combination of Tremelimumab (Pfizer/MedImmune) and MSB-0010718C (Merck), a combination of Tremelimumab (Pfizer/MedImmune) and MIH1 (Affymetrix), a combination of Tremelimumab (Pfizer/MedImmune) and AMP-224 and a combination of Tremelimumab (Pfizer/MedImmune) and Lambrolizumab.

In the context of the present invention it is also preferred if more than one immune checkpoint modulator (e.g., checkpoint inhibitor) of the same checkpoint pathway is used, in particular at least 2, 3, 4, 5, 6, 7, 8, 9 or 10 immune checkpoint modulators (e.g., checkpoint inhibitors) of the same checkpoint pathway are used, preferably 2, 3, 4 or 5 immune checkpoint modulators (e.g., checkpoint inhibitors) of the same checkpoint pathway are used, more preferably 2, 3 or 4 immune checkpoint modulators (e.g., checkpoint inhibitors) of the same checkpoint pathway are used, even more preferably 2 or 3 immune checkpoint modulators (e.g., checkpoint inhibitors) of the same checkpoint pathway are used and most preferably 2 immune checkpoint modulators (e.g., checkpoint inhibitors) of the same checkpoint pathway are used. Preferred checkpoint pathways to be modulated are the PD-1 pathway, the CTLA-4 pathway, the CD40 pathway or the IDO pathway, more preferably the PD-1 pathway, the CTLA-4 pathway or the CD40 pathway and even more preferably the PD-1 pathway or the CTLA-4 pathway. For example, a combination of MEDI4736 and MEDI0680 may be used to modulate, in particular to inhibit, the PD-1 pathway.

In the context of the present invention immune checkpoint modulators may be any kind of molecule or agent, as long as it totally or partially reduces, inhibits, interferes with, activates, stimulates, increases, reinforces or supports the function of one or more checkpoint molecules as described above. In particular, the immune checkpoint modulator binds to one or more checkpoint molecules, such as checkpoint proteins, or to its precursors, e.g. on DNA- or RNA-level, thereby modulating (e.g., totally or partially reducing, inhibiting, interfering with, activating, stimulating, increasing, reinforcing or supporting) the function of one or more checkpoint molecules as described above. Preferred immune checkpoint modulators are oligonucleotides, siRNA, shRNA, ribozymes, anti-sense RNA molecules, immunotoxins, small molecule inhibitors and (e.g., checkpoint molecule blocking, antagonist or agonist of checkpoint molecule) antibodies or antigen binding fragments thereof.

Preferably, the immune checkpoint modulator is an oligonucleotide. Such an oligonucleotide is preferably used to decrease protein expression, in particular to decrease the expression of a checkpoint protein, such as the checkpoint receptors or ligands described above. Oligonucleotides are short DNA or RNA molecules, typically comprising from 2 to 50 nucleotides, preferably from 3 to 40 nucleotides, more preferably from 4 to 30 nucleotides and even more preferably from 5 to 25 nucleotides, such as, for example 4, 5, 6, 7, 8, 9 or 10 nucleotides. Oligonucleotides are usually made in the laboratory by solid-phase chemical synthesis. Oligonucleotides maybe single-stranded or double-stranded, however, in the context of the present invention the oligonucleotide is preferably single-stranded. More preferably, the checkpoint modulator oligonucleotide is an antisense-oligonucleotide. Antisense-oligonucleotides are single strands of DNA or RNA that are complementary to a chosen sequence, in particular to a sequence chosen from the DNA or RNA sequence (or a fragment thereof) of a checkpoint protein. Antisense RNA is typically used to prevent protein translation of messenger RNA strands, e.g. of mRNA for a checkpoint protein, by binding to the mRNA. Antisense DNA is typically used to target a specific, complementary (coding or non-coding) RNA. If binding takes place, such a DNA/RNA hybrid can be degraded by the enzyme RNase H. Moreover, morpholino-antisense oligonucleotides can be used for gene knockdowns in vertebrates. For example, Kryczek et al., 2006 (Kryczek I, Zou L, Rodriguez P, Zhu G, Wei S, Mottram P, et al. B7-H4 expression identifies a novel suppressive macrophage population in human ovarian carcinoma. J Exp Med. 2006; 203:871-81) designed a B7-H4-specific morpholino that specifically blocked B7-H4 expression in macrophages, resulting in increased T-cell proliferation and reduced tumor volumes in mice with tumor associated antigen (TAA)-specific T cells.

Preferably, the immune checkpoint modulator is an siRNA. Small interfering RNA (siRNA), sometimes known as short interfering RNA or silencing RNA, is a class of double-stranded RNA molecules, which is typically 20-25 base pairs in length. In the RNA interference (RNAi) pathway, siRNA interferes with the expression of specific genes, such as genes coding for checkpoint proteins, with complementary nucleotide sequences. siRNA functions by causing mRNA to be broken down after transcription, resulting in no translation. Transfection of exogenous siRNA may be used for gene knockdown, however, the effect maybe only transient, especially in rapidly dividing cells. This may be overcome, for example, by RNA modification or by using an expression vector for the siRNA. The siRNA sequence may also be modified to introduce a short loop between the two strands. The resulting transcript is a short hairpin RNA (shRNA, also "small hairpin RNA"), which can be processed into a functional siRNA by Dicer in its usual fashion. shRNA is an advantageous mediator of RNAi in that it has a relatively low rate of degradation and turnover. Accordingly, the immune checkpoint modulator is preferably an shRNA. shRNA typically requires the use of an expression vector, e.g. a plasmid or a viral or bacterial vector.

Preferably, the immune checkpoint modulator is an immunotoxin. Immunotoxins are chimeric proteins that contain a targeting moiety (such as an antibody), which is typically targeting an antigen on a certain cell, such as a cancer cell, linked to a toxin. In the context of the present invention, an immunotoxin comprising a targeting moiety, which targets a checkpoint molecule, is preferred. When the immunotoxin binds to a cell carrying the antigen, e.g. the checkpoint molecule, it is taken in through endocytosis, and the toxin can then kill the cell. Immunotoxins preferably comprise a (modified) antibody or antibody fragment, linked to a (fragment of a) toxin. For linkage, methods are well known in the art and the same methods as described herein for linkage of the components of the complex may be used. The targeting portion of the immunotoxin typically comprises a Fab portion of an antibody that targets a specific cell type. The toxin is usually cytotoxic, such as a protein derived from a bacterial or plant protein, from which the natural binding domain has been removed so that the targeting moiety of the immunotoxin directs the toxin to the antigen on the target cell. However, immunotoxins can also comprise a targeting moiety other than an antibody or antibody fragment, such as a growth factor. For example, recombinant fusion proteins containing a toxin and a growth factor are also referred to as recombinant immunotoxins.

Preferably, the immune checkpoint modulator is a small molecule drug (also referred to as "small molecule inhibitor"). A small molecule drug is a low molecular weight (up to 900 daltons) organic compound that typically interacts with (the regulation of) a biological process. In the context of the present invention, a small molecule drug which is an immune checkpoint modulator, is an organic compound having a molecular weight of no more than 900 daltons, which totally or partially reduces, inhibits, interferes with, or negatively modulates the function of one or more checkpoint molecules as described above. The upper molecular weight limit of 900 daltons allows for the possibility to rapidly diffuse across cell membranes and for oral bioavailability. More preferably, the molecular weight of the small molecule drug which is an immune checkpoint modulator, is no more than 500 daltons. For example, various A2AR antagonists known in the art are organic compounds having a molecular weight below 500 daltons.

Most preferably, the immune checkpoint modulator is an antibody or an antigen-binding fragment thereof, in particular antibodies, or antigen binding fragments thereof, that bind to immune checkpoint receptors or antibodies that bind to immune checkpoint receptor ligands. Preferably, such antibodies, or antigen binding fragments thereof, are agonists or antagonists of immune checkpoint receptors or of immune checkpoint receptor ligands. Examples of antibody-type checkpoint modulators include immune checkpoint modulators, which are currently approved as described above, namely, Yervoy® (Ipilimumab; Bristol Myers Squibb), Opdivo® (Nivolumab; Bristol Myers Squibb) and Keytruda® (Pembrolizumab; Merck) and further anti-checkpoint receptor antibodies or anti-checkpoint ligand antibodies as described above.

As used herein, the term "antibody" encompasses various forms of antibodies, preferably monoclonal antibodies, including but not being limited to whole antibodies, antibody fragments, human antibodies, chimeric antibodies, humanized antibodies and genetically engineered antibodies (variant or mutant antibodies) as long as the characteristic properties according to the invention are retained, which means that the antibody (or the antigen-binding fragment) modulates (e.g., totally or partially reduces, inhibits, interferes with, activates, stimulates, increases, reinforces or supports) the function of one or more checkpoint molecules as described above. In particular, the antibody (or the antigen-binding fragment) mediates this function by binding to a checkpoint molecule. Accordingly, the antibody (or the antigen-binding fragment) is preferably a "blocking" antibody (or the antigen-binding fragment), in particular an "antagonist" antibody (or the antigen-binding fragment), or an "agonist" antibody (or the antigen-binding fragment). In particular, the term "antibody" includes both, glycosylated and non-glycosylated immunoglobulins of any isotype or subclass (preferably lgG) or to an antigen-binding region thereof that competes with the intact antibody for specific binding, unless otherwise specified. Preferred examples of antibodies include monoclonal antibodies, bispecific antibodies, minibodies, domain antibodies, synthetic antibodies, antibody mimetics, chimeric antibodies, humanized antibodies, human antibodies, antibody fusions, antibody conjugates, single chain antibodies, antibody derivatives, antibody analogues and fragments thereof, respectively. Unless otherwise indicated, the term "antibody" includes, in addition to antibodies comprising two full-length heavy chains and two full-length light chains, derivatives, variants, and fragments thereof. In some instances an "antibody" may include fewer chains. Especially preferred are human or humanized monoclonal antibodies and/or recombinant antibodies, especially as recombinant human monoclonal antibodies. Particularly preferred are human IgG-type antibodies.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germline immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 3340). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole et al. and Boerner et al. are also available for the preparation of human monoclonal antibodies (Cole et al., Monoclonal Antibodies and Cancer Therapy, Alan R. Liss, p. 77 (1985); and Boerner, P., et al., J. Immunol. 147 (1991) 86-95). The term "human antibody" as used herein also comprises such antibodies which are modified, e.g. in the variable region to generate the properties according to the invention.

As used herein, the term "recombinant antibody" is intended to include all antibodies that are prepared, expressed, created or isolated by recombinant means, such as antibodies isolated from a host cell such as for example a CHO cell or from an animal (e.g. a mouse) that is transgenic for, e.g. human, immunoglobulin genes or antibodies expressed using a recombinant expression vector transfected into a host cell. Thus, recombinant antibodies are antibodies that are prepared, expressed, created or isolated by recombinant means, such as (i) antibodies isolated from an animal (e.g., a mouse) that is transgenic for human immunoglobulin genes or a hybridoma prepared therefrom, (ii) antibodies isolated from a host cell transfected to express the antibody, e.g., from a transfectoma, (iii) antibodies isolated from a recombinant, combinatorial antibody library, and (iv) antibodies prepared, expressed, created or isolated by any other means that involve splicing of immunoglobulin gene sequences to other DNA sequences. Such antibodies may have variable and constant regions derived from germline immunoglobulin sequences of two distinct species of animals. Antibodies subjected to in vitro mutagenesis (or, when an animal transgenic for human immunoglobulin sequences is used, in vivo somatic mutagenesis) are also preferred, while the amino acid sequences of the VH and Vu regions of such antibodies may be sequences that, while derived from and related to the germline VH and VL sequences of a particular species (e.g., human), may not naturally exist within that species' antibody germline repertoire in vivo. Recombinant antibodies may have variable and constant regions in a rearranged form and/or, for example, certain mutations, which do not occur in nature.

As used herein, the terms "antigen binding fragment," "fragment," and "antibody fragment" are used interchangeably to refer to any fragment of an antibody of the invention that retains the specific binding activity of the antibody according to the invention. Examples of antibody fragments include, but are not limited to, a single chain antibody, Fab, Fab', F(ab')$_2$, Fv or scFv. Fragments of the antibodies of the invention can be obtained from the antibodies by methods that include digestion with enzymes, such as pepsin or papain, and/or by cleavage of disulfide bonds by chemical reduction. Alternatively, fragments of antibodies can be obtained by cloning and expression of part of the sequences of the heavy and/or light chains. "Fragments" include, but are not limited to, Fab, Fab', F(ab')$_2$ and Fv fragments. The invention also encompasses single-chain Fv fragments (scFv) derived from the heavy and light chains of an antibody of the invention. For example, the invention includes a scFv comprising the CDRs from an antibody of the invention. Also included are heavy or light chain monomers and dimers, single domain heavy chain antibodies, single domain light chain antibodies, as well as single chain antibodies, e.g., single chain Fv in which the heavy and light chain variable domains are joined by a peptide linker. Antibody fragments of the invention may impart monovalent or multivalent interactions and be contained in a variety of structures as described above. For instance, scFv molecules may be synthesized to create a trivalent "triabody" or a tetravalent "tetrabody." The scFv molecules may include a domain of the Fc region resulting in bivalent minibodies. In addition, the sequences of the invention may be a component of multispecific molecules in which the sequences of the invention target the checkpoint molecule and other regions of the molecule bind to other targets. Exemplary molecules include, but are not limited to, bispecific Fab2, trispecific Fab3, bispecific scFv, and diabodies (Holliger and Hudson, 2005, Nature Biotechnology 9:1126-1136). Although the specification, including the claims, may, in some places, refer explicitly to antigen binding fragment(s), antibody fragment(s), variant(s) and/or derivative(s) of antibodies, it is understood that the term "antibody" or "antibody of the invention" includes all categories of antibodies, namely, antigen binding fragment(s), antibody fragment(s), variant(s) and derivative(s) of antibodies. Further, the term "antibody" as used herein includes both antibodies and antigen binding fragments thereof.

Preferably, the immune checkpoint modulators in the combination used according to the present invention are antibodies or antigen-binding fragments that can partially or totally block the PD-1 pathway (e.g., they can be partial or full antagonists of the PD-1 pathway), in particular PD-1, PD-L1 or PD-L2, more preferably, the antibody can partially or totally block PD-1 (e.g., they can be partial or full antagonists of PD-1). Such antibodies or antigen-binding fragments include anti-PD-1 antibodies, human anti-PD-1 antibodies, mouse anti-PD-1 antibodies, mammalian anti-PD-1 antibodies, humanized anti-PD-1 antibodies, monoclonal anti-PD-1 antibodies, polyclonal anti-PD-1 antibodies, chimeric anti-PD-1 antibodies, anti-PD-L1 antibodies, anti-PD-L2 antibodies, anti-PD-1 adnectins, anti-PD-1 domain antibodies, single chain anti-PD-1 fragments, heavy chain anti-PD-1 fragments, and light chain anti-PD-1 fragments. For example, the anti-PD-1 antibody may be an antigen-binding fragment. Preferably, the anti-PD-1 antibody is able to bind to human PD-1 and to partially or totally block the activity of PD-1 (e.g., they can be partial or full antagonists of PD-1), thereby in particular unleashing the function of immune cells expressing PD-1.

Preferably, the immune checkpoint modulators in the combination used according to the present invention are antibodies or antigen-binding fragments that can partially or totally block the CTLA-4 pathway (e.g., they can be partial or full antagonists of the CTLA-4 pathway). Such antibodies or antigen-binding fragments include anti-CTLA4 antibodies, human anti-CTLA4 antibodies, mouse anti-CTLA4 antibodies, mammalian anti-CTLA4 antibodies, humanized anti-CTLA4 antibodies, monoclonal anti-CTLA4 antibodies, polyclonal anti-CTLA4 antibodies, chimeric anti-CTLA4 antibodies, MDX-010 (ipilimumab), tremelimumab, anti-CD28 antibodies, anti-CTLA4 adnectins, anti-CTLA4 domain antibodies, single chain anti-CTLA4 fragments, heavy chain anti-CTLA4 fragments, and light chain anti-CTLA4 fragments. For example, the anti-CTLA4 antibody may be an antigen-binding fragment. Preferably, the anti-CTLA4 antibody is able to bind to human CTLA4 and to partially or totally block the activity of CTLA4 (e.g., they can be partial or full antagonists of CTLA-4), thereby in particular unleashing the function of immune cells expressing CTLA4.

Complex Comprising a Cell Penetrating Peptide, at Least One Antigen or Antigenic Epitope In addition to the immune checkpoint modulator described above, the combination for use according to the present invention comprises a complex comprising:
 a) a cell penetrating peptide;
 b) at least one antigen or antigenic epitope; and
 c) at least one TLR peptide agonist,
wherein the components a)-c), i.e. the cell penetrating peptide, the at least one antigen or antigenic epitope and the at least one TLR peptide agonist, are covalently linked. In the following, it is also referred to such a complex comprising a cell penetrating peptide, at least one antigen or antigenic epitope and at least one TLR peptide agonist, which are covalently linked, by using the term "the complex" or "the complex comprised by the combination for use according to the present invention".

Such a complex comprised by the combination for use according to the present invention provides simultaneous (i) stimulation of multi-epitopic cytotoxic T cell-mediated immunity, (ii) induction of $T_h$ cells and (iii) promotion of immunological memory. Thereby, a complex comprised by the combination for use according to the present invention provides a potent vaccine, in particular having improved anti-tumor activity.

Preferably, the complex comprised by the combination for use according to the present invention is a polypeptide or a protein, in particular a recombinant polypeptide or a recombinant protein, preferably a recombinant fusion protein or a recombinant fusion polypeptide. The term "recombinant" as used herein (i.e. throughout the specification) means that it (here: the polypeptide or the protein) does not occur naturally. Accordingly, the complex comprised by the combination for use according to the present invention, which is a recombinant polypeptide or a recombinant protein, typically comprises components a) to c), wherein components a) to c) are of different origins, i.e. do not naturally occur in this combination.

In the context of the present invention, i.e. throughout the present application, the terms "peptide", "polypeptide", "protein" and variations of these terms refer to peptide, oligopeptide, oligomer or protein including fusion protein, respectively, comprising at least two amino acids joined to each other, preferably by a normal peptide bond, or, alternatively, by a modified peptide bond, such as for example in the cases of isosteric peptides. A peptide, polypeptide or protein can be composed of L-amino acids and/or D-amino acids. Preferably, a peptide, polypeptide or protein is either (entirely) composed of L-amino acids or (entirely) of D-amino acids, thereby forming "retro-inverso peptide sequences". The term "retro-inverso (peptide) sequences" refers to an isomer of a linear peptide sequence in which the direction of the sequence is reversed and the chirality of each amino acid residue is inverted (see e.g. Jameson et al., Nature, 368,744-746 (1994); Brady et al., Nature, 368,692-693 (1994)). In particular, the terms "peptide", "polypeptide", "protein also include "peptidomimetics" which are defined as peptide analogs containing non-peptidic structural elements, which peptides are capable of mimicking or antagonizing the biological action(s) of a natural parent peptide. A peptidomimetic lacks classical peptide characteristics such as enzymatically scissile peptide bonds. In particular, a peptide, polypeptide or protein can comprise amino acids other than the 20 amino acids defined by the genetic code in addition to these amino acids, or it can be composed of amino acids other than the 20 amino acids defined by the genetic code. In particular, a peptide, polypeptide or protein in the context of the present invention can equally be composed of amino acids modified by natural processes, such as post-translational maturation processes or by chemical processes, which are well known to a person skilled in the art. Such modifications are fully detailed in the literature. These modifications can appear anywhere in the polypeptide: in the peptide skeleton, in the amino acid chain or even at the carboxy- or amino-terminal ends. In particular, a peptide or polypeptide can be branched following an ubiquitination or be cyclic with or without branching. This type of modification can be the result of natural or synthetic post-translational processes that are well known to a person skilled in the art. The terms "peptide", "polypeptide", "protein" in the context of the present invention in particular also include modified peptides, polypeptides and proteins. For example, peptide, polypeptide or protein modifications can include acetylation, acylation, ADP-ribosylation, amidation, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, glycosylation including pegylation, hydroxylation, iodization, methylation, myristoylation, oxidation, proteolytic processes, phosphorylation, prenylation, racemization, seneloylation, sulfatation, amino acid addition such as arginylation or ubiquitination. Such modifications are fully detailed in the literature (Proteins Structure and Molecular Properties (1993) 2nd Ed., T. E. Creighton, New York; Post-translational Covalent Modifications of Proteins (1983) B. C. Johnson, Ed., Academic Press, New York; Seifter et al. (1990) Analysis for protein modifications and nonprotein cofactors, Meth. Enzymol. 182:626-646 and Rattan et al., (1992) Protein Synthesis: Post-translational Modifications and Aging, Ann NY Acad Sci, 663:48-62). Accordingly, the terms "peptide", "polypeptide", "protein" preferably include for example lipopeptides, lipoproteins, glycopeptides, glycoproteins and the like.

However, in a particularly preferred embodiment, the complex as described herein is a "classical" peptide, polypeptide or protein, whereby a "classical" peptide, polypeptide or protein is typically composed of amino acids selected from the 20 amino acids defined by the genetic code, linked to each other by a normal peptide bond.

If the complex comprised by the combination for use according to the present invention is a polypeptide or a protein, it is preferred that it comprises at least 50, at least 60, at least 70, preferably at least 80, at least 90, more preferably at least 100, at least 110, even more preferably at least 120, at least 130, particularly preferably at least 140, or most preferably at least 150 amino acid residues.

Component a)—Cell Penetrating Peptide

The CPP allows for efficient delivery, i.e. transport and loading, in particular of at least one antigen or antigenic epitope, into the antigen presenting cells (APCs), in particular into the dendritic cells (DCs) and thus to the dendritic cells' antigen processing machinery.

The term "cell penetrating peptides" ("CPPs") is generally used to designate short peptides that are able to transport different types of cargo molecules across plasma membrane, and, thus, facilitate cellular uptake of various molecular cargoes (from nanosize particles to small chemical molecules and large fragments of DNA). "Cellular internalization" of the cargo molecule linked to the cell penetrating peptide generally means transport of the cargo molecule across the plasma membrane and thus entry of the cargo molecule into the cell. Depending on the particular case, the cargo molecule can, then, be released in the cytoplasm, directed to an intracellular organelle, or further presented at the cell surface. Cell penetrating ability, or internalization, of the cell penetrating peptide or of the complex (comprising said cell penetrating peptide) comprised by the combination for use according to the invention can be checked by standard methods known to one skilled in the art, including flow cytometry or fluorescence microscopy of live and fixed cells, immunocytochemistry of cells transduced with said peptide or complex, and Western blot.

Cell penetrating peptides typically have an amino acid composition that either contains a high relative abundance of positively charged amino acids such as lysine or arginine or have a sequence that contains an alternating pattern of polar/charged amino acids and non-polar, hydrophobic amino acids. These two types of structures are referred to as polycationic or amphipathic, respectively. Cell-Penetrating peptides are of different sizes, amino acid sequences, and charges but all CPPs have a common characteristic that is the ability to translocate the plasma membrane and facilitate the delivery of various molecular cargoes to the cytoplasm or to an organelle of a cell. At present, the theories of CPP translocation distinguish three main entry mechanisms: direct penetration in the membrane, endocytosis-mediated entry, and translocation through the formation of a transitory structure. CPP transduction is an area of ongoing research. Cell-penetrating peptides have found numerous applications in medicine as drug delivery agents in the treatment of different diseases including cancer and virus inhibitors, as well as contrast agents for cell labeling and imaging.

Typically, cell penetrating peptides (CPPs) are peptides of 8 to 50 residues that have the ability to cross the cell membrane and enter into most cell types. Alternatively, they are also called protein transduction domain (PTDs) reflecting their origin as occurring in natural proteins. Frankel and Pabo simultaneously to Green and Lowenstein described the ability of the trans-activating transcriptional activator from the human immunodeficiency virus 1 (HIV-TAT) to penetrate into cells (Frankel, A. D. and C. O. Pabo, Cellular uptake of the tat protein from human immunodeficiency virus. Cell, 1988. 55 (6): p. 1189-93). In 1991, transduction into neural cells of the Antennapedia homeodomain (DNA-binding domain) from *Drosophila melanogaster* was described (Joliot, A., et al., Antennapedia homeobox peptide regulates neural morphogenesis. Proc Natl Acad Sci USA, 1991. 88 (5): p. 1864-8).

In 1994, the first 16-mer peptide CPP called Penetratin, having the amino acid sequence RQIKIYFQNRRMKWKK (SEQ ID NO: 1) was characterized from the third helix of the homeodomain of Antennapedia (Derossi, D., et al., The third helix of the Antennapedia homeodomain translocates through biological membranes. J Biol Chem, 1994. 269 (14): p. 10444-50), followed in 1998 by the identification of the minimal domain of TAT, having the amino acid sequence YGRKKRRQRRR (SEQ ID NO: 2) required for protein transduction (Vives, E., P. Brodin, and B. Lebleu, A truncated HIV-1 Tat protein basic domain rapidly translocates through the plasma membrane and accumulates in the cell nucleus. J Biol Chem, 1997. 272 (25): p. 16010-7). Over the past two decades, dozens of peptides were described from different origins including viral proteins, e.g. VP22 (Elliott, G. and P. O'Hare, Intercellular trafficking and protein delivery by a herpesvirus structural protein. Cell, 1997. 88 (2): p. 223-33) and ZEBRA (Rothe, R., et al., Characterization of the cell-penetrating properties of the Epstein-Barr virus ZEBRA trans-activator. J Biol Chem, 2010. 285 (26): p. 20224-33), or from venoms, e.g. melittin (Dempsey, C. E., The actions of melittin on membranes. Biochim Biophys Acta, 1990. 1031 (2): p. 143-61), mastoporan (Konno, K., et al., Structure and biological activities of eumenine mastoparan-AF (EMP-AF), a new mast cell degranulating peptide in the venom of the solitary wasp (Anterhynchium flavomarginatum micado). Toxicon, 2000. 38 (11): p. 1505-15), maurocalcin (Esteve, E., et al., Transduction of the scorpion toxin maurocalcine into cells. Evidence that the toxin crosses the plasma membrane. J Biol Chem, 2005. 280 (13): p. 12833-9), crotamine (Nascimento, F. D., et al., Crotamine mediates gene delivery into cells through the binding to heparan sulfate proteoglycans. J Biol Chem, 2007. 282 (29): p. 21349-60) or buforin (Kobayashi, S., et al., Membrane translocation mechanism of the antimicrobial peptide buforin 2. Biochemistry, 2004. 43 (49): p. 15610-6). Synthetic CPPs were also designed including the polyarginine (R8, R9, R10 and R12) (Futaki, S., et al., Arginine-rich peptides. An abundant source of membrane-permeable peptides having potential as carriers for intracellular protein delivery. J Biol Chem, 2001. 276 (8): p. 5836-40) or transportan (Pooga, M., et al., Cell penetration by transportan. FASEB J, 1998. 12 (1): p. 67-77). Any of the above described CPPs may be used as cell penetrating peptide, i.e. as component a), in the complex comprised by the combination for use according to the present invention. In particular, the component a), i.e. the CPP, in the complex comprised by the combination for use according to the present invention may comprise the minimal domain of TAT, having the amino acid sequence YGRKKRRORRR (SEQ ID NO: 2). In particular, the component a), i.e. the CPP, in the complex comprised by the combination for use according to the present invention may comprise Penetratin having the amino acid sequence RQIKIYFQNRRMKWKK (SEQ ID NO: 1).

Various CPPs, which can be used as cell penetrating peptide, i.e. as component a), in the complex comprised by the composition for use according to the present invention, are also disclosed in the review: Milletti, F., Cell-penetrating peptides: classes, origin, and current landscape. Drug Discov Today 17 (15-16): 850-60, 2012. In other words, the CPPs disclosed in Milletti, F., 2012, Cell-penetrating peptides: classes, origin, and current landscape. Drug Discov Today 17 (15-16): 850-60 can be used as cell penetrating peptide, i.e. as component a), in the complex comprised by the combination for use according to the present invention. This includes in particular cationic CPPs, amphipatic CPPs, and hydrophobic CPPs as well as CPPs derived from heparan-, RNA- and DNA-binding proteins (cf. Table 1 of Milletti, F., Cell-penetrating peptides: classes, origin, and current landscape. Drug Discov Today 17 (15-16): 850-60, 2012), CPPs derived from signal peptides (cf. Table 2 of Milletti, F., Cell-penetrating peptides: classes, origin, and current landscape. Drug Discov Today 17 (15-16): 850-60, 2012), CPPs derived from antimicrobial peptides (cf. Table 3 of Milletti, F., Cell-penetrating peptides: classes, origin, and current landscape. Drug Discov Today 17 (15-16): 850-60, 2012), CPPs derived from viral proteins (cf. Table 4 of Milletti, F., Cell-penetrating peptides: classes, origin, and current landscape. Drug Discov Today 17 (15-16): 850-60, 2012), CPPs derived from various natural proteins (cf. Table 5 of Milletti, F., Cell-penetrating peptides: classes, origin, and current landscape. Drug Discov Today 17 (15-16): 850-60, 2012), and Designed CPPs and CPPs derived from peptide libraries (cf. Table 6 of Milletti, F., Cell-penetrating peptides: classes, origin, and current landscape. Drug Discov Today 17 (15-16): 850-60, 2012).

Preferably, the cell penetrating peptide, which is comprised by the complex,
i) has a length of the amino acid sequence of said peptide of 5 to 50 amino acids in total, preferably of 10 to 45 amino acids in total, more preferably of 15 to 45 amino acids in total; and/or ii) has an amino acid sequence comprising a fragment of the minimal domain of ZEBRA, said minimal domain extending from residue 170 to residue 220 of the ZEBRA amino acid sequence according to SEQ ID NO: 3, wherein, optionally, 1, 2, 3, 4, or 5 amino acids have been substituted, deleted, and/or added without abrogating said peptide's cell penetrating ability, or a sequence variant of such a fragment.

Thereby, it is preferred that the cell penetrating peptide, which is comprised by the complex i) has a length of the amino acid sequence of said peptide of 5 to 50 amino acids in total, preferably of 10 to 45 amino acids in total, more preferably of 15 to 45 amino acids in total; and ii) has an amino acid sequence comprising a fragment of the minimal domain of ZEBRA, said minimal domain extending from residue 170 to residue 220 of the ZEBRA amino acid sequence according to SEQ ID NO: 3, wherein, optionally, 1, 2, 3, 4, or 5 amino acids have been substituted, deleted, and/or added without abrogating said peptide's cell penetrating ability, or a sequence variant of such a fragment.

Such preferred CPPs are disclosed in WO 2014/041505.

The term "ZEBRA" (also known as Zta, Z, EB1, or BZLF1) generally means the basic-leucine zipper (bZIP) transcriptional activator of the Epstein-Barr virus (EBV). The minimal domain of ZEBRA, which exhibits cell penetrating properties, has been identified as spanning from residue 170 to residue 220 of ZEBRA. The amino acid sequence of ZEBRA is disclosed under NCBI accession number YP_401673 and comprises 245 amino acids represented in SEQ ID NO: 3:

```
MMDPNSTSEDVKFTPDPYQVPFVQAFDQATRVYQDLGGPSQAPLPCVLWP

VLPEPLPQGQLTAYHVSTAPTGSWFSAPQPAPENAYQAYAAPQLFPVSDI
```

-continued

```
TQNQQTNQAGGEAPQPGDNSTVQTAAAVVFACPGANQGQQLADIGVPQPA

PVAAPARRTRKPQQPESLEECDSELEIKRYKNRVASRKCRAKFKQLLQHY

REVAAAKSSENDRLRLLLKQMCPSLDVDSIIPRTPDVLHEDLLNF
(SEQ ID NO: 3-ZEBRA amino acid sequence (natural
sequence from Epstein-Barr virus (EBV))
(YP_401673))
```

Recently, a CPP derived from the viral protein ZEBRA was described to transduce protein cargoes across biological membranes by both (i) direct translocation and (ii) lipid raft-mediated endocytosis (Rothe R, Liguori L, Villegas-Mendez A, Marques B, Grunwald D, Drouet E, et al. Characterization of the cell-penetrating properties of the Epstein-Barr virus ZEBRA trans-activator. The Journal of biological chemistry 2010; 285 (26): 20224-33). The present inventors assume that these two mechanisms of entry should promote both MHC class I and II restricted presentation of cargo antigens to CD8+ and CD4+ T cells, respectively. Accordingly, such a CPP can deliver multi-epitopic peptides to dendritic cells (DCS), and subsequently to promote CTL and Th cell activation and anti-tumor function. Such a CPP can thus efficiently deliver the complex comprised by the combination for use according to the present invention to antigen presenting cells (APCs) and lead to multi-epitopic MHC class I and II restricted presentation.

In the context of the present invention, the term "MHC class I" designates one of the two primary classes of the Major Histocompatibility Complex molecules. The MHC class I (also noted "MHC I") molecules are found on every nucleated cell of the body. The function of MHC class I is to display an epitope to cytotoxic cells (CTLs). In humans, MHC class I molecules consist of two polypeptide chains, α- and β2-microglobulin (b2m). Only the α chain is polymorphic and encoded by a HLA gene, while the b2m subunit is not polymorphic and encoded by the Beta-2 microglobulin gene. In the context of the present invention, the term "MHC class II" designates the other primary class of the Major Histocompatibility Complex molecules. The MHC class II (also noted "MHC II") molecules are found only on a few specialized cell types, including macrophages, dendritic cells and B cells, all of which are dedicated antigen-presenting cells (APCs).

Preferably, the sequence variant of a fragment of the minimal domain of ZEBRA as described above shares, in particular over the whole length, at least 70%, at least 75%, preferably at least 80%, more preferably at least 85%, even more preferably at least 90%, particularly preferably at least 95%, most preferably at least 99% amino acid sequence identity with the fragment of the minimal domain of ZEBRA as described above without abrogating the cell penetrating ability of the cell penetrating peptide. In particular, a "fragment" of the minimal domain of ZEBRA as defined above is preferably to be understood as a truncated sequence thereof, i.e. an amino acid sequence, which is N-terminally, C-terminally and/or intrasequentially truncated compared to the amino acid sequence of the native sequence. Moreover, such a "fragment" of the minimal domain of ZEBRA has preferably a length of 5 to 50 amino acids in total, preferably of 10 to 45 amino acids in total, more preferably of 15 to 45 amino acids in total.

Accordingly, the term "sequence variant" as used in the context of the present invention, i.e. throughout the present application, refers to any alteration in a reference sequence. The term "sequence variant" includes nucleotide sequence variants and amino acid sequence variants. Preferably, a reference sequence is any of the sequences listed in the "Table of Sequences and SEQ ID Numbers" (Sequence listing), i.e. SEQ ID NO: 1 to SEQ ID NO: 47. Preferably, a sequence variant shares, in particular over the whole length of the sequence, at least 70%, at least 75%, preferably at least 80%, more preferably at least 85%, even more preferably at least 90%, particularly preferably at least 95%, most preferably at least 99% sequence identity with a reference sequence, whereby sequence identity is calculated as described below. In particular, a sequence variant preserves the specific function of the reference sequence. Sequence identity is calculated as described below. In particular, an amino acid sequence variant has an altered sequence in which one or more of the amino acids in the reference sequence is deleted or substituted, or one or more amino acids are inserted into the sequence of the reference amino acid sequence. As a result of the alterations, the amino acid sequence variant has an amino acid sequence which is at least 70%, at least 75%, preferably at least 80%, more preferably at least 85%, even more preferably at least 90%, particularly preferably at least 95%, most preferably at least 99% identical to the reference sequence. For example, variant sequences which are at least 90% identical have no more than 10 alterations, i.e. any combination of deletions, insertions or substitutions, per 100 amino acids of the reference sequence.

In the context of the present invention, an amino acid sequence "sharing a sequence identity" of at least, for example, 95% to a query amino acid sequence of the present invention, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted, preferably within the above definitions of variants or fragments. The same, of course, also applies similarly to nucleic acid sequences.

For (amino acid or nucleic acid) sequences without exact correspondence, a "% identity" of a first sequence may be determined with respect to a second sequence. In general, these two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length.

Methods for comparing the identity and homology of two or more sequences are well known in the art. The percentage to which two sequences are identical can e.g. be determined using a mathematical algorithm. A preferred, but not limiting, example of a mathematical algorithm which can be used is the algorithm of Karlin et al. (1993), PNAS USA, 90:5873-5877. Such an algorithm is integrated in the BLAST family of programs, e.g. BLAST or NBLAST program (see also Altschul et al., 1990, J. Mol. Biol. 215, 403-410 or Altschul et al. (1997), Nucleic Acids Res, 25:3389-3402), accessible through the home page of the NCBI at world wide web site ncbi.nlm.nih.gov) and FASTA (Pearson (1990), Methods Enzymol. 183, 63-98; Pearson and Lipman (1988), Proc. Natl. Acad. Sci. U.S.A 85, 2444-2448). Sequences which are identical to other sequences to a certain extent can be identified by these programmes. Furthermore, programs available in the Wisconsin Sequence Analysis Package, version 9.1 (Devereux et al., 1984, Nucleic Acids Res., 387-395), for example the programs BESTFIT and GAP, may be used to determine the % identity between two polynucleotides and the % identity and the % homology or identity between two polypeptide sequences. BESTFIT uses the "local homology" algorithm of (Smith and Waterman (1981), J. Mol. Biol. 147, 195-197) and finds the best single region of similarity between two sequences.

More preferably, the fragments of the cell penetrating peptide or the variants thereof as described above further retain said peptide's ability to present a cargo molecule such as antigens or antigenic epitopes at the surface of a cell, such as an antigen-presenting cell, in the context of MHC class I and/or MHC class II molecules. The ability of a cell penetrating peptide or complex comprising said cell penetrating peptide to present a cargo molecule such as antigens or antigenic epitopes at the surface of a cell in the context of MHC class I and/or MHC class II molecules can be checked by standard methods known to one skilled in the art, including capacity to stimulate proliferation and/or function of MHC-restricted $CD4^+$ or $CD8^+$ T cells with specificity for these epitopes.

The preferred cell penetrating peptide, which
i) has a length of the amino acid sequence of said peptide of 5 to 50 amino acids in total, preferably of 10 to 45 amino acids in total, more preferably of 15 to 45 amino acids in total; and/or
ii) has an amino acid sequence comprising a fragment of the minimal domain of ZEBRA, said minimal domain extending from residue 170 to residue 220 of the ZEBRA amino acid sequence according to SEQ ID NO: 3, wherein, optionally, 1, 2, 3, 4, or 5 amino acids have been substituted, deleted, and/or added without abrogating said peptide's cell penetrating ability, or a variant of such a fragment preferably comprises an amino acid sequence having at least one conservatively substituted amino acid compared to the referenced sequence, meaning that a given amino acid residue is replaced by a residue having similar physiochemical characteristics.

Generally, substitutions for one or more amino acids present in the referenced amino acid sequence should be made conservatively. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity properties, are well known (Kyte and Doolittle, 1982, J. Mol. Biol. 157 (1): 105-132). Substitutions of one or more L-amino acids with one or more D-amino acids are to be considered as conservative substitutions in the context of the present invention. Exemplary amino acid substitutions are presented in Table 1 below:

TABLE 1

| Original residues | Examples of substitutions |
|---|---|
| Ala (A) | Val, Leu, Ile, Gly |
| Arg (R) | His, Lys |
| Asn (N) | Gln |

TABLE 1-continued

| Original residues | Examples of substitutions |
|---|---|
| Asp (D) | Glu |
| Cys (C) | Ser |
| Gln (Q) | Asn |
| Glu (E) | Asp |
| Gly (G) | Pro, Ala |
| His (H) | Lys, Arg |
| Ile (I) | Leu, Val, Met, Ala, Phe |
| Leu (L) | Ile, Val, Met, Ala, Phe |
| Lys (K) | Arg, His |
| Met (M) | Leu, Ile, Phe |
| Phe (F) | Leu, Val, Ile, Tyr, Trp, Met |
| Pro (P) | Ala, Gly |
| Ser (S) | Thr |
| Thr (T) | Ser |
| Trp (W) | Tyr, Phe |
| Tyr (Y) | Trp, Phe |
| Val (V) | Ile, Met, Leu, Phe, Ala |

Particularly preferably, the preferred cell penetrating peptide, which
  i) has a length of the amino acid sequence of said peptide of 5 to 50 amino acids in total, preferably of 10 to 45 amino acids in total, more preferably of 15 to 45 amino acids in total; and/or
  ii) has an amino acid sequence comprising a fragment of the minimal domain of ZEBRA, said minimal domain extending from residue 170 to residue 220 of the ZEBRA amino acid sequence according to SEQ ID NO: 3, wherein, optionally, 1, 2, 3, 4, or 5 amino acids have been substituted, deleted, and/or added without abrogating said peptide's cell penetrating ability, or a variant of such a fragment comprises a Cys (C) substituted into a Ser(S), at the equivalent of position 189 relative to ZEBRA amino acid sequence of SEQ ID NO: 3.

Thereby, it is preferred that such a preferred cell penetrating peptide has an amino acid sequence comprising a sequence according to the following general formula (I):

$$X_1X_2X_3X_4X_5X_6X_7X_8X_9X_{10}X_{11}SX_{13}X_{14}X_{15}X_{16}X_{17}$$

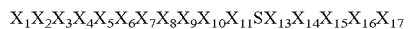

with 0, 1, 2, 3, 4, or 5 amino acids which are substituted, deleted, and/or added without abrogating said peptide's cell penetrating ability, wherein
  $X_1$ is K, R, or H, preferably $X_1$ is K or R;
  $X_2$ is R, K, or H, preferably $X_2$ is R or K;
  $X_3$ is Y, W, or F, preferably $X_3$ is Y, W, or F;
  $X_4$ is K, R, or H, preferably $X_4$ is K or R;
  $X_5$ is N or Q;
  $X_6$ is R, K, or H, preferably $X_6$ is R or K;
  $X_7$ is V, I, M, L, F, or A, preferably $X_7$ is V, I, M or L;
  $X_8$ is A, V, L, I, or G, preferably $X_8$ is A or G;
  $X_9$ is S or T;
  $X_{10}$ is R, K, or H, preferably $X_{10}$ is R or K;
  $X_{11}$ is K, R, or H, preferably $X_{11}$ is K or R;
  $X_{13}$ is R, K, or H, preferably $X_{13}$ is R or K;
  $X_{14}$ is A, V, L, I, or G, preferably $X_{14}$ is A or G;
  $X_{15}$ is K, R, or H, preferably $X_{15}$ is K or R;
  $X_{16}$ is F, L, V, I, Y, W, or M, preferably $X_{16}$ is F, Y or W; and
  $X_{17}$ is K, R, or H, preferably $X_{17}$ is K or R.

Preferably, such a peptide, polypeptide or protein is either (entirely) composed of L-amino acids or (entirely) of D-amino acids, thereby forming "retro-inverso peptide sequences". The term "retro-inverso (peptide) sequences" refers to an isomer of a linear peptide sequence in which the direction of the sequence is reversed and the chirality of each amino acid residue is inverted (see e.g. Jameson et al., Nature, 368,744-746 (1994); Brady et al., Nature, 368,692-693 (1994)).

In a particular embodiment, the cell penetrating peptide is as generically defined above by general formula (I), wherein $X_1$ is K.

In a particular embodiment, the cell penetrating peptide is as generically defined above by general formula (I), wherein $X_2$ is R.

In a particular embodiment, the cell penetrating peptide is as generically defined above by general formula (I), wherein $X_3$ is Y.

In a particular embodiment, the cell penetrating peptide is as generically defined above by general formula (I), wherein $X_4$ is K.

In a particular embodiment, the cell penetrating peptide is as generically defined above by general formula (I), wherein $X_5$ is N.

In a particular embodiment, the cell penetrating peptide is as generically defined above by general formula (I), wherein $X_6$ is R.

In a particular embodiment, the cell penetrating peptide is as generically defined above by general formula (I), wherein $X_7$ is V.

In a particular embodiment, the cell penetrating peptide is as generically defined above by general formula (I), wherein $X_8$ is A.

In a particular embodiment, the cell penetrating peptide is as generically defined above by general formula (I), wherein $X_9$ is S.

In a particular embodiment, the cell penetrating peptide is as generically defined above by general formula (I), wherein $X_{10}$ is R.

In a particular embodiment, the cell penetrating peptide is as generically defined above by general formula (I), wherein $X_{11}$ is K.

In a particular embodiment, the cell penetrating peptide is as generically defined above by general formula (I), wherein $X_{13}$ is R.

In a particular embodiment, the cell penetrating peptide is as generically defined above by general formula (I), wherein $X_{14}$ is A.

In a particular embodiment, the cell penetrating peptide is as generically defined above by general formula (I), wherein $X_{15}$ is K.

In a particular embodiment, the cell penetrating peptide is as generically defined above by general formula (I), wherein $X_{16}$ is F.

In a particular embodiment, the cell penetrating peptide is as generically defined above by general formula (I), wherein $X_{17}$ is K.

In a particular embodiment, the cell penetrating peptide is as generically defined above by general formula (I), wherein the amino acid at position equivalent to position 12 relative to general formula (I) is a Ser(S).

It is also particularly preferred, that the preferred cell penetrating peptide, which
  i) has a length of the amino acid sequence of said peptide of 5 to 50 amino acids in total, preferably of 10 to 45 amino acids in total, more preferably of 15 to 45 amino acids in total; and/or
  ii) has an amino acid sequence comprising a fragment of the minimal domain of ZEBRA, said minimal domain extending from residue 170 to residue 220 of the ZEBRA amino acid sequence according to SEQ ID NO: 3, wherein, optionally, 1, 2, 3, 4, or 5 amino acids have been substituted, deleted, and/or added without abrogating said peptide's cell penetrating ability, or a variant of such a fragment comprises or consists of an amino acid sequence selected from the group consisting of amino acid sequences according to SEQ ID NO: 4-13, or sequence variants thereof without abrogating said peptide's cell penetrating ability, preferably sequence variants having 0, 1, 2, 3, 4, or 5 amino acids substituted, deleted and/or added without abrogating said peptide's cell penetrating ability.

```
CPP1 (Z11):
                                        (SEQ ID NO: 4)
KRYKNRVASRKCRAKFKQLLQHYREVAAAKSSENDRLRLLLKQMC

CPP2 (Z12):
                                        (SEQ ID NO: 5)
KRYKNRVASRKCRAKFKQLLQHYREVAAAKSSENDRLRLLLK

CPP3 (Z13):
                                        (SEQ ID NO: 6)
KRYKNRVASRKSRAKFKQLLQHYREVAAAKSSENDRLRLLLK

CPP4 (Z14):
                                        (SEQ ID NO: 7)
KRYKNRVASRKSRAKFKQLLQHYREVAAAK

CPP5 (Z15):
                                        (SEQ ID NO: 8)
KRYKNRVASRKSRAKFK

CPP6 (Z16):
                                        (SEQ ID NO: 9)
QHYREVAAAKSSEND

CPP7 (Z17):
                                        (SEQ ID NO: 10)
QLLQHYREVAAAK

CPP8 (Z18):
                                        (SEQ ID NO: 11)
REVAAAKSS END RLRLLLK

CPP9 (Z19):
                                        (SEQ ID NO: 12)
KRYKNRVA

CPP10 (Z20):
                                        (SEQ ID NO: 13)
VASRKSRAKFK
```

Thereby, a cell penetrating peptide is particularly preferred, which has an amino acid sequence comprising or consisting of an amino acid sequence according to SEQ ID NO: 6 (CPP3/Z13), SEQ ID NO: 7 (CPP4/Z14), SEQ ID NO: 8 (CPP5/Z15), or SEQ ID NO: 11 (CPP8/Z18), or sequence variants thereof without abrogating said peptide's cell penetrating ability, preferably sequence variants having 0, 1, 2, 3, 4, or 5 amino acids substituted, deleted and/or added without abrogating said peptide's cell penetrating ability. Moreover, a cell penetrating peptide is more preferred, which has an amino acid sequence comprising or consisting of an amino acid sequence according to SEQ ID NO: 6 (CPP3/Z13) or SEQ ID NO: 7 (CPP4/Z14) or sequence variants thereof without abrogating said peptide's cell penetrating ability, preferably sequence variants having 0, 1, 2, 3, 4, or 5 amino acids substituted, deleted and/or added without abrogating said peptide's cell penetrating ability. Moreover, a cell penetrating peptide is most preferred, which has an amino acid sequence comprising or consisting of an amino acid sequence according to SEQ ID NO: 6 (CPP3/Z13) or sequence variants thereof without abrogating said peptide's cell penetrating ability, preferably sequence variants having 0, 1, 2, 3, 4, or 5 amino acids substituted, deleted and/or added without abrogating said peptide's cell penetrating ability.

In one preferred embodiment, the cell penetrating peptide according to the invention has an amino acid sequence comprising or consisting of SEQ ID NO: 6 (CPP3/Z13).

In another preferred embodiment, the cell penetrating peptide according to the invention has an amino acid sequence comprising or consisting of SEQ ID NO: 7 (CPP4/Z14).

In another preferred embodiment, the cell penetrating peptide according to the invention has an amino acid sequence comprising or consisting of SEQ ID NO: 8 (CPP5/Z15).

In another preferred embodiment, the cell penetrating peptide according to the invention has an amino acid sequence comprising or consisting of SEQ ID NO: 11 (CPP8/Z18).

It will be understood by one skilled in the art that the primary amino acid sequence of the cell penetrating peptide may further be post-translationally modified, such as by glycosylation or phosphorylation, without departing from the invention.

In a further embodiment, the cell penetrating peptide optionally further comprises, in addition to its amino acid sequence as described above, any one of, or any combination of:

(i) a nuclear localization signal (NLS). Such signals are well known to the skilled person and are described in Nair et al. (2003, *Nucleic Acids Res.* 31 (1): 397-399)

(ii) a targeting peptide, including tumor homing peptides such as those described in Kapoor et al. (2012, *PLOS listed in ONE* 7 (4): e35187) and crdd.osdd.net/raghava/tumorhope/general.php?

Preferably, the cell penetrating peptide is linked to an antigen or antigenic epitope and facilitates the cellular internalization of said antigen or antigenic epitope.

The complex comprised by the combination for use according to the present invention may comprise one single cell penetrating peptide or more than one cell penetrating peptides. Preferably, the complex comprised by the combination for use according to the present invention comprises no more than five cell penetrating peptides, more preferably the complex comprised by the combination for use according to the present invention comprises no more than four cell penetrating peptides, even more preferably the complex comprised by the combination for use according to the present invention comprises no more than three cell penetrating peptides, particularly preferably the complex comprised by the combination for use according to the present invention comprises no more than two cell penetrating peptides and most preferably the complex comprised by the combination for use according to the present invention comprises one single cell penetrating peptide.

Component b)—Antigen/Antigenic Epitope

The complex comprised by the combination for use according to the present invention comprises as component b) at least one antigen or antigenic epitope.

As used herein, an "antigen" is any structural substance which serves as a target for the receptors of an adaptive immune response, in particular as a target for antibodies, T cell receptors, and/or B cell receptors. An "epitope", also known as "antigenic determinant", is the part (or fragment) of an antigen that is recognized by the immune system, in particular by antibodies, T cell receptors, and/or B cell receptors. Thus, one antigen has at least one epitope, i.e. a single antigen has one or more epitopes. In the context of the present invention, the term "epitope" is mainly used to designate T cell epitopes, which are presented on the surface of an antigen-presenting cell, where they are bound to Major Histocompatibility Complex (MHC). T cell epitopes presented by MHC class I molecules are typically, but not exclusively, peptides between 8 and 11 amino acids in length, whereas MHC class II molecules present longer peptides, generally, but not exclusively, between 12 and 25 amino acids in length.

Preferably, in the complex comprised by the combination for use according to the present invention, the at least one antigen or antigenic epitope is selected from the group consisting of: (i) a peptide, a polypeptide, or a protein, (ii) a polysaccharide, (iii) a lipid, (iv) a lipoprotein or a lipopeptide, (v) a glycolipid, (vi) a nucleic acid, and (vii) a small molecule drug or a toxin. Thus, the at least one antigen or antigenic epitope may be a peptide, a protein, a polysaccharide, a lipid, a combination thereof including lipoproteins and glycolipids, a nucleic acid (e.g. DNA, siRNA, shRNA, antisense oligonucleotides, decoy DNA, plasmid), or a small molecule drug (e.g. cyclosporine A, paclitaxel, doxorubicin, methotrexate, 5-aminolevulinic acid), or any combination thereof in particular if more than one antigen or antigenic epitope is comprised by the complex comprised by the combination for use according to the present invention.

It is understood that the at least one antigen or antigenic epitope can comprise for example at least one, i.e. one or more, peptides, polypeptides or proteins linked together and/or at least one, i.e. one or more, nucleic acids, e.g. where each one encodes one peptide or polypeptide. Also the at least one antigen or antigenic epitope can be a combination of a protein, a lipid, and/or a polysaccharide including lipoproteins and glycolipids. Thus, in particular if the complex comprised by the combination for use according to the present invention comprises more than one antigen or antigenic epitope, it can comprise more than one peptide, polypeptide, or protein, more than one polysaccharide, more than one lipid, more than one lipoprotein, more than one glycolipid, more than one nucleic acid, more than one small molecule drug or toxin, or a combination thereof.

Preferably, the complex comprised by the combination for use according to the invention comprises at least one antigen or antigenic epitope comprising one or more epitope(s) from a cancer/tumor-associated antigen, a cancer/tumor-specific antigen, and/or an antigenic protein from a pathogen, including viral, bacterial, fungal, protozoal and multicellular parasitic antigenic protein.

More preferably, the at least one antigen or antigenic epitope comprises or consists of (i) at least one pathogen epitope and/or (ii) at least one cancer/tumor epitope, in particular at least one tumor epitope. Most preferably, the at least one antigen or antigenic epitope comprises or consists of at least one cancer/tumor epitope, in particular at least one tumor epitope.

It is particularly preferred that the complex comprised by the combination for use according to the present invention comprises only such antigen(s) or antigenic epitope(s), which are cancer/tumor-associated antigen(s), cancer/tumor-specific antigen(s) and/or cancer/tumor epitope(s); in particular, which are tumor-associated antigen(s), tumor-specific antigen(s), and/or tumor epitope(s).

As used herein, "cancer epitope" means an epitope from a cancer-associated antigen or from a cancer-specific antigen. Accordingly, "tumor epitope" means an epitope from a tumor-associated antigen or from a tumor-specific antigen. Such epitopes are typically specific (or associated) for a certain kind of cancer/tumor. For instance, cancer/tumor epitopes include glioma epitopes. In particular, cancer/tumor-associated (also cancer/tumor-related) antigens are antigens, which are expressed by both, cancer/tumor cells and normal cells. Accordingly, those antigens are normally present since birth (or even before). Accordingly, there is a chance that the immune system developed self-tolerance to those antigens. Cancer/tumor-specific antigens, in contrast, are antigens, which are expressed specifically by cancer/tumor cells, but not by normal cells. Cancer/tumor-specific antigens include in particular neoantigens. In general neoantigens are antigens, which were not present before and are, thus, "new" to the immune system. Neoantigens are typically due to somatic mutations. In the context of cancer/tumors, cancer/tumor-specific neoantigens were typically not present before the cancer/tumor developed and cancer/tumor-specific neoantigens are usually encoded by somatic gene mutations in the cancerous cells/tumor cells. Since neoantigens are new to the immune system, the risk of self-tolerance of those antigens is considerably lower as compared to cancer/tumor-associated antigens. However, every cancer's set of tumor-specific mutations appears to be unique. Accordingly, in the context of the present invention it is preferred that such cancer/tumor-specific antigens, in particular neoantigens, are identified in a subject diagnosed with a cancer by methods known to the skilled person, e.g., cancer genome sequencing. After identification, the respective cancer/tumor-specific neoantigens and/or cancer/tumor-specific neoantigenic epitopes are used in the complex comprised by the combination for use according to the present invention.

Preferably, a complex comprised by the combination for use according to the present invention comprises one or more cancer/tumor-associated epitopes and/or one or more cancer/tumor-associated antigens (but preferably no cancer/tumor-specific epitopes). It is also preferred that a complex comprised by the combination for use according to the present invention comprises one or more cancer/tumor-specific epitopes and/or one or more cancer/tumor-specific antigens (but preferably no cancer/tumor-associated epitopes). A complex comprised by the combination for use according to the present invention may also preferably comprise both, (i) one or more cancer/tumor-associated epitopes and/or one or more cancer/tumor-associated antigens and (ii) one or more cancer/tumor-specific epitopes and/or one or more cancer/tumor-specific antigens.

Suitable cancer/tumor epitopes can be retrieved for example from cancer/tumor epitope databases, e.g. from van der Bruggen P, Stroobant V, Vigneron N, Van den Eynde B. Peptide database: T cell-defined tumor antigens. *Cancer Immun* 2013; URL: www.cancerimmunity.org/peptide/, wherein human tumor antigens recognized by CD4+ or CD8+ T cells are classified into four major groups on the basis of their expression pattern, or from the database "Tantigen" (TANTIGEN version 1.0, Dec. 1, 2009; developed by Bioinformatics Core at Cancer Vaccine Center, Dana-Farber Cancer Institute; URL: cvc.dfci.harvard.edu/tadb/). Examples of cancer/tumor epitopes include e.g. TRP2-derived epitopes, glycoprotein 100 (gp100) melanoma antigen-derived epitopes, glycoprotein 70 (gp70) antigen-derived epitopes, survivin epitopes, IEa epitopes, IL13rα2, Epha2 (ephrin type-A receptor 2), immunogenic fragments thereof, and fusions of such antigens and/or fragments. Furthermore, examples of cancer/tumor epitopes include epitopes of neoantigens, such as, for example, a neoantigen from MC-38 tumor cell line as described by Yadav et al. Nature. 2014 Nov. 27;515 (7528): 572-6. As described above, neoantigens are antigens, which are entirely absent from the normal human genome. As compared with nonmutated self-antigens, neoantigens are of relevance to tumor control, as the quality of the T cell pool that is available for these antigens is not affected by central T cell tolerance. In particular, neoantigens may be based on individual tumor genomes. Potential neoantigens may be predicted by methods known to the skilled person, such as cancer genome sequencing or deep-sequencing technologies identifying mutations within the protein-coding part of the (cancer) genome.

Specific examples of cancer/tumor-associated, in particular tumor-related, or tissue-specific antigens useful in a complex comprised by the combination for use according to the present invention include, but are not limited to, the following antigens: Prostate: prostate-specific antigen (PSA), prostate-specific membrane antigen (PSMA), PAP, PSCA (PNAS 95 (4) 1735-1740 1998), prostate mucin antigen (PMA) (Beckett and Wright, 1995, Int. J. Cancer 62:703-710), Prostase, Her-2neu, SPAS-1; Melanoma: TRP-2, tyrosinase, Melan A/Mart-1, gpIOO, BAGE, GAGE, GM2 ganglioside; Breast: Her2-neu, kinesin 2, TATA element modulatory factor 1, tumor protein D52, MAGE D, ING2, HIP-55, TGF-1 anti-apoptotic factor, HOM-Mel-40/SSX2, epithelial antigen (LEA 135), DF31MUC1 antigen (Apostolopoulos et al., 1996 Immunol. Cell. Biol. 74:457-464; Pandey et al., 1995, Cancer Res. 55:4000-4003); Testis: MAGE-1, HOM-Mel-40/SSX2, NY-ESO-1; Colorectal: EGFR, CEA; Lung: MAGE D, EGFR Ovarian Her-2neu; Baldder: transitional cell carcinoma (TCC) (Jones et al., 1997, Anticancer Res. 17:685-687), Several cancers: Epha2, Epha4, PCDGF, HAAH, Mesothelin; EPCAM; NY-ESO-1, glycoprotein MUC1 and NIUC10 mucins p5 (especially mutated versions), EGFR; Miscellaneous tumor: cancer-associated serum antigen (CASA) and cancer antigen 125 (CA 125) (Kierkegaard et al., 1995, Gynecol. Oncol. 59:251-254), the epithelial glycoprotein 40 (EGP40) (Kievit et al., 1997, Int. J. Cancer 71:237-245), squamous cell carcinoma antigen (SCC) (Lozza et al., 1997 Anticancer Res. 17:525-529), cathepsin E (Mota et al., 1997, Am. J Pathol. 150:1223-1229), tyrosinase in melanoma (Fishman et al., 1997 Cancer 79:1461-1464), cell nuclear antigen (PCNA) of cerebral cavernomas (Notelet et al., 1997 Surg. Neurol. 47:364-370), a 35 kD tumor-associated autoantigen in papillary thyroid carcinoma (Lucas et al., 1996 Anticancer Res. 16:2493-2496), CDC27 (including the mutated form of the protein), antigens triosephosphate isomerase, 707-AP, A60 mycobacterial antigen (Macs et al., 1996, J. Cancer Res. Clin. Oncol. 122:296-300), Annexin II, AFP, ART-4, BAGE, β-catenin/m, BCL-2, bcr-abl, bcr-abl p190, bcr-abl p210, BRCA-1, BRCA-2, CA 19-9 (Tolliver and O'Brien, 1997, South Med. J. 90:89-90; Tsuruta at al., 1997 Urol. Int. 58:20-24), CAMEL, CAP-1, CASP-8, CDC27/m, CDK-4/m, CEA (Huang et al., Exper Rev. Vaccines (2002) 1:49-63), CT9, CT10, Cyp-B, Dek-cain, DAM-6 (MAGE-B2), DAM-10 (MAGE-B1), EphA2 (Zantek et al., Cell Growth Differ. (1999) 10:629-38; Carles-Kinch et al., Cancer Res. (2002) 62:2840-7), EphA4 (Cheng at al., 2002, Cytokine Growth Factor Rev. 13:75-85), tumor associated Thomsen-Friedenreich antigen (Dahlenborg et al., 1997, Int. J Cancer 70:63-71), ELF2M, ETV6-AML1, G250, GAGE-1, GAGE-2, GAGE-3, GAGE-4, GAGE-5, GAGE-6, GAGE-7B, GAGE-8, GnT-V, gp100 (Zajac et al., 1997, Int. J Cancer 71:491-496), HAGE, HER2/neu, HLA-A*0201-R1701, HPV-E7, HSP70-2M, HST-2, hTERT, hTRT, iCE, inhibitors of apoptosis (e.g., survivin), KH-1 adenocarcinoma antigen (Deshpande and Danishefsky, 1997, Nature 387:164-166), KIAA0205, K-ras, LAGE, LAGE-1, LDLR/FUT, MAGE-1, MAGE-2, MAGE-3, MAGE-6, MAGE-A1, MAGE-A2, MAGE-A3, MAGE-A4, MAGE-A6, MAGE-A10, MAGE-A12, MAGE-B5, MAGE-B6, MAGE-C2, MAGE-C3, MAGE D, MART-1, MART-1/Melan-A (Kawakami and Rosenberg, 1997, Int. Rev. Immunol. 14:173-192), MC1R, MDM-2, Myosin/m, MUC1, MUC2, MUM-1, MUM-2, MUM-3, neo-polyA polymerase, NA88-A, NY-ESO-1, NY-ESO-1a (CAG-3), PAGE-4, PAP, Proteinase 3 (Molldrem et al., Blood (1996) 88:2450-7; Molldrem et al., Blood (1997) 90:2529-34), P15, p190, Pm1/RARa, PRAME, PSA, PSM, PSMA, RAGE, RAS, RCAS1, RU1, RU2, SAGE, SART-1, SART-2, SART-3, SP17, SPAS-1, TEL/AML1, TPI/m, Tyrosinase, TARP, TRP-1 (gp75), TRP-2, TRP-2/INT2, WT-1, and alternatively translated NY-ESO-ORF2 and CAMEL proteins, derived from the NY-ESO-1 and LAGE-1 genes. Numerous other cancer antigens are well known in the art.

Preferably, the cancer/tumor antigen or the cancer/tumor epitope is a recombinant cancer/tumor antigen or a recombinant cancer/tumor epitope. Such a recombinant cancer/tumor antigen or a recombinant cancer/tumor epitope may be designed by introducing mutations that change (add, delete or substitute) particular amino acids in the overall amino acid sequence of the native cancer/tumor antigen or the native cancer/tumor epitope. The introduction of mutations does not alter the cancer/tumor antigen or the cancer/tumor epitope so much that it cannot be universally applied across a mammalian subject, and preferably a human or dog subject, but changes it enough that the resulting amino acid sequence breaks tolerance or is considered a foreign antigen in order to generate an immune response. Another manner may be creating a consensus recombinant cancer/tumor antigen or cancer/tumor epitope that has at least 85% and up to 99% amino acid sequence identity to its' corresponding native cancer/tumor antigen or native cancer/tumor epitope; preferably at least 90% and up to 98% sequence identity; more preferably at least 93% and up to 98% sequence identity; or even more preferably at least 95% and up to 98% sequence identity. In some instances the recombinant cancer/tumor antigen or the recombinant cancer/tumor epitope has 95%, 96%, 97%, 98%, or 99% amino acid sequence identity to its' corresponding native cancer/tumor antigen or cancer/tumor epitope. The native cancer/tumor antigen is the antigen normally associated with the particular cancer or cancer tumor. Depending upon the cancer/tumor antigen, the consensus sequence of the cancer/tumor antigen can be across mammalian species or within subtypes of a species or across viral strains or serotypes. Some cancer/tumor antigen do not vary greatly from the wild type amino acid sequence of the cancer/tumor antigen. The aforementioned approaches can be combined so that the final recombinant cancer/tumor antigen or cancer/tumor epitope has a percent similarity to native cancer antigen amino acid sequence as discussed above. Preferably, however, the amino acid sequence of an epitope of a cancer/tumor antigen as described herein is not mutated and, thus, identical to the reference epitope sequence.

As used herein "pathogen epitope" means an epitope from an antigenic protein, an antigenic polysaccharide, an antigenic lipid, an antigenic lipoprotein or an antigenic glycolipid from a pathogen including viruses, bacteria, fungi, protozoa and multicellular parasites. Antigenic proteins, polysaccharides, lipids, lipoproteins or glycolipids from pathogens include, herewith, proteins, polysaccharides, lipids, lipoproteins and glycolipids, respectively, from pathogens responsible of diseases which can be a target for vaccination including, for instance, Amoebiasis, Anthrax, Buruli Ulcer (*Mycobacterium ulcerans*), Caliciviruses associated diarrhoea, *Campylobacter* diarrhoea, Cervical Cancer (Human papillomavirus), *Chlamydia trachomatis* associated genital diseases, Cholera, Crimean-Congo haemorrhagic fever, Dengue Fever, Diptheria, Ebola haemorrhagic fever, Enterotoxigenic *Escherichia coli* (ETEC) diarrhoea, Gastric Cancer (*Helicobacter pylori*), Gonorrhea, Group A *Streptococcus* associated diseases, Group B *Streptococcus* associated diseases, *Haemophilus influenzae* B pneumonia and invasive disease, Hepatitis A, Hepatitis B, Hepatitis C, Hepatitis E diarrhoea, Herpes simplex type 2 genital ulcers, HIV/AIDS, Hookworm Disease, Influenza, Japanese encephalitis, Lassa Fever, Leishmaniasis, Leptospirosi, Liver cancer (Hepatitis B), Liver Cancer (Hepatitis C), Lyme Disease, Malaria, Marburg haemorrhagic fever, Measles, Mumps, Nasopharyngeal cancer (Epstein-Barr virus), *Neisseria meningitidis* Meningitis, Parainfluenza associated pneumonia, Pertussis, Plague, Poliomyelitis, Rabies, Respiratory syncytial virus (RSV) pneumonia, Rift Valley fever, Rotavirus diarrhoea, Rubella, Schistosomiasis, Severe Acute Respiratory Syndrome (SARS), Shigellosis, Smallpox, *Staphylococcus aureus* associated diseases, Stomach Cancer (*Helicobacter pylori*), *Streptococcus pneumoniae* and invasive disease, Tetanus, Tick-borne encephalitis, Trachoma, Tuberculosis, Tularaemia, Typhoid fever, West-Nile virus associated disease, Yellow fever.

Preferably, the at least one antigen or antigenic epitope will be presented at the cell surface in an MHC class I and/or MHC class II context and/or in a CD1 context, whereby presentation at the cell surface in an MHC class I and/or MHC class II context is preferred. The phrase "epitope presentation in the MHC class I context" refers in particular to a $CD8^+$ epitope lying in the groove of a MHC class I molecule at the surface of a cell. The phrase "epitope presentation in the MHC class II context" refers in particular to a $CD4^+$ epitope lying in the groove of a MHC class II molecule at the surface of a cell. The phrase "epitope presentation in the CD1 context" refers in particular to a lipidic epitope lying in the groove of a cluster of differentiation 1 molecule at the surface of a cell.

Advantageously, the complex comprised by the combination for use according to the invention comprises a cell penetrating peptide and at least one antigen or antigenic epitope, and allows the transport and presentation of said epitopes at the cell surface of antigen presenting cells in an MHC class I and MHC class II context, and is, thus, useful in vaccination and immunotherapy.

Preferably, the complex comprised by the combination for use according to the present invention comprises at least one antigen or antigenic epitope, which is at least one $CD4^+$ epitope and/or at least one $CD8^+$ epitope.

The terms "$CD4^+$ epitope" or "$CD4^+$-restricted epitope", as used herein, designate an epitope recognized by a $CD4^+$ T cell, said epitope in particular consisting of an antigen fragment lying in the groove of a MHC class II molecule. A single $CD4^+$ epitope comprised in the complex comprised by the combination for use according to the present invention preferably consists of about 12-25 amino acids. It can also consist of, for example, about 8-25 amino acids or about 6-100 amino acids.

The terms "$CD8^+$ epitope" or "$CD8^+$-restricted epitope", as used herein, designate an epitope recognized by a $CD8^+$ T cell, said epitope in particular consisting of an antigen fragment lying in the groove of a MHC class I molecule. A single $CD8^+$ epitope comprised in the complex comprised by the combination for use according to the present invention preferably consists of about 8-11 amino acids. It can also consist of, for example, about 8-15 amino acids or about 6-100 amino acids.

Preferably, the at least one antigen can comprise or the at least one antigenic epitope can consist of a $CD4^+$ epitope and/or a $CD8^+$ epitope corresponding to antigenic determinant(s) of a cancer/tumor-associated antigen, a cancer/tumor-specific antigen, or an antigenic protein from a pathogen. More preferably, the at least one antigen can comprise or the at least one antigenic epitope can consist of a $CD4^+$ epitope and/or a $CD8^+$ epitope corresponding to antigenic determinant(s) of a cancer/tumor-associated antigen or a cancer/tumor-specific antigen. Most preferably, the at least one antigen can comprise or the at least one antigenic epitope can consist of a $CD4^+$ epitope and/or a $CD8^+$ epitope corresponding to antigenic determinant(s) of a tumor-associated antigen or a tumor-specific antigen.

It is also preferred that the complex comprised by the combination for use according to the present invention comprises at least two antigens or antigenic epitopes, wherein at least one antigen or antigenic epitope comprises or consists a $CD4^+$ epitope and at least one antigen or antigenic epitope comprises or consists a $CD8^+$ epitope. It is now established that $T_h$ cells ($CD4^+$) play a central role in the anti-tumor immune response both in DC licensing and in the recruitment and maintenance of CTLs ($CD8^+$) at the tumor site. Therefore, a complex comprised by the combination for use according to the present invention comprising at least two antigens or antigenic epitopes, wherein at least one antigen or antigenic epitope comprises or consists of a $CD4^+$ epitope and at least one antigen or antigenic epitope comprises or consists a $CD8^+$ epitope, provides an integrated immune response allowing simultaneous priming of CTLs and $T_h$ cells and is thus preferable to immunity against only one $CD8^+$ epitope or only one $CD4^+$ epitope. For example, the complex comprised by the combination for use according to the present invention may preferably comprise an Ealpha-$CD4^+$ epitope and a gp100-$CD8^+$ epitope.

Preferably, the complex comprised by the combination for use according to the present invention comprises at least two antigens or antigenic epitopes, wherein the at least two antigens or antigenic epitopes comprise or consist of at least two, e.g. 2, 3, 4, 5, 6, 7, 8, 9, or more, $CD4^+$ epitopes and/or at least two, e.g. 2, 3, 4, 5, 6, 7, 8, 9, or more, $CD8^+$ epitopes. Thereby, the at least two antigens or antigenic epitopes are preferably different antigens or antigenic epitopes, more preferably the at least two antigens or antigenic epitopes are different from each other but relating to the same kind of tumor. A multi-antigenic vaccine will (i) avoid outgrowth of antigen-loss variants, (ii) target different tumor cells within a heterogeneous tumor mass and (iii) circumvent patient-to-patient tumor variability. Thus, the complex comprised by the combination for use according to the present invention particularly preferably comprises at least four antigens or antigenic epitopes, in particular with at least two $CD8^+$ epitopes and at least two $CD4^+$ epitopes. Such a complex comprised by the combination for use according to the present invention induces multi-epitopic CD8 CTLs and CD4 $T_h$ cells to function synergistically to counter tumor cells and promote efficient anti-tumor immunity. $T_h$ cells are also involved in the maintenance of long-lasting cellular immunity that was monitored after vaccination. Such a complex comprised by the combination for use according to the present invention induces polyclonal, multi-epitopic immune responses and poly-functional $CD8^+$ and $CD4^+$ T cells, and thus efficacious anti-tumor activity.

Preferably, the complex comprised by the combination for use according to the present invention comprises at least two antigens or antigenic epitopes, more preferably the complex comprised by the combination for use according to the present invention comprises at least three antigens or antigenic epitopes, even more preferably the complex comprised by the combination for use according to the present invention comprises at least four antigens or antigenic epitopes, particularly preferably the complex comprised by the combination for use according to the present invention comprises at least five antigens or antigenic epitopes and most preferably the complex comprised by the combination for use according to the present invention comprises at least six antigens or antigenic epitopes. The antigens or antigenic epitopes comprised by the complex may be the same or different, preferably the antigens or antigenic epitopes comprised by the complex are different from each other. Preferably, the complex comprises at least one CD4+ epitope and at least one CD8+ epitope.

Preferably, the complex comprised by the combination for use according to the present invention comprises more than one CD4+ epitope, e.g. two or more CD4+ epitopes from the same antigen or from different antigens, and preferably no CD8+ epitope. It is also preferred that the complex comprised by the combination for use according to the present invention comprises more than one CD8+ epitope, e.g. two or more CD8+ epitopes from the same antigen or from different antigens, and preferably no CD4+ epitope. Most preferably, however, the complex comprised by the combination for use according to the present invention comprises (i) at least one CD4+ epitope, e.g. two or more CD4+ epitopes from the same antigen or from different antigens, and (ii) at least one CD8+ epitope, e.g. two or more CD8+ epitopes from the same antigen or from different antigens.

For example, the complex comprised by the combination for use according to the present invention may preferably comprise a gp100-CD8+ epitope, an Ealpha-CD4+ epitope, and a further CD4+ epitope and a further CD8+ epitope. Even more preferably, the complex comprised by the combination for use according to the present invention may comprise a polypeptide or protein comprising a gp100-CD8+ epitope and an Ealpha-CD4+ epitope. For example, such a polypeptide or protein comprised by the complex comprised by the combination for use according to the present invention comprises or consists of an amino acid sequence according to SEQ ID NO: 14 or sequence variants thereof as defined above:

```
                                                    SEQ ID NO: 14
ESLKIS QAVHAAHAEI NEAGREVVGV GALKVPRNQD WLGVPRFAKF ASFEAQGALA

NIAVDKANLD VEQLESIINF EKLTEWTGS (MAD5-cargo comprising OVA-CD4+, gp100-CD8+, Ealpha-CD4+,
and OVA-CD8+ epitopes)
```

For example, the complex comprised by the combination for use according to the present invention may preferably comprise a gp70-CD8+ epitope and/or a gp70-CD4+ epitope. Even more preferably, the complex comprised by the combination for use according to the present invention may comprise a polypeptide or protein comprising a gp70-CD8+ epitope and/or a gp70-CD4+ epitope. For example, such a polypeptide or protein comprised by the complex comprised by the combination for use according to the present invention comprises or consists of an amino acid sequence according to SEQ ID NO: 36 or sequence variants thereof as defined above:

```
                                                    SEQ ID NO: 36
VTYHSPSYAYHQFERRAILNRLVQFIKDRI (Mad8-cargo comprising a gp70-CD8+ and
a gp70-CD4+ epitope)
```

For example, the complex comprised by the combination for use according to the present invention may preferably comprise at least one survivin epitope, such as a survivin CD8+ epitope and/or a survivin CD4+ epitope. More preferably, the complex comprised by the combination for use according to the present invention may comprise a polypeptide or protein comprising a survivin CD8+ epitope and/or a survivin CD4+ epitope. More preferably, the complex comprised by the combination for use according to the present invention may comprise a polypeptide or protein comprising more than one survivin CD8+ epitope and/or more than one survivin CD4+ epitope, such as two different survivin CD8+ epitopes. For example, such a polypeptide or protein comprised by the complex comprised by the combination for use according to the present invention comprises or consists of an amino acid sequence according to SEQ ID NO: 37 or sequence variants thereof as defined above:

```
                                                    SEQ ID NO: 37
NYRIATFKNWPFLEDCAMEELTVSEFLKLDRQR (Mad11-cargo comprising survivin CD8+ epitope 1
and survivin CD8+ epitope 2)
```

For example, the complex comprised by the combination for use according to the present invention may preferably comprise an epitope from a neoantigen. Even more preferably, the complex comprised by the combination for use according to the present invention may comprise a polypeptide or protein comprising an epitope from a neoantigen, such as the neoantigen from MC-38 tumor cell line identified by Yadav et al. Nature. 2014 Nov. 27;515 (7528): 572-6. For example, such a polypeptide or protein comprised by the complex comprised by the combination for use according to the present invention comprises or consists of an amino acid sequence according to SEQ ID NO: 38 or sequence variants thereof as defined above:

```
                                                    SEQ ID NO: 38
HLELASMTNMELMSSIV
(Mad9-cargo comprising the epitope from a
neoantigen as described by Yadav et al.
Nature. 2014 Nov. 27;515(7528):572-6).
```

For example, the complex comprised by the combination for use according to the present invention may preferably comprise more than one, e.g. two or three, epitopes from neoantigens. Even more preferably, the complex comprised by the combination for use according to the present invention may comprise a polypeptide or protein comprising more than one, e.g. two or three, epitopes from neoantigens, such as the neoantigens from MC-38 tumor cell line identified by Yadav et al. Nature. 2014 Nov. 27;515 (7528): 572-6. For example, such a polypeptide or protein comprised by the complex comprised by the combination for use according to the present invention comprises or consists of an amino acid sequence according to SEQ ID NO: 39 or sequence variants thereof as defined above:

```
                                            SEQ ID NO: 39
LFRAAQLANDVVLQIMEHLELASMTNMELMSSIVVISASIIVFNLLELEG
(Mad12-cargo comprising the epitope from a
neoantigen as described by Yadav et al.
Nature. 2014 Nov. 27;515(7528):572-6).
```

Preferably, the at least one antigen or antigenic epitope comprised by the complex comprised by the combination for use according to the present invention is a peptide, polypeptide, or a protein.

Examples of antigen or antigenic epitope of peptidic, polypeptidic, or proteic nature useful in the invention, include cancer/tumor antigens or antigenic epitopes thereof, allergy antigens or antigenic epitopes thereof, auto-immune self-antigens or antigenic epitopes thereof, pathogenic antigens or antigenic epitopes thereof, and antigens or antigenic epitopes thereof from viruses, preferably from cytomegalovirus (CMV), orthopox variola virus, orthopox alastrim virus, parapox *ovis* virus, molluscum contagiosum virus, herpes simplex virus 1, herpes simplex virus 2, herpes B virus, varicella zoster virus, pseudorabies virus, human cytomegaly virus, human herpes virus 6, human herpes virus 7, Epstein-Barr virus, human herpes virus 8, hepatitis B virus, chikungunya virus, O'nyong'nyong virus, rubivirus, hepatitis C virus, GB virus C, West Nile virus, dengue virus, yellow fever virus, louping ill virus, St. Louis encephalitis virus, Japan B encephalitis virus, Powassan virus, FSME virus, SARS, SARS-associated corona virus, human corona virus 229E, human corona virus Oc43, Torovirus, human T cell lymphotropic virus type I, human T cell lymphotropic virus type II, HIV (AIDS), i.e. human immunodeficiency virus type 1 or human immunodeficiency virus type 2, influenza virus, Lassa virus, lymphocytic choriomeningitis virus, Tacaribe virus, Junin virus, Machupo virus, Borna disease virus, Bunyamwera virus, California encephalitis virus, Rift Valley fever virus, sand fly fever virus, Toscana virus, Crimean-Congo haemorrhagic fever virus, Hazara virus, Khasan virus, Hantaan virus, Seoul virus, Prospect Hill virus, Puumala virus, Dobrava Belgrade virus, Tula virus, sin nombre virus, Lake Victoria Marburg virus, Zaire Ebola virus, Sudan Ebola virus, Ivory Coast Ebola virus, influenza virus A, influenza virus B, influenza viruses C, parainfluenza virus, malaria parasite (*Plasmodium falciparum, Plasmodium vivax, Plasmodium ovale, Plasmodium malariae, Plasmodium knowlesi*), Marburg virus, measles virus, mumps virus, respiratory syncytial virus, human metapneumovirus, vesicular stomatitis Indiana virus, rabies virus, Mokola virus, Duvenhage virus, European bat lyssavirus 1+2, Australian bat lyssavirus, adenoviruses A-F, human papilloma viruses, condyloma virus 6, condyloma virus 11, polyoma viruses, adeno-associated virus 2, rotaviruses, orbiviruses, varicella including varizella zoster, etc., or antigens or antigenic epitopes from *leishmania*, typanosomes, amibes, bacteria, etc., or may be selected from epitopes or from variants of the above antigens or antigenic epitopes. Preferably, epitopes as well as variants of antigens as defined above exhibit a sequence homology or identity of about 10%, in particular at least 10%, about 20%, in particular at least 20%, about 30%, in particular at least 30%, about 40%, in particular at least 40%, about 50%, in particular at least 50%, about 60%, in particular at least 60%, about 70%, in particular at least 70%, about 80%, in particular at least 80%, about 90% in particular at least 90%, at least 95% or at least 98% with one of the antigens or antigen sequences as shown or described above. In this context, the definition of epitopes and variants similarly applies as defined.

Examples of antigens or antigenic epitopes in the category of peptide, polypeptide or protein include a combination of multiple glioma epitopes such as those described in Novellino et al. (2005, *Cancer Immunol Immunother*, 54 (3): 187-207), Vigneron et al. (2013, *Cancer Immun.* 13:15). However, a single complex comprised by the combination for use according to the present invention may also comprise only a subset, i.e. one or more of all of said glioma epitopes. In such a case preferably different complexes comprised by the combination for use according to the present invention comprise different subsets of all of said glioma epitopes, so that for example a vaccine according to the present invention comprising such different complexes comprises all of said glioma epitopes but distributed in the different complexes.

Moreover, a complex comprised by the combination for use according to the invention may also comprise at least one antigen or antigenic epitope, wherein said antigen or antigenic epitope is a polysaccharide, a lipid, a lipoprotein, and/or a glycolipid, in particular a polysaccharidic, lipidic, lipoproteic, and/or glycolipidic epitope, which can be, for example, pathogen epitopes as defined herewith.

In particular, the complex comprised by the combination for use according to the invention may comprise at least one antigen or antigenic epitope, wherein said antigen or antigenic epitope is polysaccharidic, lipidic, lipoproteic, and/or glycolipidic, including viral, bacterial, fungal, protozoal and multicellular parasitic antigens or antigenic epitopes.

Preferably, said epitopes will be presented at the cell surface in an MHC class I and/or MHC class II context.

Preferably, said lipidic epitopes will be presented at the cell surface in a CD1 (cluster of differentiation 1) context.

The complex comprised by the combination for use according to the present invention may also comprise at least one antigen or antigenic epitope, wherein said antigen or antigenic epitope is a small molecule drug or toxin.

Examples of cargo molecules within the category of small molecule drugs or toxins useful in the invention include cyclosporine A, paclitaxel, doxorubicin, methotrexate, 5-aminolevulinic acid, diphtheria toxin, sunitinib and those molecules reviewed in *De wit Amer* (2010, *Neuro Oncol,* 12 (3): 304-16).

The complex comprised by the combination for use according to the present invention comprises at least one antigen or antigenic epitope, preferably the complex comprised by the combination for use according to the present invention comprises more than one antigen or antigenic epitope, in particular 2, 3, 4, 5, 6, 7, 8, 9, 10 or more antigens or antigenic epitopes, more preferably the complex comprised by the combination for use according to the present invention comprises (at least) two or three antigens or antigenic epitopes, even more preferably the complex comprised by the combination for use according to the present invention comprises (at least) four or five antigens or antigenic epitopes. If more than one antigen or antigenic epitope is comprised by the complex comprised by the combination for use according to the present invention it is understood that said antigen or antigenic epitope is in particular also covalently linked in the complex comprised by the combination for use according to the present invention, e.g. to another antigen or antigenic epitope and/or to a component a), i.e. a cell penetrating peptide, and/or to a component c), i.e. a TLR peptide agonist.

The various antigens or antigenic epitopes comprised by the complex may be the same or different. Preferably, the various antigens or antigenic epitopes comprised by the complex are different from each other, thus providing a multi-antigenic and/or multi-epitopic complex.

Moreover, it is preferred that the more than one antigen or antigenic epitope, in particular 2, 3, 4, 5, 6, 7, 8, 9, 10 or more antigens or antigenic epitopes, are positioned consecutively in the complex comprised by the combination for use according to the present invention. This means in particular that all antigens and/or antigenic epitopes comprised by the complex are positioned in a stretch, which is neither interrupted by component a), i.e. a cell penetrating peptide, nor by component c), i.e. a TLR peptide agonist. Rather, component a) and component c) are positioned in the complex for example before or after such a stretch of all antigens and/or antigenic epitopes. However, the antigens and/or antigenic epitopes positioned consecutively in such a way may be linked to each other for example by a spacer or linker as described below, which is neither component a), i.e. a cell penetrating peptide, nor component c), i.e. a TLR peptide agonist.

Alternatively, however, the various antigens and/or antigenic epitopes may also be positioned in any other way in the complex comprised by the combination for use according to the present invention, for example with component a) and/or component c) positioned in between two or more antigens and/or antigenic epitopes, i.e. with one or more antigens and/or antigenic epitopes positioned between component a) and component c) (or vice versa) and, optionally, one or more antigens and/or antigenic epitopes positioned at the respective other end of component a) and/or component c).

It is understood that a number of different antigens or antigenic epitopes relating to the same kind of disease, in particular to the same kind of tumor, may be advantageously comprised by a single complex. Alternatively, a number of different antigens or antigenic epitopes relating to the same kind of disease, in particular to the same kind of tumor, may be distributed to subsets of different antigens or antigenic epitopes, in particular subsets complementing each other in the context of a certain kind of disease, e.g. tumor, which are comprised by different complexes, whereby such different complexes comprising different subsets may advantageously be administered simultaneously, e.g. in a single vaccine, to a subject in need thereof.

Preferably, the complex according to the present invention comprises at least one tumor epitope, which is an epitope of an antigen selected from the group consisting of EpCAM, HER-2/neu, MUC-1, TOMM34, RNF 43, KOC1, VEGFR, BhCG, survivin, CEA, TGFβR2, p53, KRas, OGT, CASP5, COA-1, MAGE, SART, IL13Ralpha2, CMV, EGFRvIII, EphA2, gp100, hTert, TRP-2, YKL-40, brevican, neuroligin 4 and PTPRz1. More preferably, the complex according to the present invention comprises at least one tumor antigen selected from the group consisting of EpCAM, HER-2/neu, MUC-1, TOMM34, RNF 43, KOC1, VEGFR, BhCG, survivin, CEA, TGFβR2, p53, KRas, OGT, CASP5, COA-1, MAGE, SART, IL13Ralpha2, CMV, EGFRvIII, EphA2, gp100, hTert, TRP-2, YKL-40, brevican, neuroligin 4 and PTPRz1 or a fragment thereof, or a sequence variant of a tumor antigen or a sequence variant of a fragment thereof. It is also preferred that the complex according to the present invention comprises at least one tumor epitope, which is an epitope of an antigen selected from the glioma antigens disclosed by Reardon, D. A., et al., *An update on vaccine therapy and other immunotherapeutic approaches for glioblastoma.* Expert Rev Vaccines, 2013. 12 (6): p. 597-615.

As used herein, a "fragment" of an antigen comprises at least 10 consecutive amino acids of the antigen, preferably at least 15 consecutive amino acids of the antigen, more preferably at least 20 consecutive amino acids of the antigen, even more preferably at least 25 consecutive amino acids of the antigen and most preferably at least 30 consecutive amino acids of the antigen. A "sequence variant" is as defined above, namely a sequence variant has an (amino acid) sequence which is at least 70%, at least 75%, preferably at least 80%, more preferably at least 85%, even more preferably at least 90%, particularly preferably at least 95%, most preferably at least 99% identical to the reference sequence. A "functional" sequence variant means in the context of an antigen/antigen fragment/epitope, that the function of the epitope(s), e.g. comprised by the antigen (fragment), is not impaired or abolished. Preferably, however, the amino acid sequence of the epitope(s), e.g. comprised by the cancer/tumor antigen (fragment) as described herein, is not mutated and, thus, identical to the reference epitope sequence.

As described above, suitable cancer/tumor epitopes of those antigens are known from the literature or can be identified by using cancer/tumor epitope databases, e.g. from van der Bruggen P, Stroobant V, Vigneron N, Van den Eynde B. Peptide database: T cell-defined tumor antigens. *Cancer Immun* 2013; URL: www.cancerimmunity.org/peptide/, wherein human tumor antigens recognized by $CD4^+$ or $CD8^+$ T cells are classified into four major groups on the basis of their expression pattern, or from the database "Tantigen" (TANTIGEN version 1.0, Dec. 1, 2009; developed by Bioinformatics Core at Cancer Vaccine Center, Dana-Farber Cancer Institute; URL: cvc.dfci.harvard.edu/tadb/).

Component c)—TLR Peptide Agonist

In the complex comprised by the combination for use according to the present invention, the TLR peptide agonist allows an increased targeting of the vaccine towards dendritic cells along with self-adjuvancity. Physical linkage of a TLR peptide agonist to the CPP and the at least one antigen or antigenic epitope in the complex comprised by the combination for use according to the present invention provides an enhanced immune response by simultaneous stimulation of antigen presenting cells, in particular dendritic cells, that internalize, metabolize and display antigen(s).

As used in the context of the present invention, a "TLR peptide agonist" is an agonist of a Toll-like receptor (TLR), i.e. it binds to a TLR and activates the TLR, in particular to produce a biological response. Moreover, the TLR peptide agonist is a peptide, a polypeptide or a protein as defined above. Preferably, the TLR peptide agonist comprises from 10 to 150 amino acids, more preferably from 15 to 130 amino acids, even more preferably from 20 to 120 amino acids, particularly preferably from 25 to 110 amino acids, and most preferably from 30 to 100 amino acids.

Toll like receptors (TLRs) are transmembrane proteins that are characterized by extracellular, transmembrane, and cytosolic domains. The extracellular domains containing leucine-rich repeats (LRRs) with horseshoe-like shapes are involved in recognition of common molecular patterns derived from diverse microbes. Toll like receptors include TLRs1-10. Compounds capable of activating TLR receptors and modifications and derivatives thereof are well documented in the art. TLR1 may be activated by bacterial lipoproteins and acetylated forms thereof, TLR2 may in addition be activated by Gram positive bacterial glycolipids, LPS, LP A, LTA, fimbriae, outer membrane proteins, heat shock proteins from bacteria or from the host, and Mycobacterial lipoarabinomannans. TLR3 may be activated by dsRNA, in particular of viral origin, or by the chemical compound poly (LC). TLR4 may be activated by Gram negative LPS, LTA, Heat shock proteins from the host or from bacterial origin, viral coat or envelope proteins, taxol or derivatives thereof, hyaluronan containing oligosaccharides and fibronectins. TLR5 may be activated with bacterial flagellae or flagellin. TLR6 may be activated by mycobacterial lipoproteins and group B *streptococcus* heat labile soluble factor (GBS-F) or *staphylococcus* modulins. TLR7 may be activated by imidazoquinolines. TLR9 may be activated by unmethylated CpG DNA or chromatin-IgG complexes.

Preferably, the TLR peptide agonist comprised by the complex comprised by the combination for use according to the present invention is an agonist of TLR1, 2, 4, 5, 6, and/or 10. TLRs are expressed either on the cell surface (TLR1, 2, 4, 5, 6, and 10) or on membranes of intracellular organelles, such as endosomes (TLR3, 4, 7, 8, and 9). The natural ligands for the endosomal receptors turned out to be nucleic acid-based molecules (except for TLR4). The cell surface-expressed TLR1, 2, 4, 5, 6, and 10 recognize molecular patterns of extracellular microbes (Monie, T. P., Bryant, C. E., et al. 2009: Activating immunity: Lessons from the TLRs and NLRs. Trends Biochem. Sci. 34 (11), 553-561). TLRs are expressed on several cell types but virtually all TLRs are expressed on DCs allowing these specialized cells to sense all possible pathogens and danger signals.

However, TLR2, 4, and 5 are constitutively expressed at the surface of DCs. Accordingly, the TLR peptide agonist comprised by the complex comprised by the combination for use according to the present invention is more preferably a peptide agonist of TLR2, TLR4 and/or TLR5. Even more preferably, the TLR peptide agonist is a TLR2 peptide agonist and/or a TLR4 peptide agonist. Particularly preferably, the TLR peptide agonist is a TLR4 peptide agonist. Most preferably, the TLR peptide agonist is one TLR peptide agonist, which is both, a TLR2 and a TLR4 agonist. TLR2 can detect a wide variety of ligands derived from bacteria, viruses, parasites, and fungi. The ligand specificity is often determined by the interaction of TLR2 with other TLRs, such as TLR1, 6, or 10, or non-TLR molecules, such as dectin-1, CD14, or CD36. The formation of a heterodimer with TLR1 enables TLR2 to identify triacyl lipoproteins or lipopeptides from (myco) bacterial origin, such as Pam3CSK4 and peptidoglycan (PGA; Gay, N. J., and Gangloff, M. (2007): Structure and function of Toll receptors and their ligands. Annu. Rev. Biochem. 76, 141-165; Spohn, R., Buwitt-Beckmann, U., et al. (2004): Synthetic lipopeptide adjuvants and Toll-like receptor 2-Structure-activity relationships. Vaccine 22 (19), 2494-2499). Heterodimerization of TLR2 and 6 enables the detection of diacyl lipopeptides and zymosan. Lipopolysaccharide (LPS) and its derivatives are ligands for TLR4 and flagellin for TLR5 (Bryant, C. E., Spring, D. R., et al. (2010). The molecular basis of the host response to lipopolysaccharide. Nat. Rev. Microbiol. 8 (1), 8-14).

TLR2 interacts with a broad and structurally diverse range of ligands, including molecules expressed by microbes and fungi. Multiple TLR2 agonists have been identified, including natural and synthetic lipopeptides (e.g. *Mycoplasma fermentas* macrophage-activating lipopeptide (MALP-2)), peptidoglycans (PG such as those from *S. aureus*), lipopolysaccharides from various bacterial strains (LPS), polysaccharides (e.g. zymosan), glycosylphosphatidyl-inositol-anchored structures from gram positive bacteria (e.g. lipoteichoic acid (LTA) and lipo-arabinomannan from mycobacteria and lipomannas from *M. tuberculosis*). Certain viral determinants may also trigger via TLR2 (Barbalat R, Lau L, Locksley R M, Barton G M. Toll-like receptor 2 on inflammatory monocytes induces type I interferon in response to viral but not bacterial ligands. Nat Immunol. 2009: 10 (11): 1200-7). Bacterial lipopeptides are structural components of cell walls. They consist of an acylated s-glycerylcysteine moiety to which a peptide can be conjugated via the cysteine residue. Examples of TLR2 agonists, which are bacterial lipopeptides, include MALP-2 and it's synthetic analogue di-palmitoyl-S-glyceryl cysteine ($Pam_2Cys$) or tri-palmitoyl-S-glyceryl cysteine ($Pam_3Cys$).

A diversity of ligands interact with TLR4, including Monophosphoryl Lipid A from *Salmonella minnesota* R595 (MPLA), lipopolysaccharides (LPS), mannans (*Candida albicans*), glycoinositolphospholipids (*Trypanosoma*), viral envelope proteins (RSV and MMTV) and endogenous antigens including fibrinogen and heat-shock proteins. Such agonists of TLR4 are for example described in Akira S, Uematsu S, Takeuchi O. Pathogen recognition and innate immunity. Cell. February 24; 2006: 124 (4): 783-801 or in Kumar H, Kawai T, Akira S. Toll-like receptors and innate immunity. Biochem Biophys Res Commun. October 30; 2009 388 (4): 621-5. LPS, which is found in the outer membrane of gram negative bacteria, is the most widely studied of the TLR4 ligands. Suitable LPS-derived TLR4 agonist peptides are described for example in WO 2013/120073 (A1).

TLR5 is triggered by a region of the flagellin molecule expressed by nearly all motile bacteria. Thus, flagellin, or peptides or proteins derived from flagellin and/or variants or fragments of flagellin are also suitable as TLR peptide agonists comprised by the complex.

Examples of TLR peptide agonists thus include the TLR2 lipopeptide agonists MALP-2, $Pam_2Cys$ and $Pam_3Cys$ or modifications thereof, different forms of the TLR4 agonist LPS, e.g. *N. meningitidis* wild-type L3-LPS and mutant penta-acylated LpxL1-LPS, and the TLR5 agonist flagellin.

However, it is preferred that the TLR peptide agonist comprised by the complex is neither a lipopeptide nor a lipoprotein, neither a glycopeptide nor a glycoprotein, more preferably, the TLR peptide agonist comprised by the complex is a classical peptide, polypeptide or protein as defined herein.

A preferred TLR2 peptide agonist is annexin II or an immunomodulatory fragment thereof, which is described in detail in WO 2012/048190 A1 and U.S. patent application Ser. No. 13/033,1546, in particular a TLR2 peptide agonist comprising an amino acid sequence according to SEQ ID NO: 4 or SEQ ID NO: 7 of WO 2012/048190 A1 or fragments or variants thereof are preferred.

Thereby, a TLR2 peptide agonist comprising or consisting of an amino acid sequence according to SEQ ID NO: 15 or a sequence variant thereof as described above is particularly preferred as component c), i.e. as the at least one TLR peptide agonist, comprised by the complex.

SEQ ID NO: 15
STVHEILCKLSLEGDHSTPPSAYGSVKPYTNFDAE
(TLR2 peptide agonist Anaxa)

A particularly preferred functional sequence variant of the TLR peptide agonist according to SEQ ID NO: 15 is the TLR peptide agonist according to SEQ ID NO: 47:

SEQ ID NO: 47
STVHEILSKLSLEGDHSTPPSAYGSVKPYTNFDAE

Accordingly, a TLR2 peptide agonist comprising or consisting of an amino acid sequence according to SEQ ID NO: 47 or a sequence variant thereof as described above is particularly preferred as component c), i.e. as the at least one TLR peptide agonist, comprised by the complex.

Regarding TLR4, TLR peptides agonists are particularly preferred, which in particular correspond to motifs that bind to TLR4, in particular (i) peptides mimicking the natural LPS ligand (RS01: Gln-Glu-Ile-Asn-Ser-Ser-Tyr and RS09: Ala-Pro-Pro-His-Ala-Leu-Ser) and (ii) Fibronectin derived peptides. The cellular glycoprotein Fibronectin (FN) has multiple isoforms generated from a single gene by alternative splicing of three exons. One of these isoforms is the extra domain A (EDA), which interacts with TLR4.

Further suitable TLR peptide agonists comprise a fibronectin EDA domain or a fragment or variant thereof. Such suitable fibronectin EDA domains or a fragments or variants thereof are disclosed in EP 1 913 954 B1, EP 2 476 440 A1, US 2009/0220532 A1, and WO 2011/101332 A1. Thereby, a TLR4 peptide agonist comprising or consisting of an amino acid sequence according to SEQ ID NO: 40 or a sequence variant thereof as described above is particularly preferred as component c), i.e. as the at least one TLR peptide agonist, comprised by the complex comprised by the combination for use according to the present invention.

SEQ ID NO: 40
NIDRPKGLAFTDVDVDSIKIAWESPQGQVSRYRVTYSSPEDGIRELFPAP
DGEDDTAELQGL RPGSEYTVSVVALHDDMESQPLIGIQST
(TLR4 peptide agonist EDA)

In addition, high-mobility group box 1 protein (HMGB1) and peptide fragments thereof are assumed to be TLR4 agonists. Such HMGB1-derived peptides are for example disclosed in US 2011/0236406 A1.

Moreover, also the TLR agonist according to SEQ ID NO: 15 and the TLR agonist according to SEQ ID NO: 47 may act as TLR4 agonist. Accordingly, a TLR4 peptide agonist comprising or consisting of an amino acid sequence according to SEQ ID NO: 15 or 47 or a functional sequence variant thereof is particularly preferred as component c), i.e. as the at least one TLR peptide agonist, comprised by the complex.

The complex comprised by the combination for use according to the present invention comprises at least one TLR peptide agonist, preferably the complex comprised by the combination for use according to the present invention comprises more than one TLR peptide agonist, in particular 2, 3, 4, 5, 6, 7, 8, 9, 10 or more TLR peptide agonists, more preferably the complex comprised by the combination for use according to the present invention comprises (at least) two or three TLR peptide agonists, even more preferably the complex comprised by the combination for use according to the present invention comprises (at least) four or five TLR peptide agonists. If more than one TLR peptide agonist is comprised by the complex it is understood that said TLR peptide agonist is in particular also covalently linked in the complex comprised by the combination for use according to the present invention, e.g. to another TLR peptide agonist and/or to a component a), i.e. a cell penetrating peptide, and/or to a component b), i.e. an antigen or antigenic epitope.

In a particularly preferred embodiment, the complex comprised by the combination for use according to the present invention comprises one single TLR peptide agonist. In particularly, in this particularly preferred embodiment, the complex comprised by the combination for use according to the present invention comprises one single TLR peptide agonist and no further component having TLR agonist properties except the one single TLR peptide agonist as described.

The various TLR peptide agonists comprised by the complex may be the same or different. Preferably, the various TLR peptide agonists comprised by the complex are different from each other.

Moreover, it is preferred that the more than one antigen or antigenic epitope, in particular 2, 3, 4, 5, 6, 7, 8, 9, 10 antigens or antigenic epitopes, or more TLR peptide agonists, in particular 2, 3, 4, 5, 6, 7, 8, 9, 10 TLR agonists, are positioned consecutively in the complex comprised by the combination for use according to the present invention. This means in particular that all TLR peptide agonists comprised by the complex are positioned in a stretch, which is neither interrupted by component a), i.e. a cell penetrating peptide, nor by component b), i.e. at least one antigen or antigenic epitope. Rather, component a) and component b) are positioned in the complex for example before or after such a stretch of all TLR peptide agonists. However, the TLR peptide agonists positioned consecutively in such a way may be linked to each other for example by a spacer or linker as described below, which is neither component a), i.e. a cell penetrating peptide, nor component b), i.e. at least one antigen or antigenic epitope.

Alternatively, however, the various TLR peptide agonists may also be positioned in any other way in the complex comprised by the combination for use according to the present invention, for example with component a) and/or component b) positioned in between two or more TLR peptide agonists, i.e. with one or more TLR peptide agonist positioned between component a) and component b) (or vice versa) and, optionally, one or more TLR peptide agonists positioned at the respective other end of component a) and/or component b).

It is understood that a number of different TLR peptide agonists activating the same or different TLR receptors may be advantageously comprised by a single complex. Alternatively, a number of different TLR peptide agonists activating the same or different TLR receptors may be distributed to subsets of different TLR peptide agonists activating the same or different TLR receptors, which are comprised by different complexes, whereby such different complexes comprising different subsets may advantageously be administered simultaneously, e.g. in a single vaccine, to a subject in need thereof.

Linkage of Components a), b), and c) in the Complex

In the complex comprised by the combination for use according to the present invention, components a), b) and c) are covalently linked, i.e. the linkage between two out of the three components a), b), and c) of the complex is a covalent linkage. Preferably, two out of the three components a), b), and c) of the complex are covalently linked to each other (i.e. the "first" and the "second" component), and the third component out of the three components a), b), and c) is covalently linked either to the first component out of the three components a), b), and c) or to the second component out of the three components a), b), and c). Thereby, preferably a linear molecule is formed. However, it is also conceivable that each of the three components a), b), and c) is covalently linked to both of the other components out of the three components a), b), and c).

A "covalent linkage" (also covalent bond), as used in the context of the present invention, refers to a chemical bond that involves the sharing of electron pairs between atoms. A "covalent linkage" (also covalent bond) in particular involves a stable balance of attractive and repulsive forces between atoms when they share electrons. For many molecules, the sharing of electrons allows each atom to attain the equivalent of a full outer shell, corresponding to a stable electronic configuration. Covalent bonding includes many kinds of interactions, including for example σ-bonding, π-bonding, metal-to-metal bonding, agostic interactions, and three-center two-electron bonds. Accordingly, the complex comprised by the combination for use according to the present invention, may also be referred to as "compound", in particular it may be referred to as "molecule".

Preferably, in the complex comprised by the combination for use according to the present invention, components a), b), and c) are covalently linked by chemical coupling in any suitable manner known in the art, such as cross-linking methods. However, attention is drawn to the fact that many known chemical cross-linking methods are non-specific, i.e., they do not direct the point of coupling to any particular site on the components a), b), and c). Thus, the use of non-specific cross-linking agents may attack functional sites or sterically block active sites, rendering the fused components of the complex biologically inactive. It is referred to the knowledge of the skilled artisan to block potentially reactive groups by using appropriate protecting groups. Alternatively, the use of the powerful and versatile oxime and hydrazone ligation techniques, which are chemo-selective entities that can be applied for the cross-linking of components a), b), and c) may be employed. This linking technology is described e.g. by Rose et al. (1994), JACS 116, 30.

Coupling specificity can be increased by direct chemical coupling to a functional group found only once or a few times in components a), b), and/or c), which functional group is to be cross-linked to the another of the components a), b), and c). As an example, the cystein thiol group may be used, if just one cystein residue is present in a certain component a), b), or c) of complex comprised by the combination for use according to the present invention. Also, for example, if a certain component a), b), or c) contains no lysine residues, a cross-linking reagent specific for primary amines will be selective for the amino terminus of the respective component. Alternatively, cross-linking may also be carried out via the side chain of a glutamic acid residue placed at the N-terminus of the peptide such that a amide bond can be generated through its side-chain. Therefore, it may be advantageous to link a glutamic acid residue to the N-terminus of a certain component a), b), or c). However, if a cysteine residue is to be introduced into a certain component a), b), or c), introduction at or near its N- or C-terminus is preferred. Conventional methods are available for such amino acid sequence alterations based on modifications of certain component a), b), or c) by either adding one or more additional amino acids, e.g. inter alia an cystein residue, to the translocation sequence or by substituting at least one residue of the translocation sequence(s) being comprised in the respective component. In case a cystein side chain is used for coupling purposes, a certain component a), b), or c) has preferably one cystein residue. Any second cystein residue should preferably be avoided and can, optionally, be replaced when they occur in the respective component comprised by the complex. When a cysteine residue is replaced in the original sequence of a certain component a), b), or c), it is typically desirable to minimize resulting changes in the peptide folding of the respective component. Changes in folding are minimized when the replacement is chemically and sterically similar to cysteine. Therefore, serine is preferred as a replacement for cystein.

Coupling of two out of the three components a), b), and c) can be accomplished via a coupling or conjugating agent including standard peptide synthesis coupling reagents such as HOBt, HBTU, DICI, TBTU. There are several intermolecular cross-linking agents which can be utilized, see for example, Means and Feeney, Chemical Modification of Proteins, Holden-Day, 1974, pp. 39-43. Among these reagents are, for example, N-succinimidyl 3-(2-pyridyldithio) propionate (SPDP) or N,N'-(1,3-phenylene)bismaleimide; N,N'-ethylene-bis-(iodoacetamide) or other such reagent having 6 to 11 carbon methylene bridges; and 1,5-difluoro-2,4-dinitrobenzene. Other cross-linking agents useful for this purpose include: p,p'-difluoro-m,m'-dinitrodiphenylsulfone; dimethyl adipimidate; phenol-1,4-disulfonylchloride; hexamethylenediisocyanate or diisothiocyanate, or azophenyl-p-diisocyanate; glutaraldehyde and disdiazobenzidine. Cross-linking agents may be homobifunctional, i.e., having two functional groups that undergo the same reaction. A preferred homobifunctional cross-linking agent is bismaleimidohexane (BMH). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of proteins (or polypeptides) that contain cysteine residues. Cross-linking agents may also be heterobifunctional. Heterobifunctional cross-linking agents have two different functional groups, for example an amine-reactive group and a thiol-reactive group, that will cross-link two proteins having free amines and thiols, respectively. Examples of heterobifunctional cross-linking agents are Succinimidyl-4-(N-maleimidomethyl)-cyclohexane-1-carboxylate (SMCC), m-maleimidobenzoyl-N-hydroxysuccinimide ester (MBS), and succinimide 4-(p-maleimidophenyl) butyrate (SMPB), an extended chain analog of MBS. The succinimidyl group of these cross-linkers reacts with a primary amine, and the thiol-reactive maleimide forms a covalent bond with the thiol of a cysteine residue. Because cross-linking agents often have low solubility in water, a hydrophilic moiety, such as a sulfonate group, may be added to the cross-linking agent to improve its water solubility. Sulfo-MBS and sulfo-SMCC are examples of cross-linking agents modified for water solubility. Many cross-linking agents yield a conjugate that is essentially non-cleavable under cellular conditions. Therefore, some cross-linking agents contain a covalent bond, such as a disulfide, that is cleavable under cellular conditions. For example, Traut's reagent, dithiobis (succinimidylpropionate) (DSP), and N-succinimidyl 3-(2-pyridyldithio) propionate (SPDP) are well-known cleavable cross-linkers. The use of a cleavable cross-linking agent permits the cell penetrating peptide, the at least one antigen or antigenic epitope and the at least one TLR peptide agonist comprised by the complex to separate from each other after delivery into the target cell. For this purpose, direct disulfide linkage may also be useful. Chemical cross-linking may also include the use of spacer arms.

Spacer arms provide intramolecular flexibility or adjust intramolecular distances between conjugated moieties and thereby may help preserve biological activity. A spacer arm may be in the form of a protein (or polypeptide) moiety that includes spacer amino acids, e.g. proline. Alternatively, a spacer arm may be part of the cross-linking agent, such as in "long-chain SPDP" (Pierce Chem. Co., Rockford, Ill., cat. No. 21651 H). Numerous cross-linking agents, including the ones discussed above, are commercially available. Detailed instructions for their use are readily available from the commercial suppliers. More detailed information on protein cross-linking and conjugate preparation, which is useful in the context of linkage of components a), b), and c) comprised by the complex can be retrieved from: Wong, Chemistry of Protein Conjugation and Cross-Linking, CRC Press (1991).

Cross-linking agents for peptide or protein crosslinking include for example (i) amine-to-amine crosslinkers, e.g. homobifunctional amine-specific protein crosslinking reagents based on NHS-ester and imidoester reactive groups for selective conjugation of primary amines; available in short, long, cleavable, irreversible, membrane permeable, and cell surface varieties; (ii) sulfhydryl-to-carbohydrate crosslinkers, e.g. crosslinking reagents based on maleimide and hydrazide reactive groups for conjugation and formation of covalent crosslinks; (iii) sulfhydryl-to-sulfhydryl crosslinkers, e.g. homobifunctional sulfhydryl-specific crosslinking reagents based on maleimide or pyridyldithiol reactive groups for selective covalent conjugation of protein and peptide thiols (reduced cysteines) to form stable thioether bonds; (iv) photoreactive crosslinkers, e.g. aryl azide, diazirine, and other photo-reactive (light-activated) chemical heterobifunctional crosslinking reagents to conjugate proteins, nucleic acids and other molecular structures involved in receptor-ligand interaction complexes via two-step activation; (v) amine-to-sulfhydryl crosslinkers, e.g. heterobifunctional protein crosslinking reagents for conjugation between primary amine (lysine) and sulfhydryl (cysteine) groups of proteins and other molecules; available with different lengths and types of spacer arms; and (vi) amine-to-amine crosslinkers, e.g. carboxyl-to-amine crosslinkers, e.g. Carbodiimide crosslinking reagents, DCC and EDC (EDAC), for conjugating carboxyl groups (glutamate, aspartate, C-termini) to primary amines (lysine, N-termini) and also N-hydroxysuccinimide (NHS) for stable activation of carboxylates for amine-conjugation.

Examples of crosslinkers in general, which can be used in the complex comprised by the combination for use according to the present invention, include N-(α-Maleimidoacetoxy)-succinimide ester, N-5-Azido-2-nitrobenzyloxy-succinimide, 1,4-Bis-Maleimidobutane, 1,4-Bis-Maleimmidyl-2,3-dihydroxy-butane, Bis-Maleimidohexane, Bis-Maleimidoethane, N-(β-Maleimidopropionic acid) hydrazide*TFA, N-(β-Maleimidopropyloxy) succinimide ester, 1,8-Bis-Maleimidodiethylene-glycol, 1,11-Bis-Maleimidotriethyleneglycol, Bis (sulfosuccinimidyl) suberate, Bis (sulfosuccinimidyl) glutarate-d0, Bis (sulfosuccinimidyl) 2,2,4,4-glutarate-d4, Bis (sulfosuccinimidyl) suberate-d0, Bis (sulfosuccinimidyl) 2,2,7,7-suberate-d4, Bis (NHS) PEG5, Bis (NHS) PEG9, Bis (2-[succinimidoxycarbonyloxy]ethyl) sulfone, N,N-Dicyclohexylcarbodiimide, 1-5-Difluoro-2,4-dinitrobenzene, Dimethyl adipimidate*2HCl, Dimethyl pimelimidate*2HCl, Dimethyl suberimidate*2HCl, Disuccinimidyl glutarate, Dithiobis (succimidylpropionate) (Lomant's Reagent), Disuccinimidyl suberate, Disuccinimidyl tartarate, Dimethyl 3,3'-dithiobispropionimidate*2HCl, Dithiobis-maleimidoethane, 3,3'-Dithiobis (sulfosuccinimidylpropionate), 1-Ethyl-3-(3-dimethylaminopropyl) carbodiimide hydrochloride, Ethylene glycol bis (succinimidylsuccinate), N-ε-Maleimidocaproic acid, N-(ε-Maleimidocaproic acid) hydrazide, N-(ε-Maleimidocaproyloxy) succinimide ester, N-(γ-Maleimidobutryryloxy) succinimide ester, N-(κ-Maleimidoundecanoic acid) hydrazide, NHS-LC-Diazirine, Succinimidyl 4-(N-maleimidomethyl) cyclohexane-1-carboxy-(6-amidocaproate, Succinimidyl 6-(3'-[2-pyridyldithio]propionamido) hexanoate, L-Photo-Leucine, L-Photo-Methionine, m-Maleimidobenzoyl-N-hydroxysuccinimide ester, 4-(4-N-Maleimidophenyl)-butyric acid hydrazide*HCl, 2-[N2-(4-Azido-2,3,5,6-tetrafluorobenzoyl)-N6-(6-biotinamidocaproyl)-L-lysinyl]ethylmethanethiosulfate, 2-{N2-[N6-(4-Azido-2,3,5,6-tetrafluorobenzoyl)-N6-(6-biotinamidocaproyl)-L-lysinyl]}ethylmethanethiosulfate, N-Hydroxysuccinimide, N-hydroxysuccinimide ester ethane azide, N-hydroxysuccinimide ester tetraoxapentadecane azide, N-hydroxysuccinimide ester dodecaoxanonatriacontane azide, NHS-Phosphine, 3-(2-Pyridyldithio) propionylhydrazide, 2-pyridyldithiol-tetraoxatetradecane-N-hydroxysuccinimide, 2-pyridyldithiol-tetraoxaoctatriacontane-N-hydroxysuccinimide, N-(p-Maleimidophenyl) isocyanate, Succinimdyl 3-(bromoacetamido) propionate, NHS-Diazirine, NHS-SS-Diazirine, N-succinimidyl iodoacetate, N-Succinimidyl(4-iodoacetyl)aminobenzoate, Succinimidyl 4-(N-maleimido-methyl) cyclohexane-1-carboxylate, NHS-PEG2-Maliemide, NHS-PEG4-Maliemide, NHS-PEG6-Maleimide, NHS-PEG8-Maliemide, NHS-PEG12-Maliemide, NHS-PEG24-Maleimide, Succinimidyl 4-(p-maleimido-phenyl) butyrate, Succinimidyl-6-(β-maleimidopropionamido) hexanoate, 4-Succinimidyloxycarbonyl-methyl-α-(2-pyridyldithio) toluene, Succinimidyl-(4-psoralen-8-yloxy) butyrate, N-Succinimidyl 3-(2-pyridyldithio) propionate, Ethylene glycol bis (sulfo-succinimidyl succinate), N-(ε-Maleimidocaproyloxy) sulfosuccinimide ester, N-(γ-Maleimidobutryloxy) sulfosuccinimide ester, N-(κ-Maleimidoundecanoyloxy) sulfosuccinimide ester, Sulfo-NHS-LC-Diazirine, Sulfosuccinimidyl 6-(3'-[2-pyridyldithio]propionamido) hexanoate, m-Maleimidobenzoyl-N-hydroxysulfosuccinimide ester, N-Hydroxysuccinimide, Sulfo-NHS-Phosphine, Sulfosuccinimidyl 6-(4'-azido-2'-nitrophenylamino) hexanoate, Sulfo-NHS-(2-6-[Biotinamido]-2-(p-azidobezamido), Sulfo-NHS-Diazirine, Sulfo-NHS-SS-Diazirine, Sulfosuccinimidyl (4-iodo-acetyl) aminobenzoate, Sulfosuccinimidyl 4-(N-maleimidomethyl)cyclohexane-1-carboxylate, Sulfosuccinimidyl 4-(p-maleimidophenyl) butyrate, Tris-(2-Maleimidoethyl)amine (Trifunctional), and Tris-(succimimidyl aminotricetate) (Trifunctional).

The linkage between two out of the three components a), b), and c) of the complex comprised by the combination for use according to the present invention may be directly or indirectly, i.e. two components directly adjoin or they may be linked by an additional component of the complex, e.g. a spacer or a linker.

A direct linkage may be realized preferably by an amide bridge, if the components to be linked have reactive amino or carboxy groups. More specifically, if the components to be linked are peptides, polypeptides or proteins, a peptide bond is preferred. Such a peptide bond may be formed using a chemical synthesis involving both components (an N-terminal end of one component and the C-terminal end of the other component) to be linked, or may be formed directly via a protein synthesis of the entire peptide sequence of both components, wherein both (protein or peptide) components are preferably synthesized in one step. Such protein synthesis methods include e.g., without being limited thereto, liquid phase peptide synthesis methods or solid peptide synthesis methods, e.g. solid peptide synthesis methods according to Merrifield, t-Boc solid-phase peptide synthesis, Fmoc solid-phase peptide synthesis, BOP (Benzotriazole-1-yl-oxy-tris-(dimethylamino)-phosphonium hexafluorophosphate) based solid-phase peptide synthesis, etc., Alternatively, ester or ether linkages are preferred.

Moreover, in particular if the components to be linked are peptides, polypeptides or proteins, a linkage may occur via the side chains, e.g. by a disulfide bridge. Further components of other chemical nature, e.g. the at least one antigen or antigenic epitope if it is not of peptidic nature, may be likewise attached to the components of peptidic nature, e.g. the cell penetrating peptide, the at least one TLR peptide agonist, and the at least one antigen or antigenic epitope if it is of peptidic nature. The linkage via a side chain will preferably be based on side chain amino, thiol or hydroxyl groups, e.g. via an amide or ester or ether linkage. A linkage of a peptide main chain with a peptide side chain of another component may also be via an isopeptide bond. An isopeptide bond is an amide bond that is not present on the main chain of a protein. The bond forms between the carboxyl terminus of one peptide or protein and the amino group of a lysine residue on another (target) peptide or protein.

The complex comprised by the combination for use according to the present invention may optionally comprise a spacer or linker, which are non-immunologic moieties, which are preferably cleavable, and which link component a) and b) and/or component a) and c), and/or component b) and c), and/or link consecutive antigens or antigenic epitopes, and/or link consecutive TLR peptide agonists, and/or link consecutive cell penetrating peptides, and/or which can be placed at the C-terminal part of components b) and/or c). A linker or spacer may preferably provide further functionalities in addition to linking of the components, and preferably being cleavable, more preferably naturally cleavable inside the target cell, e.g. by enzymatic cleavage. However, such further functionalities do in particular not include any immunological functionalities. Examples of further functionalities, in particular regarding linkers in fusion proteins, can be found in Chen X. et al., 2013: Fusion Protein Linkers: Property, Design and Functionality. Adv Drug Deliv Rev. 65 (10): 1357-1369, wherein for example also in vivo cleavable linkers are disclosed. Moreover, Chen X. et al., 2013: Fusion Protein Linkers: Property, Design and Functionality. Adv Drug Deliv Rev. 65 (10): 1357-1369 also discloses various linkers, e.g. flexible linkers and rigid linkers, and linker designing tools and databases, which can be useful in the complex comprised by the combination for use according to the present invention or to design a linker to be used in the complex.

Said spacer may be peptidic or non-peptidic, preferably the spacer is peptidic. Preferably, a peptidic spacer consists of about 1, 2, 3, 4, 5, 6, 7, 8, 9, or 10 amino acids, more preferably of about 1, 2, 3, 4, or 5 amino acids. The amino acid sequence of the peptidic spacer may be identical to that of the N-terminal or C-terminal flanking region of any of the components a), b), or c). Alternatively a peptidic spacer can consist of non-natural amino acid sequences such as an amino acid sequence resulting from conservative amino acid substitutions of said natural flanking regions or sequences of known cleavage sites for proteases such as an enterokinase target site (amino acid sequence: DDDK, SEQ ID NO: 16), factor Xa target site (amino acid sequence: IEDGR, SEQ ID NO: 17), thrombin target site (amino acid sequence: LVPRGS, SEQ ID NO: 18), protease TEV target site (amino acid sequence: ENLYFQG, SEQ ID NO: 19), PreScission protease target site (amino acid sequence LEVLFQGP, SEQ ID NO: 20), polycationic amino acids, e.g. poly K, furin target site (amino acid sequence RX(R/K)R, SEQ ID NO: 21). In a particular embodiment, the peptidic spacer does not contain any Cys (C) residues. In a preferred embodiment the linker sequence contains at least 20%, more preferably at least 40% and even more preferably at least 50% Gly or β-alanine residues, e.g. GlyGlyGlyGlyGly (SEQ ID NO: 22), GlyGlyGlyGly (SEQ ID NO: 23), GlyGlyGly, CysGlyGly or GlyGlyCys, etc. Appropriate linker sequences can be easily selected and prepared by a person skilled in the art. They may be composed of D and/or L amino acids. Further examples of a peptidic spacer include the amino acid sequences EQLE (SEQ ID NO: 24) or TEWT (SEQ ID NO: 25) or any conservative substitutions thereof.

A non-peptidic spacer can include or may be an ester, a thioester, and a di-sulfide.

In particular, the complex comprised by the combination for use according to the invention may comprise a spacer or linker, in particular a peptidic spacer, placed between component a) and b) and/or between component a) and c), and/or between component b) and c). This peptidic spacer can be chosen by one skilled in the art so that it may be cut by the cell machinery once the complex comprising the cell penetrating peptide and the cargo molecule has been internalized.

When the complex comprises several antigens or antigenic epitopes or when the complex comprises several TLR peptide agonists, it will be clear for one skilled in the art that each of the antigens or antigenic epitopes and/or each of the TLR peptide agonists comprised in the complex can be either directly linked to each other or linked via spacers or linkers such as, e.g., a peptidic spacer consisting of a few amino acids. Alternatively, when the complex comprised by the combination for use according to the present invention comprises several antigens or antigenic epitopes or when the complex comprises several TLR peptide agonists, it is also possible that some antigens or antigenic epitopes and/or some TLR peptide agonists comprised by the complex are directly linked to each other and some other antigens or antigenic epitopes and/or some other TLR peptide agonists are linked via spacers or linkers such as a peptidic spacer consisting of a few amino acids.

For example, two successive antigens or antigenic epitopes or two successive TLR peptide agonists comprised in the complex are linked to each other by spacers consisting of the natural flanking regions of said antigens or antigenic epitopes or of said TLR peptide agonists, respectively. For example, the spacer used to link a first antigen/antigenic epitope or a first TLR peptide agonist to a second antigen/antigenic epitope or to a second TLR peptide agonist, respectively, may consists of up to about 8 amino acids corresponding to up to about 4 amino acids of the N-terminal or C-terminal flanking region of the first antigen/antigenic epitope or the first TLR peptide agonist, followed by up to about 4 amino acids of the N-terminal or C-terminal flanking region of the second antigen/antigenic epitope or the second TLR peptide agonist. In an illustration of the complex comprised by the combination for use according to the present invention, the spacer used to link a first antigen/antigenic epitope or a first TLR peptide agonist ("antigen/epitope/TLR peptide agonist 1") to a second epitope ("antigen/epitope/TLR peptide agonist 2") consists of about 8 amino acids corresponding to any possible combination ranging from: 0 flanking amino acid of antigen/epitope/TLR peptide agonist 1 and 8 flanking amino acids of antigen/ epitope/TLR peptide agonist 2, to 8 flanking amino acids of antigen/epitope/TLR peptide agonist 1 and 0 flanking amino acid of antigen/epitope/TLR peptide agonist 2, i.e. including 1 flanking amino acid of antigen/epitope/TLR peptide agonist 1 and 7 flanking amino acids of antigen/epitope/TLR peptide agonist 2, 2 flanking amino acid of antigen/epitope/ TLR peptide agonist 1 and 6 flanking amino acids of antigen/epitope/TLR peptide agonist 2, 3 flanking amino acid of antigen/epitope/TLR peptide agonist 1 and 5 flanking amino acids of antigen/epitope/TLR peptide agonist 2, 4 flanking amino acid of antigen/epitope/TLR peptide agonist 1 and 4 flanking amino acids of antigen/epitope/TLR peptide agonist 2, 5 flanking amino acid of antigen/epitope/TLR peptide agonist 1 and 3 flanking amino acids of antigen/ epitope/TLR peptide agonist 2, 6 flanking amino acid of antigen/epitope/TLR peptide agonist 1 and 2 flanking amino acids of antigen/epitope/TLR peptide agonist 2, 7 flanking amino acid of antigen/epitope/TLR peptide agonist 1 and 1 flanking amino acid of antigen/epitope/TLR peptide agonist 2, 8 flanking amino acid of antigen/epitope/TLR peptide agonist 1 and 0 flanking amino acids of antigen/epitope/TLR peptide agonist 2. It will be understood that the total of 8 amino acids constituting a spacer linking two consecutive antigen/epitope/TLR peptide agonist is not an absolute value and the spacer could also be composed of a total of, for instance, 3 amino acids, 4 amino acids, 5 amino acids, 6 amino acids, 7 amino acids, 9 amino acids or 10 amino acids. Similarly, equivalent combinations as mentioned above are also an illustration of the complex in the situation where a spacer has less or more than 8 amino acids.

In another particular illustration of the complex comprised by the combination for use according to the present invention, the spacer used to link a first antigen/antigenic epitope or a first TLR peptide agonist ("antigen/epitope/TLR peptide agonist 1") to a second antigen/antigenic epitope or to a second TLR peptide agonist, respectively, ("antigen/ epitope/TLR peptide agonist 2") consists of e.g. 1, 2, 3, 4, or 5 amino acids. More particularly, said spacer's amino acid sequence can correspond to the 4 amino acids of the N-terminal or C-terminal flanking region of antigen/epitope/TLR peptide agonist 1 or antigen/epitope/TLR peptide agonist 2. A spacer as described above may also be placed at the C-terminal part of the last antigen/epitope/TLR peptide agonist comprised in the complex.

The technics for linking two of the three components a), b), and c) are well documented in the literature and can depend on the nature of the at least one antigen or antigenic epitope. For instance, linkages between two of the three components a), b), and c) can be achieved via cleavable disulphide linkages through total stepwise solid-phase synthesis or solution-phase or solid-phase fragment coupling, stable amide, thiazolidine, oxime and hydrazine linkage, disulphide linkage, stable thiomaleimide linkage, peptide bond (including peptide bonds between amino acids of a fusion protein), or electrostatic or hydrophobic interactions.

Preferably, the at least one antigen or antigenic epitope comprised by the complex as well as any optional spacer or linker comprised by the complex are of peptidic nature. More preferably, all components of the complex comprised by the combination for use according to the present invention, e.g. the cell penetrating peptide, the at least one antigen or antigenic epitope, which is a peptide, polypeptide or protein, the at least one TLR peptide agonist and any optional peptidic linker or spacer are linked in the complex comprised by the combination for use according to the present invention by a peptide bond. Most preferably, the complex comprised by the combination for use according to the present invention is thus a peptide, polypeptide or protein, such as a fusion protein, e.g. a recombinant fusion protein.

In this context, a complex comprising or consisting of an amino acid sequence according to SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, SEQ ID NO: 42, SEQ ID NO: 43, SEQ ID NO: 44, or SEQ ID NO: 45; or a complex comprising or consisting of an amino acid sequence sharing at least 50%, at least 60%, at least 70%, at least 75%, at least 80%, at least 85%, at least 90%, at least 95% or at least 98% sequence identity with any of SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 41, SEQ ID NO: 42, SEQ ID NO: 43, SEQ ID NO: 44, or SEQ ID NO: 45 is preferred. A complex comprising or consisting of an amino acid sequence according to SEQ ID NO: 27, SEQ ID NO: 28, SEQ ID NO: 29, SEQ ID NO:31, SEQ ID NO: 41, SEQ ID NO: 42, SEQ ID NO: 43 or SEQ ID NO: 45 or a complex comprising or consisting of an amino acid sequence sharing at least 50%, at least 60%, at least 70%, at least 75%, at least 80%, at least 85%, at least 90%, at least 95% or at least 98% sequence identity with any of SEQ ID NO: 27, SEQ ID NO: 28, SEQ ID NO: 29, SEQ ID NO: 31, SEQ ID NO: 41, SEQ ID NO: 42, SEQ ID NO: 43 or SEQ ID NO: 45 is more preferred. A complex comprising or consisting of an amino acid sequence according to SEQ ID NO: 28, SEQ ID NO: 31, SEQ ID NO: 41, SEQ ID NO: 42, SEQ ID NO: 43 or SEQ ID NO: 45 or a complex comprising or consisting of an amino acid sequence sharing at least 50%, at least 60%, at least 70%, at least 75%, at least 80%, at least 85%, at least 90%, at least 95% or at least 98% sequence identity with SEQ ID NO: 28, SEQ ID NO: 31, SEQ ID NO: 41, SEQ ID NO: 42, SEQ ID NO: 43 or SEQ ID NO: 45 is even more preferred. A complex comprising or consisting of an amino acid sequence according to SEQ ID NO: 28, SEQ ID NO: 41, SEQ ID NO: 42, SEQ ID NO: 43 or SEQ ID NO: 45 or a complex comprising or consisting of an amino acid sequence sharing at least 50%, at least 60%, at least 70%, at least 75%, at least 80%, at least 85%, at least 90%, at least 95% or at least 98% sequence identity with SEQ ID NO: 28, SEQ ID NO: 41, SEQ ID NO: 42, SEQ ID NO: 43 or SEQ ID NO: 45 is particularly preferred.

```
SEQ ID NO: 26:
MHHHHHHNID RPKGLAFTDV DVDSIKIAWE SPQGQVSRYR VTYSSPEDGI

RELFPAPDGEDDTAELQGLR PGSEYTVSVV ALHDDMESQP LIGIQSTKRY KNRVASRKSR

AKFKQLLQHY REVAAAKSSE NDRLRLLLKE SLKISQAVHA AHAEINEAGR EVVGVGALKV

PRNQDWLGVP RFAKFASFEA QGALANIAVD KANLDVEQLE SIINFEKLTE WTGS
```

-continued

SEQ ID NO: 27:
MHHHHHHSTV HEILCKLSLE GDHSTPPSAY GSVKPYTNFD AEKRYKNRVA

SRKSRAKFKQ LLQHYREVAA AKSSENDRLR LLLKESLKIS QAVHAAHAEI NEAGREVVGV

GALKVPRNQD WLGVPRFAKF ASFEAQGALA NIAVDKANLD VEQLESIINF EKLTEWTGS

SEQ ID NO: 28:
MHHHHHHKRYKNRVA SRKSRAKFKQ LLQHYREVAA AKSSENDRLR LLLKESLKIS

QAVHAAHAEI NEAGREVVGV GALKVPRNQD WLGVPRFAKF ASFEAQGALA

NIAVDKANLD VEQLESIINF EKLTEWTGSS TVHEILCKLS LEGDHSTPPS AYGSVKPYTN

FDAE

SEQ ID NO: 29:
MHHHHHHKRY KNRVASRKSR AKFKQLLQHY REVAAAKESL KISQAVHAAH

AEINEAGREV VGVGALKVPR NQDWLGVPRF AKFASFEAQG ALANIAVDKA

NLDVEQLESI INFEKLTEWT GSSTVHEILC KLSLEGDHST PPSAYGSVKP YTNFDAE

SEQ ID NO: 30:
MHHHHHHREV AAAKSSENDR LRLLLKESLK ISQAVHAAHA EINEAGREVV

GVGALKVPRN QDWLGVPRFA KFASFEAQGA LANIAVDKAN LDVEQLESII

NFEKLTEWTG SSTVHEILCK LSLEGDHSTP PSAYGSVKPY TNFDAE

SEQ ID NO: 31:
MHHHHHHNID RPKGLAFTDV DVDSIKIAWE SPQGQVSRYR VTYSSPEDGI

RELFPAPDGE DDTAELQGLR PGSEYTVSVV ALHDDMESQP LIGIQSTKRY KNRVASRKSR

AKFKQLLQHY REVAAAKESL KISQAVHAAH AEINEAGREV VGVGALKVPR

NQDWLGVPRF AKFASFEAQG ALANIAVDKA NLDVEQLESI INFEKLTEWT GS

SEQ ID NO: 32:
MHHHHHHNID RPKGLAFTDV DVDSIKIAWE SPQGQVSRYR VTYSSPEDGI

RELFPAPDGE DDTAELQGLR PGSEYTVSVV ALHDDMESQP LIGIQSTREV AAAKSSENDR

LRLLLKESLK ISQAVHAAHA EINEAGREVV GVGALKVPRN QDWLGVPRFA KFASFEAQGA

LANIAVDKAN LDVEQLESII NFEKLTEWTG S

SEQ ID NO: 41:
KRYKNRVASRKSRAKFKQLLQHYREVAAAKSSENDRLRLLLKVTYHSPSYAYHQFERRAILN

RLVQFIKDRISVVQALVLTSTVHEILCKLSLEGDHSTPPSAYGSVKPYTN FDAE

SEQ ID NO: 42:
KRYKNRVASRKSRAKFKQLLQHYREVAAAKSSENDRLRLLLKNYRIATFKNWPFLEDCAME

ELTVSEFLKLDRQRSTVHEILCKLSLEGDHSTPPSAYGSVKPYTNFDAE

SEQ ID NO: 43:
KRYKNRVASRKSRAKFKQLLQHYREVAAAKSSENDRLRLLLKHLELASMTNMELMSSIVST

VHEILCKLSLEGDHSTPPSAYGSVKPYTNFDAE

SEQ ID NO: 44:
RKKRRQRRRVKRISQAVHAAHAEINEAGRRVKRKVPRNQDWLRVKRASFEAQGALANIAV

DKARVKRSIINFEKLRVKRSTVHEILCKLSLEGDHSTPPSAYGSVKPYTNFDAE

SEQ ID NO: 45:
KRYKNRVASRKSRAKFKQLLQHYREVAAAKSSENDRLRLLLKLFRAAQLANDVVLQIMEHLELA

SMTNMELMSSIVVISASIIVFNLLELEGSTVHEILCKLSLEGDHSTPPSAYGSVKPYTNFDAE

Arrangement of Components a), b), and c) in the Complex

The components a), b), and c) may be arranged in the complex comprised by the combination for use according to the present invention in any way.

In particular if more than one cell penetrating peptide and/or more than one antigen or antigenic epitope and/or more than one TLR peptide agonist are comprised by the complex, the more than one cell penetrating peptide may be positioned in a non-consecutive manner, i.e. at least one antigen or antigenic epitope (component b)) and/or at least one TLR peptide agonist (component c)) may interrupt a stretch of consecutively positioned cell penetrating peptides and/or the cell penetrating peptides may be positioned with component b) and/or with component c) in an alternating manner. Similarly, the more than one antigen or antigenic epitope may be positioned in a non-consecutive manner, i.e. at least one cell penetrating peptide (component a)) and/or at least one TLR peptide agonist (component c)) may interrupt a stretch of consecutively positioned antigens or antigenic epitopes and/or the antigens or antigenic epitopes may be positioned with component a) and/or with component c) in an alternating manner. Similarly, the more than one TLR peptide agonist may be positioned in a non-consecutive manner, i.e. at least one cell penetrating peptide (component a)) and/or at least one antigen or antigenic epitope (component b)) may interrupt a stretch of consecutively positioned TLR peptide agonists and/or the TLR peptide agonists may be positioned with component a) and/or with component b) in an alternating manner.

However, it is preferred that the more than one cell penetrating peptide is positioned in the complex comprised by the combination for use according to the present invention in a consecutive manner and/or the more than one antigen or antigenic epitope is positioned in the complex comprised by the combination for use according to the present invention in a consecutive manner and/or the more than one TLR peptide agonist is positioned in the complex comprised by the combination for use according to the present invention in a consecutive manner. This means in particular that all single units of a certain component, i.e. all cell penetrating peptides, all antigens or antigenic epitopes or all TLR peptide agonists, which are comprised by the complex are positioned in a stretch, which is not interrupted by any of the other two components. Rather, the other two components are positioned in the complex for example before or after such a stretch of all single units of said certain component. However, the single units of said certain component positioned consecutively in such a way may be linked to each other for example by a spacer or linker as described herein, which is not of the other two components.

It is particularly preferred that each of the components a), b), and c) is positioned in a consecutive manner.

Structurally each component a), b), and c) typically comprises a single main chain and at least one side chain. The term "main chain" (also "backbone chain"), as used in the context of the present invention, refers to the main continuous chain of covalently bond atoms in a molecule. For example, in peptides, polypeptides and proteins, the main chain (backbone) typically comprises alpha-carbon atoms and nitrogen atoms of the constituent amino acids linked by the peptide bond. The backbone does not include the side chains. The term "side chain" (also "pendant chain"), as used in the context of the present invention, refers to a chemical group that is attached to a core part of the molecule called "main chain" or backbone. For example, in peptides, polypeptides and proteins, the side chains typically represent the (main) parts of the constituent amino acids, which are attached to the alpha-carbon atoms of the backbone.

In the complex comprised by the combination for use according to the present invention, the components a), b), and c) may be covalently linked via a linker or spacer as described herein or they may be directly covalently linked. Independently of whether a spacer or linker is used for covalent linkage or not, there are in principle four options of how two of the three components are linked to each other in the complex comprised by the combination for use according to the present invention, namely:

(i) via main-chain/main-chain linkage,
(ii) via main-chain/side-chain linkage,
(iii) via side-chain/main-chain linkage or
(iv) via side-chain/side chain linkage.

Preferably, all three components a), b), and c) are linked via main-chain/main-chain linkage, thus resulting in particular in a main chain of the complex, which comprises the main chain of one or more cell penetrating peptide(s), the main chain of one or more antigen(s) or antigenic epitope(s), and the main chain of one or more TLR peptide agonist(s). In other words, the main chain of one or more cell penetrating peptide(s), the main chain of one or more antigen(s) or antigenic epitope(s), and the main chain of one or more TLR peptide agonist(s) constitute the main chain of the complex, optionally together with further components, for example linker(s), spacer(s), etc., Accordingly, the following arrangements of the components a), b), and c) are preferred, in particular if the at least one antigen or antigenic epitope is a peptide, polypeptide or protein, whereby said preferred arrangements are shown below in N-terminus→C-terminus direction of the main chain of the complex and wherein all three components a), b), and c) are linked via main-chain/main-chain linkage and may be optionally linked by a linker, a spacer or another additional component:

(α) component a) (cell penetrating peptide)-component b) (at least one antigen or antigenic epitope)-component c) (at least one TLR peptide agonist);

(β) component c) (at least one TLR peptide agonist)-component a) (cell penetrating peptide)-component b) (at least one antigen or antigenic epitope);

(γ) component a) (cell penetrating peptide)-component c) (at least one TLR peptide agonist)-component b) (at least one antigen or antigenic epitope);

(δ) component c) (at least one TLR peptide agonist)-component b) (at least one antigen or antigenic epitope)-component a) (cell penetrating peptide);

(ε) component b) (at least one antigen or antigenic epitope)-component a) (cell penetrating peptide)-component c) (at least one TLR peptide agonist); or (ζ) component b) (at least one antigen or antigenic epitope)-component c) (at least one TLR peptide agonist)-component a) (cell penetrating peptide).

In particular if all three components a), b), and c) are linked via main-chain/main-chain linkage, it is preferred that the at least one antigen or antigenic epitope is positioned C-terminally of the cell penetrating peptide, whereby the cell penetrating peptide and the at least one antigen or antigenic epitope are optionally linked by a further component, e.g. a linker, a spacer, or by the at least one TLR peptide agonist. Accordingly, this corresponds to the arrangements (a), (B), and (y) from the arrangements shown above, i.e. from the above arrangements (a), (B), and (y) are more preferred.

Even more preferably, the at least one antigen or antigenic epitope is positioned C-terminally of the cell penetrating peptide, whereby the cell penetrating peptide and the at least one antigen or antigenic epitope are optionally linked by a further component, e.g. a linker, a spacer, but not by the at least one TLR peptide agonist. Accordingly, this corresponds to the arrangements (a) and (B) from the arrangements shown above, i.e. from the above arrangements (a) and (B) are even more preferred. Particularly preferably, the complex comprised by the combination for use according to the present invention is a recombinant polypeptide or a recombinant protein and the components a) to c) are positioned in N-terminus→C-terminus direction of the main chain of said complex in the order:

(α) component a)-component b)-component c); or (β) component c)-component a)-component b), wherein the components may be linked by a further component, in particular by a linker or a spacer.

Particularly preferred is arrangement (a), wherein the at least one TLR agonist comprises or consists of at least one TLR2 agonist, for example:

(α1) component a) (cell penetrating peptide)-component b) (at least one antigen or antigenic epitope)-one or more TLR2 peptide agonist, e.g. 1, 2, 3, 4, or 5 TLR2 peptide agonist(s);

(α2) component a) (cell penetrating peptide)-component b) (at least one antigen or antigenic epitope)-one or more TLR2 peptide agonist, e.g. 1, 2, 3, 4, or 5 TLR2 peptide agonist(s), one or more TLR4 peptide agonist, e.g. 1, 2, 3, 4, or 5 TLR4 peptide agonist(s) and one or more TLR5 peptide agonist, e.g. 1, 2, 3, 4, or 5 TLR5 peptide agonist(s);

(α3) component a) (cell penetrating peptide)-component b) (at least one antigen or antigenic epitope)-one or more TLR2 peptide agonist, e.g. 1, 2, 3, 4, or 5 TLR2 peptide agonist(s) and one or more TLR4 peptide agonist, e.g. 1, 2, 3, 4, or 5 TLR4 peptide agonist(s); or (α4) component a) (cell penetrating peptide)-component b) (at least one antigen or antigenic epitope)-one or more TLR2 peptide agonist, e.g. 1, 2, 3, 4, or 5 TLR2 peptide agonist(s) and one or more TLR5 peptide agonist, e.g. 1, 2, 3, 4, or 5 TLR5 peptide agonist(s).

Alternatively, in such an arrangement comprising a TLR2 peptide agonist, additional TLR peptide agonists may also be arranged at other positions in the complex, for example:

(α5) one or more TLR4 peptide agonist, e.g. 1, 2, 3, 4, or 5 TLR4 peptide agonist(s)-component a) (cell penetrating peptide)-component b) (at least one antigen or antigenic epitope)-one or more TLR2 peptide agonist, e.g. 1, 2, 3, 4, or 5 TLR2 peptide agonist(s);

(α6) one or more TLR5 peptide agonist, e.g. 1, 2, 3, 4, or 5 TLR5 peptide agonist(s)-component a) (cell penetrating peptide)-component b) (at least one antigen or antigenic epitope)-one or more TLR2 peptide agonist, e.g. 1, 2, 3, 4, or 5 TLR2 peptide agonist(s); or (α7) one or more TLR4 peptide agonist, e.g. 1, 2, 3, 4, or 5 TLR4 peptide agonist(s) and one or more TLR5 peptide agonist, e.g. 1, 2, 3, 4, or 5 TLR5 peptide agonist(s)-component a) (cell penetrating peptide)-component b) (at least one antigen or antigenic epitope)-one or more TLR2 peptide agonist, e.g. 1, 2, 3, 4, or 5 TLR2 peptide agonist(s).

Particularly preferred is arrangement (B), wherein the at least one TLR agonist comprises or consists of at least one TLR4 agonist, for example:

(β1) one or more TLR4 peptide agonist, e.g. 1, 2, 3, 4, or 5 TLR4 peptide agonist(s)-component a) (cell penetrating peptide)-component b) (at least one antigen or antigenic epitope);

(β2) one or more TLR4 peptide agonist, e.g. 1, 2, 3, 4, or 5 TLR4 peptide agonist(s), one or more TLR2 peptide agonist, e.g. 1, 2, 3, 4, or 5 TLR2 peptide agonist(s) and one or more TLR5 peptide agonist, e.g. 1, 2, 3, 4, or 5 TLR5 peptide agonist(s)-component a) (cell penetrating peptide) component b) (at least one antigen or antigenic epitope);

(β3) one or more TLR4 peptide agonist, e.g. 1, 2, 3, 4, or 5 TLR4 peptide agonist(s) and one or more TLR2 peptide agonist, e.g. 1, 2, 3, 4, or 5 TLR2 peptide agonist(s)-component a) (cell penetrating peptide)-component b) (at least one antigen or antigenic epitope); or (β4) one or more TLR4 peptide agonist, e.g. 1, 2, 3, 4, or 5 TLR4 peptide agonist(s) and one or more TLR5 peptide agonist, e.g. 1, 2, 3, 4, or 5 TLR5 peptide agonist(s)-component a) (cell penetrating peptide)-component b) (at least one antigen or antigenic epitope).

Alternatively, in such an arrangement comprising a TLR4 peptide agonist, additional TLR peptide agonists may also be arranged at other positions in the complex, for example:

(β5) one or more TLR4 peptide agonist, e.g. 1, 2, 3, 4, or 5 TLR4 peptide agonist(s)-component a) (cell penetrating peptide)-component b) (at least one antigen or antigenic epitope)-one or more TLR2 peptide agonist, e.g. 1, 2, 3, 4, or 5 TLR2 peptide agonist(s);

(β6) one or more TLR4 peptide agonist, e.g. 1, 2, 3, 4, or 5 TLR4 peptide agonist(s)-component a) (cell penetrating peptide)-component b) (at least one antigen or antigenic epitope)-one or more TLR5 peptide agonist, e.g. 1, 2, 3, 4, or 5 TLR5 peptide agonist(s); or (β7) one or more TLR4 peptide agonist, e.g. 1, 2, 3, 4, or 5 TLR4 peptide agonist(s)-component a) (cell penetrating peptide)-component b) (at least one antigen or antigenic epitope)-one or more TLR2 peptide agonist, e.g. 1, 2, 3, 4, or 5 TLR2 peptide agonist(s) and one or more TLR5 peptide agonist, e.g. 1, 2, 3, 4, or 5 TLR5 peptide agonist(s).

Alternatively, only two of the three components a), b), and c) are linked via main-chain/main-chain linkage in the complex comprised by the combination for use according to the present invention.

For example components a) and b) are linked via main-chain/main-chain linkage, resulting thus in the following arrangements of the components a) and b) in the complex, shown in N-terminus→C-terminus direction of the main chain of the complex, whereby the components a) and b) may be optionally linked by a further component, e.g. a linker, a spacer etc.:

(1) cell penetrating peptide (a)-antigen/antigenic epitope (b); or (2) antigen/antigenic epitope (b)-cell penetrating peptide (a).

In such a case, component c), i.e. the at least one TLR peptide agonist, may then be arranged via main-chain/side-chain linkage, via side-chain/main-chain linkage or via side-chain/side chain linkage to either the cell penetrating peptide (a) or to the antigen/antigenic epitope (b) or, if present, to an additional component like a spacer or linker, which may be, for example, positioned between the cell penetrating peptide (a) and the antigen/antigenic epitope (b). This includes the following arrangements:

(i) component c) may be linked—optionally via a spacer or a linker—via main-chain/side-chain linkage to component a), i.e. the main chain of the at least one TLR peptide agonist is covalently linked—optionally via a spacer or a linker—to the side chain of the cell penetrating peptide;

(ii) component c) may be linked—optionally via a spacer or a linker—via side-chain/main-chain linkage to component a), i.e. the side chain of the at least one TLR peptide agonist is covalently linked—optionally via a spacer or a linker—to the main chain of the cell penetrating peptide;

(iii) component c) may be linked—optionally via a spacer or a linker—via side-chain/side-chain linkage to component a), i.e. the side chain of the at least one TLR peptide agonist is covalently linked—optionally via a spacer or a linker—to the side chain of the cell penetrating peptide;
(iv) component c) may be linked—optionally via a spacer or a linker—via main-chain/side-chain linkage to component b), i.e. the main chain of the at least one TLR peptide agonist is covalently linked—optionally via a spacer or a linker—to the side chain of the at least one antigen or antigenic epitope;
(v) component c) may be linked—optionally via a spacer or a linker—via side-chain/main-chain linkage to component b), i.e. the side chain of the at least one TLR peptide agonist is covalently linked—optionally via a spacer or a linker—to the main chain of the at least one antigen or antigenic epitope;
(vi) component c) may be linked—optionally via a spacer or a linker—via side-chain/side-chain linkage to component b), i.e. the side chain of the at least one TLR peptide agonist is covalently linked—optionally via a spacer or a linker—to the side chain of the at least one antigen or antigenic epitope;
(vii) component c) may be linked—optionally via a spacer or a linker—via main-chain/side-chain linkage to a linker or a spacer positioned between component a) and component b), i.e. the main chain of the at least one TLR peptide agonist is covalently linked—optionally via a spacer or a linker—to the side chain of a linker or a spacer positioned between component a) and component b);
(viii) component c) may be linked—optionally via a spacer or a linker—via side-chain/main-chain linkage to a linker or a spacer positioned between component a) and component b), i.e. the side chain of the at least one TLR peptide agonist is covalently linked—optionally via a spacer or a linker—to the main chain of a linker or a spacer positioned between component a) and component b); or
(ix) component c) may be linked—optionally via a spacer or a linker—via side-chain/side-chain linkage to a linker or a spacer positioned between component a) and component b), i.e. the side chain of the at least one TLR peptide agonist is covalently linked—optionally via a spacer or a linker—to the side chain of a linker or a spacer positioned between component a) and component b).

For example components b) and c) are linked via main-chain/main-chain linkage, resulting thus in the following arrangements of the components b) and c) in the complex, shown in N-terminus→C-terminus direction of the main chain of the complex, whereby the components b) and c) may be optionally linked by a further component, e.g. a linker, a spacer etc.:
(3) antigen/antigenic epitope (b)-TLR peptide agonist (c); or
(4) TLR peptide agonist (c)-antigen/antigenic epitope (b).

In such a case, component a), i.e. the cell penetrating peptide, may then be arranged via main-chain/side-chain linkage, via side-chain/main-chain linkage or via side-chain/side chain linkage to either the antigen/antigenic epitope (b) or to the TLR peptide agonist (c) or, if present, to an additional component like a spacer or linker, which may be, for example, positioned between the antigen/antigenic epitope (b) and the TLR peptide agonist (c). This includes the following arrangements:
(x) component a) may be linked—optionally via a spacer or a linker—via main-chain/side-chain linkage to component b), i.e. the main chain of the cell penetrating peptide is covalently linked—optionally via a spacer or a linker—to the side chain of the at least one antigen or antigenic epitope;
(xi) component a) may be linked—optionally via a spacer or a linker—via side-chain/main-chain linkage to component b), i.e. the side chain of the cell penetrating peptide is covalently linked—optionally via a spacer or a linker—to the main chain of the at least one antigen or antigenic epitope;
(xii) component a) may be linked—optionally via a spacer or a linker—via side-chain/side-chain linkage to component b), i.e. the side chain of the cell penetrating peptide is covalently linked—optionally via a spacer or a linker—to the side chain of the at least one antigen or antigenic epitope;
(xiii) component a) may be linked—optionally via a spacer or a linker—via main-chain/side-chain linkage to component c), i.e. the main chain of the cell penetrating peptide is covalently linked—optionally via a spacer or a linker—to the side chain of the at least one TLR peptide agonist;
(xiv) component a) may be linked—optionally via a spacer or a linker—via side-chain/main-chain linkage to component c), i.e. the side chain the cell penetrating peptide is covalently linked—optionally via a spacer or a linker—to the main chain of the at least one TLR peptide agonist;
(xv) component a) may be linked—optionally via a spacer or a linker—via side-chain/side-chain linkage to component c), i.e. the side chain of the cell penetrating peptide is covalently linked—optionally via a spacer or a linker—to the side chain of the at least one TLR peptide agonist;
(xvi) component a) may be linked—optionally via a spacer or a linker—via main-chain/side-chain linkage to a linker or a spacer positioned between component b) and component c), i.e. the main chain of the cell penetrating peptide is covalently linked—optionally via a spacer or a linker—to the side chain of a linker or a spacer positioned between component b) and component c);
(xvii) component a) may be linked—optionally via a spacer or a linker—via side-chain/main-chain linkage to a linker or a spacer positioned between component b) and component c), i.e. the side chain of the cell penetrating peptide is covalently linked—optionally via a spacer or a linker—to the main chain of a linker or a spacer positioned between component b) and component c); or
(xviii) component a) may be linked—optionally via a spacer or a linker—via side-chain/side-chain linkage to a linker or a spacer positioned between component b) and component c), i.e. the side chain of the cell penetrating peptide is covalently linked—optionally via a spacer or a linker—to the side chain of a linker or a spacer positioned between component b) and component c).

For example components a) and c) are linked via main-chain/main-chain linkage, resulting thus in the following arrangements of the components a) and b) in the complex, shown in N-terminus→C-terminus direction of the main chain of the complex, whereby the components a) and c) may be optionally linked by a further component, e.g. a linker, a spacer etc.:
(5) cell penetrating peptide (a)-TLR peptide agonist (c); or
(6) TLR peptide agonist (c)-cell penetrating peptide (a).

In such a case, component b), i.e. the at least one antigen or antigenic epitope, may then be arranged via main-chain/side-chain linkage, via side-chain/main-chain linkage or via side-chain/side chain linkage to either the cell penetrating peptide (a) or to the TLR peptide agonist (c) or, if present, to an additional component like a spacer or linker, which may be, for example, positioned between the cell penetrating peptide (a) and the TLR peptide agonist (c). This includes the following arrangements:

(xix) component b) may be linked—optionally via a spacer or a linker—via main-chain/side-chain linkage to component a), i.e. the main chain of the at least one antigen or antigenic epitope is covalently linked—optionally via a spacer or a linker—to the side chain of the cell penetrating peptide;

(xx) component b) may be linked—optionally via a spacer or a linker—via side-chain/main-chain linkage to component a), i.e. the side chain of the at least one antigen or antigenic epitope is covalently linked—optionally via a spacer or a linker—to the main chain of the cell penetrating peptide;

(xxi) component b) may be linked—optionally via a spacer or a linker—via side-chain/side-chain linkage to component a), i.e. the side chain of the at least one antigen or antigenic epitope is covalently linked—optionally via a spacer or a linker—to the side chain of the cell penetrating peptide;

(xxii) component b) may be linked—optionally via a spacer or a linker—via main-chain/side-chain linkage to component c), i.e. the main chain of the at least one antigen or antigenic epitope is covalently linked—optionally via a spacer or a linker—to the side chain of the at least one TLR peptide agonist;

(xxiii) component b) may be linked—optionally via a spacer or a linker—via side-chain/main-chain linkage to component c), i.e. the side chain of the at least one antigen or antigenic epitope is covalently linked—optionally via a spacer or a linker—to the main chain of the at least one TLR peptide agonist;

(xxiv) component b) may be linked—optionally via a spacer or a linker—via side-chain/side-chain linkage to component c), i.e. the side chain of the at least one antigen or antigenic epitope is covalently linked—optionally via a spacer or a linker—to the side chain of the at least one TLR peptide agonist;

(xxv) component b) may be linked—optionally via a spacer or a linker—via main-chain/side-chain linkage to a linker or a spacer positioned between component a) and component c), i.e. the main chain of the at least one antigen or antigenic epitope is covalently linked—optionally via a spacer or a linker—to the side chain of a linker or a spacer positioned between component a) and component c);

(xxvi) component b) may be linked—optionally via a spacer or a linker—via side-chain/main-chain linkage to a linker or a spacer positioned between component a) and component c), i.e. the side chain of the at least one antigen or antigenic epitope is covalently linked—optionally via a spacer or a linker—to the main chain of a linker or a spacer positioned between component a) and component c); or (xxvii) component b) may be linked—optionally via a spacer or a linker—via side-chain/side-chain linkage to a linker or a spacer positioned between component a) and component c), i.e. the side chain of the at least one antigen or antigenic epitope is covalently linked—optionally via a spacer or a linker—to the side chain of a linker or a spacer positioned between component a) and component c).

Alternatively, it is also conceivable that in the complex comprised by the combination for use according to the present invention all three of the components a), b), and c) are arranged via main-chain/side-chain linkage, via side-chain/main-chain linkage or via side-chain/side chain linkage, optionally linked by an additional component, e.g. a spacer or a linker.

Preferred Combinations of a Preferred Immune Checkpoint Modulator and a Preferred Complex Comprising a Cell Penetrating Peptide, at Least One Antigen or Antigenic Epitope As described above, a preferred combination for use according to the present invention comprises a preferred immune checkpoint modulator as described herein. Moreover, a preferred combination for use according to the present invention comprises a preferred complex as described herein comprising a (preferred) cell penetrating peptide, at least one (preferred) antigen or antigenic epitope and at least one (preferred) TLR peptide agonist.

A more preferred combination for use according to the present invention comprises (i) a preferred immune checkpoint modulator as described herein and (ii) a preferred complex comprising as described herein comprising a (preferred) cell penetrating peptide, at least one (preferred) antigen or antigenic epitope and at least one (preferred) TLR peptide agonist. In the following preferred embodiments of a preferred combination for use according to the present invention are described.

In a preferred combination for use according to the present invention the complex is a recombinant polypeptide or a recombinant protein wherein a) the cell penetrating peptide has an amino acid sequence comprising or consisting of an amino acid sequence according to SEQ ID NO: 6 (CPP3/Z13), SEQ ID NO: 7 (CPP4/Z14), SEQ ID NO: 8 (CPP5/Z15), or SEQ ID NO: 11 (CPP8/Z18), or sequence variants thereof as described herein without abrogating said peptide's cell penetrating ability;

b) the at least one antigen or antigenic epitope is a peptide, polypeptide or protein and, preferably, comprises or consists of at least one cancer epitope or tumor epitope; and c) the TLR peptide agonist is a TLR2 peptide agonist and/or a TLR4 peptide agonist.

It is also preferred in the combination for use according to the present invention that the immune checkpoint modulator is a modulator of CD40, CTLA-4, PD-L1, PD-L2, PD-1 and/or IDO, preferably the immune checkpoint modulator is an inhibitor of CTLA-4, PD-L1, PD-L2, PD-1 and/or IDO or an activator of CD40, more preferably the immune checkpoint modulator is an inhibitor of CTLA-4, PD-L1, PD-1 and/or IDO and even more preferably the immune checkpoint modulator is an inhibitor of CTLA-4 and/or PD-1.

It is also preferred in the combination for use according to the present invention that the immune checkpoint modulator is a modulator of CD40, LAG3, CTLA-4, PD-L1, PD-L2, PD-1 and/or IDO, preferably the immune checkpoint modulator is an inhibitor of LAG3, CTLA-4, PD-L1, PD-L2, PD-1 and/or IDO or an activator of CD40, more preferably the immune checkpoint modulator is an inhibitor of LAG3, CTLA-4, PD-L1, PD-1 and/or IDO and even more preferably the immune checkpoint modulator is an inhibitor of LAG3, CTLA-4 and/or PD-1.

For example, in a preferred combination for use according to the present invention
the complex is a recombinant polypeptide or a recombinant protein wherein
a) the cell penetrating peptide has an amino acid sequence comprising or consisting of an amino acid sequence according to SEQ ID NO: 6 (CPP3/Z13), SEQ ID NO: 7 (CPP4/Z14), SEQ ID NO: 8 (CPP5/Z15), or SEQ ID NO: 11 (CPP8/Z18), or sequence variants thereof as described herein without abrogating said peptide's cell penetrating ability;
b) the at least one antigen or antigenic epitope is a peptide, polypeptide or protein and, preferably, comprises or consists of at least one cancer epitope or tumor epitope; and
c) the TLR peptide agonist is a TLR2 peptide agonist and/or a TLR4 peptide agonist; and
the immune checkpoint modulator is a modulator of the CD40 pathway, of the CTLA-4 pathway and/or of the PD-1 pathway, in particular the immune checkpoint modulator is an activator of CD40 or an inhibitor of CD40, CTLA-4, PD-L1, PD-L2 and/or PD-1, more preferably the immune checkpoint modulator is an inhibitor of CTLA-4, PD-L1, PD-L2 and/or PD-1, and even more preferably the immune checkpoint modulator is an inhibitor of CTLA-4 and/or PD-1.

For example, in a preferred combination for use according to the present invention
the complex is a recombinant polypeptide or a recombinant protein wherein
a) the cell penetrating peptide has an amino acid sequence comprising or consisting of an amino acid sequence according to SEQ ID NO: 6 (CPP3/Z13), SEQ ID NO: 7 (CPP4/Z14), SEQ ID NO: 8 (CPP5/Z15), or SEQ ID NO: 11 (CPP8/Z18), or sequence variants thereof as described herein without abrogating said peptide's cell penetrating ability;
b) the at least one antigen or antigenic epitope is a peptide, polypeptide or protein and, preferably, comprises or consists of at least one cancer epitope or tumor epitope; and
c) the TLR peptide agonist is a TLR2 peptide agonist and/or a TLR4 peptide agonist; and
the immune checkpoint modulator is a modulator of the CD40 pathway, of the CTLA-4 pathway, of the LAG3 pathway, and/or of the PD-1 pathway, in particular the immune checkpoint modulator is an activator of CD40 or an inhibitor of CD40, LAG3, CTLA-4, PD-L1, PD-L2 and/or PD-1, more preferably the immune checkpoint modulator is an inhibitor of LAG3, CTLA-4, PD-L1, PD-L2 and/or PD-1, and even more preferably the immune checkpoint modulator is an inhibitor of LAG3, CTLA-4 and/or PD-1.

In a preferred combination for use as described herein, in particular in such a preferred combination for use as described above, it is preferred if more than one immune checkpoint modulator, e.g. checkpoint inhibitor, is used, in particular if at least 2, 3, 4, 5, 6, 7, 8, 9 or 10 distinct immune checkpoint modulators, e.g. checkpoint inhibitors, are used, preferably 2, 3, 4 or 5 distinct immune checkpoint modulators, e.g. checkpoint inhibitors, are used, more preferably 2, 3 or 4 distinct immune checkpoint modulators, e.g. checkpoint inhibitors, are used, even more preferably 2 or 3 distinct immune checkpoint modulators, e.g. checkpoint inhibitors, are used and most preferably 2 distinct immune checkpoint modulators, e.g. checkpoint inhibitors, are used.

Thereby it is preferred that at least (i) an inhibitor of the CTLA-4 pathway, in particular an inhibitor of CTLA-4 and (ii) an inhibitor of the PD-1 pathway, in particular an inhibitor of PD-1, PD-L1 or PD-L2 are used; preferably at least (i) an inhibitor of CTLA-4 and (ii) an inhibitor of PD-1 are used.

Use in Medicine

The combination of the immune checkpoint modulator as described herein and of the complex comprising a cell penetrating peptide, at least one antigen or antigenic epitope and at least one TLR peptide agonist as described herein is for use in medicine.

Such a combination of the immune checkpoint modulator as described herein and of the complex comprising a cell penetrating peptide, at least one antigen or antigenic epitope and at least one TLR peptide agonist as described herein is able to initiate or enhance the efficacy of checkpoint modulators. Moreover, such a combination as described herein can simultaneously (i) stimulate multi-epitopic cytotoxic T cell-mediated immunity, (ii) induce $T_h$ cells and (iii) promote immunological memory, thereby generating potent, long lasting (anti-tumor) immunity. Immunological memory is essential to protect against relapse, in particular against tumor relapse. Taken together, the present invention thus provides to a combination as described herein which is able to initiate, enable, enhance or improve an immune response, in particular which enables, enhances or improves the subject's or tumor response to checkpoint modulators.

The combination for use according to the present invention can be useful in a variety of diseases. Preferably the combination as described herein is for use (for the preparation of a medicament) for the prevention, treatment or stabilization of a disease or disorder, such as those which can be treated by immunotherapy, including cancers, infectious diseases, autoimmunity disorders, hematological diseases and transplant rejections. Accordingly, a combination as described herein for use in the prevention, treatment or stabilization of a disease or disorder, such as those which can be treated by immunotherapy, including cancers, infectious diseases, autoimmunity disorders, hematological diseases and transplant rejections is preferred.

In the context of the present invention, it is particularly preferred that the combination of the immune checkpoint modulator as described herein and of the complex comprising a cell penetrating peptide, at least one antigen or antigenic epitope and at least one TLR peptide agonist as described herein is used in the prevention and/or treatment of cancer.

The term "disease" as used in the context of the present invention is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

Preferred diseases to be treated and/or prevented by use of the combination of the immune checkpoint modulator as described herein and of the complex comprising a cell penetrating peptide, at least one antigen or antigenic epitope and at least one TLR peptide agonist as described herein include cancer, hematological disorders, infectious diseases, autoimmunity disorders and transplant rejections. Thereby, treatment and/or prevention of cancer and infectious diseases is preferred and treatment and/or prevention of cancer is more preferred. For cancer, a malignant neoplasm of the brain or a malignant neoplasm of lymphoid, hematopoietic and related tissue are preferred and glioblastoma is more preferred.

Preferably, the combination of the immune checkpoint modulator as described herein and of the complex comprising a cell penetrating peptide, at least one antigen or antigenic epitope and at least one TLR peptide agonist as described herein may be used for (the preparation of a medicament for) the prophylaxis, treatment and/or amelioration of cancer or tumor diseases, including diseases caused by defective apoptosis, preferably selected from acusticus neurinoma, anal carcinoma, astrocytoma, basalioma, Behcet's syndrome, bladder cancer, blastomas, bone cancer, brain metastases, brain tumors, brain cancer (glioblastomas), breast cancer (mamma carcinoma), Burkitt's lymphoma, carcinoids, cervical colon carcinoma, colorectal cancer, corpus carcinoma, craniopharyngeomas, CUP syndrome, endometrial carcinoma, gall bladder cancer, genital tumors, including cancers of the genitourinary tract, glioblastoma, gliomas, head/neck tumors, hepatomas, histocytic lymphoma, Hodgkin's syndromes or lymphomas and non-Hodgkin's lymphomas, hypophysis tumor, intestinal cancer, including tumors of the small intestine, and gastrointestinal tumors, Kaposi's sarcoma, kidney cancer, kidney carcinomas, laryngeal cancer or larynx cancer, leukemia, including acute myeloid leukaemia (AML), erythroleukemia, acute lymphoid leukaemia (ALL), chronic myeloid leukaemia (CML), and chronic lymphocytic leukaemia (CLL), lid tumor, liver cancer, liver metastases, lung carcinomas (=lung cancer=bronchial carcinoma), small cell lung carcinomas and non-small cell lung carcinomas, and lung adenocarcinoma, lymphomas, lymphatic cancer, malignant melanomas, mammary carcinomas (=breast cancer), medulloblastomas, melanomas, meningiomas, Mycosis fungoides, neoplastic diseases neurinoma, oesophageal cancer, oesophageal carcinoma (=oesophageal cancer), oligodendroglioma, ovarian cancer (=ovarian carcinoma), ovarian carcinoma, pancreatic carcinoma (=pancreatic cancer), penile cancer, penis cancer, pharyngeal cancer, pituitary tumour, plasmocytoma, prostate cancer (=prostate tumors), rectal carcinoma, rectal tumors, renal cancer, renal carcinomas, retinoblastoma, sarcomas, Schneeberger's disease, skin cancer, e.g. melanoma or non-melanoma skin cancer, including basal cell and squamous cell carcinomas as well as psoriasis, pemphigus vulgaris, soft tissue tumours, spinalioma, stomach cancer, testicular cancer, throat cancer, thymoma, thyroid carcinoma, tongue cancer, urethral cancer, uterine cancer, vaginal cancer, various virus-induced tumors such as, for example, papilloma virus-induced carcinomas (e.g. cervical carcinoma=cervical cancer), adenocarcinomas, herpes virus-induced tumors (e.g. Burkitt's lymphoma, EBV-induced B-cell lymphoma, cervix carcinoma), hepatitis B-induced tumors (hepatocell carcinomas), HTLV-1- and HTLV-2-induced lymphomas, vulval cancer, wart conditions or involvement, etc. In the present context, the terms "therapy" and "therapeutic" preferably mean to have at least some minimal physiological effect upon being administered to a living body. For example, a physiological effect upon administering a "therapeutic" anti-tumor compound may be the inhibition of tumor growth, or decrease in tumor size, or prevention reoccurrence of the tumor. Preferably, in the treatment of cancer or neoplastic disease, a compound which inhibits the growth of a tumor or decreased the size of the tumor or prevents the reoccurrence of the tumor would be considered therapeutically effective. The term "anti-tumor drug" therefore preferably means any therapeutic agent having therapeutic effect against a tumor, neoplastic disease or cancer.

Further preferred examples of cancers to be treated with the combination of the immune checkpoint modulator as described herein and of the complex comprising a cell penetrating peptide, at least one antigen or antigenic epitope and at least one TLR peptide agonist as described herein include brain cancer, prostate cancer, breast cancer, ovarian cancer, esophageal cancer, lung cancer, liver cancer, kidney cancer, melanoma, gut carcinoma, lung carcinoma, head and neck squamous cell carcinoma, chronic myeloid leukemia, colorectal carcinoma, gastric carcinoma, endometrial carcinoma, myeloid leukemia, lung squamous cell carcinoma, acute lymphoblastic leukemia, acute myelogenous leukemia, bladder tumor, promyelocytic leukemia, non-small cell lung carcinoma, and sarcoma. Most preferably, the combination of the immune checkpoint modulator as described herein and of the complex comprising a cell penetrating peptide, at least one antigen or antigenic epitope and at least one TLR peptide agonist as described herein are used to treat colorectal cancer.

The cancer may be a solid tumor, blood cancer, or lymphatic cancer. The cancer may be benign or metastatic.

Preferably, the cancer to be prevented and/or treated is a glioma, more preferably highly invasive glioblastoma multiforme (GBM). Gliomas are the most frequent form of primary brain tumors in adults, with glioblastoma multiforme (GBM) having the poorest prognosis. This tumor is notorious for its highly invasive and aggressive behavior. In particular, the combination of the immune checkpoint modulator as described herein and of the complex comprising a cell penetrating peptide, at least one antigen or antigenic epitope and at least one TLR peptide agonist as described herein may be used in conjunction with existing modalities for glioma, more specifically highly invasive GBM. T lymphocytes can actively seek out neoplastic cells in the brain, and have the potential to safely eliminate specific tumor cells without damaging the surrounding healthy tissues.

Moreover, the combination of the immune checkpoint modulator as described herein and of the complex comprising a cell penetrating peptide, at least one antigen or antigenic epitope and at least one TLR peptide agonist as described herein may be used for (the preparation of a medicament for) the prophylaxis, treatment and/or amelioration of infectious diseases, preferably viral, retroviral, bacterial or protozoological infectious diseases. Such infectious diseases are typically selected from AIDS, anthrax, Japanese encephalitis, bacterial infectious diseases such as miscarriage (prostate inflammation), anthrax, appendicitis, borreliosis, botulism, Camphylobacter, *Chlamydia trachomatis* (inflammation of the urethra, conjunctivitis), cholera, diphtheria, donavanosis, epiglottitis, typhus fever, gas gangrene, gonorrhoea, rabbit fever, Heliobacter *pylori*, whooping cough, climatic bubo, osteomyelitis, Legionnaire's disease, chicken-pox, condyloma *acuminata*, cytomegalic virus (CMV), dengue fever, early summer meningoencephalitis (ESME), Ebola virus, colds, fifth disease, foot-and-mouth disease, herpes simplex type I, herpes simplex type II, herpes zoster, HSV, infectious diseases caused by parasites, protozoa or fungi, such as amoebiasis, bilharziosis, Chagas disease, *Echinococcus*, fish tapeworm, fish poisoning (Ciguatera), fox tapeworm, athlete's foot, canine tapeworm, candidosis, yeast fungus spots, scabies, cutaneous Leishmaniosis, lambliasis (giardiasis), lice, onchocercosis (river blindness), fungal diseases, bovine tapeworm, schistosomiasis, porcine tapeworm, toxoplasmosis, trichomoniasis, trypanosomiasis (sleeping sickness), visceral Leishmaniosis, nappy/diaper dermatitis or miniature tapeworm, infectious erythema, influenza, Kaposi's sarcoma, Lassa fever, Leishmaniasis, leprosy, listeriosis, Lyme borreliosis, malaria, Marburg virus infection, measles, meningitis, including bacterial meningitis, molluscum contagiosum, mononucleosis, mumps, *Mycoplasma hominis*, neonatal sepsis (Chorioamnionitis), noma, Norwalk virus infection, otitis media, paratyphus, Pfeiffer's glandular fever, plague, pneumonia, polio (poliomyelitis, childhood lameness), pseudo-croup, rabies, Reiter's syndrome, Rocky Mountain spotted fever, *Salmonella* paratyphus, *Salmonella* typhus, SARS, scarlet fever, shingles, hepatitis, smallpox, soft chancre, syphilis, tetanus, three-day fever, tripper, tsutsugamushi disease, tuberculosis, typhus, vaginitis (colpitis), viral diseases caused by cytomegalovirus (CMV), orthopox variola virus, orthopox alastrim virus, parapox *ovis* virus, molluscum contagiosum virus, herpes simplex virus 1, herpes simplex virus 2, herpes B virus, varicella zoster virus, pseudorabies virus, human cytomegaly virus, human herpes virus 6, human herpes virus 7, Epstein-Barr virus, human herpes virus 8, hepatitis B virus, chikungunya virus, O'nyong'nyong virus, rubivirus, hepatitis C virus, GB virus C, West Nile virus, dengue virus, yellow fever virus, louping ill virus, St. Louis encephalitis virus, Japan B encephalitis virus, Powassan virus, FSME virus, SARS, SARS-associated corona virus, human corona virus 229E, human corona virus Oc43, Torovirus, human T cell lymphotropic virus type I, human T cell lymphotropic virus type II, HIV (AIDS), i.e. human immunodeficiency virus type 1 or human immunodeficiency virus type 2, influenza virus, Lassa virus, lymphocytic choriomeningitis virus, Tacaribe virus, Junin virus, Machupo virus, Borna disease virus, Bunyamwera virus, California encephalitis virus, Rift Valley fever virus, sand fly fever virus, Toscana virus, Crimean-Congo haemorrhagic fever virus, Hazara virus, Khasan virus, Hantaan virus, Seoul virus, Prospect Hill virus, Puumala virus, Dobrava Belgrade virus, Tula virus, sin nombre virus, Lake Victoria Marburg virus, Zaire Ebola virus, Sudan Ebola virus, Ivory Coast Ebola virus, influenza virus A, influenza virus B, influenza viruses C, parainfluenza virus, measles virus, mumps virus, respiratory syncytial virus, human metapneumovirus, vesicular stomatitis Indiana virus, rabies virus, Mokola virus, Duvenhage virus, European bat lyssavirus 1+2, Australian bat lyssavirus, adenoviruses A-F, human papilloma viruses, condyloma virus 6, condyloma virus 11, polyoma viruses, adeno-associated virus 2, rotaviruses, or orbiviruses, Varicella including Varizella zoster, and malaria parasite (*Plasmodium falciparum, Plasmodium vivax, Plasmodium ovale, Plasmodium malariae, Plasmodium knowlesi*), viral infectious diseases such as AIDS, infectious diseases caused by Condyloma *acuminata*, hollow warts, Dengue fever, three-day fever, Ebola virus, cold, early summer meningoencephalitis (FSME), flu, shingles, hepatitis, herpes simplex type I, herpes simplex type II, Herpes zoster, influenza, Japanese encephalitis, Lassa fever, Marburg virus, warts, West Nile fever, yellow fever, etc.

Further preferred examples of infectious diseases include diseases caused by viruses, bacteria, fungi, protozoa and multicellular parasites. They include, for instance, Amoebiasis, Anthrax, Buruli Ulcer (*Mycobacterium ulcerans*), Caliciviruses associated diarrhoea, *Campylobacter* diarrhoea, Cervical Cancer (Human papillomavirus), *Chlamydia trachomatis* associated genital diseases, Cholera, Crimean-Congo haemorrhagic fever, Dengue Fever, Diptheria, Ebola haemorrhagic fever, Enterotoxigenic *Escherichia coli* (ETEC) diarrhoea, Gastric Cancer (*Helicobacter pylori*), Gonorrhea, Group A *Streptococcus* associated diseases, Group B *Streptococcus* associated diseases, *Haemophilus influenzae* B pneumonia and invasive disease, Hepatitis A, Hepatitis B, Hepatitis C, Hepatitis E diarrhoea, Herpes simplex type 2 genital ulcers, HIV/AIDS, Hookworm Disease, Influenza, Japanese encephalitis, Lassa Fever, Leishmaniasis, Leptospirosi, Liver cancer (Hepatitis B), Liver Cancer (Hepatitis C), Lyme Disease, Malaria, Marburg haemorrhagic fever, Measles, Mumps, Nasopharyngeal cancer (Epstein-Barr virus), *Neisseria meningitidis* Meningitis, Parainfluenza associated pneumonia, Pertussis, Plague, Poliomyelitis, Rabies, Respiratory syncytial virus (RSV) pneumonia, Rift Valley fever, Rotavirus diarrhoea, Rubella, Schistosomiasis, Severe Acute Respiratory Syndrome (SARS), Shigellosis, Smallpox, *Staphylococcus aureus* associated diseases, Stomach Cancer (*Helicobacter pylori*), *Streptococcus pneumoniae* and invasive disease, Tetanus, Tick-borne encephalitis, Trachoma, Tuberculosis, Tularaemia, Typhoid fever, West-Nile virus associated disease, Yellow fever.

Moreover, the combination of the immune checkpoint modulator as described herein and of the complex comprising a cell penetrating peptide, at least one antigen or antigenic epitope and at least one TLR peptide agonist as described herein may be used for (the preparation of a medicament for) the prophylaxis, treatment and/or amelioration of autoimmune disorders, for example autoimmune diseases of the CNS, auto-inflammatory diseases, Celiac disease; Sjogren's syndrome, systemic lupus erythematosus etc., Typically, autoimmune diseases arise from an abnormal immune response of the body against substances and tissues normally present in the body (autoimmunity). This may be restricted to certain organs (e.g. in autoimmune thyroiditis) or may involve a particular tissue in different places (e.g. Goodpasture's disease which may affect the basement membrane in both the lung and the kidney). Autoimmune diseases may be classified by corresponding type of hypersensitivity: type I (i.e. urticaria induced by autologous serum), type II, type III, or type IV.

Examples of autoimmune diseases include Blau syndrome, Bullous pemphigoid, Cancer, Castleman's disease, Celiac disease, Chagas disease, Chronic inflammatory demyelinating polyneuropathy, Chronic recurrent multifocal osteomyelitis, chronic obstructive pulmonary disease, Churg-Strauss syndrome, Cicatricial pemphigoid, Cogan syndrome, Cold agglutinin disease, Complement component 2 deficiency, Contact dermatitis, Cranial arteritis, CREST syndrome, Crohn's disease, Cushing's Syndrome, Dercum's disease, Dermatitis herpetiformis, Dermatomyositis, Diabetes mellitus type 1, Diffuse cutaneous systemic sclerosis, Dressler's syndrome, lupus, Discoid lupus erythematosus, Eczema, Acute disseminated encephalomyelitis (ADEM), Addison's disease, Agammaglobulinemia, Amyotrophic lateral sclerosis (Also Lou Gehrig's disease; Motor Neuron Disease), Ankylosing Spondylitis Antiphospholipid syndrome, Antisynthetase syndrome, Atopic dermatitis, Autoimmune aplastic anemia, Autoimmune cardiomyopathy, Autoimmune hemolytic anemia, Autoimmune hepatitis, Autoimmune inner ear disease, Autoimmune lymphoproliferative syndrome, Autoimmune peripheral neuropathy, Autoimmune pancreatitis, Autoimmune polyendocrine syndrome, Autoimmune progesterone dermatitis, Autoimmune thrombocytopeniarpura, Autoimmune urticarial, Autoimmune uveitis, Balo disease/Balo concentric sclerosis, Behcet's disease, Berger's disease, Bickerstaff's encephalitis, Endometriosis, Enthesitis-related arthritis, Eosinophilic gastroenteritis, Epidermolysis bullosa acquisita, Erythroblastosis fetalis, Evan's syndrome, Fibrodysplasia ossificans, Fibrosing alveolitis (or Idiopathic pulmonary fibrosis), Gastritis, Glomerulonephritis, Goodpasture's syndrome, Graves' disease, Guillain-Barre syndrome, Hashimoto's encephelopathy, Hashimoto's thyroiditis, Gestational Pemphigoid, Hidradenitis suppurativa, Hypogammaglobulinemia, Idiopathic thrombocytopeni purpura (Autoimmune thrombocytopenia purpura), IgA nephropathy, Occular cicatricial pemphigoid, Inclusion body myositis, Rheumatoid arthritis, Chronic inflammatory Rheumatic fever, demyelinating polyneuropathy, Sarcoidosis, Palindromic rheumatism, Interstitial cystitis, Juvenile idiopathic Schizophrenia, PANDAS (pediatric arthritis aka Juvenile autoimmune rheumatoid arthritis), Schmidt syndrome, neuropsychiatric Kawasaki's disease another form of APS, Schnitzler syndrome, Paraneoplastic cerebellar myasthenic syndrome, Leukocytoclastic Serum Sickness, Lichen planus, Sjogren's syndrome, Lichen sclerosus, Parsonage-Turner, Linear IgA disease, Still's disease, Pemphigus vulgaris, Lupoid hepatitis, Autoimmune hepatitis, Stiff person syndrome, Pernicious anaemia, Subacute bacterial endocarditis (SBE), POEMS syndrome, Lupus erythematosus, Sweet's syndrome, Sympathetic ophthalmia, Meniere's disease, Systemic lupus, Primary biliary cirrhosis, Miller-Fisher syndrome, Takayasu's arteritis, cholangitis, Progressive inflammatory neuropathy, Mucha-Habermann disease, Psoriasis, Psoriatic arthritis, Pyoderma gangrenosum, Multiple sclerosis, Pure red cell aplasia, Rasmussen's encephalitis, Myasthenia gravis, Transverse myelitis, Raynaud phenomenon, Microscopic colitis, Ulcerative colitis, Myositis, idiopathic inflammatory bowel disease (IBD), Neuromyelitis optica, Devic's disease, and Neuromyotonia.

Moreover, the combination of the immune checkpoint modulator as described herein and of the complex comprising a cell penetrating peptide, at least one antigen or antigenic epitope and at least one TLR peptide agonist as described herein may be used for (the preparation of a medicament for) the prophylaxis, treatment and/or amelioration of hematological disorders, which are typically disorders which primarily affect the blood. Thereby, hematological malignancies are preferred.

Examples of hematological diseases include myeloid disorders, including Hemoglobinopathies (congenital abnormality of the hemoglobin molecule or of the rate of hemoglobin synthesis), e.g. Sickle-cell disease, Thalassemia, Methemoglobinemia; Anemias (lack of red blood cells or hemoglobin), e.g. Iron deficiency anemia, Megaloblastic anemia including Vitamin B12 deficiency, Pernicious anemia, and Folate deficiency, Hemolytic anemias (destruction of red blood cells) including Genetic disorders of RBC membrane such as Hereditary spherocytosis, Hereditary elliptocytosis, and Congenital dyserythropoietic anemia, Genetic disorders of RBC metabolism such as Glucose-6-phosphate dehydrogenase deficiency (G6PD), and Pyruvate kinase deficiency, Immune mediated hemolytic anemia (direct Coombs test is positive) such as Autoimmune hemolytic anemia including Warm antibody autoimmune hemolytic anemia (such as Idiopathic, Systemic lupus erythematosus (SLE), and Evans' syndrome (antiplatelet antibodies and hemolytic antibodies)) and Cold antibody autoimmune hemolytic anemia (such as Idiopathic cold hemagglutinin syndrome, Infectious mononucleosis, and Paroxysmal cold hemoglobinuria), Alloimmune hemolytic anemia including Hemolytic disease of the newborn (HDN) (such as Rh disease (Rh D), ABO hemolytic disease of the newborn, Anti-Kell hemolytic disease of the newborn, Rhesus c hemolytic disease of the newborn, Rhesus E hemolytic disease of the newborn, and other blood group incompatibility (RhC, Rhe, Kid, Duffy, MN, P and others)), Drug induced immune mediated hemolytic anemia including Penicillin (high dose) and Methyldopa, Hemoglobinopathies (i.e. where these is an unstable or crystalline hemoglobin), Paroxysmal nocturnal hemoglobinuria (rare acquired clonal disorder of red blood cell surface proteins), Direct physical damage to RBCs including Microangiopathic hemolytic anemia and Secondary to artificial heart valve(s), Aplastic anemia such as Fanconi anemia, Diamond-Blackfan anemia (inherited pure red cell aplasia), and Acquired pure red cell aplasia; Decreased numbers of cells, e.g. Myelodysplastic syndrome, Myelofibrosis, Neutropenia (decrease in the number of neutrophils), Agranulocytosis, Glanzmann's thrombasthenia, and Thrombocytopenia (decrease in the number of platelets) including Idiopathic thrombocytopenia purpura (ITP), Thrombotic thrombocytopeniaurpura (TTP), and Heparin-induced thrombocytopenia (HIT); Myeloproliferative disorders (Increased numbers of cells), e.g. Polycythemia vera (increase in the number of cells in general), Erythrocytosis (increase in the number of red blood cells), Leukocytosis (increase in the number of white blood cells), Thrombocytosis (increase in the number of platelets), and Myeloproliferative disorder; Coagulopathies (disorders of bleeding and coagulation), e.g. Thrombocytosis, Recurrent thrombosis, Disseminated intravascular coagulation, Disorders of clotting proteins including Hemophilia such as Hemophilia A, Hemophilia B (also known as Christmas disease), and Hemophilia C, Von Willebrand disease, Disseminated intravascular coagulation, Protein S deficiency, and Antiphospholipid syndrome, and Disorders of platelets including Thrombocytopenia, Glanzmann's thrombasthenia, and Wiskott-Aldrich syndrome. Moreover, examples of hematological diseases also include hematological malignancies, e.g. lymphomas including Hodgkin's disease and Non-Hodgkin's lymphoma such as Burkitt's lymphoma, Anaplastic large cell lymphoma, Splenic marginal zone lymphoma, Hepatosplenic T-cell lymphoma, and Angioimmunoblastic T-cell lymphoma (AILT), Myelomas such as Multiple myeloma, Waldenström macroglobulinemia, and Plasmacytoma, Leukemias such as Acute lymphocytic leukemia (ALL), Chronic lymphocytic leukemia (CLL), Acute myelogenous leukemia (AML), Chronic Idiopathic Myleofibrosis (MF), Chronic myelogenous leukemia (CML), T-cell prolymphocytic leukemia (T-PLL), B-cell prolymphocytic leukemia (B-PLL), Chronic neutrophilic leukemia (CNL), Hairy cell leukemia (HCL), T-cell large granular lymphocyte leukemia (T-LGL), and Aggressive NK-cell leukemia. Moreover, examples of hematological diseases also include miscellaneous haematological diseases including Hemochromatosis, Asplenia, Hypersplenism such as Gauchers disease, Monoclonal gammopathy of undetermined significance, Hemophagocytic lymphohistiocytosis, and Tempi syndrome. Moreover, examples of hematological diseases also include hematological changes secondary to non-hematological disorders including Anemia of chronic disease, Infectious mononucleosis, AIDS, Malaria, and Leishmaniasis.

Moreover, the combination of the immune checkpoint modulator as described herein and of the complex comprising a cell penetrating peptide, at least one antigen or antigenic epitope and at least one TLR peptide agonist as described herein may be used for (the preparation of a medicament for) the prophylaxis, treatment and/or amelioration of transplant rejection, including e.g. graft-versus-host reaction. Transplant rejection includes hyperacute rejection, acute rejection and chronic rejection of a transplant. Examples of transplant rejection include skin, kidney, heart, lung, pancreas, liver, blood cell, bone marrow, cornea, accidental severed limb, in particular fingers, hand, foot, face, nose, bone, cardiac valve, blood vessel or intestine transplant rejection reaction.

In general, "combination of the immune checkpoint modulator as described herein and of the complex comprising a cell penetrating peptide, at least one antigen or antigenic epitope and at least one TLR peptide agonist as described herein" means that the therapy with the immune checkpoint modulator as described herein is combined with the therapy with the complex comprising a cell penetrating peptide, at least one antigen or antigenic epitope and at least one TLR peptide agonist as described herein. In other words, even if one component (the checkpoint modulator or the complex) is not administered, e.g., at the same day as the other component (the other of checkpoint modulator or complex), their treatment schedules are typically intertwined. This means that "a combination" in the context of the present invention does in particular not include the start of a therapy with one component (the checkpoint modulator or the complex) after the therapy with the other component (the other of checkpoint modulator or complex) is finished. Thereby, a "finished" therapy means in particular that the active component does not exert its effects anymore—i.e. a "therapy" may in particular be finished several minutes, hours or days after the last administration of the active component, depending on how long the active component exerts its effects. In more general, an "intertwined" treatment schedule of the checkpoint modulator and the complex—and, thus, a combination of the checkpoint modulator and the complex-means that (i) not every administration of the checkpoint modulator (and therefore the complete checkpoint modulator therapy) is completed for more than one week (preferably for more than 3 days, more preferably for more than 2 days, even more preferably for more than a day) before the first administration of the complex (and therefore the complete therapy with the complex) starts; or (ii) not every administration of the complex (and therefore the complete therapy with the complex) is completed for more than one week (preferably for more than 3 days, more preferably for more than 2 days, even more preferably for more than a day) before the first administration of the checkpoint modulator (and therefore the complete checkpoint modulator therapy) starts.

For example, in the combination of the immune checkpoint modulator as described herein and of the complex comprising a cell penetrating peptide, at least one antigen or antigenic epitope and at least one TLR peptide agonist as described herein for use according to the present invention, one component (the checkpoint modulator or the complex) may be administered once a week and the other component (the other of checkpoint modulator or complex) may be administered once a month. To achieve in this example "a combination" in the sense of the present invention the monthly administered component is to be administered at least once in the same week, in which also the weekly administered other component is administered.

As outlined above, the administration of the immune checkpoint modulator and/or of the complex comprised by the combination for use according to the present invention may require multiple successive administrations, e.g. multiple injections. Thus, the administration may be repeated at least two times, for example once as primary immunization injections and, later, as booster injections.

In particular, the immune checkpoint modulator and/or the complex comprised by the combination for use according to the present invention may be administered repeatedly or continuously. The immune checkpoint modulator and/or the complex comprised by the combination for use according to the present invention may be administered repeatedly or continuously for a period of at least 1, 2, 3, or 4 weeks; 2, 3, 4, 5, 6, 8, 10, or 12 months; or 2, 3, 4, or 5 years. For example, the immune checkpoint modulator comprised by the combination for use according to the present invention may be administered twice per day, once per day, every two days, every three days, once per week, every two weeks, every three weeks, once per month or every two months. For example, the complex comprised by the combination for use according to the present invention may be administered twice per day, once per day, every two days, every three days, once per week, every two weeks, every three weeks, once per month or every two months. Preferably, the complex comprised by the combination for use according to the present invention may be administered repeatedly, for example once per week or (once) every two weeks.

In the combination of the immune checkpoint modulator as described herein and of the complex comprising a cell penetrating peptide, at least one antigen or antigenic epitope and at least one TLR peptide agonist as described herein for use according to the present invention, the immune checkpoint modulator and the complex are preferably administered at about the same time.

"At about the same time", as used herein, means in particular simultaneous administration or that directly after administration of the immune checkpoint modulator the complex is administered or directly after administration of the complex the immune checkpoint modulator is administered. The skilled person understands that "directly after" includes the time necessary to prepare the second administration—in particular the time necessary for exposing and disinfecting the location for the second administration as well as appropriate preparation of the "administration device" (e.g., syringe, pump, etc.). Simultaneous administration also includes if the periods of administration of the checkpoint modulator and of the complex overlap or if, for example, one component (checkpoint modulator or complex) is administered over a longer period of time, such as 30 min, 1 h, 2 h or even more, e.g. by infusion, and the other component (checkpoint modulator or complex) is administered at some time during such a long period. Administration of the immune checkpoint modulator and of the complex at about the same time is in particular preferred if different routes of administration and/or different administration sites are used.

It is also preferred in the combination of the immune checkpoint modulator as described herein and of the complex comprising a cell penetrating peptide, at least one antigen or antigenic epitope and at least one TLR peptide agonist as described herein for use according to the present invention that the immune checkpoint modulator and the complex are administered consecutively. For example, the immune checkpoint modulator is preferably administered before the complex. It is also preferred that the immune checkpoint modulator is administered after the complex.

In consecutive administration, the time between administration of the first component (the checkpoint modulator or the complex) and administration of the second component (the other of the checkpoint modulator and the complex) is preferably no more than one week, more preferably no more than 3 days, even more preferably no more than 2 days and most preferably no more than 24 h. It is particularly preferred that the checkpoint modulator and the complex are administered at the same day with the time between administration of the first component (the checkpoint modulator of the complex) and administration of the second component (the other of the checkpoint modulator and the complex) being preferably no more than 6 hours, more preferably no more than 3 hours, even more preferably no more than 2 hours and most preferably no more than 1 h.

Preferably, the immune checkpoint modulator comprised by the combination for use according to the present invention and the complex comprised by the combination for use according to the present invention are administered in a therapeutically effective amount. A "therapeutically effective amount", as used herein, is the amount which is sufficient for the alleviation of the symptoms of the disease or condition being treated and/or for prophylaxis of the symptoms of the disease or condition being prevented. In other words, a "therapeutically effective amount" means an amount of the complex and/or of the checkpoint modulator that is sufficient to significantly induce a positive modification of a disease or disorder, i.e. an amount of the complex and/or of the checkpoint modulator, that elicits the biological or medicinal response in a tissue, system, animal or human that is being sought. The term also includes the amount of the complex and/or of the immune checkpoint modulator sufficient to reduce the progression of the disease, notably to reduce or inhibit the tumor growth or infection and thereby elicit the response being sought, in particular such response could be an immune response directed against the antigens or antigenic epitopes comprised in by the complex (i.e. an "inhibition effective amount"). At the same time, however, a "therapeutically effective amount" is preferably small enough to avoid serious side-effects, that is to say to permit a sensible relationship between advantage and risk. The determination of these limits typically lies within the scope of sensible medical judgment. A "therapeutically effective amount" of the complex and/or of the checkpoint modulator, will furthermore vary in connection with the particular condition to be treated and also with the age and physical condition of the patient to be treated, the body weight, general health, sex, diet, time of administration, rate of excretion, drug combination, the activity of the specific components (checkpoint modulator and complex), the severity of the condition, the duration of the treatment, the nature of the accompanying therapy, of the particular pharmaceutically acceptable carrier used, and similar factors, within the knowledge and experience of the accompanying doctor.

The dosage administered, as single or multiple doses, to an individual will thus vary depending upon a variety of factors, including pharmacokinetic properties, subject conditions and characteristics (sex, age, body weight, health, size), extent of symptoms, concurrent treatments, frequency of treatment and the effect desired.

Preferably, for cancer treatment, the therapeutically effective dose of the complex comprised by the combination for use according to the present invention is from about 0.001 mg to 10 mg, preferably from about 0.01 mg to 5 mg, more preferably from about 0.1 mg to 2 mg per injection or from about 0.01 nmol to 1 mmol per injection, in particular from 1 nmol to 1 mmol per injection, preferably from 1 µmol to 1 mmol per injection. It is also preferred if the therapeutically effective dose of the complex comprised by the combination for use according to the present invention is (per kg body weight), in particular for cancer treatment, from about 0.01 mg/kg to 100 mg/kg, preferably from about 0.05 mg/kg to 50 mg/kg, more preferably from about 0.1 mg/kg to 25 mg/kg, even more preferably from about 0.5 mg/kg to 10 mg/kg and most preferably from about 1 mg/kg to 5 mg/kg.

Preferably, the therapeutically effective dose of the immune checkpoint modulator comprised by the combination for use according to the present invention is (per kg body weight), in particular for cancer treatment, from about 0.01 mg/kg to 100 mg/kg, preferably from about 0.05 mg/kg to 50 mg/kg, more preferably from about 0.1 mg/kg to 25 mg/kg, even more preferably from about 0.5 mg/kg to 15 mg/kg and most preferably from about 1 mg/kg to 10 mg/kg.

The complex comprised by the combination for use according to the present invention and the immune checkpoint modulator comprised by the combination for use according to the present invention can be administered by various routes of administration, for example, systemically or locally. Routes for systemic administration in general include, for example, transdermal, oral and parenteral routes, which include subcutaneous, intravenous, intramuscular, intraarterial, intradermal and intraperitoneal routes and/or intranasal administration routes. Routes for local administration in general include, for example, topical administration routes, but also administration directly at the site of affliction, such as intratumoral administration.

Preferably, the complex comprised by the combination for use according to the present invention and the immune checkpoint modulator comprised by the combination for use according to the present invention are administered by a parenteral route of administration. More preferably, the complex comprised by the combination for use according to the present invention and the immune checkpoint modulator comprised by the combination for use according to the present invention are administered via intravenous, intratumoral, intradermal, subcutaneous, intramuscular, intranasal, or intranodal route. Even more preferably, the complex comprised by the combination for use according to the present invention and the immune checkpoint modulator comprised by the combination for use according to the present invention are administered intravenously and/or subcutaneously. It is also more preferred that the complex comprised by the combination for use according to the present invention and the immune checkpoint modulator comprised by the combination for use according to the present invention are administered intradermally and/or subcutaneously.

Preferably, the complex comprised by the combination for use according to the present invention and the immune checkpoint modulator comprised by the combination for use according to the present invention are administered via the same route of administration, preferably via the same parenteral route of administration, more preferably intravenously or subcutaneously.

However, it is more preferred that the complex comprised by the combination for use according to the present invention and the immune checkpoint modulator comprised by the combination for use according to the present invention are administered via distinct routes of administration, preferably via distinct parenteral routes of administration, more preferably the immune checkpoint modulator comprised by the combination for use according to the present invention is administered intravenously and the complex comprised by the combination for use according to the present invention is administered via intratumoral, intradermal, subcutaneous, intramuscular, intranasal, or intranodal route, preferably the complex comprised by the combination for use according to the present invention is administered subcutaneously. Even more preferably the immune checkpoint modulator comprised by the combination for use according to the present invention is administered intravenously and/or the complex comprised by the combination for use according to the present invention is administered subcutaneously or intradermally.

The complex comprised by the combination for use according to the present invention and the immune checkpoint modulator comprised by the combination for use according to the present invention may be provided in the same or in distinct compositions.

Preferably, the complex comprised by the combination for use according to the present invention and the immune checkpoint modulator comprised by the combination for use according to the present invention are provided in distinct compositions. Thereby, different other components, e.g. different vehicles, can be used for the complex and for the checkpoint modulator. Moreover, the complex and the immune checkpoint modulator can be administered via different routes of administration and the doses (in particular the relation of the doses) can be adjusted according to the actual need.

However, it is also preferred that the immune checkpoint modulator and the complex are provided in the same composition. Such a composition comprising both, the immune checkpoint modulator and the complex is described in more detail below ("composition according to the present invention").

No matter whether a composition comprises only the immune checkpoint modulator (and not the complex), only the complex (and not the checkpoint modulator) or both, such a composition may be a pharmaceutical composition and/or a vaccine composition.

In particular, such a composition, which comprises only the immune checkpoint modulator (and not the complex), only the complex (and not the checkpoint modulator) or both, is preferably a (pharmaceutical) composition which optionally comprises a pharmaceutically acceptable carrier and/or vehicle, or any excipient, buffer, stabilizer or other materials well known to those skilled in the art.

As a further ingredient, the (pharmaceutical) composition may in particular comprise a pharmaceutically acceptable carrier and/or vehicle. In the context of the present invention, a pharmaceutically acceptable carrier typically includes the liquid or non-liquid basis of the (pharmaceutical) composition. If the (pharmaceutical) composition is provided in liquid form, the carrier will typically be pyrogen-free water; isotonic saline or buffered (aqueous) solutions, e.g phosphate, citrate etc. buffered solutions. Particularly for injection of the (pharmaceutical) composition, water or preferably a buffer, more preferably an aqueous buffer, may be used, containing a sodium salt, preferably at least 30 mM of a sodium salt, a calcium salt, preferably at least 0.05 mM of a calcium salt, and optionally a potassium salt, preferably at least 1 mM of a potassium salt. According to a preferred embodiment, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, $K_2CO_3$, $KHCO_3$, $K_2SO_4$, and examples of calcium salts include e.g. $CaCl_2$), $CaI_2$, $CaBr_2$, $CaCO_3$, $CaSO_4$, $Ca(OH)_2$. Furthermore, organic anions of the aforementioned cations may be contained in the buffer. According to a more preferred embodiment, the buffer suitable for injection purposes as defined above, may contain salts selected from sodium chloride (NaCl), calcium chloride ($CaCl_2$)) and optionally potassium chloride (KCl), wherein further anions may be present additional to the chlorides. $CaCl_2$) can also be replaced by another salt like KCl. Typically, the salts in the injection buffer are present in a concentration of at least 30 mM sodium chloride (NaCl), at least 1 mM potassium chloride (KCl) and at least 0.05 mM calcium chloride ($CaCl_2$)). The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Saline (0.9% NaCl) and Ringer-Lactate solution are particularly preferred as a liquid basis.

Preferably, the (pharmaceutical) composition, which comprises the immune checkpoint modulator and/or the complex as described herein, further comprises arginine, such as L-arginine.

However, one or more compatible solid or liquid fillers or diluents or encapsulating compounds may be used as well for the (pharmaceutical) composition, which are suitable for administration to a subject to be treated. The term "compatible" as used herein means that these constituents of the (pharmaceutical) composition are capable of being mixed with the complex according to the present invention as defined above in such a manner that no interaction occurs which would substantially reduce the pharmaceutical effectiveness of the (pharmaceutical) composition under typical use conditions. Pharmaceutically acceptable carriers, fillers and diluents must, of course, have sufficiently high purity and sufficiently low toxicity to make them suitable for administration to a subject to be treated. Some examples of compounds which can be used as pharmaceutically acceptable carriers, fillers or constituents thereof are sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from *theobroma*; polyols, such as, for example, polypropylene glycol, glycerol, sorbitol, mannitol and polyethylene glycol; alginic acid.

As described above, the (pharmaceutical) composition may be administered orally, parenterally, by inhalation spray, topically, rectally, nasally, buccally, vaginally or via an implanted reservoir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Preferably, the (pharmaceutical) composition may be administered by parenteral injection, more preferably by subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or via infusion techniques. Sterile injectable forms of the (pharmaceutical) compositions may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation of the (pharmaceutical) composition.

For intravenous, cutaneous or subcutaneous injection, or injection at the site of affliction, the active ingredient will preferably be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required. Whether it is a polypeptide, peptide, or nucleic acid molecule, other pharmaceutically useful compound according to the present invention that is to be given to an individual, administration is preferably in a "therapeutically effective amount", this being sufficient to show benefit to the individual. The actual amount administered, and rate and time-course of administration, will depend on the nature and severity of what is being treated.

The (pharmaceutical) composition as described herein may also be administered orally in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient, i.e. the inventive transporter cargo conjugate molecule as defined above, is combined with emulsifying and suspending agents. If desired, certain sweetening, flavoring or coloring agents may also be added.

The (pharmaceutical) composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the (pharmaceutical) composition may be formulated in a suitable ointment, containing the inventive immunostimulatory composition, particularly its components as defined above, suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the (pharmaceutical) composition can be formulated in a suitable lotion or cream. In the context of the present invention, suitable carriers include, but are not limited to, mineral oil, sorbitan monostearate, polysorbate 60, cetyl esters wax, cetearyl alcohol, 2-octyldodecanol, benzyl alcohol and water.

In this context, prescription of treatment, e.g. decisions on dosage etc. when using the above (pharmaceutical) composition is typically within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in REMINGTON'S PHARMACEUTICAL SCIENCES, 16th edition, Osol, A. (ed), 1980.

Accordingly, the (pharmaceutical) composition typically comprises a therapeutically effective amount of the components of the (pharmaceutical) composition, in particular of the complex and/or of the checkpoint modulator. The (pharmaceutical) composition may be used for human and also for veterinary medical purposes, preferably for human medical purposes, as a (pharmaceutical) composition in general or as a vaccine.

(Pharmaceutical) compositions, in particular vaccine compositions, or formulations according to the invention may be administered as a pharmaceutical formulation which can contain the complex as described herein and/or the checkpoint modulator as described herein in any form described herein.

The terms "pharmaceutical formulation" and "pharmaceutical composition" as used in the context of the present invention refer in particular to preparations which are in such a form as to permit biological activity of the active ingredient(s) to be unequivocally effective and which contain no additional component which would be toxic to subjects to which the said formulation would be administered.

In the context of the present invention, an "efficacy" of a treatment can be measured based on changes in the course of a disease in response to a use or a method according to the present invention. For example, the efficacy of a treatment of cancer can be measured by a reduction of tumor volume, and/or an increase of progression free survival time, and/or a decreased risk of relapse post-resection for primary cancer. More specifically for cancer treated by immunotherapy, assessment of efficacy can be by the spectrum of clinical patterns of antitumor response for immunotherapeutic agents through novel immune-related response criteria (irRC), which are adapted from Response Evaluation Criteria in Solid Tumors (RECIST) and World Health Organization (WHO) criteria (J. Natl. Cancer Inst. 2010, 102 (18): 1388-1397). The efficacy of prevention of infectious disease is ultimately assessed by epidemiological studies in human populations, which often correlates with titres of neutralizing antibodies in sera, and induction of multifunctional pathogen specific T cell responses. Preclinical assessment can include resistance to infection after challenge with infectious pathogen. Treatment of an infectious disease can be measured by inhibition of the pathogen's growth or elimination of the pathogen (and, thus, absence of detection of the pathogen), correlating with pathogen specific antibodies and/or T cell immune responses.

(Pharmaceutical) compositions, in particular vaccine compositions, or formulations according to the invention may also be administered as a pharmaceutical formulation which can contain antigen presenting cells loaded with the complex as described herein in any form described herein.

The vaccine and/or the composition according to the present invention may also be formulated as (pharmaceutical) compositions and unit dosages thereof, in particular together with a conventionally employed adjuvant, immunomodulatory material, carrier, diluent or excipient as described above and below, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous and intradermal) use by injection or continuous infusion.

In the context of the present invention, in particular in the context of a (pharmaceutical) composition and vaccines according to the present invention, injectable compositions are typically based upon injectable sterile saline or phosphate-buffered saline or other injectable carriers known in the art. Such (pharmaceutical) compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Examples of suitable adjuvants and/or immunomodulatory materials in the context of the present invention include MPL® (Corixa), aluminum-based minerals including aluminum compounds (generically called Alum), ASO1-4, MF59, Calcium Phosphate, Liposomes, Iscom, polyinosinic: polycytidylic acid (polyIC), including its stabilized form poly-ICLC (Hiltonol), CpG oligodeoxynucleotides, Granulocyte-macrophage colony-stimulating factor (GM-CSF), lipopolysaccharide (LPS), Montanide, polylactide co-glycolide (PLG), Flagellin, Soap Bark tree saponins (QS21), amino alkyl glucosamide compounds (e.g. RC529), two component antibacterial peptides with synthetic oligodeoxynucleotides (e.g. IC31), Imiquimod, Resiquimod, Immunostimulatory sequences (ISS), monophosphoryl lipid A (MPLA), and Fibroblast-stimulating lipopeptide (FSL1).

Compositions, in particular pharmaceutical compositions and vaccines, according to the present invention may be liquid formulations including, but not limited to, aqueous or oily suspensions, solutions, emulsions, syrups, and elixirs. The compositions may also be formulated as a dry product for reconstitution with water or other suitable vehicle before use. Such liquid preparations may contain additives including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, Tween®, Span®.

Compositions, in particular pharmaceutical compositions and vaccines, according to the present invention may also be formulated as a depot preparation, which may be administered by implantation or by intramuscular injection.

Compositions, in particular pharmaceutical compositions and vaccines, according to the present invention may also be solid compositions, which may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Compositions, in particular pharmaceutical compositions and vaccines, according to the present invention may also be administered in sustained release forms or from sustained release drug delivery systems.

Moreover, the compositions, in particular pharmaceutical compositions and vaccines, according to the present invention may be adapted for delivery by repeated administration.

Further materials as well as formulation processing techniques and the like, which are useful in the context of compositions, in particular pharmaceutical compositions and vaccines, according to the present invention or in the context of their preparation are set out in "Part 5 of Remington's "The Science and Practice of Pharmacy", 22nd Edition, 2012, University of the Sciences in Philadelphia, Lippincott Williams & Wilkins".

Kit According to the Present Invention

In a further aspect, the present invention also provides a kit, in particular a kit of parts, comprising
  (i) an immune checkpoint modulator and
  (ii) a complex comprising:
    a) a cell penetrating peptide;
    b) at least one antigen or antigenic epitope; and
    c) at least one TLR peptide agonist,
    wherein the components a)-c) comprised by the complex are covalently linked.

In particular, such a kit according to the present invention comprises (i) the immune checkpoint modulator as described above (in the context of the combination for use according to the present invention) and (ii) the complex as described above (in the context of the combination for use according to the present invention). In other words, preferred embodiments of the immune checkpoint modulator as described above (in the context of the combination for use according to the present invention) are also preferred in the kit according to the present invention. Accordingly, preferred embodiments of the complex as described above (in the context of the combination for use according to the present invention) are also preferred in the kit according to the present invention.

The various components of the kit may be packaged in one or more containers. The above components may be provided in a lyophilized or dry form or dissolved in a suitable buffer. For example, the kit may comprise a (pharmaceutical) composition comprising the immune checkpoint modulator as described above and a (pharmaceutical) composition comprising the complex as described above, e.g. with each composition in a separate container. The kit may also comprise a (pharmaceutical) composition comprising both, the immune checkpoint modulator and the complex, as described above.

The kit may also comprise additional reagents including, for instance, preservatives, growth media, and/or buffers for storage and/or reconstitution of the above-referenced components, washing solutions, and the like.

In addition, the kit-of-parts according to the present invention may optionally contain instructions of use. Preferably, the kit further comprises a package insert or label with directions to treat a disease as described herein, for example cancer, by using a combination of the immune checkpoint modulator and the complex.

Such a kit may preferably be for use in medicine as described herein, in particular for use in the prevention and/or treatment of cancer as described herein.

Moreover, the present invention also provides a vaccination kit for treating, preventing and/or stabilizing a disease, e.g. a cancer or an infectious disease, comprising the pharmaceutical composition comprising the immune checkpoint modulator as described herein and the pharmaceutical composition, in particular the vaccine, comprising the complex as described herein (wherein the pharmaceutical compositions may be the same or different) and instructions for use of said pharmaceutical composition or of said vaccine.

Composition According to the Present Invention

In a further aspect, the present invention also provides a composition comprising
(i) an immune checkpoint modulator and
(ii) a complex comprising:
   a) a cell penetrating peptide;
   b) at least one antigen or antigenic epitope; and
   c) at least one TLR peptide agonist,
   wherein the components a)-c) comprised by the complex are covalently linked.

In particular, such a composition according to the present invention comprises (i) the immune checkpoint modulator as described above (in the context of the combination for use according to the present invention) and (ii) the complex as described above (in the context of the combination for use according to the present invention). In other words, preferred embodiments of the immune checkpoint modulator as described above (in the context of the combination for use according to the present invention) are also preferred in the composition according to the present invention. Accordingly, preferred embodiments of the complex as described above (in the context of the combination for use according to the present invention) are also preferred in the composition according to the present invention.

Moreover, a composition comprising the immune checkpoint modulator as described above and the complex as described above and preferred embodiments of such a composition are described above (in the context of the combination for use according to the present invention). It is understood that the same description, in particular the same preferred embodiments as described above for the composition apply accordingly to the composition as described here.

Accordingly, the composition preferably comprises a pharmaceutically acceptable carrier. Preferred examples of such a pharmaceutically acceptable carrier are as described above.

It is also preferred that the composition comprises at least two different complexes. Moreover, a preferred composition comprises at least two different immune checkpoint modulators.

Such a composition may preferably be for use in medicine as described herein, in particular for use in the prevention and/or treatment of cancer as described herein.

Moreover, it is preferred that the composition is a vaccine.

As used in the context of the present invention, the term "vaccine" refers to a biological preparation that provides innate and/or adaptive immunity, typically to a particular disease, preferably cancer. Thus, a vaccine supports in particular an innate and/or an adaptive immune response of the immune system of a subject to be treated. For example, the antigen or antigenic epitope of the complex as described herein typically leads to or supports an adaptive immune response in the patient to be treated, and the TLR peptide agonist of the complex as described herein may lead to or support an innate immune response.

The vaccine may also comprise a pharmaceutically acceptable carrier, adjuvant, and/or vehicle as defined below for the inventive pharmaceutical composition. In the specific context of the vaccine, the choice of a pharmaceutically acceptable carrier is determined in principle by the manner in which the inventive vaccine is administered. The inventive vaccine can be administered, for example, systemically or locally as described above. More preferably, vaccines may be administered by an intravenous, intradermal, subcutaneous, or intramuscular route. The vaccine is therefore preferably formulated in liquid (or sometimes in solid) form. The suitable amount of the vaccine to be administered can be determined by routine experiments with animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to about 7.4. Suitable carriers for injection include hydrogels, devices for controlled or delayed release, polylactic acid and collagen matrices. Suitable pharmaceutically acceptable carriers for topical application include those which are suitable for use in lotions, creams, gels and the like. If the inventive vaccine is to be administered orally, tablets, capsules and the like are the preferred unit dose form. The pharmaceutically acceptable carriers for the preparation of unit dose forms which can be used for oral administration are well known in the prior art. The choice thereof will depend on secondary considerations such as taste, costs and storability, which are not critical for the purposes of the present invention, and can be made without difficulty by a person skilled in the art.

The vaccine can additionally contain one or more auxiliary substances in order to further increase its immunogenicity. A synergistic action of the inventive complex as defined above and of an auxiliary substance, which may be optionally contained in the inventive vaccine as described above, is preferably achieved thereby. Depending on the various types of auxiliary substances, various mechanisms can come into consideration in this respect. For example, compounds that permit the maturation of dendritic cells (DCs), for example lipopolysaccharides or TNF-alpha, form a first class of suitable auxiliary substances. In general, it is possible to use as auxiliary substance any agent that influences the immune system in the manner of a "danger signal" (LPS, GP96, etc.) or cytokines, such as GM-CSF, which allow an immune response produced by the immune-stimulating adjuvant according to the invention to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta or TNF-alpha, growth factors, such as hGH.

Further additives which may be included in the vaccine are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The inventive vaccine can also additionally contain any further compound, which is known to be immune-stimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

Another class of compounds, which may be added to the vaccine in this context, may be CpG nucleic acids, in particular CpG-RNA or CpG-DNA. A CpG-RNA or CpG-DNA can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid is preferably in the form of CpG-RNA, more preferably in the form of single-stranded CpG-RNA (ss CpG-RNA). The CpG nucleic acid preferably contains at least one or more (mitogenic) cytosine/guanine dinucleotide sequence(s) (CpG motif(s)). According to a first preferred alternative, at least one CpG motif contained in these sequences, in particular the C (cytosine) and the G (guanine) of the CpG motif, is unmethylated. All further cytosines or guanines optionally contained in these sequences can be either methylated or unmethylated. According to a further preferred alternative, however, the C (cytosine) and the G (guanine) of the CpG motif can also be present in methylated form.

Preferably, the (pharmaceutical) composition, in particular the vaccine, as described above is for use in the prevention and/or treatment of diseases or disorders including for example cancers, hematological disorders, infectious diseases, autoimmunity disorders and transplant rejections, whereby cancer is preferred.

It is also preferred that the (pharmaceutical) composition, in particular the vaccine, is used in a method for treating a subject, preferably a mammalian subject, and most preferably a human subject, who is suffering from a disease or disorder, in particular from a disorder that can be treated by immunotherapy such as cancers, infectious diseases, autoimmunity disorders and transplant rejections.

Nucleic Acid Molecule

In another aspect, the invention also provides a nucleic acid molecule comprising a polynucleotide encoding the immune checkpoint modulator according to the present invention as described above, wherein the immune checkpoint modulator is a (poly) peptide or a protein, and/or encoding the complex according to the present invention as described above, wherein the complex is a (poly) peptide or a protein, in particular a fusion (poly) peptide or a fusion protein. Most preferably, the nucleic acid (molecule) encodes at least an exemplified complex as described herein or a functional sequence variant thereof. Accordingly, the nucleic acid (molecule) most preferably comprises a polynucleotide encoding an amino acid sequence according to any of SEQ ID NOs: 26-32, or 41-45 or an amino acid sequence sharing at least 50%, at least 60%, at least 70%, at least 75%, at least 80%, at least 85%, at least 90%, at least 95% or at least 98% sequence identity with any of SEQ ID NOs: 26-32, or 41-45.

Examples of nucleic acid molecules and/or polynucleotides include, e.g., a recombinant polynucleotide, a vector, an oligonucleotide, an RNA molecule such as an rRNA, an mRNA, an miRNA, an siRNA, or a tRNA, or a DNA molecule such as a cDNA.

The term "vector" refers to a nucleic acid molecule, preferably to a recombinant nucleic acid molecule, i.e. a nucleic acid molecule which does not occur in nature. A vector in the context of the present invention is suitable for incorporating or harboring a desired nucleic acid sequence. Such vectors may be storage vectors, expression vectors, cloning vectors, transfer vectors etc. A storage vector is a vector which allows the convenient storage of a nucleic acid molecule. Thus, the vector may comprise a sequence corresponding, e.g., to a desired complex according to the present invention as described above and/or a sequence corresponding, e.g., to a desired immune checkpoint modulator according to the present invention as described above. An expression vector may be used for production of expression products such as RNA, e.g. mRNA, or peptides, polypeptides or proteins. For example, an expression vector may comprise sequences needed for transcription of a sequence stretch of the vector, such as a promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors. A vector in the context of the present invention may be, e.g., an RNA vector or a DNA vector. Preferably, a vector is a DNA molecule. For example, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector.

In particular, the present invention provides a kit comprising
(i) a nucleic acid molecule comprising a polynucleotide encoding an immune checkpoint modulator, wherein the immune checkpoint modulator is a (poly) peptide or a protein; and
(ii) a nucleic acid molecule comprising a polynucleotide encoding a complex, the complex comprising:
a) a cell penetrating peptide;
b) at least one antigen or antigenic epitope; and
c) at least one TLR peptide agonist,
wherein the complex is a (poly) peptide or a protein, in particular a fusion (poly) peptide or a fusion protein.

In such a kit according to the present invention preferred immune checkpoint modulator are those as described herein and preferred complexes are those as described herein.

Moreover, a kit preferably also comprises a package insert or label, for example with directions to express the immune checkpoint modulator and the complex and/or to treat cancer by using a combination of the immune checkpoint modulator and the complex.

Such a kit is preferably for use in medicine, for example for use in the prevention and/or treatment of cancer.

As described above, the nucleic acid molecule(s) in the kit are preferably selected from the group consisting of a vector as described above, such as an expression vector; an RNA molecule such as an rRNA, an mRNA, an miRNA, an siRNA, or a tRNA; or a DNA molecule, such as a cDNA.

In the kit according to the present invention the immune checkpoint modulator and the complex may be encoded by the same nucleic acid molecule or, preferably, by distinct nucleic acid molecules.

Accordingly, the present invention also provides a nucleic acid molecule comprising
(i) a polynucleotide encoding an immune checkpoint modulator, wherein the immune checkpoint modulator is a (poly) peptide or a protein; and
(ii) a polynucleotide encoding a complex, the complex comprising:
a) a cell penetrating peptide;
b) at least one antigen or antigenic epitope; and
c) at least one TLR peptide agonist,
wherein the complex is a (poly) peptide or a protein, in particular a fusion (poly) peptide or a fusion protein.

In such a nucleic acid molecule according to the present invention preferred immune checkpoint modulator are those as described herein and preferred complexes are those as described herein. Moreover, the nucleic acid molecule is preferably selected from the group consisting of a vector as described above, such as an expression vector; an RNA molecule such as an rRNA, an mRNA, an miRNA, an siRNA, or a tRNA; or a DNA molecule, such as a cDNA. For example, the nucleic acid molecule may be an expression vector or an RNA molecule, e.g. an mRNA molecule, encoding the complex and the immune checkpoint inhibitor in a biscistronic manner.

Furthermore, the present invention also provides a composition comprising
(i) a nucleic acid molecule comprising a polynucleotide encoding an immune checkpoint modulator, wherein the immune checkpoint modulator is a (poly) peptide or a protein; and
(ii) a nucleic acid molecule comprising a polynucleotide encoding a complex, the complex comprising:
a) a cell penetrating peptide;
b) at least one antigen or antigenic epitope; and
c) at least one TLR peptide agonist,
wherein the complex is a (poly) peptide or a protein, in particular a fusion (poly) peptide or a fusion protein.

In such a composition according to the present invention preferred immune checkpoint modulator are those as described herein and preferred complexes are those as described herein. Moreover, the nucleic acid molecule(s) are preferably selected from the group consisting of a vector as described above, such as an expression vector; an RNA molecule such as an rRNA, an mRNA, an miRNA, an siRNA, or a tRNA; or a DNA molecule, such as a cDNA.

The composition may also comprise further components, for example those described above for a (pharmaceutical) composition according to the present invention comprising the complex and/or the checkpoint inhibitor as described herein.

Method and Combination Therapy According to the Present Invention

In a further aspect, the present invention provides a method for treating a subject, preferably a mammalian subject, and most preferably a human subject, who is suffering from a disease or disorder, in particular from a disorder that can be treated by immunotherapy such as cancers, infectious diseases, autoimmunity disorders and transplant rejections, comprising administering to the subject (i) an immune checkpoint modulator and
(ii) a complex comprising:
a) a cell penetrating peptide;
b) at least one antigen or antigenic epitope; and
c) at least one TLR peptide agonist,
wherein the components a)-c) comprised by the complex are covalently linked.

In particular, the present invention provides a method for treating cancer or initiating, enhancing or prolonging an anti-tumor-response in a subject in need thereof comprising administering to the subject
(i) an immune checkpoint modulator and
(ii) a complex comprising:
a) a cell penetrating peptide;
b) at least one antigen or antigenic epitope; and
c) at least one TLR peptide agonist,
wherein the components a)-c) comprised by the complex are covalently linked.

In more general, the present invention can be applied to any subject suffering from any disease or disorder, depending on the specificity in particular of the at least one antigen or antigenic epitope comprised by the complex comprised by the combination for use according to the present invention. In particular, the therapeutic effect of the complex may be to elicit an immune response directed against said antigens or antigenic epitopes, in particular a response that is dependent on $CD4^+$ helper T cells and/or $CD8^+$ cytotoxic T cells and/or that is restricted by MHC class I molecules and/or MHC class II molecules and the therapeutic effect of the checkpoint modulator may be to enable or to enhance such an effect of the complex.

Preferably, subjects according to the invention are subjects suffering from a cancer, for instance from a cancer of the brain, colon, head or neck, or from a cervical cancer. More preferably, subjects according to the invention are subjects suffering from a brain cancer including glioma.

It is also preferred that subjects according to the invention have been subjected to a surgical removal of a tumor.

Alternatively, subjects according to the invention may preferably be subjects suffering from an infectious disease.

In a further aspect, the present invention also provides a combination therapy for preventing and/or treating cancer, wherein the combination therapy comprises administration of
(i) an immune checkpoint modulator and
(ii) a complex comprising:
a) a cell penetrating peptide;
b) at least one antigen or antigenic epitope; and
c) at least one TLR peptide agonist,
wherein the components a)-c) comprised by the complex are covalently linked.

Preferred embodiments of such a combination therapy are preferred embodiments of the complex as described above, embodiments of the checkpoint modulator as described above, and/or—in more general—preferred embodiments of the combination for use according to the present invention. The kit according to the present invention and the (pharmaceutical) composition, in particular the vaccine, according to the present invention may be used in the combination therapy according to the present invention. Subjects to be treated with such a combination therapy are the same as described for the methods according to the present invention and diseases to be prevented and/or treated are the same as described herein, in the context of the combination for use according to the present invention.

EXAMPLES

In the following, particular examples illustrating various embodiments and aspects of the invention are presented.

However, the present invention shall not to be limited in scope by the specific embodiments described herein. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Example 1: Effects of Combination of a PD1 Inhibitor and a Complex Comprising a Cell Penetrating Peptide, Different Antigens and a TLR Peptide Agonist on Tumor Growth and Survival Rate In order to assess the effects of combination of a PD1 inhibitor and a complex comprising a cell penetrating peptide, different antigens and a TLR peptide agonist in treating cancer, the E.G7 tumor model was used. E.G7 is an OVA transfectant derived from the EL4 Thymoma cell line.

To this end, "Z13Mad5Anaxa" was provided, which is a complex comprising a cell penetrating peptide, different antigens and a TLR peptide agonist as described herein. Specifically, "Z13Mad5Anaxa" is a fusion protein comprising the cell-penetrating peptide "Z13", the antigenic cargo "MAD5" comprising OVA-CD4$^+$, gp100-CD8$^+$, Ealpha-CD4$^+$, and OVA-CD8$^+$ epitopes, and the TLR peptide agonist "Anaxa". In the following, the amino acid sequence of Z13Mad5Anaxa is shown with the cell-penetrating peptide "Z13" shown underlined and the TLR peptide agonist "Anaxa" shown in italics:

Example 2: Effects of Combination of a PD1 Inhibitor and a Complex Comprising a Cell Penetrating Peptide, Different Antigens and a TLR Peptide Agonist on Homing of T Cells to the e.g7 Tumor Site and on MDSCs In order to assess the effects of combination of a PD1 inhibitor and a complex comprising a cell penetrating peptide, different antigens and a TLR peptide agonist on homing of T cells to the tumor site and on MDSCs (myeloid-derived suppressor cells), the previous experiment (Example 1) was repeated with 8 mice per group and on day 22, mice were euthanized and FACS staining was performed to monitor the OVA-specific immune response and tumor microenvironment in the spleen and TILs (tumor-infiltrating lymphocytes).

Figure 2:
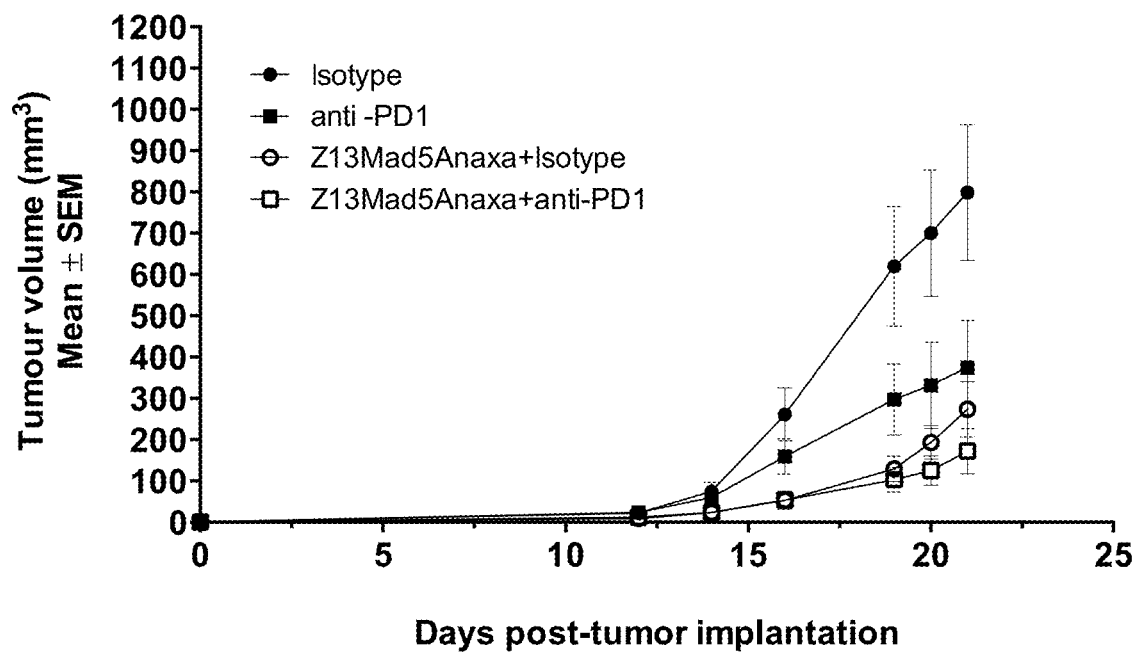
FIG. 2 shows for Example 2 tumor growth of 8 mice per group (mean±SEM). C57BL/6 mice were implanted s.c. with $3 \times 10^5$ EG7-OVA tumor cells in the left flank. Mice of the groups "Z13Mad5Anaxa+Isotype" and "Z13Mad5Anaxa+anti-PD1" were vaccinated twice (d5 and d13) by subcutaneous injection of 2 nmol of Z13Mad5Anaxa in the right flank. 200 μg of anti-PD1 antibody were administered i.p. on each of days 5, 9 and 13 to mice of groups "anti-PD1" and "Z13Mad5Anaxa+anti-PD1". For control, 200 μg of isotype 2A3 were administered i.p. on each of days 5, 9 and 13 to mice of groups "isotype" and "Z13Mad5Anaxa+isotype". Tumor size was measured with a caliper.

FIG. 2 shows the tumor growth in the experimental groups (same experimental method as in Example 1). Again, treatment with the PD1 inhibitor alone or with Z13Mad5Anaxa alone resulted in significantly reduced tumor volume (FIG. 2) as compared to the control group ("isotype"). However, the combination of both, the PD1 inhibitor and Z13Mad5Anaxa, resulted in the most pronounced improvement, namely in strongly decreased tumor volume and strongly increased survival rates. Accordingly, these data are in conformity with the results of Example 1 (cf. FIG. 1A). Thus, the data confirm that a combination of both, anti-PD1 therapy and Z13Mad5Anaxa vaccination, is more efficient than anti-PD1 therapy alone or Z13Mad5Anaxa vaccination alone and indicate a synergistic effect of anti-PD1 therapy and Z13Mad5Anaxa vaccination.

[SEQ ID NO: 28]
MHHHHHHKRYKNRVA SRKSRAKFKQ LLQHYREVAA AKSSENDRLR LLLKESLKIS

QAVHAAHAEI NEAGREVVGV GALKVPRNQD WLGVPRFAKF ASFEAQGALA

NIAVDKANLD VEQLESIINF EKLTEWTGSS TVHEILCKLS LEGDHSTPPS AYGSVKPYTN

FDAE

C57BL/6 mice (seven mice per group) were implanted s.c. with 3×10$^5$ EG7-OVA tumor cells in the left flank (day 0). After tumor implantation, mice of the groups "Z13Mad5Anaxa+Isotype" and "Z13Mad5Anaxa+anti-PD1" were vaccinated at days 5 and 13 subcutaneously with 2 nmol of Z13Mad5Anaxa in the right flank. 200 µg of anti-PD1 antibody RMP1-14 (BioXcell, West Lebanon, NH, USA) were administered i.p. on each of days 5, 9 and 13 to mice of groups "anti-PD1" and "Z13Mad5Anaxa+anti-PD1". For control, 200 µg of isotype mAB 2A3 were administered i.p. on each of days 5, 9 and 13 to mice of groups "isotype" and "Z13Mad5Anaxa+isotype". At days 5 and 13, when both, Z13Mad5Anaxa and antibody, were administered, the antibody was administered i.p. just after s.c. administration of Z13Mad5Anaxa. Tumor size was measured with a caliper.

As shown in FIG. 1, treatment with the PD1 inhibitor alone or with Z13Mad5Anaxa alone resulted in significantly reduced tumor volume (FIG. 1A) and increased survival (FIG. 1B) as compared to the control group ("isotype"). However, the combination of both, the PD1 inhibitor and Z13Mad5Anaxa, resulted in the most pronounced improvement, namely in strongly decreased tumor volume and strongly increased survival rates. These data show that a combination of both, anti-PD1 therapy and Z13Mad5Anaxa vaccination, is more efficient than anti-PD1 therapy alone or Z13Mad5Anaxa vaccination alone. These results thus indicate a synergistic effect of anti-PD1 therapy and Z13Mad5Anaxa vaccination.

Figure 3:
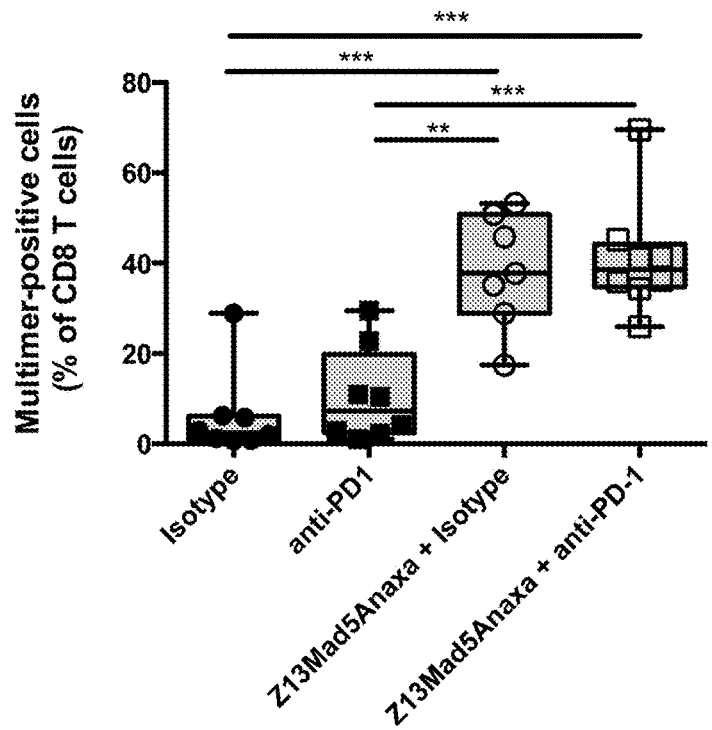
FIG. 3 shows for Example 2 the percentage of multimer-positive cells (in % of CD8 T cells) at the tumor site (Tumor-infiltrating cells, TILs) for the different experimental groups (A) and a correlation of multimer-positive cells (in % of CD8 T cells) at the tumor site (TILs) with tumor size (B). , $p<0.01$; *, $p<0.001$.
Figure 3:
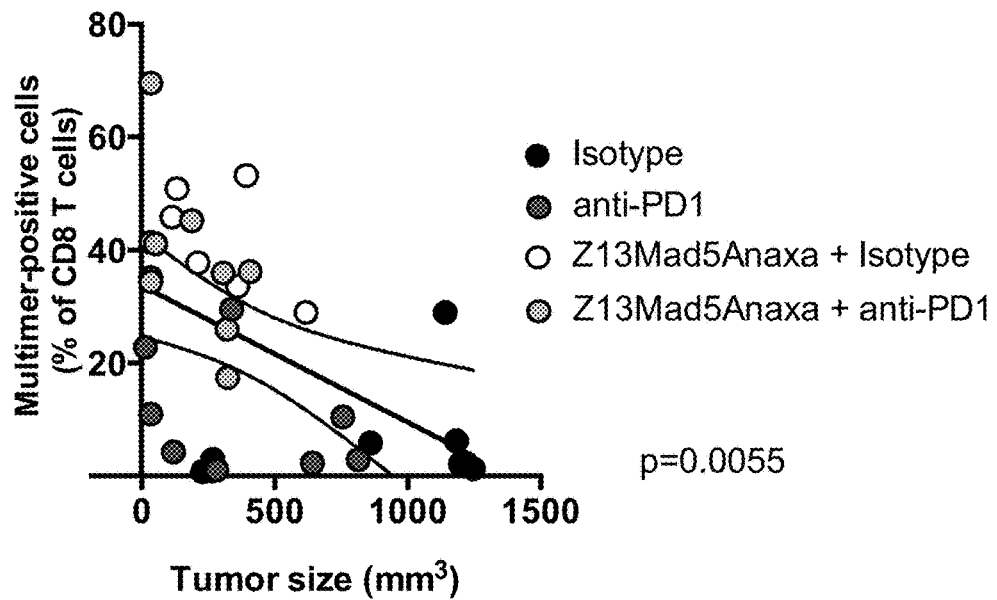

FIG. 3 shows the percentage of multimer-positive cells (in % of CD8 T cells) at the tumor site (TILs) for the different experimental groups (FIG. 3A) and a correlation of multimer-positive cells (in % of CD8 T cells) among TILs with tumor size (FIG. 3B). These data show that antigen-specific T cells accumulate at the tumor site in vaccinated mice. The lowest percentage of multimer-positive cells was found in control mice and in mice, which were treated with anti-PD1 only ("anti-PD1" group). In mice vaccinated with Z13Mad5Anaxa, the percentage of multimer-positive cells was significantly increased with the strongest and most pronounced increase observed in mice treated with both, Z13Mad5Anaxa and anti-PD1. In addition, a significant inverse correlation was observed between the percentage of multimer-positive cells (in % of CD8 T cells) and tumor size, i.e. the more the percentage of multimer-positive cells (in % of CD8 T cells), the smaller the tumor.

Figure 4:
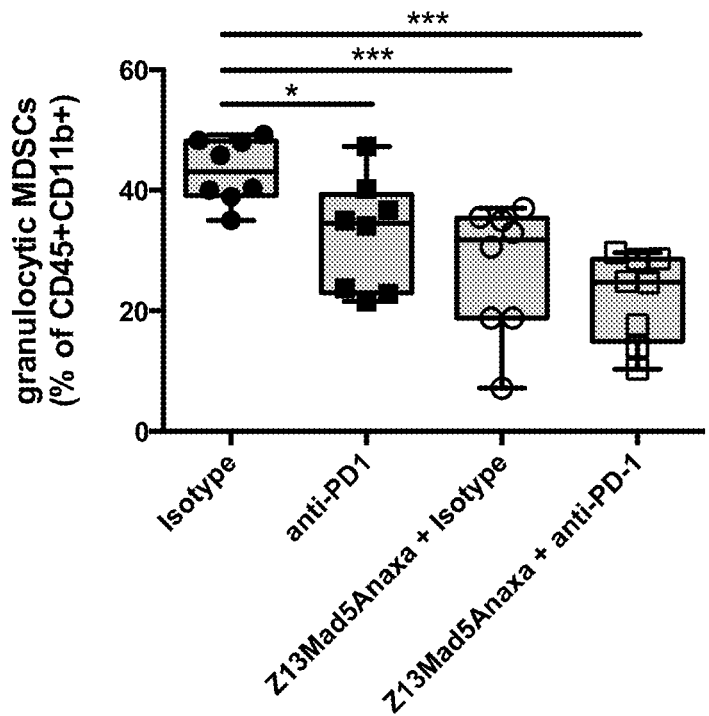
FIG. 4 shows for Example 2 the percentage of granulocytic MDSCs (in % of CD45+CD11b+ cells) for the different experimental groups in spleen (A) and TILs (B). *, $p<0.05$; , $p<0.01$; *, $p<0.001$.
Figure 4:
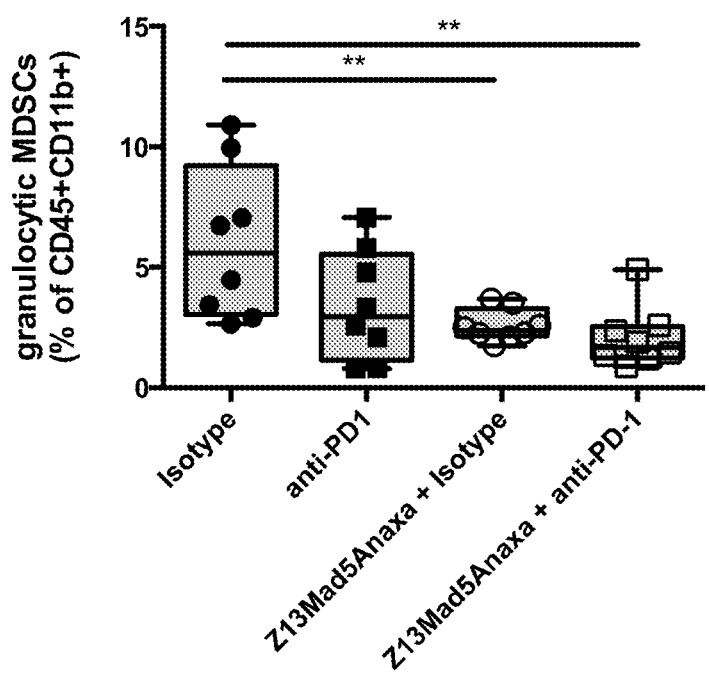
Figure 5:
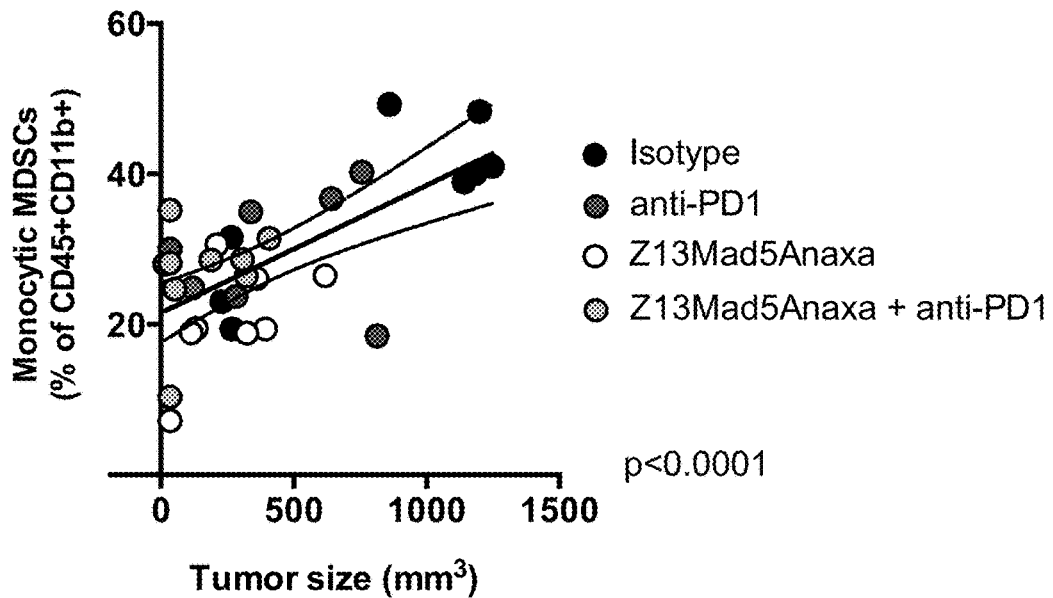
FIG. 5 shows for Example 2 the correlation of granulocytic MDSCs (in % of CD45+CD11b+ cells) with tumor size for the different experimental groups in spleen (A) and TILs (B).
Figure 5:
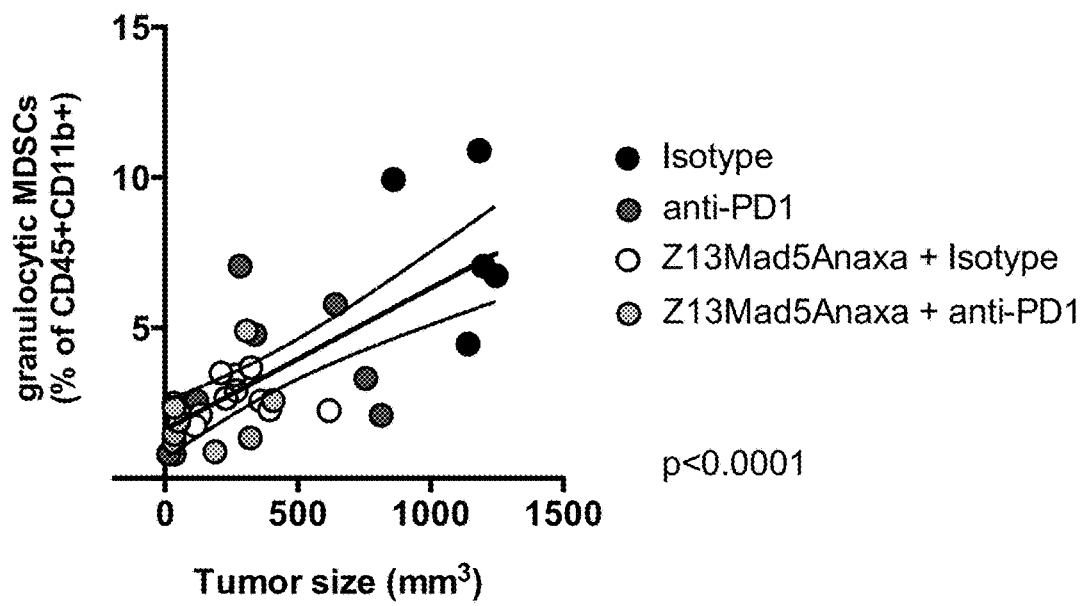

FIG. 4 shows the percentage of granulocytic MDSCs (in % of CD45+CD11b+ cells) for the different experimental groups in spleen (FIG. 4A) and TILs (FIG. 4B). The highest percentage of granulocytic MDSCs (in % of CD45+CD11b+ cells) was observed for the control group ("Isotype") in the periphery (spleen) and at the tumor site (TILs). Significantly lower percentages of granulocytic MDSCs (in % of CD45+CD11b+ cells) were observed all other experimental groups with the strongest and most pronounced decrease in granulocytic MDSCs observed in mice treated with both, Z13Mad5Anaxa and anti-PD1. FIG. 5 shows a significant correlation between the percentage of granulocytic MDSCs (in % of CD45+CD11b+ cells) and tumor size for the different experimental groups in spleen (FIG. 5A) and TILs (FIG. 5B).

Taken together, the present T cell data and MDSC data strongly support the synergistic effect of a combination of anti-PD1 therapy and Z13Mad5Anaxa vaccination observed for tumor growth and survival rate.

Example 3: Effect of the Treatment Schedule of a Combination of a PD1 Inhibitor and a Complex Comprising a Cell Penetrating Peptide, Different Antigens and a TLR Peptide Agonist on Tumor Growth In order to assess the effects of the treatment schedule of a combination of a PD1 inhibitor and a complex comprising a cell penetrating peptide, different antigens and a TLR peptide agonist in treating cancer, again the E.G7 tumor model was used.

In a first experimental group "Z13Mad5Anaxa+anti-PD1" the PD1 inhibitor and Z13Mad5Anaxa were administered as described in Example 1. Briefly, C57BL/6 mice (six-seven mice per group) were implanted s.c. with $3 \times 10^5$ EG7-OVA tumor cells in the left flank (day 0). After tumor implantation, mice were vaccinated at days 5 and 13 subcutaneously with 2 nmol of Z13Mad5Anaxa in the right flank. 200 μg of anti-PD1 antibody RMP1-14 (BioXcell, West Lebanon, NH, USA) were administered i.p. on each of days 5, 9 and 13. In the respective control group, 200 μg of isotype mAB 2A3 were administered i.p. on each of days 5, 9 and 13. At days 5 and 13, when both, Z13Mad5Anaxa and antibody, were administered, the antibody was administered i.p. just after s.c. administration of Z13Mad5Anaxa.

In a second experimental group "Z13Mad5Anaxa+anti-PD1" the PD1 inhibitor and Z13Mad5Anaxa were administered as follows: C57BL/6 mice (six-seven mice per group) were implanted s.c. with $3 \times 10^5$ EG7-OVA tumor cells in the left flank (day 0). After tumor implantation, mice were vaccinated at days 5 and 13 subcutaneously with 2 nmol of Z13Mad5Anaxa in the right flank—as in the first experimental group. However, in contrast to the first experimental group, in the second experimental group 200 μg of anti-PD1 antibody RMP1-14 (BioXcell, West Lebanon, NH, USA) were administered i.p. on each of days 17 and 20. In other words, the anti-PD1 treatment started only after the end of the Z13Mad5Anaxa treatment. In the respective control group, 200 μg of isotype mAB 2A3 were administered i.p. on each of days 17 and 20.

Figure 6:
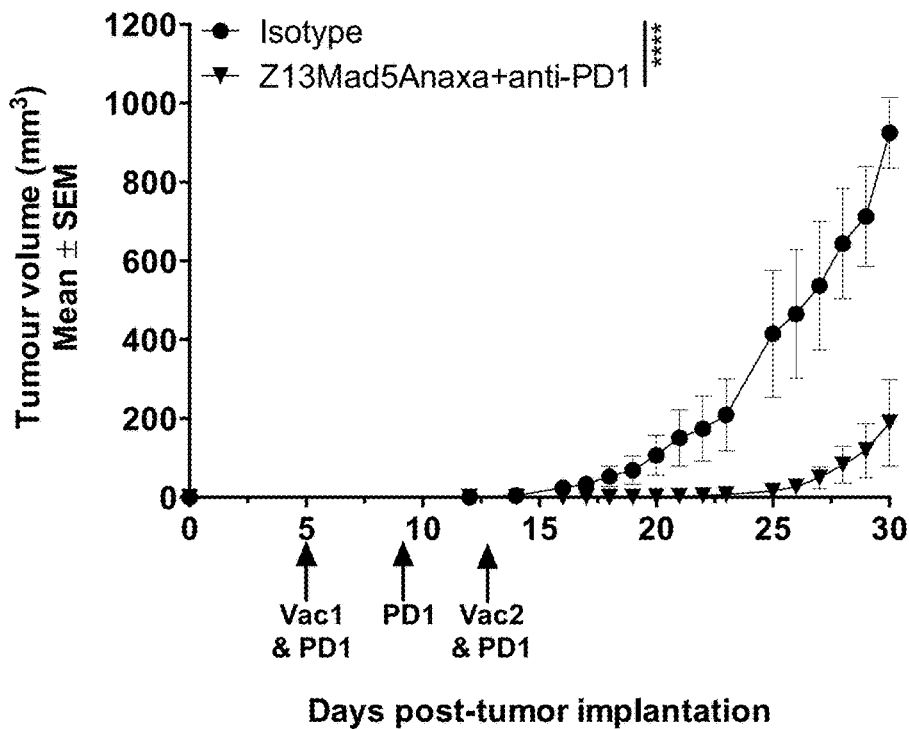
FIG. 6 shows for Example 3 the tumor growth of mice treated with anti-PD1 and Z13Mad5Anaxa in distinct treatment protocols. (A) Mice treated with anti-PD1 and Z13Mad5Anaxa according to the protocol of Example 1. (B) Tumor growth of mice treated with anti-PD1 only after vaccination with Z13Mad5Anaxa was finished. ****, $p<0.0001$.
Figure 6:
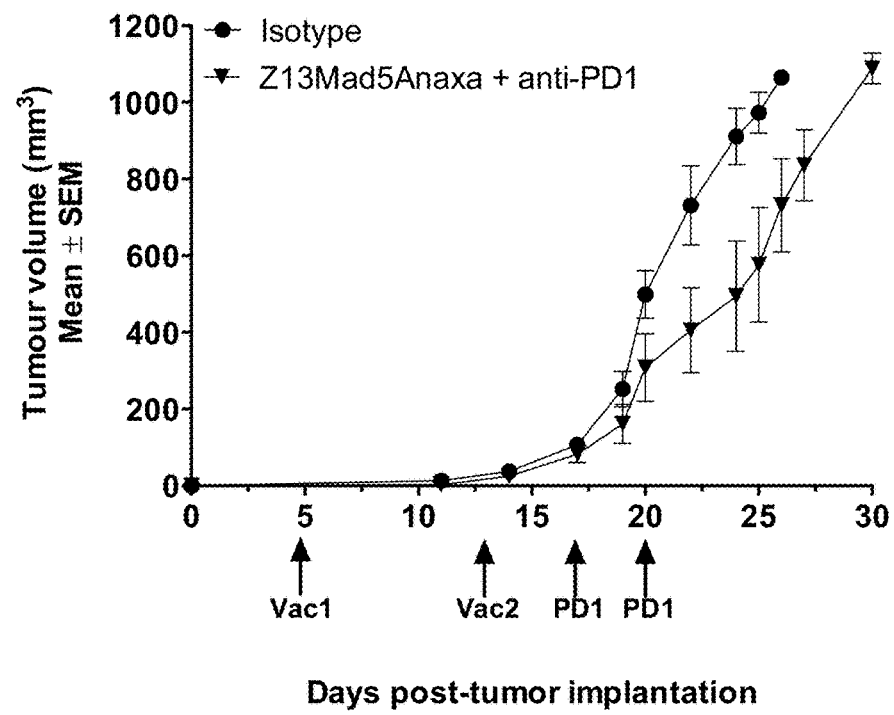

Results are shown in FIG. 6 with FIG. 6A showing the tumor growth in the first experimental group (protocol according to Example 1) and the respective control group and FIG. 6B showing the tumor growth in the second experimental group (anti-PD1 treatment only started after Z13Mad5Anaxa treatment was finished) and the respective control group. As can be retrieved from FIG. 6, the latter treatment protocol, wherein anti-PD1 treatment only started after Z13Mad5Anaxa treatment was finished, resulted in a slight improvement (slightly decreased tumor growth, cf. FIG. 6B), whereas the "true combination" of anti-PD1 and Z13Mad5Anaxa (protocol as in Example 1, cf. FIG. 6A) resulted in a considerably stronger improvement, i.e. in a strongly pronounced decrease in tumor growth.

These data further support the synergistic effect of a combination of anti-PD1 therapy and Z13Mad5Anaxa vaccination observed in the previous Examples, since the effect was much smaller when anti-PD1 therapy was only started after Z13Mad5Anaxa vaccination was finished.

Example 4: Effects of Combination of a PD1 Inhibitor and a Complex Comprising a Cell Penetrating Peptide, Different Antigens and a TLR Peptide Agonist on T Cell Homing at the Tumor Site in a Glioblastoma Model To investigate the effects of the combination of a PD1 inhibitor and a complex comprising a cell penetrating peptide, different antigens and a TLR peptide agonist in a different tumor model (other than the E.G7 model used in Examples 1-3), a murine glioblastoma model was used. T cell homing at the tumor site was thus analyzed in GI261-Quad tumor-bearing mice vaccinated twice (week 1 and week 3 after tumor implantation) with Z13Mad5Anaxa vaccine and treated or not with anti-PD1. At week 4, blood and the brain infiltrating leukocytes (BILs) were analyzed.

In particular, C57BL/6 mice were implanted intracranially with $5 \times 10^5$ G1261-Quad tumor cells at day 0. After tumor implantation, mice of the groups "Z13Mad5Anaxa+Isotype" and "Z13Mad5Anaxa+anti-PD1" were vaccinated at days 7 and 21 by subcutaneous injection of 2 nmol of Z13Mad5Anaxa in the right flank. 200 μg of anti-PD1 antibody RMP1-14 (BioXcell, West Lebanon, NH, USA) were administered i.p. on each of days 7, 10, 14, 17 and 21. to mice of groups "anti-PD1" and "Z13Mad5Anaxa+anti-PD1". For control, 200 μg of isotype mAB 2A3 were administered i.p. on each of days 7, 10, 14, 17 and 21 to mice of groups "isotype" and "Z13Mad5Anaxa+isotype". At days 7 and 21, when both, Z13Mad5Anaxa and antibody, were administered, the antibody was administered i.p. just after s.c. administration of Z13Mad5Anaxa. SIINFEKL-specific CD8 T cells were quantified in blood and in brain infiltrating leukocytes (BILs) at day 28 by multimer staining (5-8 mice per group).

Figure 7:
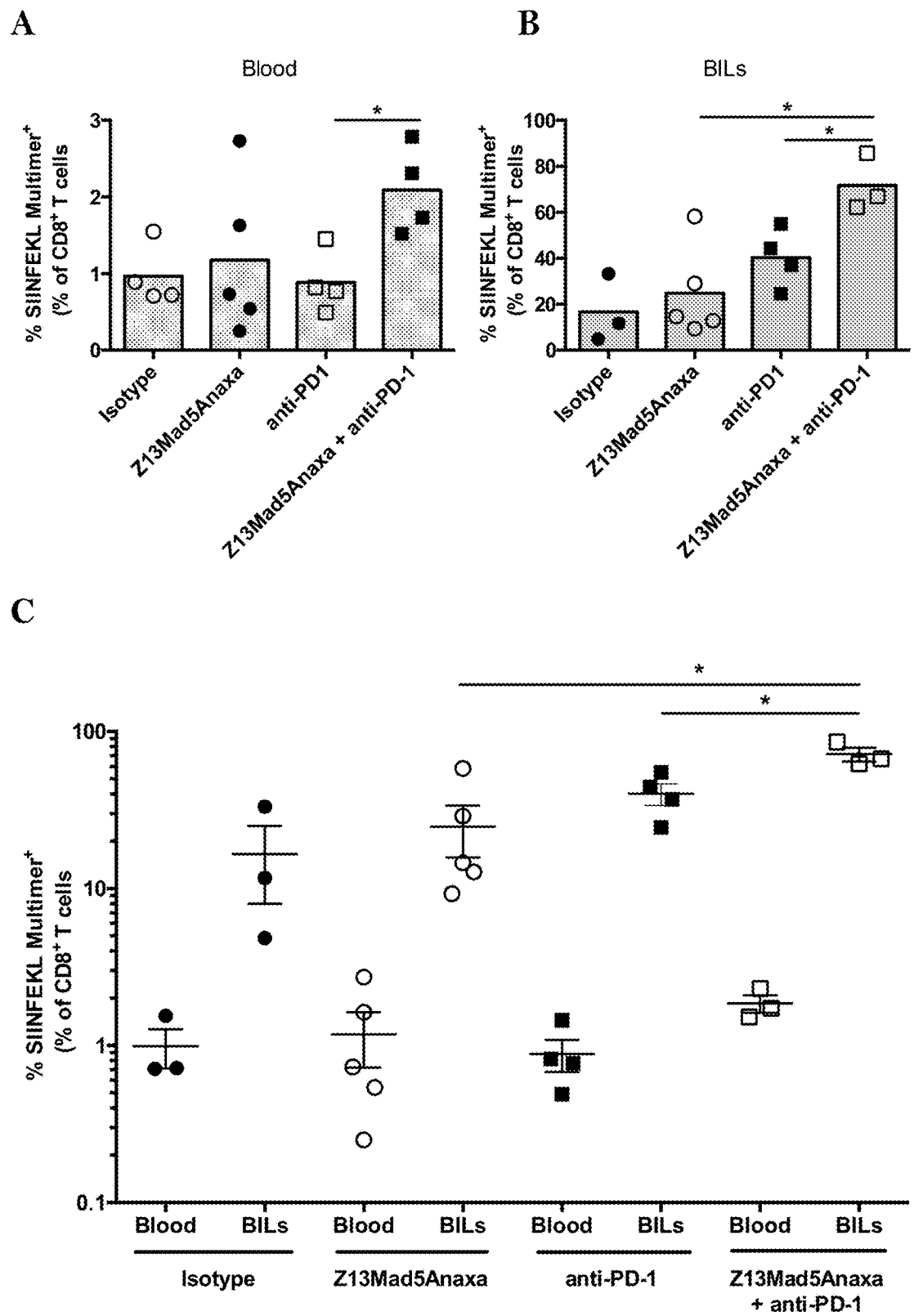
FIG. 7 shows for Example 4 the percentage of SIINFEKL-specific CD8 T cells in blood (A) and the percentage of SIINFEKL-specific CD8 T cells in BILs (B).

Results are shown in FIG. 7 with the percentage of SIINFEKL-specific CD8 T cells in blood shown in FIG. 7A and the percentage of SIINFEKL-specific CD8 T cells in BILs shown in FIG. 7B. FIG. 7C shows a summary of the percentage of SIINFEKL-specific CD8 T cells in blood and BILs. As previously observed, low frequency of SIINFEKL-specific CD8 T cells was quantified in the blood. However, a higher percentage of SIINFEKL-specific CD8 T cells was observed in the blood of Z13Mad5Anaxa-vaccinated mice treated or not with anti-PD1. In all groups, there was a sensibly stronger accumulation of SIINFEKL-specific CD8 T cells in the BILs than in blood. Importantly, the anti-PD1 therapy was able to increase the frequency of specific CD8 T cells to 42% without vaccination and even to 61% when combined with Z13Mad5Anaxa vaccination suggesting again a synergistic effect of the vaccination and the anti-PD1 therapy.

Moreover, the percentage of cytokine-producing cells was also assessed. To this end, intracellular cytokines were stained after restimulation with the SIINFEKL peptide for 6 hours in the presence of Brefeldin A (GolgiPlug, BD Biosciences) with mAb to IFN-γ (XMG1.2), tumor necrosis factor (MP6-XT22) and corresponding isotype controls (BD Biosciences).

Figure 8:
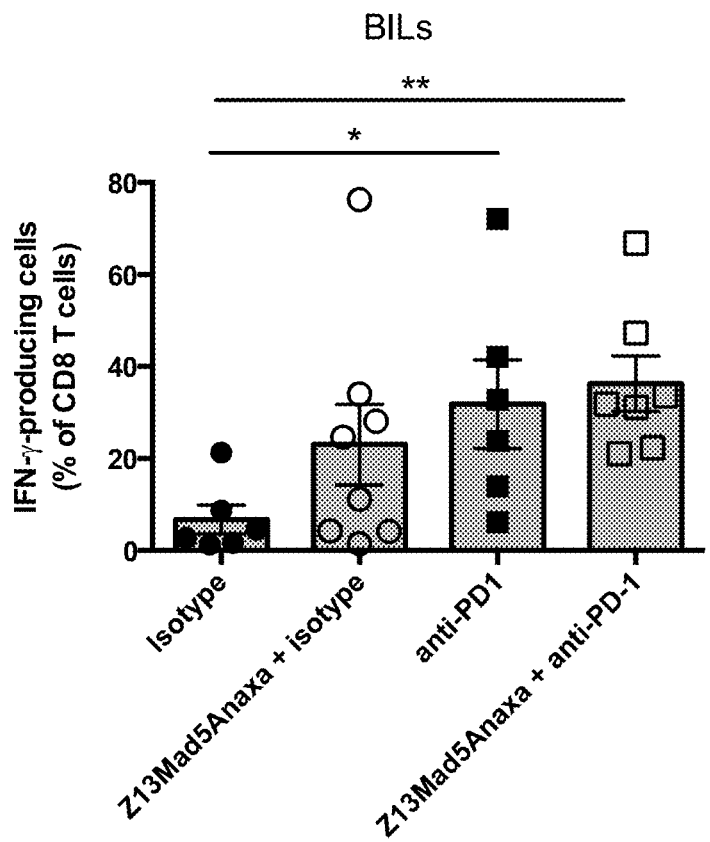
FIG. 8 shows for Example 4 the percentage of IFN-γ producing cells (% of CD8 T cells) in BILs (A) and a summary of IFN-γ and/or TNFα producing cells (% of CD8 T cells) in BILs (B) after stimulation with SIINFEKL peptide for 6 h. *, $p<0.05$; **, $p<0.01$.
Figure 8:
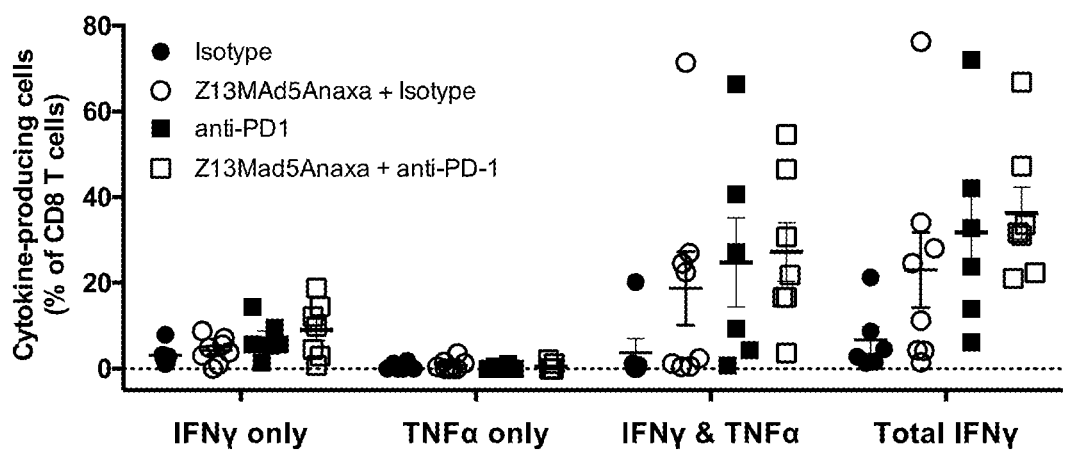

Results are shown in FIG. 8 with the percentage of IFN-γ producing cells (% of CD8 T cells) shown in FIG. 8A and a summary of IFN-γ and/or TNFα producing cells (% of CD8 T cells) shown in FIG. 8B. Those data show that vaccination with Z13Mad5Anaxa alone and treatment with anti-PD1 alone result in an increased percentage of cytokine, in particular IFN-γ, producing cells. However, the strongest increase in percentage of cytokine, in particular IFN-γ, producing cells was clearly observed in animals treated with a combination of Z13Mad5Anaxa and anti-PD1.

Taken together, the strongest SIINFEKL-specific CD8 T cell immune responses in the brains of tumor bearing mice with potent effector function were clearly observed in animals treated with a combination of Z13Mad5Anaxa and anti-PD1. These findings also indicate a synergistic effect of Z13Mad5Anaxa and anti-PD1 in the glioblastoma model.

Example 5: Effects of Combination of a PD1 Inhibitor and a Complex Comprising a Cell Penetrating Peptide, Different Antigens and a TLR Peptide Agonist on Survival in a Glioblastoma Model Next, the survival rate of mice treated with a combination of anti-PD1 and Z13Mad5Anaxa was assessed in the glioblastoma model in an independent experiment.

To this end, C57BL/6 mice were implanted intracranially with $5 \times 10^5$ GI261-Quad tumor cells at day 0. After tumor implantation, mice of the groups "Z13Mad5Anaxa+Isotype" and "Z13Mad5Anaxa+anti-PD1" were vaccinated at days 7, 21 and 35 by subcutaneous injection of 2 nmol of Z13Mad5Anaxa in the right flank. 200 µg of anti-PD1 antibody RMP1-14 (BioXcell, West Lebanon, NH, USA) were administered i.p. on each of days 7, 10, 14, 17 and 21 to mice of the group "Z13Mad5Anaxa+anti-PD1". For control, 200 µg of isotype mAB 2A3 were administered i.p. on each of days 7, 10, 14, 17 and 21 to mice of groups "isotype" and "Z13Mad5Anaxa+isotype". At days 7 and 21, when both, Z13Mad5Anaxa and antibody, were administered, the antibody was administered i.p. just after s.c. administration of Z13Mad5Anaxa. Mice were weighed daily and euthanized when weight loss was more than 15%.

Figure 9:
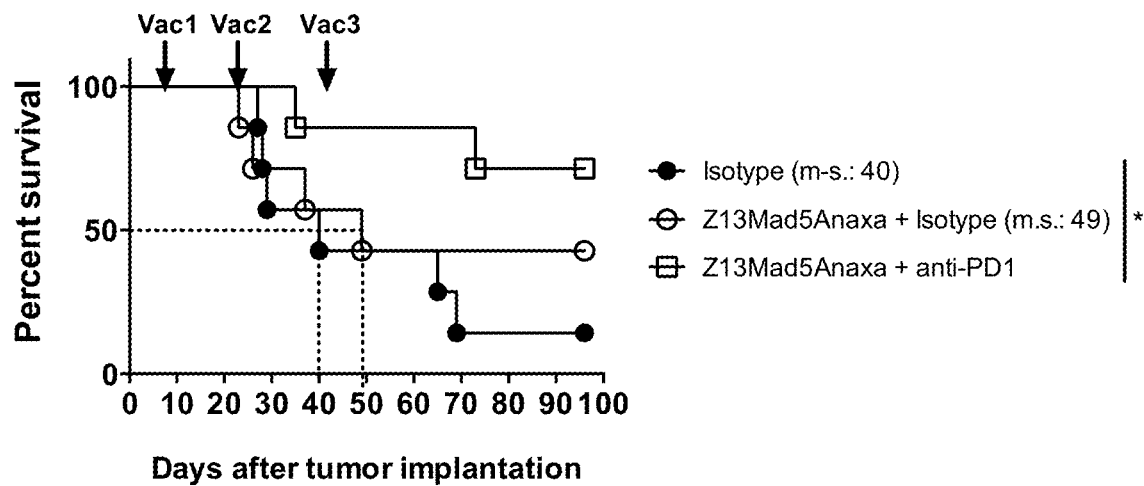
FIG. 9 shows for Example 5 the survival rate of mice. C57BL/6 mice were implanted intracranially with $5 \times 10^5$ GI261-Quad tumor cells at day 0. After tumor implantation, mice of the groups "Z13Mad5Anaxa+Isotype" and "Z13Mad5Anaxa+anti-PD1" were vaccinated at days 7, 21 and 35 by subcutaneous injection of 2 nmol of Z13Mad5Anaxa in the right flank. 200 μg of anti-PD1 antibody were administered i.p. on each of days 7, 10, 14, 17 and 21 to mice of the group "Z13Mad5Anaxa+anti-PD1". For control, 200 μg of isotype mAB 2A3 were administered i.p. on each of days 7, 10, 14, 17 and 21 to mice of groups "isotype" and "Z13Mad5Anaxa+isotype". At days 7 and 21, when both, Z13Mad5Anaxa and antibody, were administered, the antibody was administered i.p. just after s.c. administration of Z13Mad5Anaxa. Mice were weighed daily and euthanized when weight loss was more than 15%. *, $p<0.05$; **, $p<0.01$.

Results are shown in FIG. 9. These results show that Z13Mad5Anaxa therapeutic vaccination alone is more efficacious than the control group with a 10-days difference in the median survival. Again, the effects, i.e. the increase in the survival rate, are strongest for the combination of anti-PD1 and Z13Mad5Anaxa. In particular, combined anti-PD1/Z13Mad5Anaxa therapy is able to control glioblastoma growth.

Taken together, combined anti-PD1 therapy increased the effect of the vaccination with Z13Mad5Anaxa. As shown in Example 4, a combination of Z13Mad5Anaxa and anti-PD1 was able to promote the strongest secretion of cytokine by antigen-specific CD8 T cells in the brain.

Example 6: Effects of Combination of a PD1 Inhibitor and a Complex Comprising a Cell Penetrating Peptide, Different Antigens and a TLR Peptide Agonist on the Number of Metastases in a Lung Metastasis Model In this experiment the combination of a PD1 inhibitor and a complex comprising a cell penetrating peptide, different antigens and a TLR peptide agonist was investigated again in a different tumor model (other than the E.G7 model used in Examples 1-3 and the glioblastoma model used in Examples 4 and 5).

To this end, C57BL/6 mice were implanted i.v. with $1 \times 10^5$ B16-OVA melanoma tumor cells at day 0. After tumor implantation, mice of the group "Z13Mad5Anaxa+anti-PD1" ("Vaccine+anti-PD1") were vaccinated at days 0 and 10 by subcutaneous injection of 0.5 nmol of Z13Mad5Anaxa in the right flank. 200 µg of anti-PD1 antibody RMP1-14 (BioXcell, West Lebanon, NH, USA) were administered i.p. on each of days 0, 3 and 7 to mice of the groups "Z13Mad5Anaxa+anti-PD1" ("Vaccine+anti-PD1") and "anti-PD1". For control, 200 µg of isotype mAB 2A3 were administered i.p. on each of days 0, 3 and 7 to mice of the group "isotype". At day 0, when both, Z13Mad5Anaxa and antibody, were administered, the antibody was administered i.p. just after s.c. administration of Z13Mad5Anaxa. Mice were euthanized at day 17 and lung recovered. Number of metastasis foci was counted for each lung. **, p<0.01 (Unpaired T test).

Figure 10:
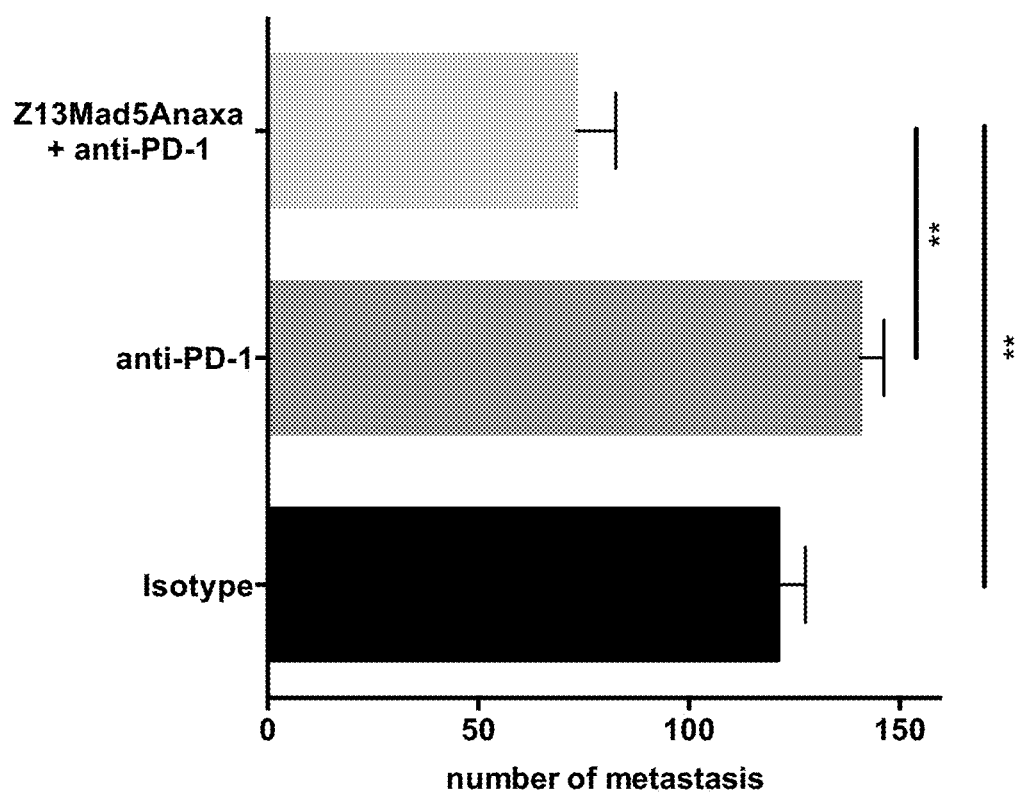
FIG. 10 shows for Example 6 the number of metastases. C57BL/6 mice were implanted i.v. with $1 \times 10^5$ B16-OVA melanoma tumor cells at day 0. After tumor implantation, mice of the group "Z13Mad5Anaxa+anti-PD1" ("Vaccine+anti-PD1") were vaccinated at days 0 and 10 by subcutaneous injection of 0.5 nmol of Z13Mad5Anaxa in the right flank. 200 μg of anti-PD1 antibody were administered i.p. on each of days 0, 3 and 7 to mice of the groups "Z13Mad5Anaxa+anti-PD1" ("Vaccine+anti-PD1") and "anti-PD1". For control, 200 μg of isotype mAB 2A3 were administered i.p. on each of days 0, 3 and 7 to mice of the group "isotype". Mice were euthanized at day 17 and lung recovered. Number of metastasis foci was counted for each lung. **, $p<0.01$ (Unpaired T test).

Results are shown in FIG. 10. Only the combined treatment with anti-PD1 and Z13Mad5Anaxa, but not the treatment with anti-PD1 alone, resulted in a significant decrease in the number of metastases. Accordingly, the combined treatment with anti-PD1 and Z13Mad5Anaxa was highly efficient in inhibiting the growth of melanoma metastasis in the lung.

Example 7: Effects of Combination of a CTLA4 Inhibitor and a Complex Comprising a Cell Penetrating Peptide, Different Antigens and a TLR Peptide Agonist on Tumor Growth in the EG7 Model To assess the effects of a combination of a complex comprising a cell penetrating peptide, different antigens and a TLR peptide agonist with a different checkpoint inhibitor, an inhibitor of CTLA4 was used in the present experiment.

C57BL/6 mice (5-6 mice per group) were implanted s.c. with $3 \times 10^5$ EG7-OVA tumor cells in the left flank (day 0). After tumor implantation, mice of the group "Z13Mad5Anaxa+aCTLA4 ip" were vaccinated at days 5 and 13 subcutaneously with 2 nmol of Z13Mad5Anaxa in the right flank. 100 µg of anti-CTLA4 antibody 9D9 (BioXcell, West Lebanon, NH, USA) were administered i.p. on each of days 5 and 13 to mice of groups "aCTLA4 ip" and "Z13Mad5Anaxa+aCTLA4 ip". In group "Z13Mad5Anaxa+aCTLA4 ip" the antibody was administered i.p. just after s.c. administration of Z13Mad5Anaxa. For control, 100 µg of isotype mAB MPC-11 (BioXcell, West Lebanon, NH, USA) were administered i.p. on each of days 5 and 13 to mice of the group "control". Tumor size was measured with a caliper.

Figure 11:
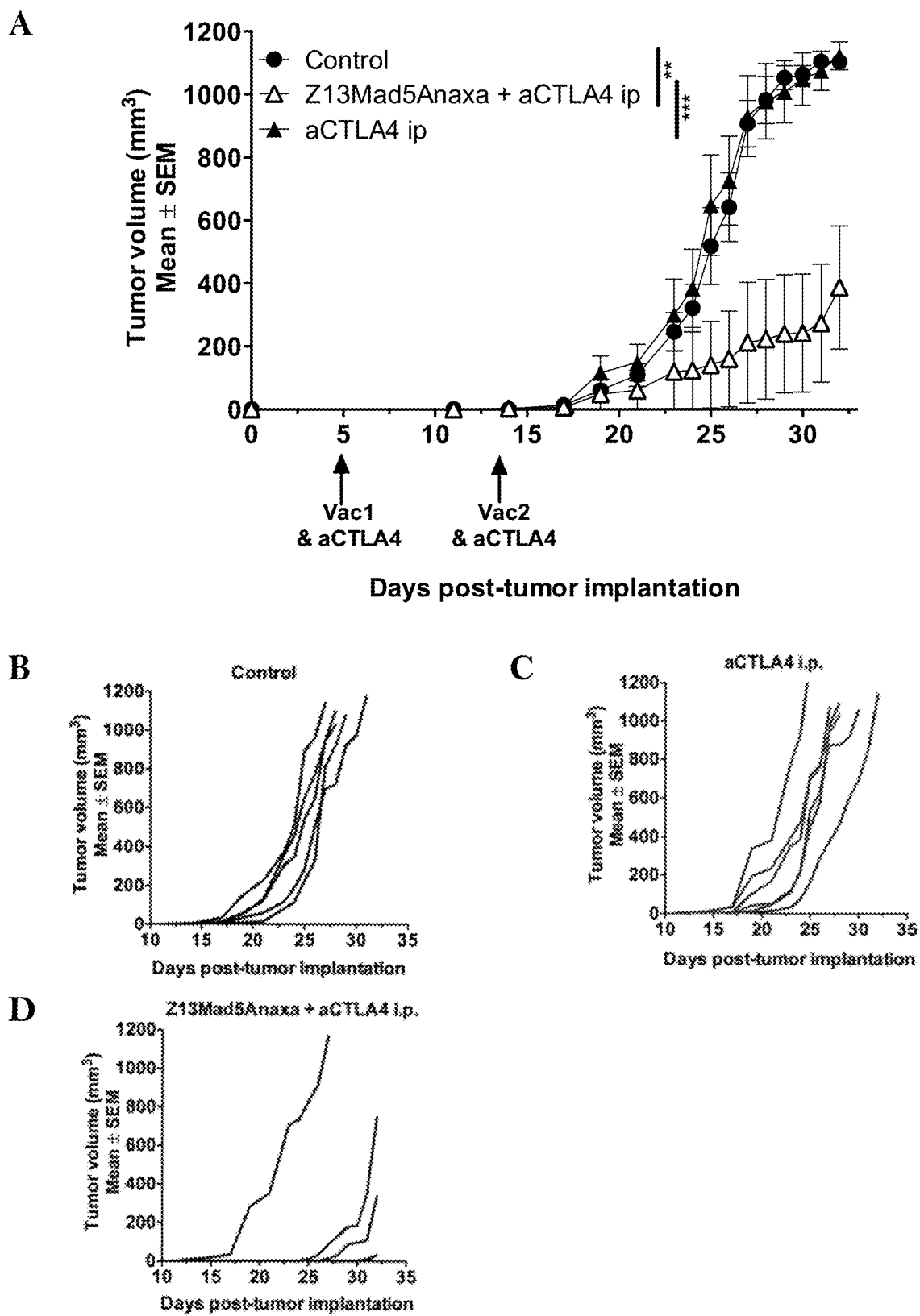
FIG. 11 shows for Example 7 the tumor growth in the EG7 tumor model. C57BL/6 mice (5-6 mice per group) were implanted s.c. with $3 \times 10^5$ EG7-OVA tumor cells in the left flank (day 0). After tumor implantation, mice of the group "Z13Mad5Anaxa+aCTLA4 ip" were vaccinated at days 5 and 13 subcutaneously with 2 nmol of Z13Mad5Anaxa in the right flank. 100 μg of anti-CTLA4 antibody were administered i.p. on each of days 5 and 13 to mice of groups "aCTLA4 ip" and "Z13Mad5Anaxa+aCTLA4 ip". In group "Z13Mad5Anaxa+aCTLA4 ip" the antibody was administered i.p. just after s.c. administration of Z13Mad5Anaxa. For control, 100 μg of isotype mAB MPC-11 were administered i.p. on each of days 5 and 13 to mice of the group "control". Tumor size was measured with a caliper. (A) Summary of all experimental groups. (B) Tumor growth in each mouse of the control group. (C) Tumor growth in each mouse of the anti-CTLA4 alone group. (D) Tumor growth in each mouse of the Z13Mad5Anaxa+aCTLA4 group. , p<0.01; *, p<0.001.

As shown in FIG. 11, treatment with the CTLA4 inhibitor alone did not result in any effect on tumor growth as compared to the control group. However, the combination of both, the CTLA4 inhibitor and Z13Mad5Anaxa, resulted in significantly decreased tumor volume. These data show that a combination of both, anti-CTLA4 therapy and Z13Mad5Anaxa vaccination efficient in decreasing tumor growth whereas anti-CTLA4 therapy alone did not result in any effect.

Example 8: Effects of the Route of Administration of the Immune Checkpoint Modulator on Tumor Growth To assess the effects of the route of administration of the immune checkpoint modulator in a combination therapy of a complex comprising a cell penetrating peptide, different antigens and a TLR peptide agonist with a checkpoint modulator, the EG7 tumor model was used.

C57BL/6 mice (5-6 mice per group) were implanted s.c. with $3 \times 10^5$ EG7-OVA tumor cells in the left flank (day 0). After tumor implantation, mice of the groups "Z13Mad5Anaxa+aCTLA4 ip" and "Z13Mad5Anaxa+aCTLA4 sc" were vaccinated at days 5 and 13 subcutaneously with 2 nmol of Z13Mad5Anaxa in the right flank. 100 µg of anti-CTLA4 antibody were administered i.p. on each of days 5 and 13 to mice of the group "Z13Mad5Anaxa+aCTLA4 ip" just after s.c. administration of Z13Mad5Anaxa. In group "Z13Mad5Anaxa+aCTLA4 sc" on each of days 5 and 13 100 µg of anti-CTLA4 antibody were administered s.c. at the same site as Z13Mad5Anaxa 1 h after injection of Z13Mad5Anaxa. For control, 100 µg of isotype mAB MPC-11 were administered i.p. on each of days 5 and 13 to mice of the group "control". Tumor size was measured with a caliper.

Figure 12:
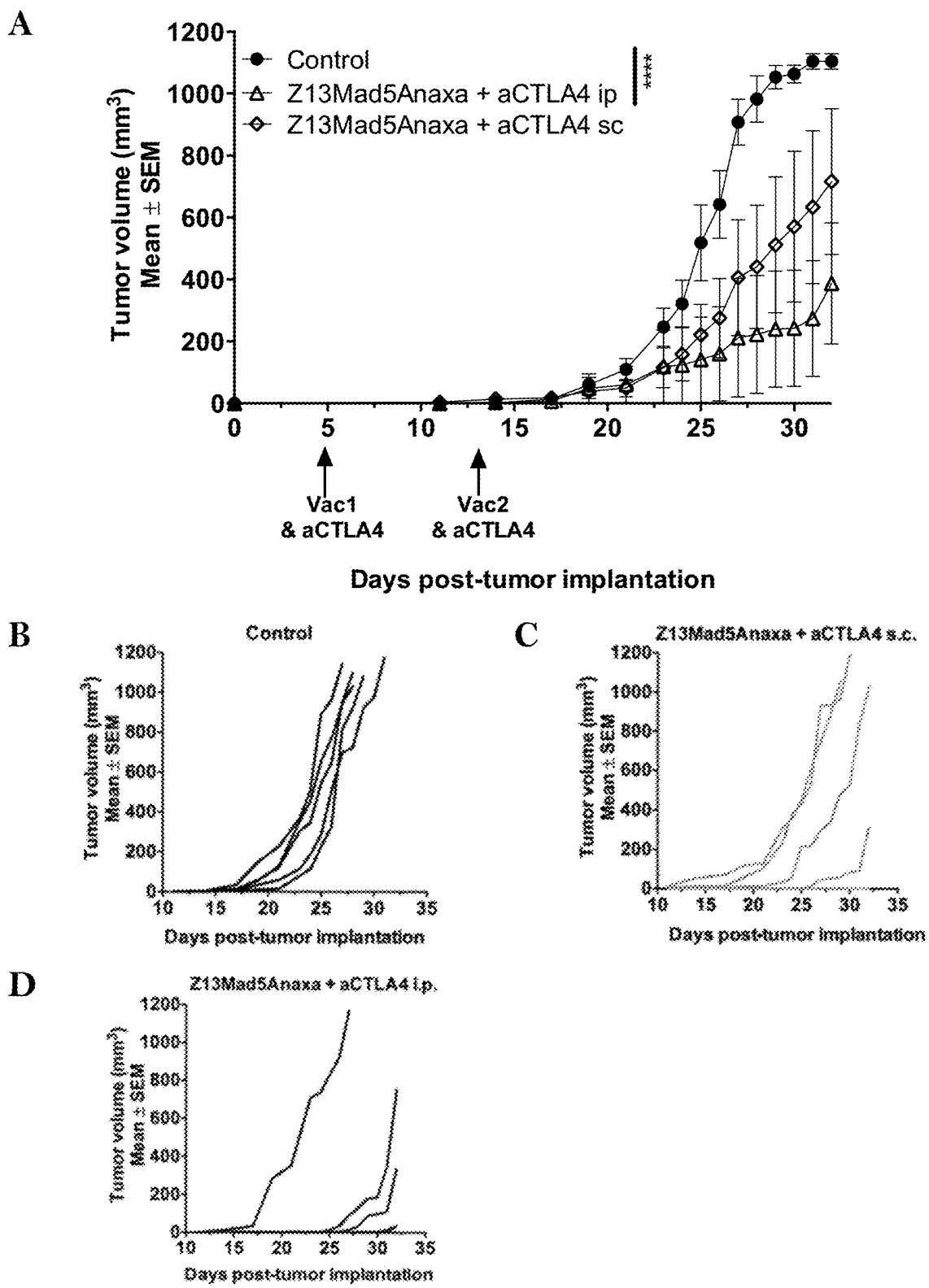
FIG. 12 shows for Example 8 the effect of the route of administration on tumor growth in the EG7 tumor model. C57BL/6 mice (5-6 mice per group) were implanted s.c. with $3\times10^5$ EG7-OVA tumor cells in the left flank (day 0). After tumor implantation, mice of the groups "Z13Mad5Anaxa+aCTLA4 ip" and "Z13Mad5Anaxa+aCTLA4 sc" were vaccinated at days 5 and 13 subcutaneously with 2 nmol of Z13Mad5Anaxa in the right flank. 100 μg of anti-CTLA4 antibody were administered i.p. on each of days 5 and 13 to mice of the group "Z13Mad5Anaxa+aCTLA4 ip" just after s.c. administration of Z13Mad5Anaxa. In group "Z13Mad5Anaxa+aCTLA4 sc" on each of days 5 and 13 100 μg of anti-CTLA4 antibody were administered s.c. at the same site as Z13Mad5Anaxa 1 h after injection of Z13Mad5Anaxa. For control, 100 μg of isotype mAB MPC-11 were administered i.p. on each of days 5 and 13 to mice of the group "control". Tumor size was measured with a caliper. (A) Summary of all experimental groups. (B) Tumor growth in each mouse of the control group. (C) Tumor growth in each mouse of the Z13Mad5Anaxa+aCTLA4 sc group. (D) Tumor growth in each mouse of the Z13Mad5Anaxa+aCTLA4 ip group. **, p<0.01.

As shown in FIG. 12, the most pronounced effect of the combination therapy of a complex comprising a cell penetrating peptide, different antigens and a TLR peptide agonist with a checkpoint modulator in decreasing tumor growth was achieved when the checkpoint modulator was administered intraperitoneally. Subcutaneous administration of the checkpoint modulator also resulted in decreased tumor growth, however, the effect was less pronounced than after i.p. administration.

Example 9: Effects of Combination of a CTLA4 Inhibitor and a Complex Comprising a Cell Penetrating Peptide, Different Antigens and a TLR Peptide Agonist on Tumor Growth in a CT26 Colon Carcinoma Model In this experiment the combination of a CTLA4 inhibitor and a complex comprising a cell penetrating peptide, different antigens and a TLR peptide agonist was investigated in a different tumor model (other than the E.G7 model used in Examples 7 and 8).

To this end, the murine CT26 colon carcinoma model was used and another complex comprising a cell penetrating peptide, different antigens and a TLR peptide agonist was designed ("Z13Mad8Anaxa"). Z13Mad8Anaxa differs from Z13Mad5Anaxa (described in Example 1) in the antigenic cargoes. In particular, "Z13Mad8Anaxa" is a fusion protein comprising the cell-penetrating peptide "Z13", the antigenic cargo "MAD8" comprising CD8 and CD4 epitopes of glycoprotein 70, and the TLR peptide agonist "Anaxa". In the following, the amino acid sequence of Z13Mad8Anaxa is shown with the cell-penetrating peptide "Z13" shown underlined and the TLR peptide agonist "Anaxa" shown in italics:

(SEQ ID NO: 33)
KRYKNRVASR KSRAKFKOLL QHYREVAAAK SSENDRLRLLLK

VTYHSPSYVY HQFERRAILN RLVQFIKDRI SVVQALVLTS

*TVHEILCKLS LEGDHSTPPS AYGSVKPYTN FDAE*

BALB/c mice (seven mice per group) were implanted s.c. with 2×10$^5$ CT26 tumor cells in the left flank (day 0). After tumor implantation, mice of the group "Z13Mad8Anaxa+ aCTLA4" were vaccinated at days 3 and 9 subcutaneously with 2 nmol of Z13Mad8Anaxa in the right flank and 100 µg of anti-CTLA4 antibody 9D9 (BioXcell, West Lebanon, NH, USA) were administered i.p. on each of days 3, 6 and 9 (on days 3 and 9 just after s.c. administration of Z13Mad8Anaxa). In the control group, 100 µg of isotype mAB MPC-11 were administered i.p. on each of days 3, 6 and 9 to mice of the group "control". Tumor size was measured with a caliper.

Figure 13:
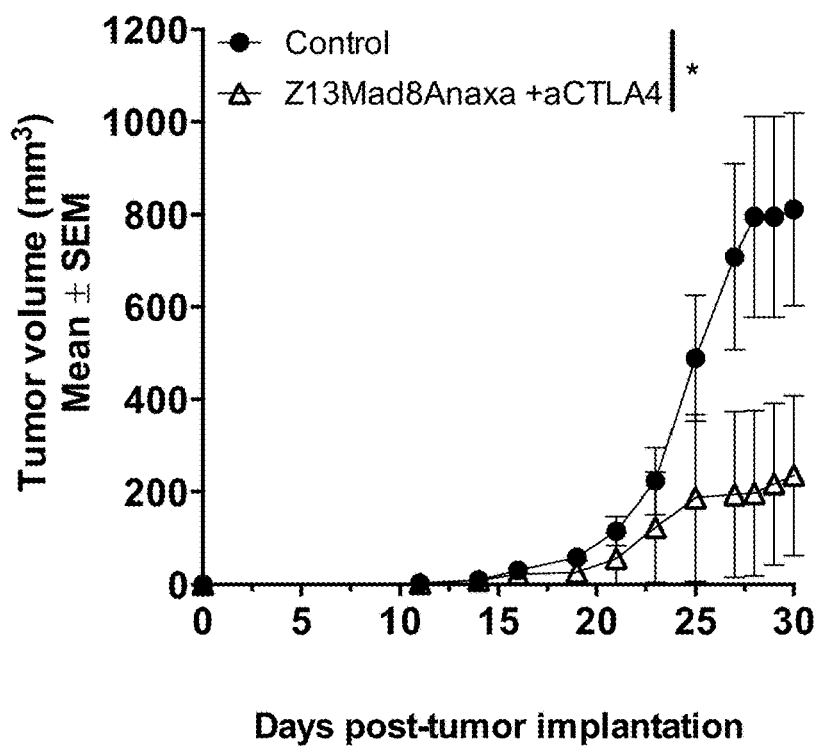
FIG. 13 shows for Example 9 the effect of a combination of a complex comprising a cell penetrating peptide, different antigens and a TLR peptide agonist and a CTLA4 inhibitor in the CT26 tumor model. BALB/c mice (5 to 6 mice per group) were implanted s.c. with $2\times10^5$ CT26 tumor cells in the left flank (day 0). After tumor implantation, mice of the group "Z13Mad8Anaxa+aCTLA4" were vaccinated at days 3 and 9 subcutaneously with 2 nmol of Z13Mad8Anaxa in the right flank and 100 μg of anti-CTLA4 antibody were administered i.p. on each of days 3, 6 and 9 (on days 3 and 9 just after s.c. administration of Z13Mad8Anaxa). In the control group, 100 μg of isotype mAB MPC-11 were administered i.p. on each of days 3, 6 and 9 to mice of the group "control". Tumor size was measured with a caliper. (A) Summary of all experimental groups. (B) Tumor growth in each mouse of the control group. (C) Tumor growth in each mouse of the Z13Mad8Anaxa+aCTLA4 group.
Figure 13:
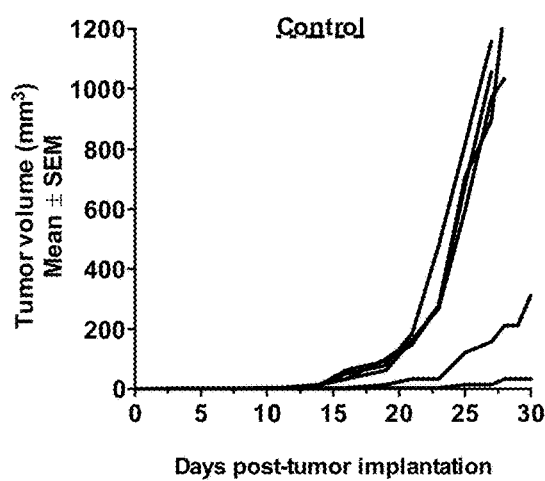
Figure 13:
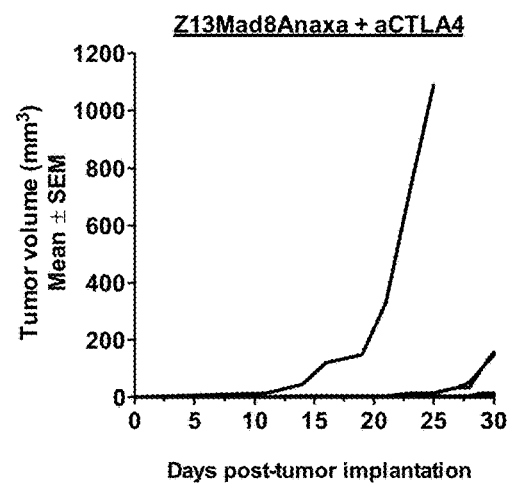

Results are shown in FIG. 13. These data show that a combination of an inhibitor of CTLA4 with complex comprising a cell penetrating peptide, different antigens and a TLR peptide agonist is able to control tumor growth also in the CT26 colon cancer tumor model.

Example 10: Effects of Combination of a Complex Comprising a Cell Penetrating Peptide, Different Antigens and a TLR Peptide Agonist with Two Different Immune Checkpoint Modulators on Tumor Growth In this experiment the effects of a combination of a complex comprising a cell penetrating peptide, different antigens and a TLR peptide agonist with two different immune checkpoint modulators, namely an inhibitor of PD1 and an inhibitor of CTLA4 was assessed. The aim of this experiment was to determine whether a combination including—in addition to the complex comprising a cell penetrating peptide, different antigens and a TLR peptide agonist-two different checkpoint modulators were even more efficacious than a combination with a single checkpoint modulator.

Care must be taken in the selection of an appropriate tumor model to avoid "floor effects" and "ceiling effects", since the effect, e.g. decrease in tumor volume, of combination with one checkpoint modulator should still be able to be improved, e.g. by an even further decrease in tumor volume. Therefore, the CT26 colon carcinoma model was chosen.

BALB/c mice (5 to 6 mice per group) were implanted s.c. with 2×10$^5$ CT26 tumor cells in the left flank (day 0). After tumor implantation, mice of the groups "Z13Mad8Anaxa+ aCTLA4" and "Z13Mad8Anaxa +aCTLA4/aPD1" were vaccinated at days 3 and 9 by subcutaneous injection of 2 nmol of Z13Mad8Anaxa in the right flank. 200 µg of anti-PD1 antibody RMP1-14 (BioXcell, West Lebanon, NH, USA) were administered i.p. on each of days 3, 6 and 9 to mice of groups "aCTLA4/aPD1" and "Z13Mad8Anaxa+ aCTLA4/aPD1". 100 µg of anti-CTLA4 antibody [name of Ab, provider?] were administered i.p. on each of days 3, 6 and 9 to groups "aCTLA4/aPD1", "Z13Mad8Anaxa+ aCTLA4" and "Z13Mad8Anaxa+aCTLA4/aPD1". At days 3 and 9, when Z13Mad8Anaxa and the antibodies were administered, the antibodies were administered i.p. just after s.c. administration of Z13Mad8Anaxa. In the control group, 100 µg of isotype mAB MPC-11 were administered i.p. on each of days 3, 6 and 9 to mice of the group "control". Tumor size was measured with a caliper.

Figure 14:
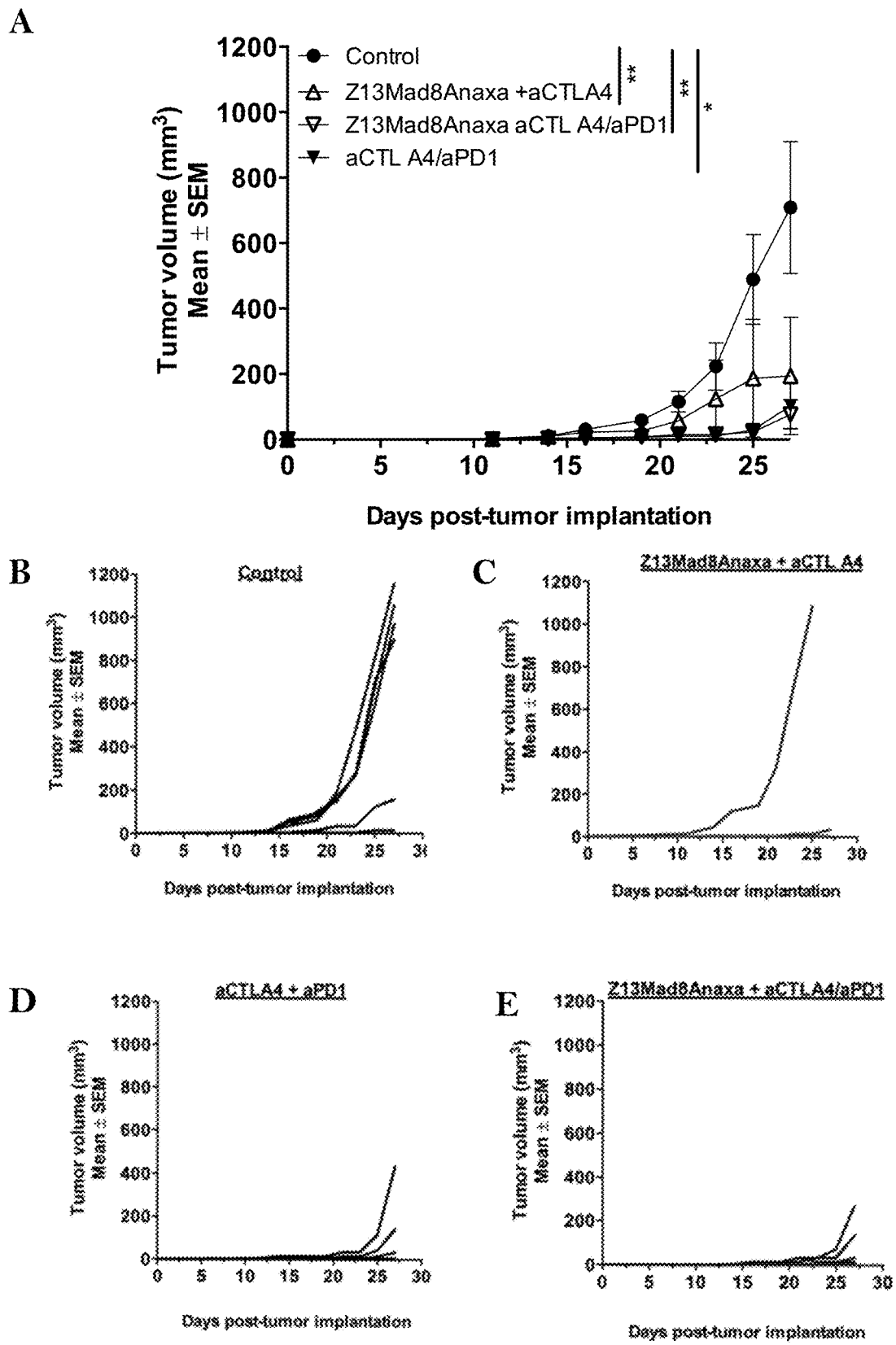
FIG. 14 shows for Example 10 the effect of a combination of a complex comprising a cell penetrating peptide, different antigens and a TLR peptide agonist, a PD1 inhibitor and a CTLA4 inhibitor. BALB/c mice (5 to 6 mice per group) were implanted s.c. with $2\times10^5$ CT26 tumor cells in the left flank (day 0). After tumor implantation, mice of the groups "Z13Mad8Anaxa+aCTLA4" and "Z13Mad8Anaxa+aCTLA4/aPD1" were vaccinated at days 3 and 9 by subcutaneous injection of 2 nmol of Z13Mad8Anaxa in the right flank. 200 μg of anti-PD1 antibody were administered i.p. on each of days 3, 6 and 9 to mice of groups "aCTLA4/aPD1" and "Z13Mad8Anaxa+aCTLA4/aPD1". 100 μg of anti-CTLA4 antibody were administered i.p. on each of days 3, 6 and 9 to groups "aCTLA4/aPD1", "Z13Mad8Anaxa+aCTLA4" and "Z13Mad8Anaxa+aCTLA4/aPD1". At days 3 and 9, when Z13Mad8Anaxa and the antibodies were administered, the antibodies were administered i.p. just after s.c. administration of Z13Mad8Anaxa. In the control group, 100 μg of isotype mAB MPC-11 and 200 μg of isotype 2A3 were administered i.p. on each of days 3, 6 and 9 to mice of the group "control". Tumor size was measured with a caliper. (A) Summary of all experimental groups. (B) Tumor growth in each mouse of the control group. (C) Tumor growth in each mouse of the Z13Mad8Anaxa+aCTLA4 group. (D) Tumor growth in each mouse of the aCTLA4/aPD1 group. (E) Tumor growth in each mouse of the Z13Mad8Anaxa+aCTLA4/aPD1 group.

Results are shown in FIG. 14. As shown in Example 9, treatment with a combination of Z13Mad8Anaxa with a CTLA4 inhibitor (but no further checkpoint modulator) resulted in a decrease in tumor growth. Similarly, treatment with a combination of checkpoint modulators (anti-CTLA4 and anti-PD1), but without Z13Mad8Anaxa, also resulted in a decrease in tumor growth. However, the combination of all three, the two distinct checkpoint modulators and Z13Mad8Anaxa, resulted in the most pronounced improvement, namely in strongly decreased tumor volume. Thus, the data show that a combination of all three, anti-PD1 therapy, anti-CTLA4 therapy and Z13Mad5Anaxa vaccination, is more efficacious than a combination of only two components. These results indicate a synergistic effect of anti-PD1 therapy, anti-CTLA4 therapy and Z13Mad5Anaxa vaccination.

Example 11: Immunogenicity of Combination of a CD40 Agonist and a Complex Comprising a Cell Penetrating Peptide, Different Antigens and a TLR Peptide Agonist To assess the potential of a combination of a complex comprising a cell penetrating peptide, different antigens and a TLR peptide agonist with again a different checkpoint modulator, an agonistic antibody targeting CD40 was used in the present experiment.

To this end, naïve C57BL/6 mice (4 mice per group) were vaccinated at days 0, 14, 28 and 42 (weeks 0, 2, 4 and 6) subcutaneously with 2 nmol of Z13Mad5Anaxa in the right flank. 100 µg of anti-CD40 antibody FGK45 (BioXcell, West Lebanon, NH, USA) were administered s.c. at day 0 to mice in the group "Z13Mad5Anaxa+aCD40 at vac1" and at days 0 and 14 to mice in the group "Z13Mad5Anaxa+ aCD40 at vac1 and vac2" (same days as first and second vaccination). The anti-CD40 antibody was administered s.c.

at the same site as Z13Mad5Anaxa 1 h after injection of Z13Mad5Anaxa. Mice were bled on days 21, 35 and 49 (weeks 3, 5 and 7) and the spleen was assessed on week 7. Multimer staining was performed on blood cells. Moreover, the percentage of cytokine-producing cells was also assessed in the spleen. To this end, intracellular cytokines were stained after restimulation with the SIINFEKL peptide for 6 hours in the presence of Brefeldin A (GolgiPlug, BD Biosciences) with mAb to IFN-γ (XMG1.2), tumor necrosis factor (MP6-XT22), CD107a (1D4B) and corresponding isotype controls (BD Biosciences).

Figure 15:
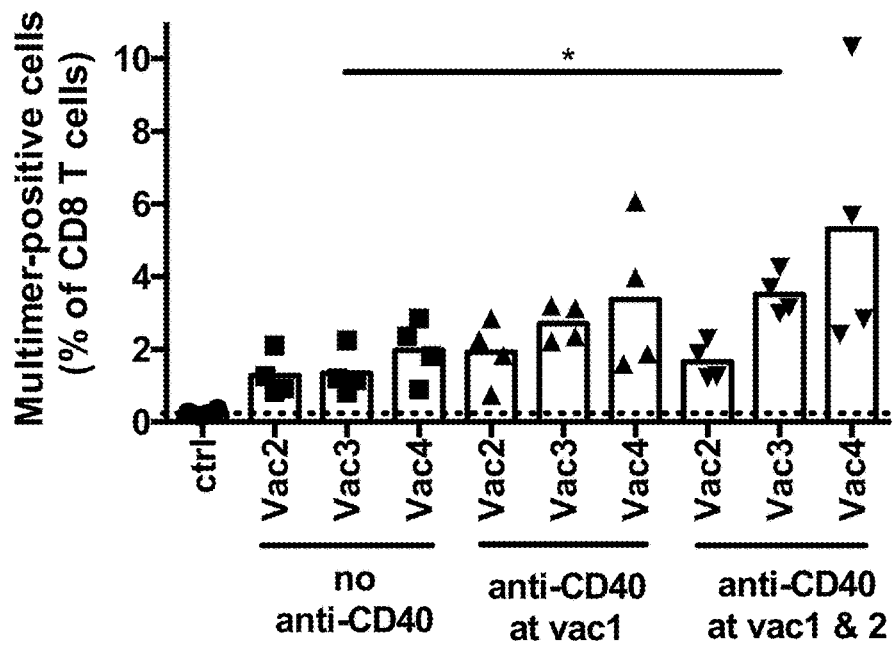
FIG. 15 shows for Example 11 the effect of a combination of a complex comprising a cell penetrating peptide, different antigens and a TLR peptide agonist, a CD40 agonist. C57BL/6 mice (4 mice per group) were vaccinated at days 0, 14, 28 and 42 by subcutaneous injection of 2 nmol of Z13Mad5Anaxa in the right flank. 100 μg of anti-CD40 antibody were administered s.c. at days 0 and days 0 and 14 to mice of groups "Z13Mad5Anaxa+aCD40 at vac1" and "Z13Mad5Anaxa+aCD40 at vac1 and vac2" respectively. (A) The percentage of multimer-positive cells (in % of CD8 T cells) for the different experimental groups. (B) The percentage of KLRG1 positive cells among multimer-positive cells. All groups are significantly different compared to naïve control group. *, p<0.05.
Figure 15:
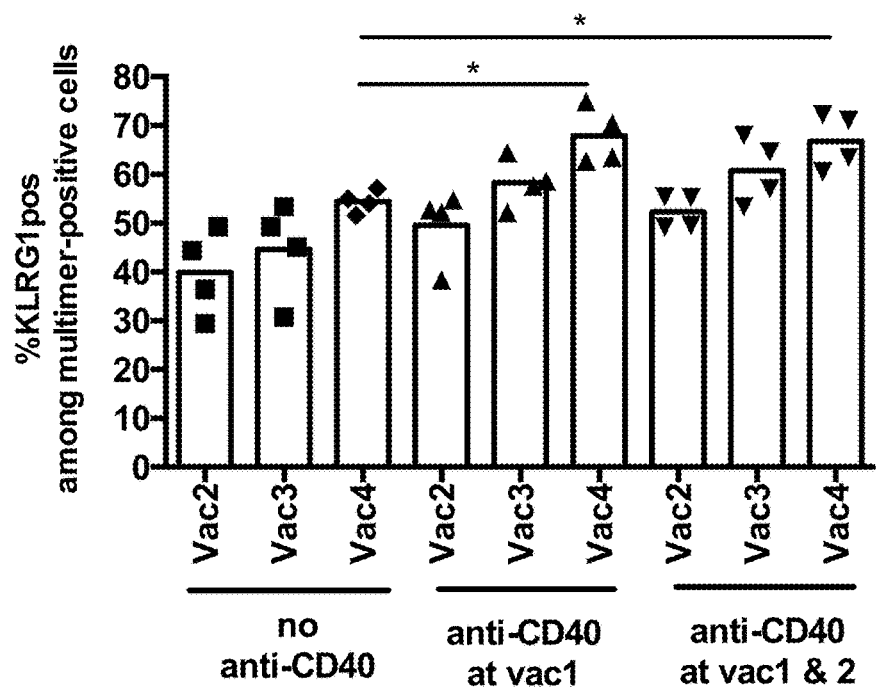

FIG. 15 shows the percentage of multimer-positive cells (in % of CD8 T cells) for the different experimental groups (FIG. 15A) and the percentage of KLRG1 positive cells among multimer-positive cells (FIG. 15B). All groups are significantly different compared to naïve control group, confirming the immunogenicity of Z13Mad5Anaxa. However, the groups treated additionally with an anti-CD40 antibody showed even more multimer-positive cells and KLRG1 positive cells, which was most pronounced in the group receiving two treatments with anti-CD40. These results indicate a synergistic effect of a combination of a CD40 agonist and Z13Mad5Anaxa on immunogenicity.

Figure 16:
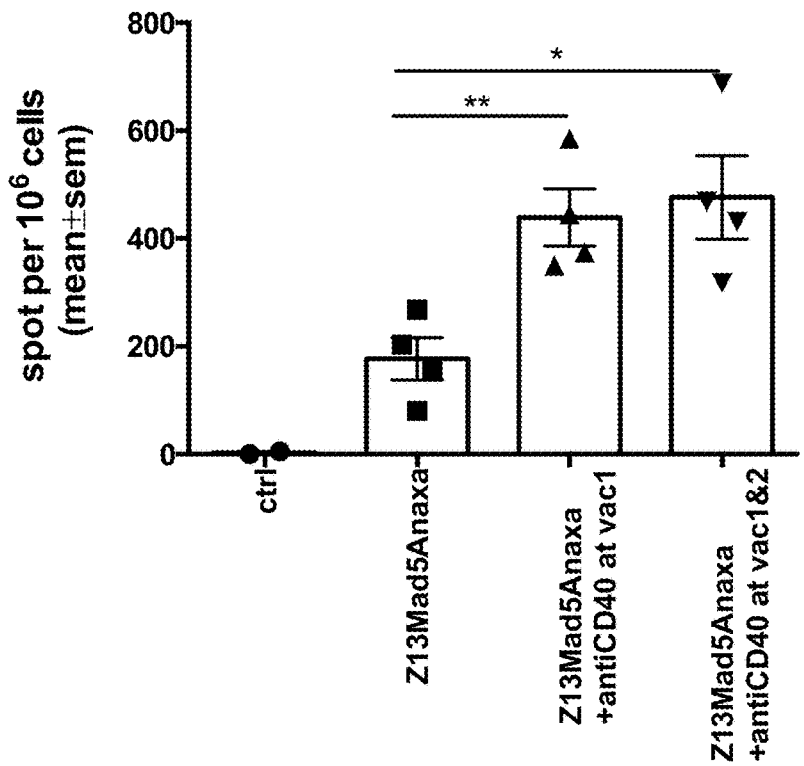
FIG. 16 shows for Example 11 (A) the amount of IFN-γ producing SIINFEKL-specific CD8 T cells (Elispot assay) and (B) the results of an intracellular staining of splenocytes for IFN-γ, CD107 and TNFα for SIINFEKL-specific CD8 T cells.
Figure 16:
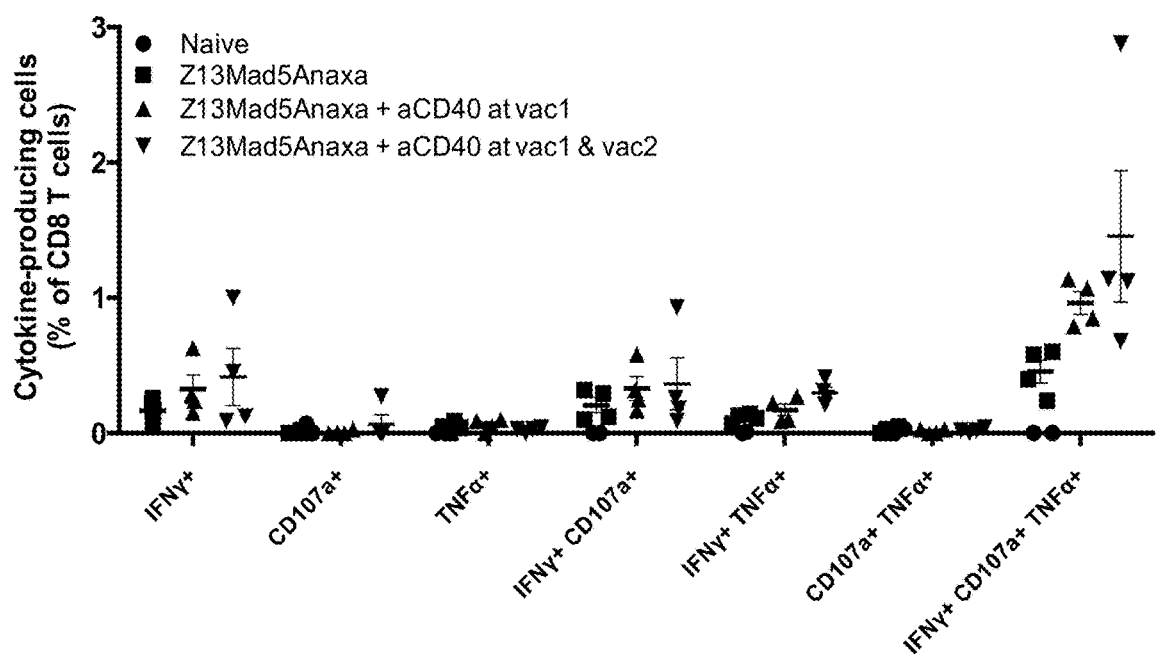
Figure 17:
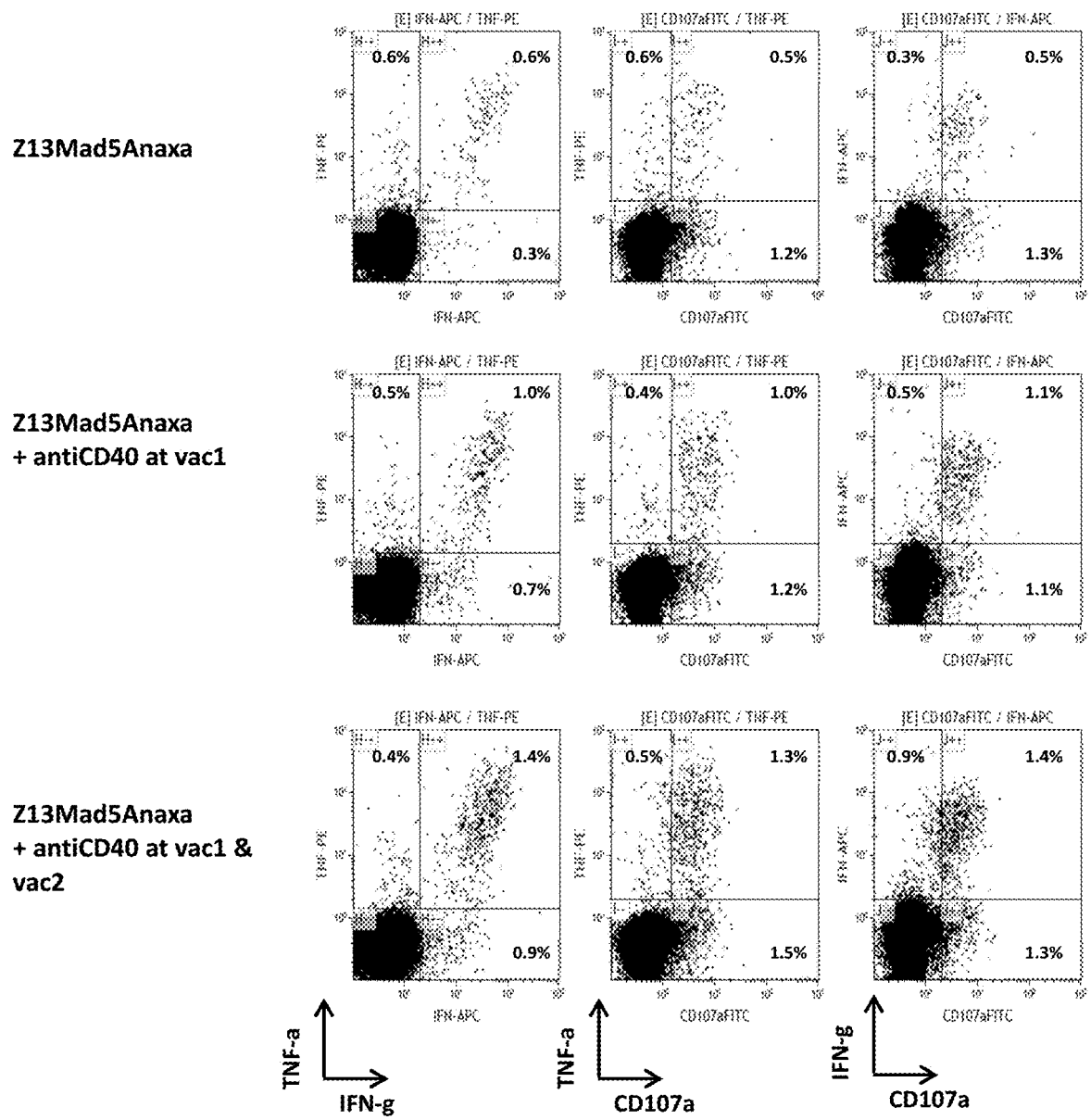
FIG. 17 shows for Example 11 the FACS plots of the intracellular staining of splenocytes for IFN-γ, CD107 and TNFα.

These data are supported by the results shown in FIGS. 16 and 17 relating to the effector function of the OVA-specific CD8 T cells, which show the strongest increase in cytokine producing cells, when vaccination with Z13Mad5Anaxa was combined with treatment with the agonistic anti-CD40 antibody.

Example 12: Efficacy of a Complex Having a Different TLR Agonist on Tumor Growth in a Benchmark EG.7-OVA Tumor Model The goal of this study was to investigate the effect of a complex as described herein having a different TLR agonist, namely "EDA" instead of "Z13", on tumor growth and survival. In the present study, the complex is a fusion protein, comprising the cell-penetrating peptide "Z13", a protein "MAD5", which consists of different CD8$^+$ and CD4$^+$ epitopes from various antigens, and the TLR4 peptide agonist "EDA". Accordingly, a fused protein with the EDA peptide at the N-terminal position and different control conjugated proteins without Z13 or EDA or both were designed.

Namely, the following constructs were designed, whereby in the amino acid sequence the cell-penetrating peptide "Z13" is shown underlined and the TLR peptide agonist "EDA" is shown in italics:

EDAZ13Mad5
Sequence:

[SEQ ID NO: 26]
M H H H H H H *N I D R P K G L A F T D V D V D S I K I A W E S P Q G Q V S R Y R V T T S S P E D G I*

*R E L F P A P D G E D D T A E L Q G L R P G S E Y T V S V V A L H D D M E S Q P L I G I Q S T* <u>K R Y K N R V A S R K S R</u>

<u>A K F K Q L L Q H Y R E V A A A K S S E N D R L R L L L K E</u> S L K I S Q A V H A A H A E I N E A G R E V V G V G A L K V

P R N Q D W L G V P R F A K F A S F E A Q G A L A N I A V D K A N L D V E Q L E S I I N F E K L T E W T G S

Molecular weight: 25'057 Da
Characteristics:
  Mad5 cargo contains OVACD4, gp100CD8, EalphaCD4 and OVACD8 epitopes
  Contains EDA TLR agonist (Lasarte, J. J., et al., The extra domain A from fibronectin targets antigens to TLR4-expressing cells and induces cytotoxic T cell responses in vivo. J Immunol, 2007. 178 (2): p. 748-56)
  Storage buffer: 50 mM Tris-HCl, 150 mM NaCl, 10% Glycerol, 2 mM DTT, 1 M L-Arginine, pH 8
  Endotoxin level: <0.01 EU/ug Mad5
Sequence:

[SEQ ID NO: 14]
MHHHHHHE SLKISQAVHA AHAEINEAGR EVVGVGALKV PRNQDWLGVP RFAKFASFEA

QGALANIAVD KANLDVEQLE SIINFEKLTE WTGS

Molecular weight: 10'154.6 Da
Characteristics:
  Mad5 cargo contains OVACD4, gp100CD8, EalphaCD4 and OVACD8 epitopes
  Storage buffer: 50 mM Tris-HCl, 150 mM NaCl, 10% Glycerol, 2 mM DTT, 0.5 M L-Arginine, pH 8
  Endotoxin level: 0.069 EU/mg EDAMad5
Sequence

[SEQ ID NO: 34]
M H H H H H H *N I D R P K G L A F T D V D V D S I K I A W E S P Q G Q V S R Y R V T Y S S P E D G I*

*R E L F P A P D G E D D T A E L Q G L R P G S E Y T V S V V A L H D D M E S Q P L I G I Q S T E* S L K I S Q A V H A

-continued

```
AHAEINEAGR EVVGVGALKV PRNQDWLGVP RFAKFASFEA QGALANIAVD

KANLDVEQLE SIINFEKLTE WTGS
```

Molecular weight: 20'017 Da

Characteristics:

Mad5 cargo contains OVACD4, gp100CD8, EalphaCD4 and OVACD8 epitopes

Contains EDA TLR agonist

Storage buffer: 50 mM Tris-HCl, 150 mM NaCl, 10% Glycerol, 2 mM DTT, 0.5 M L-Arginine, pH 8

Endotoxin level: 1.8 EU/mg

To evaluate the effect of EDA construct proteins on tumor growth control, the s.c. model of EG.7-OVA thymoma cells was chosen. C57BL/6 mice were implanted s.c. with $3 \times 10^5$ EG7-OVA tumor cells in the left flank. After tumor implantation, mice were vaccinated at day 5 and 13 with 10 nmol of one of the following constructs (cf. Examples 1 and 2 for construct description): EDAZ13Mad5, EDAMad5, Mad5, or Mad5 and MPLA (equimolar to EDA) s.c. in the right flank. Tumor size was measured with a caliper.

Figure 18:
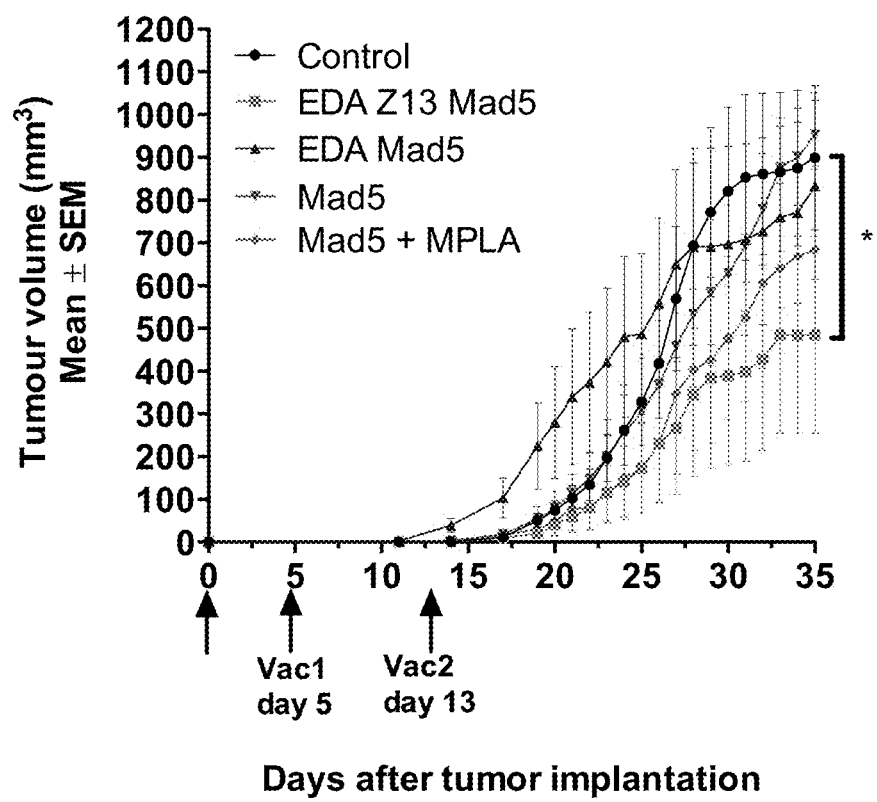
FIG. 18 shows for Example 12 the tumor growth of 7 mice per group (mean±SEM); *, p<0.05 EDAZ13Mad5 versus control group (2-way Anova test). C57BL/6 mice were implanted s.c. with $3\times10^5$ EG7-OVA tumor cells in the left flank and vaccinated twice (d5 and d13) by subcutaneous injection of 10 nmol of EDAZ13Mad5, EDAMad5, Mad5 or Mad5 and MPLA (equimolar to EDA) s.c. in the right flank. Tumor size was measured with a caliper.
Figure 19:
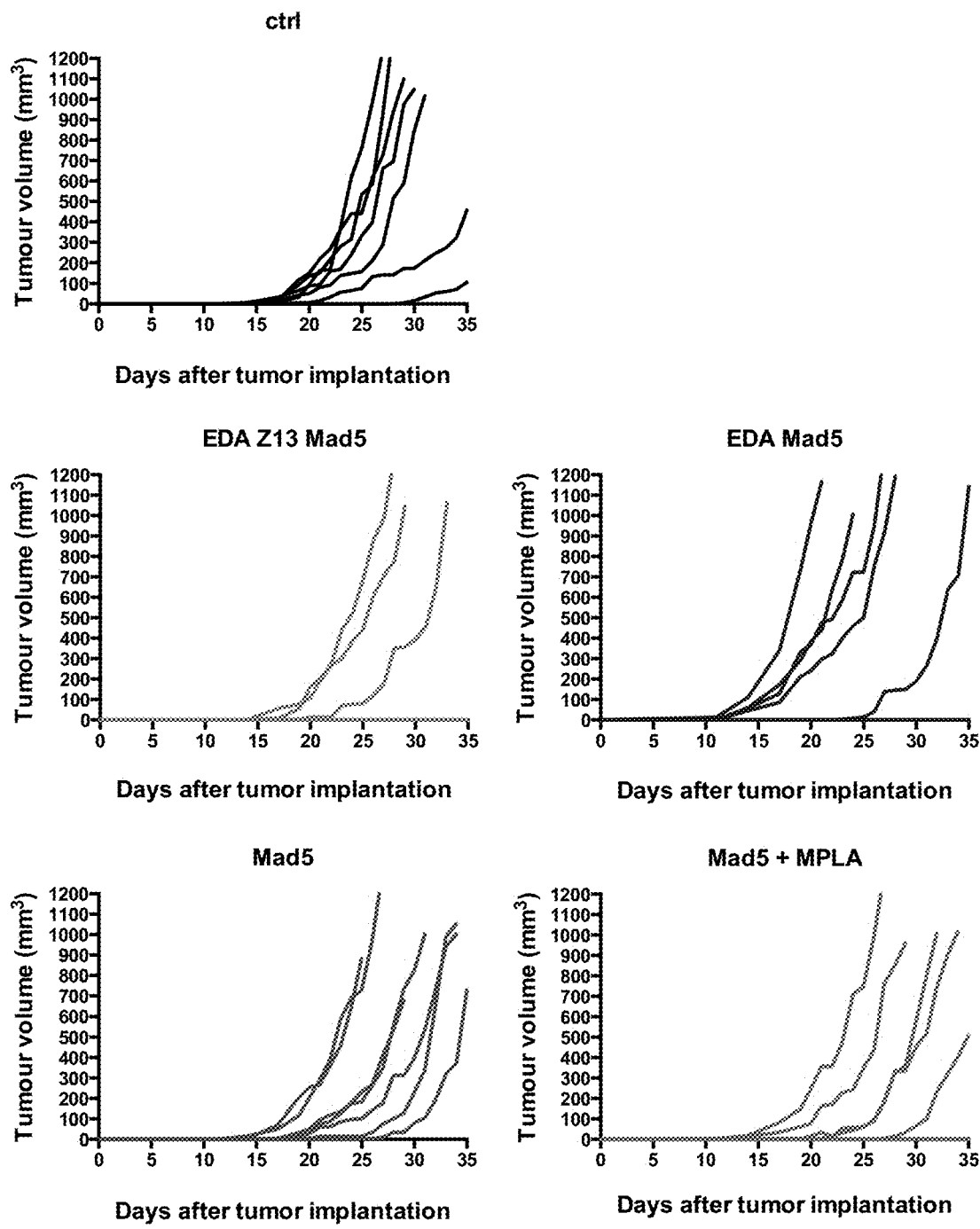
FIG. 19 shows for Example 12 individual tumor growth curves (7 individual mice per group). C57BL/6 mice were implanted s.c. with $3\times10^5$ EG7-OVA tumor cells in the left flank and vaccinated twice (d5 and d13) by subcutaneous injection of 10 nmol of EDAZ13Mad5, EDAMad5, Mad5 or Mad5 and MPLA (equimolar to EDA) s.c. in the right flank. Tumor size was measured with a caliper.
Figure 20:
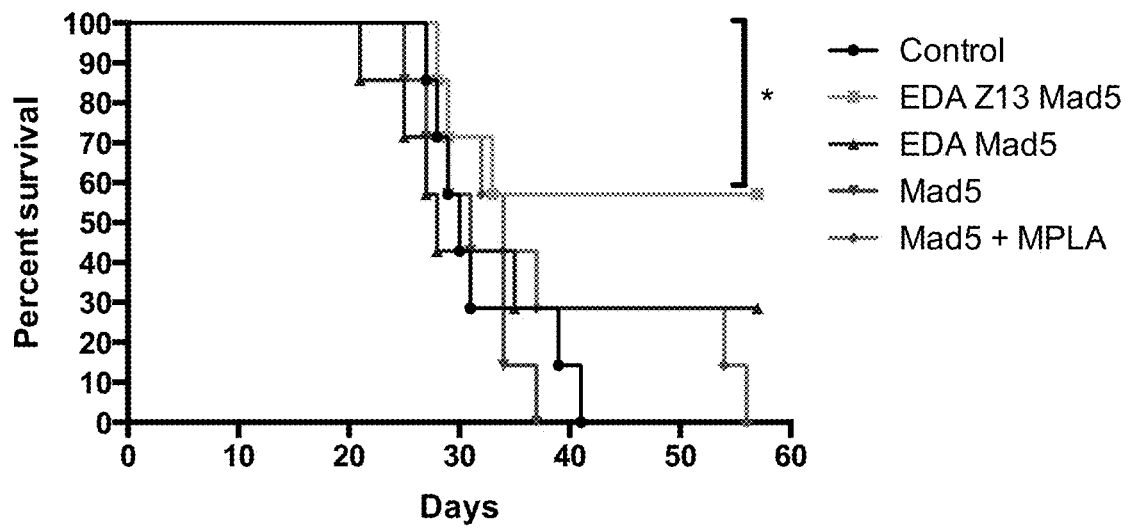
FIG. 20 shows for Example 12 (A) the survival curve of 7 mice per group; *, p<0.05 EDAZ13Mad5 versus control group (Log-rank test) and (B) the tumor-free progression curve of 7 mice per group; *, p<0.05 EDAZ13Mad5 versus control group (Log-rank test).
Figure 20:
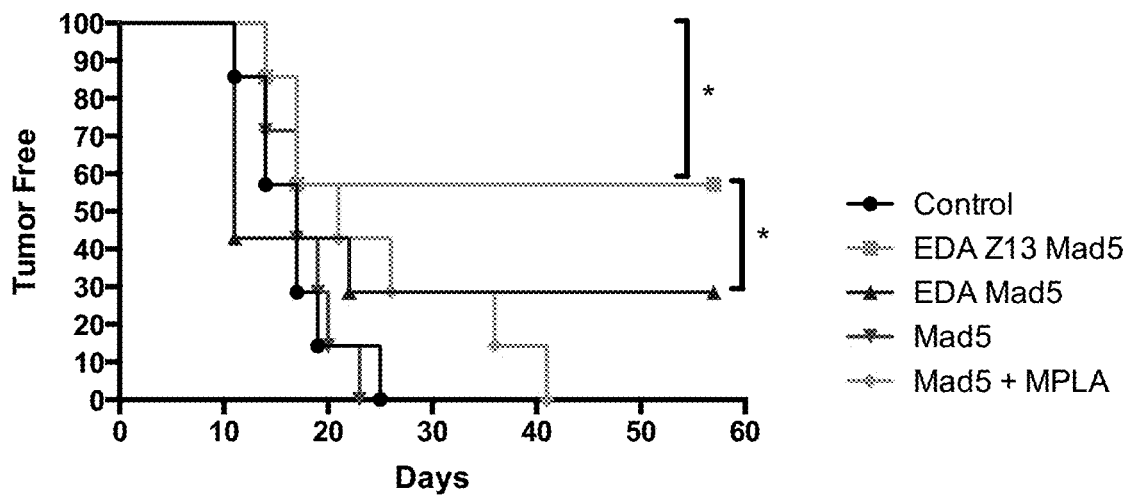

FIG. 18 shows the tumor growth of 7 mice per group (mean±SEM); *, p<0.05 EDAZ13Mad5 versus control group (2-way Anova test). FIG. 19 shows individual tumor growth curves (7 individual mice per group). FIG. 20A shows the survival curve of 7 mice per group; *, p<0.05 EDAZ13Mad5 versus control group (Log-rank test). FIG. 20B shows the tumor-free progression curve of 7 mice per group; *, p<0.05 EDAZ13Mad5 versus control group (Log-rank test).

The results show that in a therapeutic setting, EDAZ13Mad5 was the only protein vaccine to significantly control the tumor growth compared to the control group with a significant better tumor free progression curve and survival curve.

The results therefore suggest that the construct protein EDAZ13Mad5 is a highly potent vaccine for controlling the tumor growth in a therapeutic setting.

Example 13: Comparison of the Kinetic of Immune Responses with Complexes Having Different Cell Penetrating Peptides To investigate the effect of different CPPs in the complex comprised by the combination for use according to the present invention the fusion protein Z13Mad5Anaxa as described above was used.

In addition, further fusion proteins were designed, which comprise CPPs other than Z13-namely Z14 (SEQ ID NO: 7) or Z18 (SEQ ID NO: 11). Those fusion proteins also comprise the protein "MAD5", which consists of different $CD8^+$ and $CD4^+$ epitopes from various antigens, and the TLR2 peptide agonist "Anaxa". Accordingly, the following constructs were additionally designed:

Z14Mad5Anaxa

Sequence:

```
                                              (SEQ ID NO: 29)
MHHHHHHKRY KNRVASRKSR AKFKQLLQHY REVAAAKESL KISQAVHAAH

AEINEAGREV VGVGALKVPR NQDWLGVPRF AKFASFEAQG ALANIAVDKA

NLDVEQLESI INFEKLTEWT GSSTVHEILC KLSLEGDHST PPSAYGSVKP YTNFDAE
```

Z18Mad5Anaxa

Sequence:

```
                                              (SEQ ID NO: 30)
MHHHHHHREV AAAKSSENDR LRLLLKESLK ISQAVHAAHA EINEAGREVV

GVGALKVPRN QDWLGVPRFA KFASFEAQGA LANIAVDKAN LDVEQLESII

NFEKLTEWTG SSTVHEILCK LSLEGDHSTP PSAYGSVKPY TNFDAE
```

C57BL/6 mice were assigned to eight different groups (4 mice per group): three groups receiving 2 nmol of either Z13Mad5Anaxa, Z14Mad5Anaxa or Z18Mad5Anaxa and a respective control and three groups receiving 0.5 nmol of Z13Mad5Anaxa, Z14Mad5Anaxa or Z18Mad5Anaxa and a respective control. The mice were vaccinated five times (Week0, Week2, Week4, Week6 and Week8) s.c. Mice were bled 7 days after the $2^{nd}$, $3^{rd}$, $4^{th}$ and $5^{th}$ vaccination and multimer staining was performed (one experiment with 4 mice per group).

Figure 21:
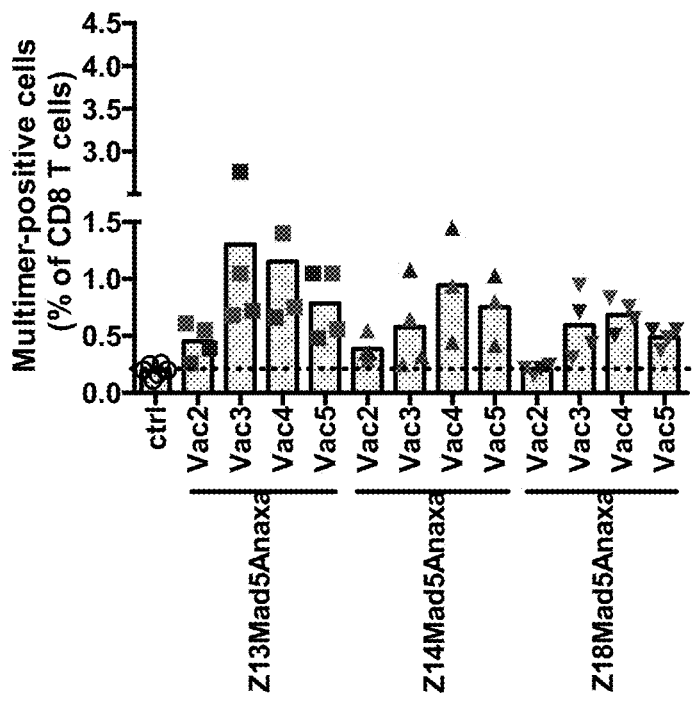
FIG. 21 shows for Example 13 the effect of complexes having different CPPs on the immune response. C57BL/6 mice were vaccinated five times (Wk0, Wk2, Wk4, Wk6 and Wk8) s.c. with either 2 nmol (A) or 0.5 nmol (B) of Z13Mad5Anaxa, Z14Mad5Anaxa or Z18Mad5Anaxa. Mice were bled 7 days after the $2^{nd}$, $3^{rd}$, $4^{th}$ and $5^{th}$ vaccination and multimer staining was performed (one experiment with 4 mice per group). *, p<0.05 between vaccinated versus naïve mice at each time point except after Vac2 for Z18Mad5Anaxa-vaccinated mice.
Figure 21:
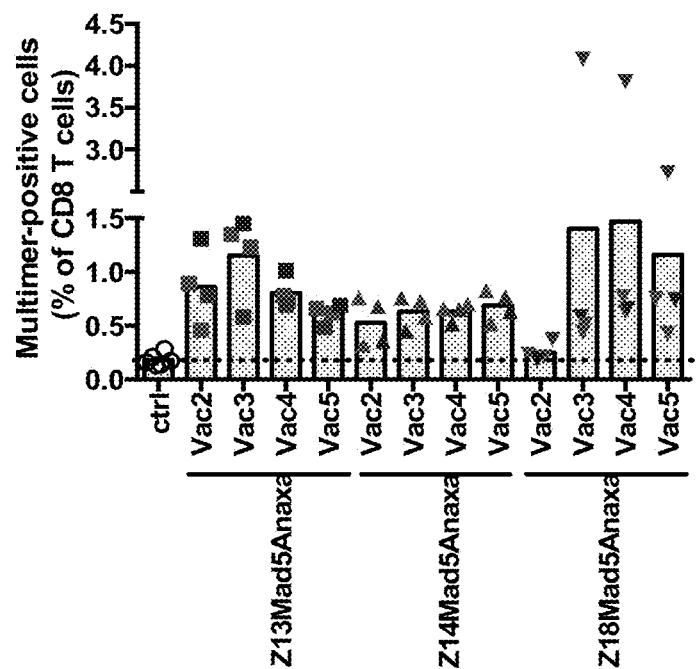

The results are shown in FIG. 21. All groups vaccinated with Z13Mad5Anaxa, Z14Mad5Anaxa or Z18Mad5Anaxa showed an increased percentage of multimer-positive cells compared to the control group (except for the second vaccination of Z18Mad5Anaxa). These results indicate that complexes according to the present invention having different cell penetrating peptides are able to elicit an immune response at different doses.

Example 14: Comparison of T Cell Immune Responses with Complexes Having Different Cell Penetrating Peptides To investigate the CD8 T cell immune responses in more detail, C57BL/6 mice were assigned to three different groups (3-4 mice per group): naïve, Z13Mad5Anaxa or Z14Mad5Anaxa.

C57BL/6 mice of the Z13Mad5Anaxa group and of the Z14Mad5Anaxa group were vaccinated five times (Week0, Week2, Week4, Week6 and Week8) s.c. with 2 nmol of either Z13Mad5Anaxa or Z14Mad5Anaxa as described above. Nine days after the $5^{th}$ vaccination, mice were euthanized, organs recovered and multimer staining was performed to identify the percentage of SIINFEKL-specific CD8 T cells in the spleen, bone marrow and draining lymph nodes (inguinal and axillary).

Figure 22:
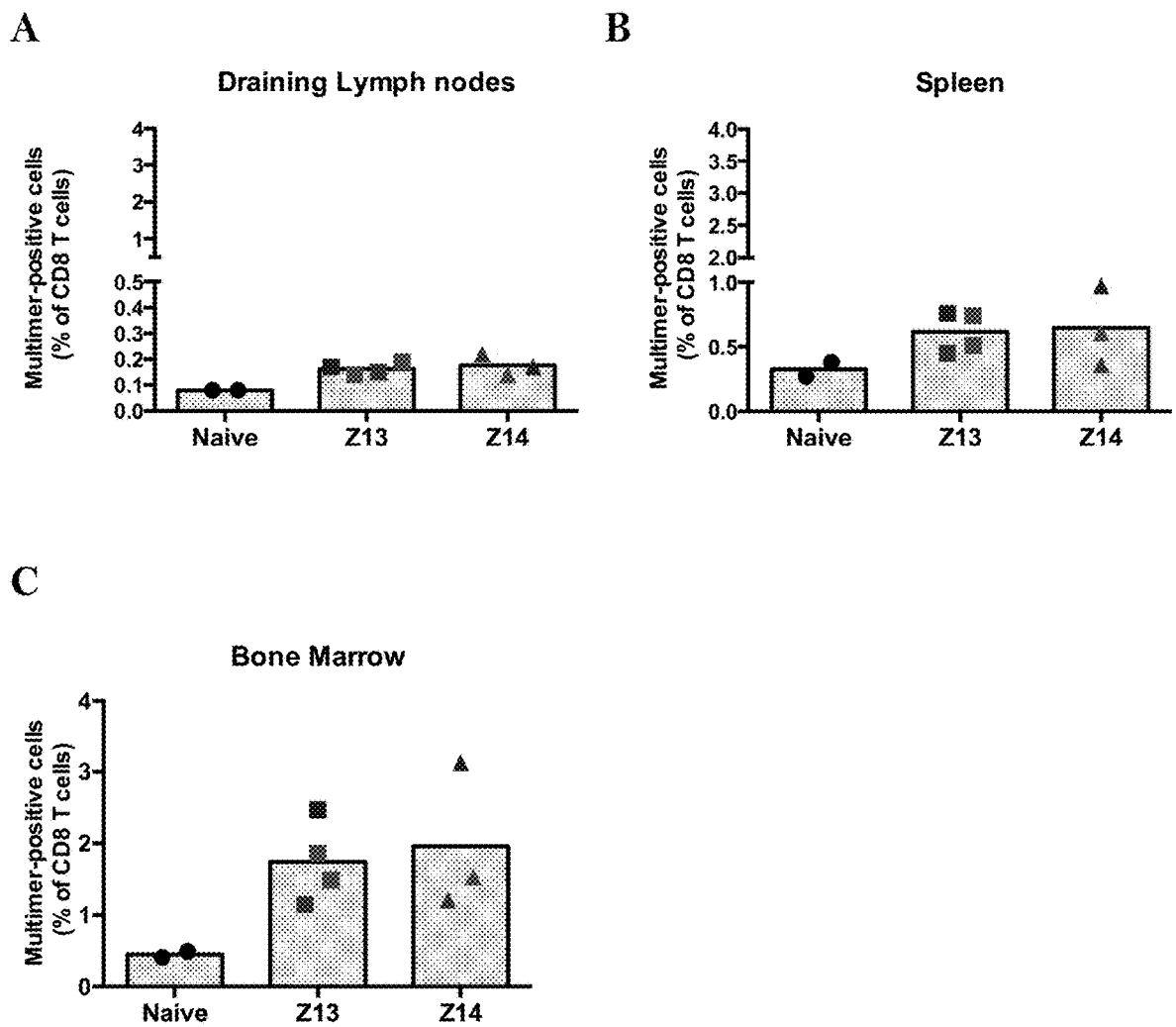
FIG. 22 shows for Example 14 the effect of complexes having different CPPs on CD8 T cells in spleen (A), draining lymph nodes (B) and bone marrow (C). C57BL/6 mice were vaccinated five times (Wk0, Wk2, Wk4, Wk6 and Wk8) s.c. with 2 nmol of Z13Mad5Anaxa or Z14Mad5Anaxa. Nine days after the $5^{th}$ vaccination, mice were euthanized, organs recovered and multimer staining was performed.

The results are shown in FIG. 22. Mice vaccinated with Z13Mad5Anaxa or with Z14Mad5Anaxa showed a similar increase in multimer-positive cells, in particular in the spleen and bone marrow as well as a slight increase in draining lymph nodes.

To further investigate the CD8 T cell effector function after vaccination with complexes with different CPPs, in the same groups of mice as described above Elispot assay was performed on spleen cells stimulated with SIINFEKL OVACD8 peptide (SEQ ID NO: 35) nine days after the $5^{th}$ vaccination in order to quantify IFN-γ producing cells.

Figure 23:
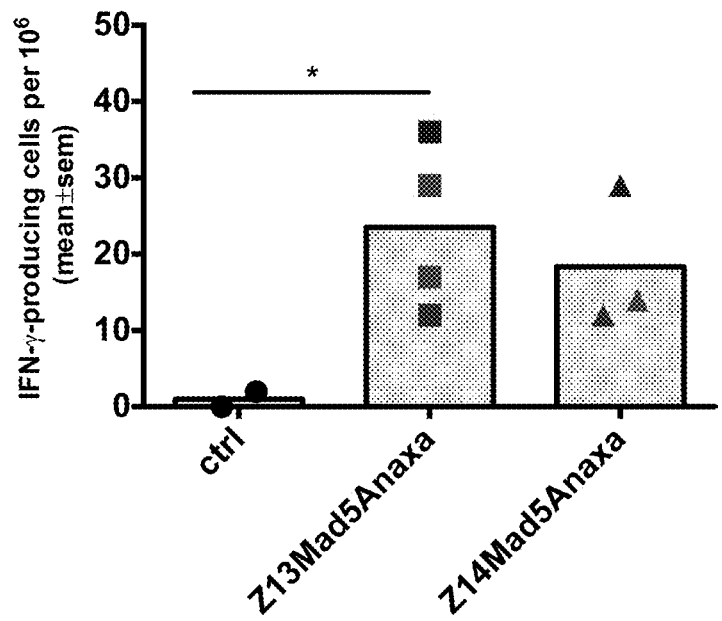
FIG. 23 shows for Example 14 the effect of complexes having different CPPs on T cells in spleen (CD8 T cell response (A) and CD4 T cell response (B)). C57BL/6 mice were vaccinated five times (Wk0, Wk2, Wk4, Wk6 and Wk8) s.c. with 2 nmol of Z13Mad5Anaxa or Z14Mad5Anaxa. (A) nine days after the 5$^{th}$ vaccination, Elispot assay was performed on spleen cells stimulated with SIINFEKL OVACD8 peptide. (B) nine days after the 5$^{th}$ vaccination, Elispot assay was performed on spleen cells stimulated with OVACD4 peptide.
Figure 23:
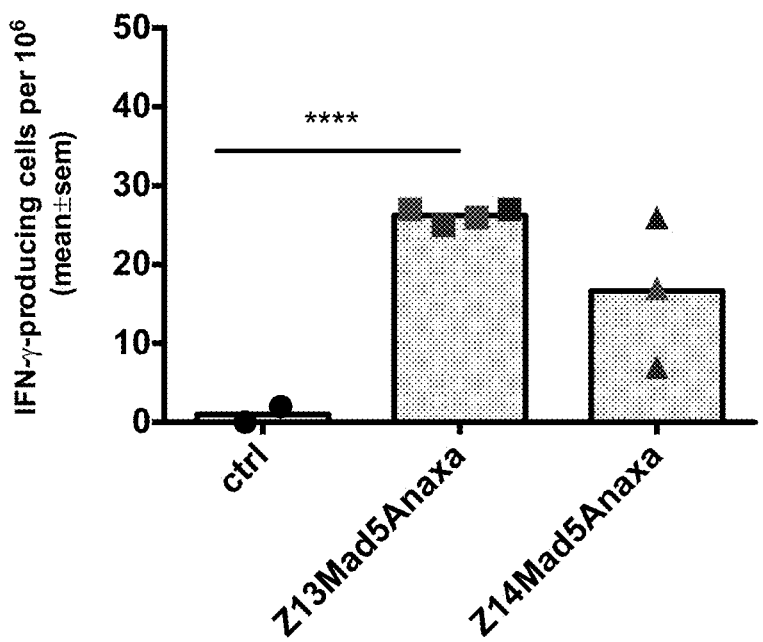

The results are shown in FIG. 23A. Mice vaccinated with Z13Mad5Anaxa showed a significant increase in IFN-γ producing cells compared to naïve mice. Mice vaccinated with Z14Mad5Anaxa showed also an increase in IFN-γ producing cells compared to naïve mice, however, the increase was not significant, which may be due to the low number of mice (3 mice in Z14Mad5Anaxa group).

To investigate the CD4 T cell responses after vaccination with complexes with different CPPs, in the same groups of mice as described above Elispot assay was performed on spleen cells stimulated with OVACD4 peptide (SEQ ID NO: 36) nine days after the $5^{th}$ vaccination in order to quantify IFN-γ producing cells.

The results are shown in FIG. 23B. Mice vaccinated with Z13Mad5Anaxa showed a highly significant increase in IFN-γ producing cells compared to naïve mice. Mice vaccinated with Z14Mad5Anaxa showed also an increase in IFN-γ producing cells compared to naïve mice, however, the increase was not significant, which may be due to the low number of mice (3 mice in Z14Mad5Anaxa group).

In addition, in the above described groups of mice, intracellular staining was performed on spleen cells stimulated with SIINFEKL OVACD8 peptide (SEQ ID NO: 35) to identify CD107a$^+$IFN-γ$^+$TNF-α$^+$ cells.

Figure 24:
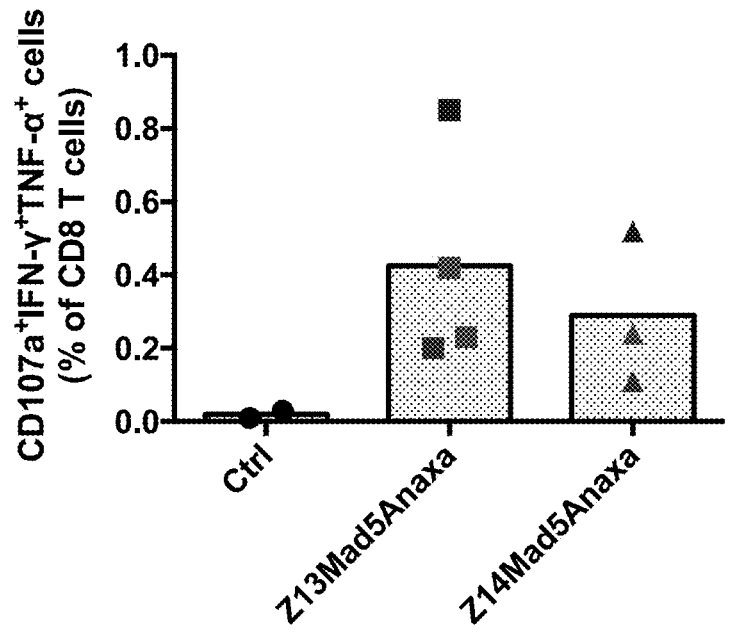
FIG. 24 shows for Example 14 the effect of complexes having different CPPs on CD8 T cell effector function. C57BL/6 mice were vaccinated five times (Wk0, Wk2, Wk4, Wk6 and Wk8) s.c. with 2 nmol of Z13Mad5Anaxa or Z14Mad5Anaxa. Nine days after the 5$^{th}$ vaccination, intracellular staining was performed on spleen cells stimulated with SIINFEKL OVACD8 peptide.

Results are shown in FIG. 24. Mice vaccinated with Z13Mad5Anaxa or with Z14Mad5Anaxa showed a similar increase in CD107a$^+$IFN-γ$^+$TNF-α$^+$ cells.

Example 15: Comparison of the Effect of Complexes Having Different Cell Penetrating Peptides on Tumor Growth and Survival in the EG.7-OVA s.c. Model To investigate the effects of complexes having different cell penetrating peptides on tumor growth and survival the EG.7-OVA s.c. model was used. On do C57BL/6 mice were implanted s.c. with $3 \times 10^5$ $^{EG}$7-OVA tumor cells in the left flank and assigned to three different groups (naïve, Z13Mad5Anaxa and Z14Mad5Anaxa). Mice were vaccinated twice at d5 and d13 after tumor implantation by s.c. injection of either 0.5 nmol of Z13Mad5Anaxa or Z14Mad5Anaxa in the right flank.

Figure 25:
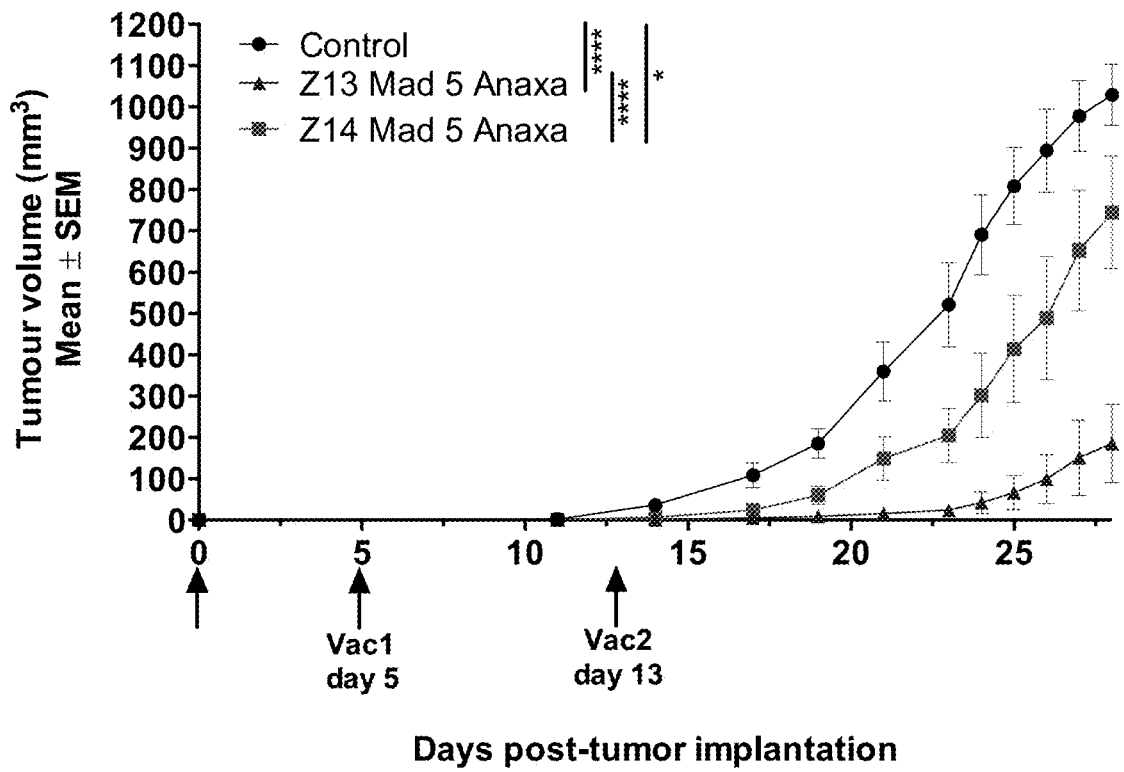
FIG. 25 shows for Example 15 the effect of complexes having different CPPs on tumor growth (A) and survival rates (B). C57BL/6 mice were implanted s.c. with 3×10$^5$ EG7-OVA tumor cells in the left flank and vaccinated twice (d5 and d13) by s.c. injection of 0.5 nmol of Z13Mad5Anaxa or Z14Mad5Anaxa in the right flank. (A) Tumor growth of 7 mice per group (mean±SEM); *, $p<0.05$; ****, $p<0.0001$ (2-way Anova test at day 28). (B) Survival curve of 7 mice per group. Median survival is indicated on the graph (m.s.). *, $p<0.05$; , $p<0.01$; *, $p<0.001$ (Log-rank test).
Figure 25:
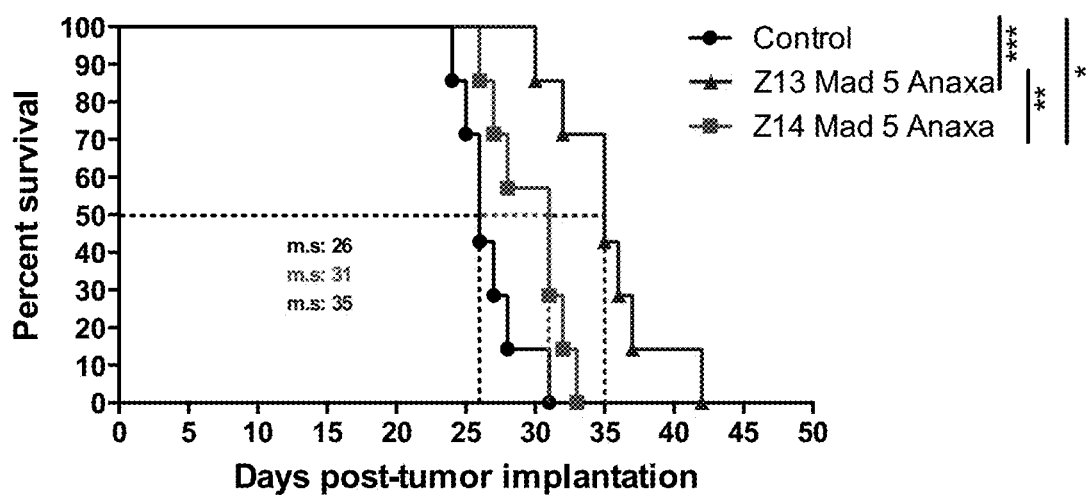

Results are shown in FIG. 25. Vaccination with Z13Mad5Anaxa or with Z14Mad5Anaxa resulted in significantly decreased tumor volumes compared to control mice (FIG. 25A) as well as to significantly increased survival rates compared to control mice (FIG. 25B). Those results indicate that both complexes, Z13Mad5Anaxa and Z14Mad5Anaxa, are able to significantly decrease tumor growth and to significantly prolong survival.

Example 16: Comparison of the Immune Responses after Vaccination with Complexes Having Different Cell Penetrating Peptides In this experiment the effect of different CPPs in the complex comprised by the combination for use according to the present invention was investigated by using a complex with the TLR agonist "EDA". Therefore, the fusion protein EDAZ13Mad5 as described above was used.

In addition, further fusion proteins were designed, which comprise CPPs other than Z13-namely Z14 (SEQ ID NO: 7) or Z18 (SEQ ID NO: 11). Those fusion proteins also comprise the protein "MAD5", which consists of different CD8$^+$ and CD4$^+$ epitopes from various antigens, and the TLR4 peptide agonist "EDA". Accordingly, the following constructs were additionally designed:

EDAZ14Mad5

Sequence:

(SEQ ID NO: 31)
```
MHHHHHHNID RPKGLAFTDV DVDSIKIAWE SPQGQVSRYR VTYSSPEDGI

RELFPAPDGE DDTAELQGLR PGSEYTVSVV ALHDDMESQP LIGIQSTKRY KNRVASRKSR

AKFKQLLQHY REVAAAKESL KISQAVHAAH AEINEAGREV VGVGALKVPR

NQDWLGVPRF AKFASFEAQG ALANIAVDKA NLDVEQLESI INFEKLTEWT GS
```

EDAZ18Mad5

Sequence:

(SEQ ID NO: 32)
```
MHHHHHHNID RPKGLAFTDV DVDSIKIAWE SPQGQVSRYR VTYSSPEDGI

RELFPAPDGE DDTAELQGLR PGSEYTVSVV ALHDDMESQP LIGIQSTREV AAAKSSENDR
```

-continued

```
LRLLLKESLK ISQAVHAAHA EINEAGREVV GVGALKVPRN QDWLGVPRFA KFASFEAQGA

LANIAVDKAN LDVEQLESII NFEKLTEWTG S
```

C57BL/6 mice were assigned to eight different groups (4 mice per group): three groups receiving 2 nmol of either EDAZ13Mad5, EDAZ14Mad5 or EDAZ18Mad5 and a respective control and three groups receiving 0.5 nmol of either EDAZ13Mad5, EDAZ14Mad5 or EDAZ18Mad5 and a respective control group. The mice were vaccinated three times (Week0, Week2 and Week4) s.c. Mice were bled 7 days after the $2^{nd}$ and $3^{rd}$ vaccination and multimer staining was performed (one experiment with 4 mice per group).

Figure 26:
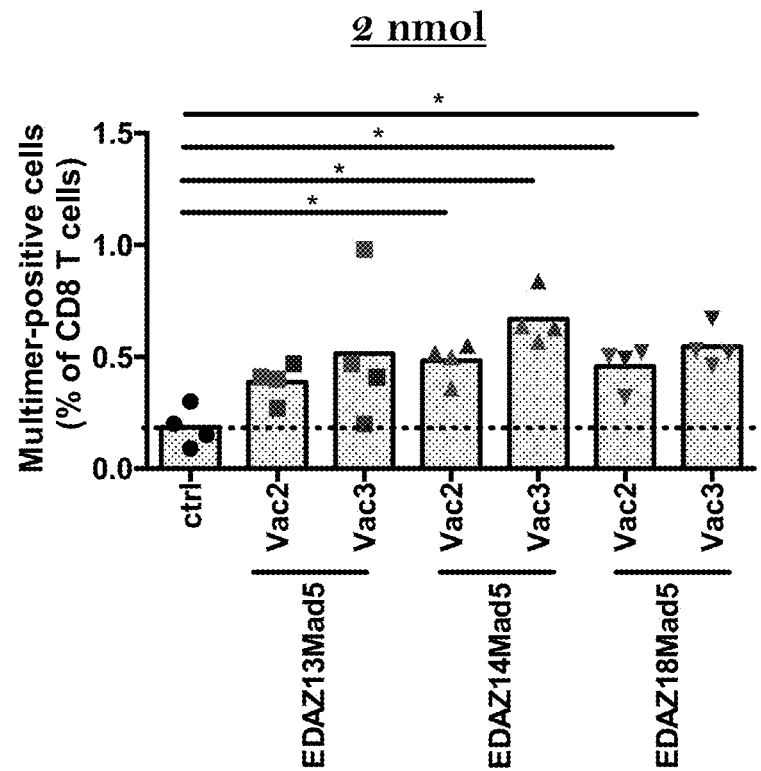
FIG. 26 shows for Example 16 the effect of complexes having different CPPs on the immune response. C57BL/6 mice were vaccinated three times (Wk0, Wk2 and Wk4) s.c. with 2 nmol (A) or 0.5 nmol (B) of EDAZ13Mad5, EDAZ14Mad5 or EDAZ18Mad5. Mice were bled 7 days after the 3$^{rd}$ vaccination and multimer staining was performed (one experiment with 4 mice per group). *, $p<0.05$
Figure 26:
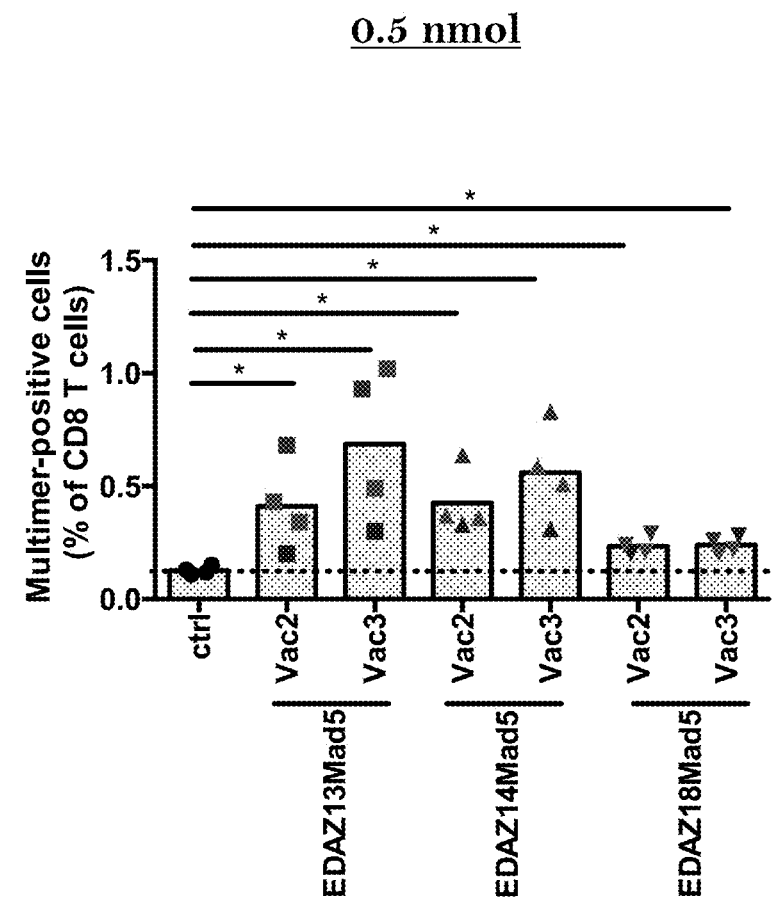

The results are shown in FIG. 26. All groups vaccinated with EDAZ13Mad5, EDAZ14Mad5 or EDAZ18Mad5 showed an increased percentage of multimer-positive cells compared to the control group. These results indicate that complexes according to the present invention having different cell penetrating peptides are able to elicit an immune response at different doses.

Example 17: Effect of EDAZ14Mad5 on Tumor Growth and Survival in the EG.7-OVA s.c. Model To investigate the effect of EDAZ14Mad5 on tumor growth and survival the EG.7-OVA s.c. model was used (cf. Example 12 and FIGS. 18-20 for the effect of EDAZ13Mad5 in the same model).

On d0 C57BL/6 mice were implanted s.c. with $3 \times 10^5$ EG7-OVA tumor cells in the left flank and assigned to two different groups (naïve and EDAZ14Mad5). Mice were vaccinated twice at d5 and d13 after tumor implantation by s.c. injection of 0.5 nmol of EDAZ14Mad5 in the right flank.

Figure 27:
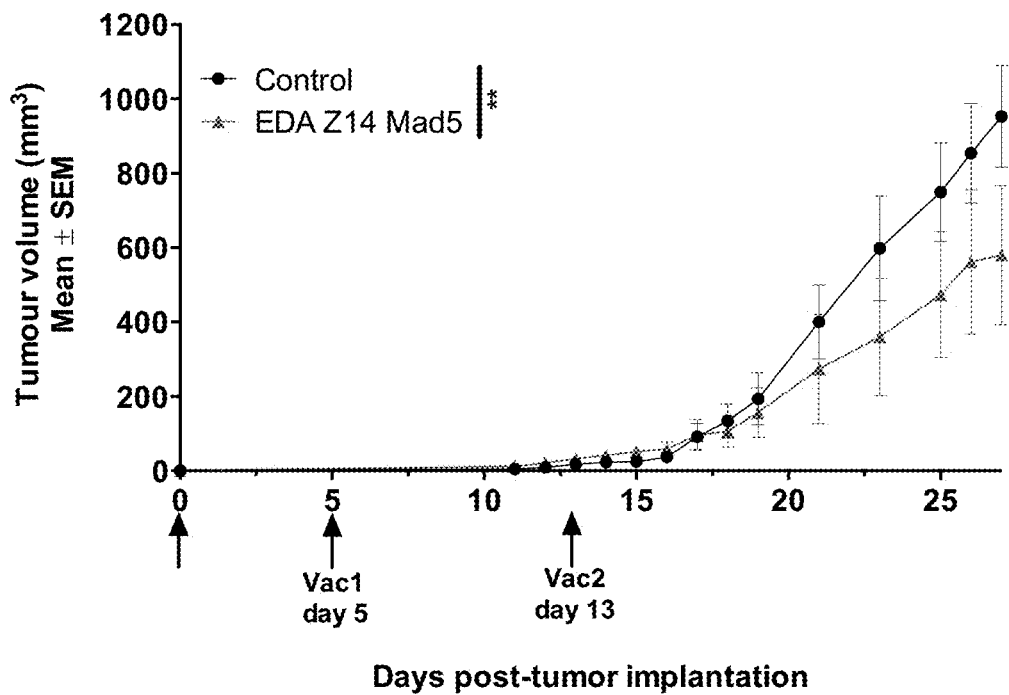
FIG. 27 shows for Example 17 the effect of EDAZ14Mad5 on tumor growth (A) and survival rates (B). C57BL/6 mice were implanted s.c. with 3×10$^5$ EG7-OVA tumor cells in the left flank and vaccinated twice (d5 and d13) by s.c. injection of 2 nmoles of EDAZ14Mad5 in the right flank. Left panel: Tumor growth of 7 mice per group (mean±SEM); **, $p<0.01$ (2-way Anova test at day 27). Right panel: Survival curve of 7 mice per group. Median survival is indicated on the graph (m.s.)
Figure 27:
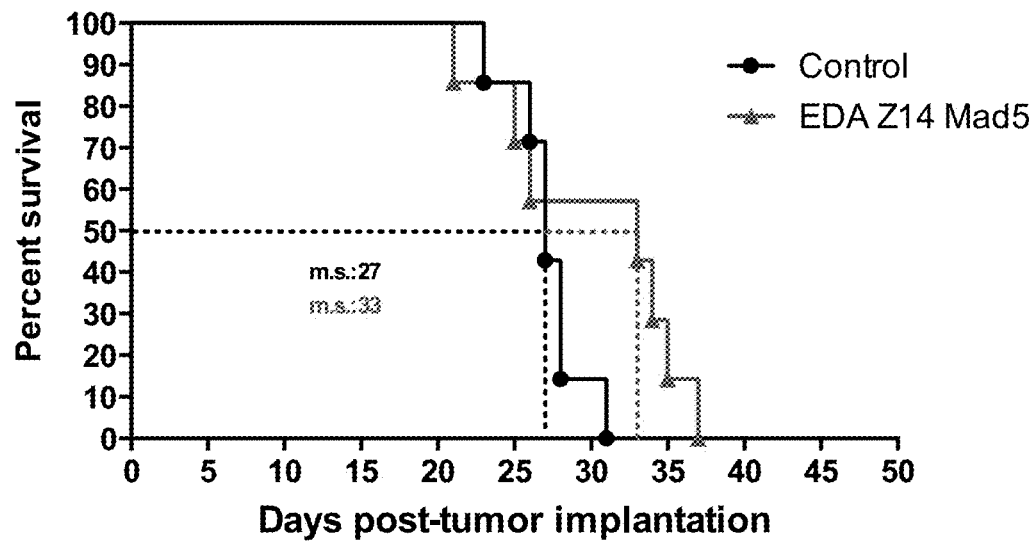

Results are shown in FIG. 27. Similarly to EDAZ13Mad5 (cf. Example 12, FIGS. 18-20) vaccination with EDAZ14Mad5 resulted in significantly decreased tumor volumes compared to control mice (FIG. 27A) as well as to significantly increased survival rates compared to control mice (FIG. 27B). Those results indicate that EDAZ14Mad5 is able to significantly decrease tumor growth and to significantly prolong survival-similarly to EDAZ13Mad5 (cf. Example 12, FIGS. 18-20).

Example 18: Superior Efficacy of Z13Mad5Anaxa Fusion Construct Compared to Z13Mad5 and a TLR Agonist Administered Separately To evaluate the effect of the conjugated TLR agonist "Anaxa" in Z13Mad5Anaxa (SEQ ID NO: 28) on tumor growth control, a benchmark tumor model was used, namely the s.c. implantation of EG.7-OVA thymoma cells. For comparison the construct "AnaxaZ13Mad5" (SEQ ID NO: 27; with N-terminal TLR agonist "Anaxa" and C-terminal antigenic cargo "Mad5") and the construct "Z13Mad5" (SEQ ID NO: 46; without TLR agonist), the latter being administered in combination with a separate TLR agonist (Pam3CSK4) were used.

Figure 28:
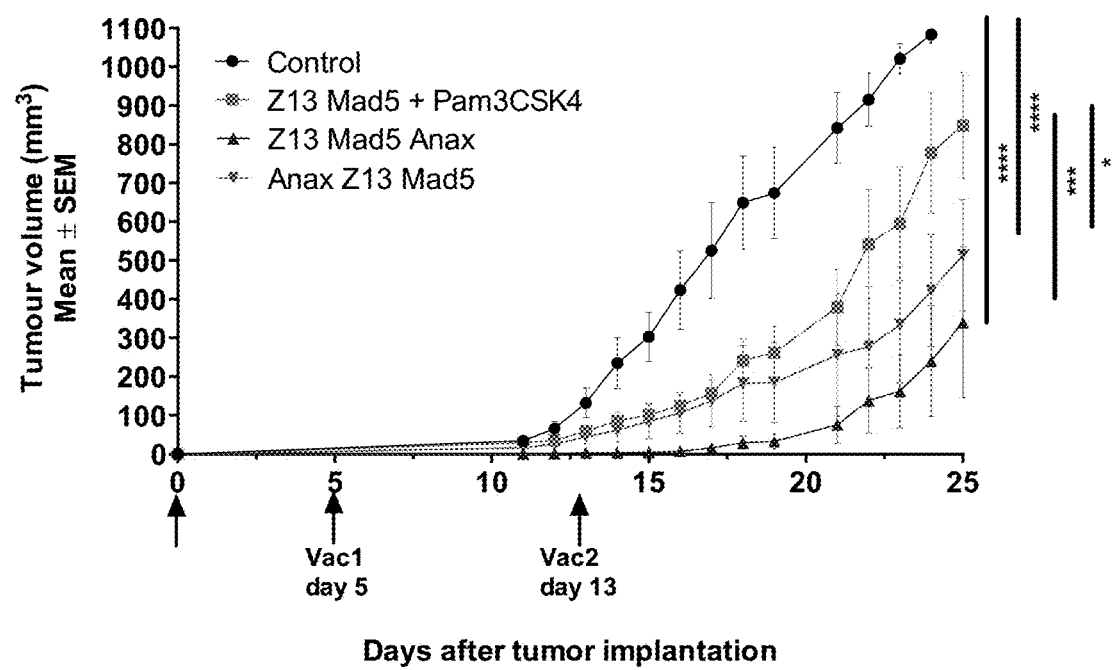
FIG. 28 shows for Example 18 the tumor growth of 7 mice per group (mean±SEM). C57BL/6 mice were implanted s.c. with 3×10$^5$ EG7-OVA tumor cells in the left flank and vaccinated twice (d5 and d13) by subcutaneous injection of 10 nmol of either AnaxZ13Mad5, Z13Mad5Anaxa or co-injection of Z13Mad5+Pam3CSK4 (equimolar to Anaxa) in the right flank. Tumor size was measured with a caliper. *, $p<0.05$; *, $p<0.001$, **, $p<0.0001$.
Figure 29:
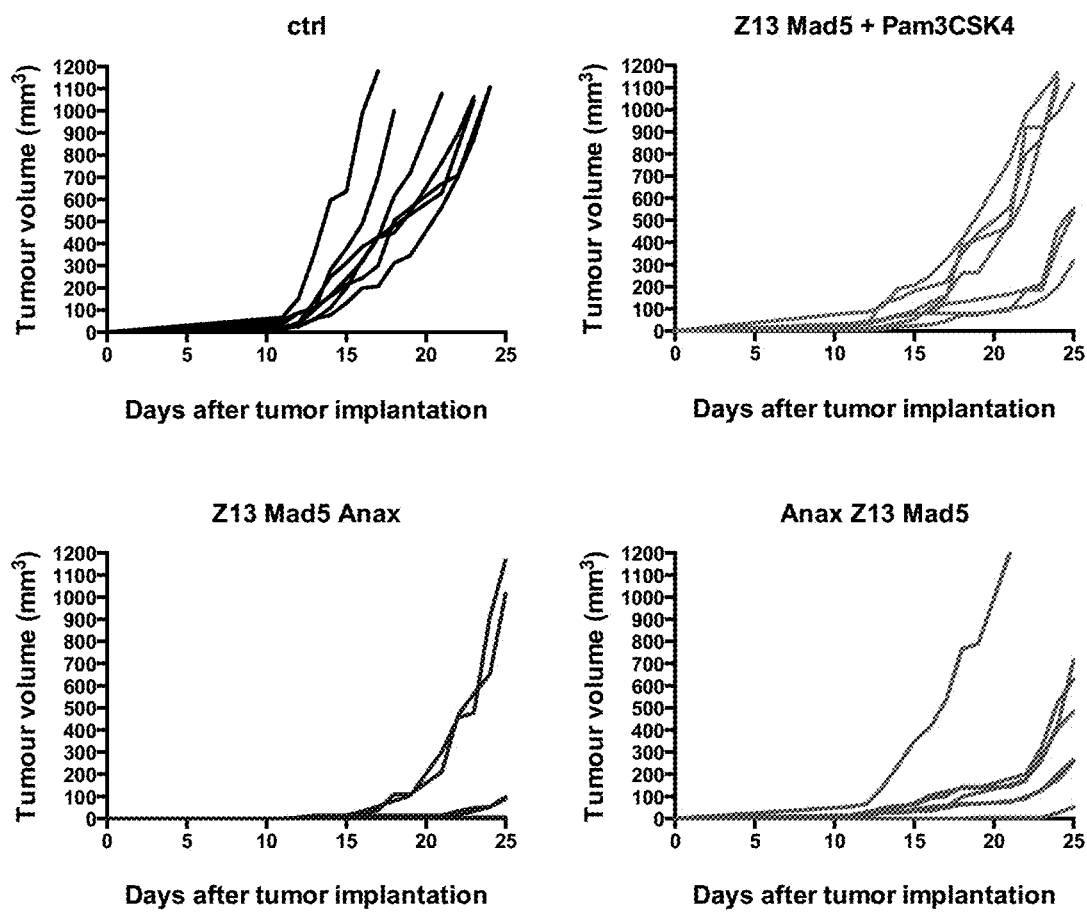
FIG. 29 shows for Example 18 the individual tumor growth curves (7 individual mice per group). C57BL/6 mice were implanted s.c. with 3×10$^5$ EG7-OVA tumor cells in the left flank and vaccinated twice (d5 and d13) by subcutaneous injection of 10 nmol of either AnaxZ13Mad5, Z13Mad5Anaxa or co-injection of Z13Mad5+Pam3CSK4 (equimolar to Anaxa) s.c. in the right flank. Tumor size was measured with a caliper.
Figure 30:
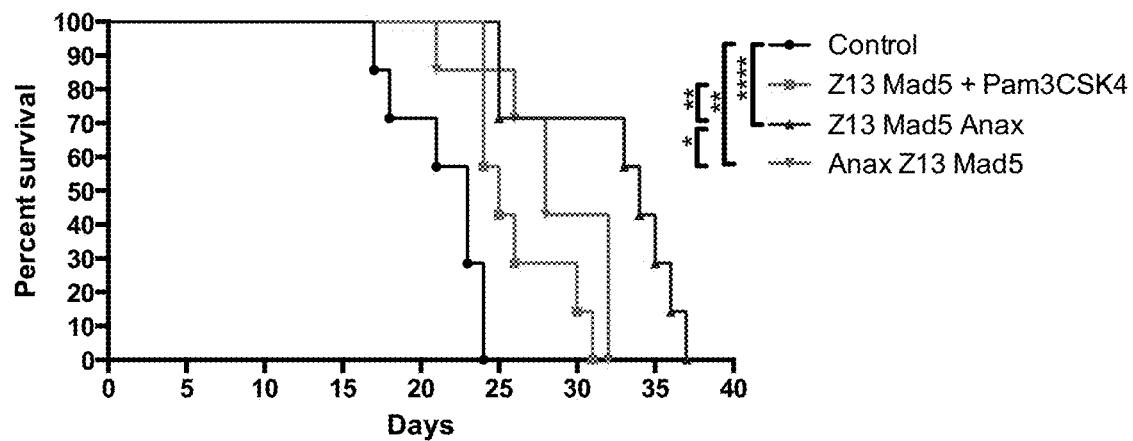
FIG. 30 shows for Example 18 the survival curve of 7 mice per group. C57BL/6 mice were implanted s.c. with 3×10$^5$ EG7-OVA tumor cells in the left flank and vaccinated twice (d5 and d13) by subcutaneous injection of 10 nmol of either AnaxZ13Mad5, Z13Mad5Anaxa or co-injection of Z13Mad5+Pam3CSK4 (equimolar to Anaxa) in the right flank. Tumor size was measured with a caliper. *, $p<0.05$, , $p<0.01$, **, $p<0.0001$ (Log-rank test).

C57BL/6 mice were implanted s.c. with $3 \times 10^5$ EG7-OVA tumor cells in the left flank. After tumor implantation, the three groups of 7 mice each were vaccinated s.c. in the right flank at day 5 and 13 by subcutaneous injection of 10 nmol of either AnaxZ13Mad5 (group 1), Z13Mad5Anaxa (group 2) or Z13Mad5 and Pam3CSK4 (equimolar to Anaxa; group 3). Tumor size was measured with a caliper. Results are shown in FIGS. 28-30.

In a therapeutic schedule, Z13Mad5Anaxa and AnaxaZ13Mad5 are better protein vaccines for controlling tumor growth compared to the control group, i.e. co-injection of Z13Mad5 and Pam3CSK4, with Z13Mad5Anaxa and AnaxaZ13Mad5 showing a significant better survival curve. In particular, Z13Mad5Anaxa and AnaxaZ13Mad5 demonstrate significantly higher efficacy than Z13Mad5 administrated separately with Pam3CSK4. The results therefore suggest that the construct proteins Z13Mad5Anaxa and AnaxaZ13Mad5 are promising conjugate-vaccines for controlling the tumor growth in a therapeutic setting.

Example 19: Therapeutic Effect on Tumor Growth-Comparison of Constructs with Different TLR Agonists The goal of this study was to compare the efficacy of the different construct protein vaccines conjugated to different TLR agonist, namely EDAZ13Mad5 (SEQ ID NO: 26) and Z13Mad5Anaxa (SEQ ID NO: 28), on tumor growth control. To this end, C57BL/6 mice were implanted s.c. with $3 \times 10^5$ EG.7-OVA thymoma cells in the left flank as described previously. Mice (7 individual mice per group) were vaccinated s.c. in the right flank at day 5 and 13 with 2 nmol of either EDAZ13Mad5, Z13Mad5Anaxa or co-injection of Z13Mad5+MPLA (equimolar to EDA).

Figure 31:
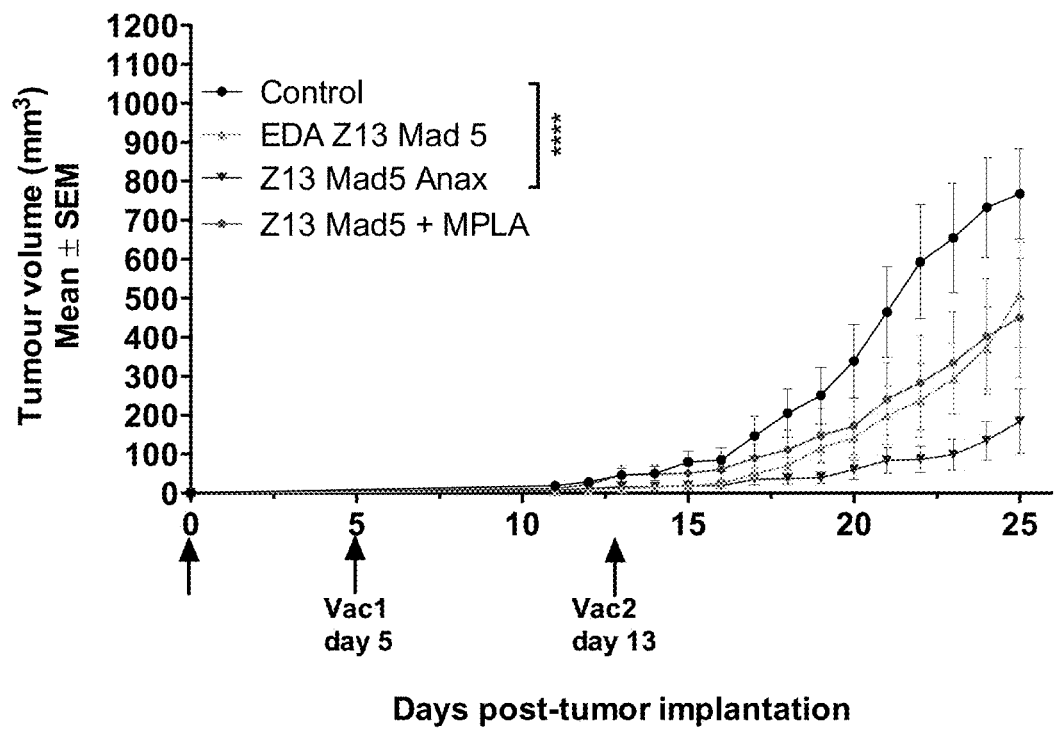
FIG. 31 shows for Example 19 the tumor growth of 7 mice per group (mean±SEM). C57BL/6 mice were implanted s.c. with 3×10$^5$ EG7-OVA tumor cells in the left flank and vaccinated twice (d5 and d13) by subcutaneous injection of 2 nmoles of Hp91Z13Mad5, EDAZ13Mad5, Z13Mad5Anaxa, Z13Mad5EDA or Z13Mad5 and MPLA (equimolar to EDA) in the right flank. *, $p<0.05$; , $p<0.01$; *, $p<0.001$; ****, $p<0.0001$ (2-way Anova test at day 23).
Figure 32:
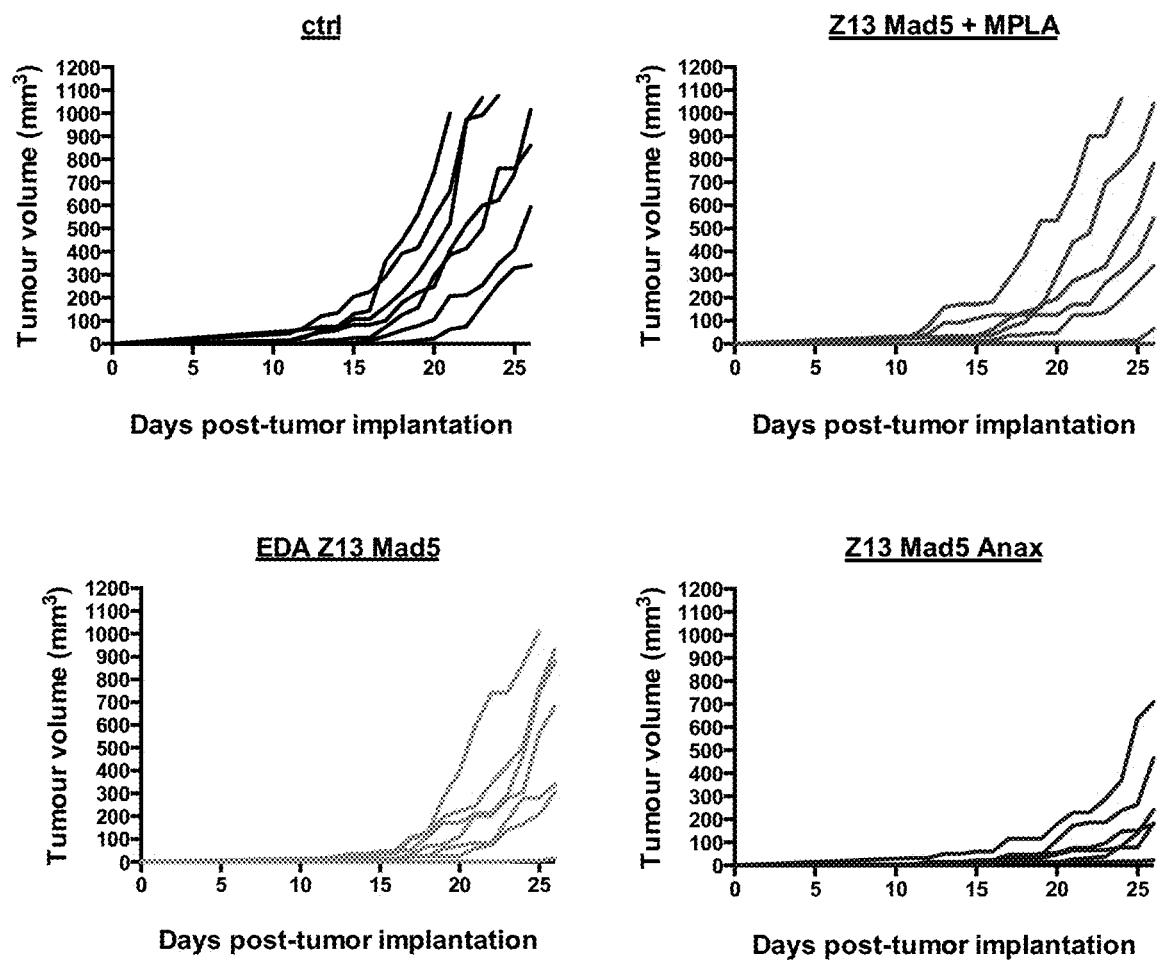
FIG. 32 shows for Example 19 the individual tumor growth curves (7 individual mice per group). C57BL/6 mice were implanted s.c. with 3×10$^5$ EG7-OVA tumor cells in the left flank and vaccinated twice (d5 and d13) by subcutaneous injection of 2 nmoles of Hp91Z13Mad5, EDAZ13Mad5, Z13Mad5Anaxa, Z13Mad5EDA or Z13Mad5 and MPLA (equimolar to EDA) s.c. in the right flank.
Figure 33:
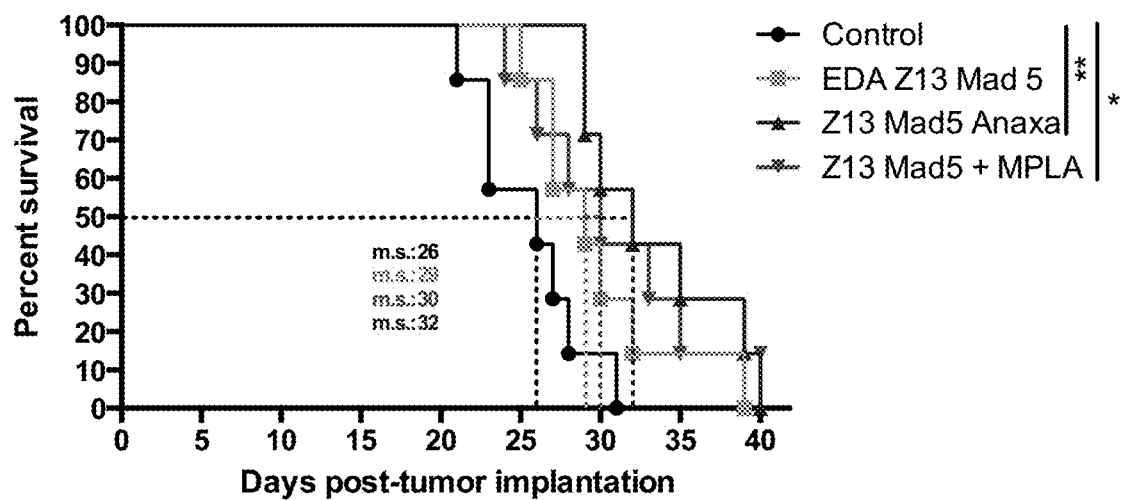
FIG. 33 shows for Example 19 the survival curves of all 7 mice per group. Median survival is indicated on the graph (m.s.). *, $p<0.05$; **, $p<0.01$ (Log-rank test).

Results are shown in FIGS. 31, 32 and 33. In this experimental setting, Z13Mad5Anaxa (SEQ ID NO: 28), EDAZ13Mad5 (SEQ ID NO: 26), and Z13Mad5 (SEQ ID NO: 46)+MPLA were similarly able to significantly control tumor growth. Moreover, these data indicate that Z13Mad5Anaxa is the best construct to significantly control tumor growth and EDAZ13Mad5 was slightly better than Z13Mad5+MPLA in this experimental setting.

Example 20: Superior Efficacy of Z13Mad5Anaxa Fusion Construct Compared to Z13Mad5 and Anaxa in a Glioblastoma Model To investigate the efficacy of a complex according to the present invention the glioblastoma model was chosen. Namely, Z13Mad5Anaxa (SEQ ID NO: 28) was administered to one group of mice, whereas Z13Mad5 (SEQ ID NO: 46) and Anaxa (SEQ ID NO: 15) were administered (both together) to another group of mice.

T cell homing at the tumor site was analyzed in Gl261-Quad tumor-bearing mice (7-16 mice per group) vaccinated twice, namely at day 7 and at day 21 after tumor implantation (day 0), with 2 nmol Z13Mad5Anaxa vaccine. A group vaccinated with both, Z13Mad5 and Anaxa (equimolar to Z13Mad5Anaxa), was used as control. Briefly, C57BL/6 mice were implanted i.e. (intracranially) with $5 \times 10^5$ G1261-Quad tumor cells and vaccinated twice (at d7 and d21 following implantation) by s.c. injection of 2 nmol of Z13Mad5Anaxa (group 1) or 2 nmol of Z13Mad5 and 2 nmol of Anaxa (group 2). At day 28, the blood and the brain infiltrating leukocytes (BILs) were analyzed, whereby SIIN-FEKL-specific CD8 T cells were quantified in blood and in BILs at d28 by multimer staining (7-16 mice per group).

Figure 34:
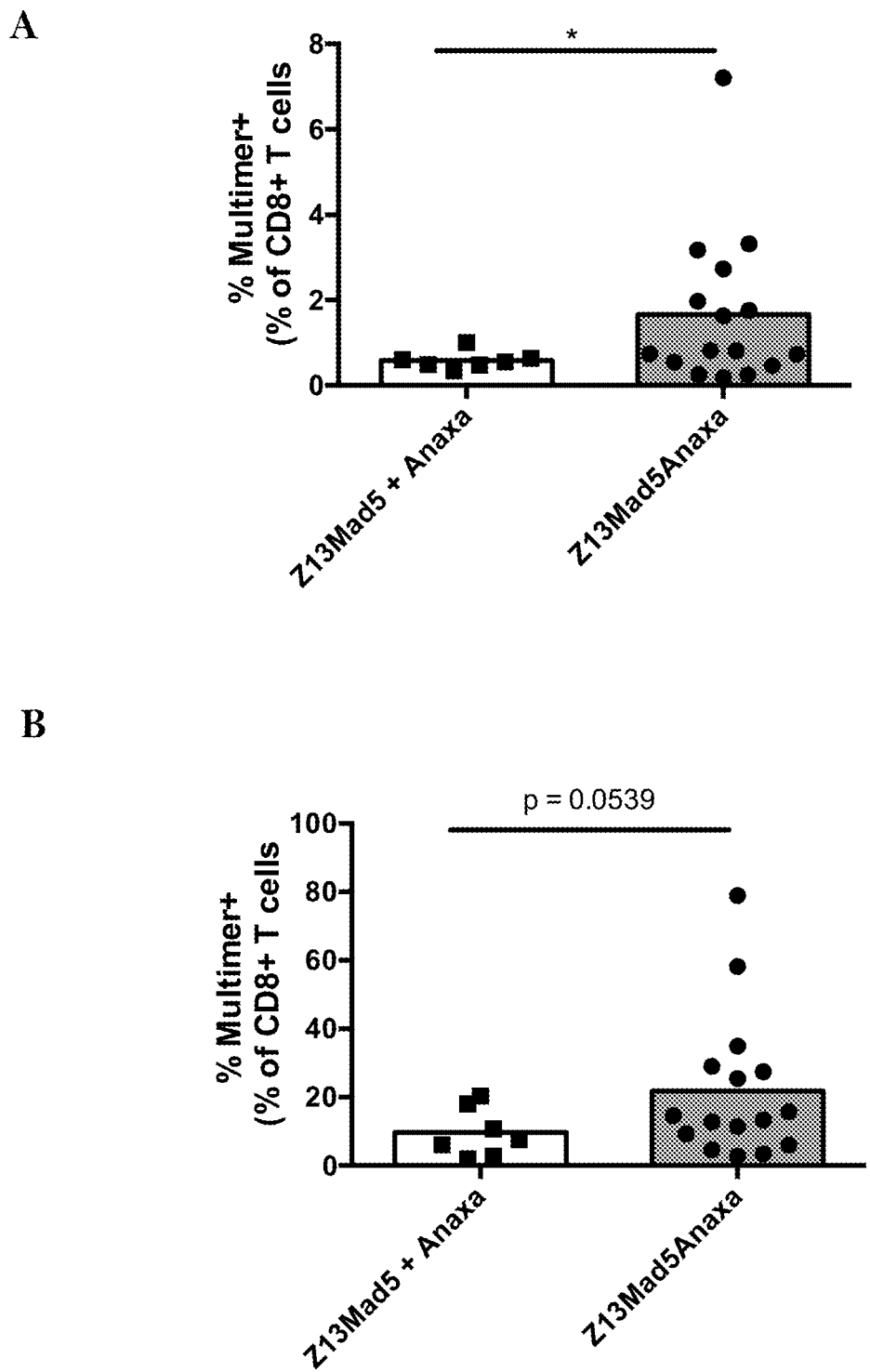
FIG. 34 shows for Example 20 the quantification of SIINFEKL-specific CD8 T cells in a Quad-GI261 glioblastoma model. Briefly, C57BL/6 mice were implanted i.e. with 5×10$^5$ G1261-Quad tumor cells and vaccinated twice (d7 and 21) by s.c. injection of 2 nmol of Z13Mad5Anaxa or 2 nmol of Z13Mad5 and 2 nmol of Anaxa. SIINFEKL-specific CD8 T cells were quantified in blood (A) and in BILs (B) at d28 by multimer staining (7-16 mice per group).

Results are shown in FIG. 34. A significantly higher percentage of SIINFEKL-specific CD8 T cells was observed in the blood of Z13Mad5Anaxa-vaccinated mice as compared to mice vaccinated with both, Z13Mad5 and Anaxa (FIG. 34A). Similarly, a stronger accumulation of SIIN-FEKL-specific CD8 T cells was observed in the BILs of Z13Mad5Anaxa-vaccinated mice as compared to mice vaccinated with Z13Mad5 and Anaxa separately (FIG. 34B, p=0.0539).

Next, cytokine secretion was assessed. To this end, C57BL/6 mice were implanted i.e. with $5\times10^5$ GI261-Quad tumor cells and vaccinated twice (d7 and 21) by s.c. injection of 2 nmol of Z13Mad5Anaxa or 2 nmol of Z13Mad5 and 2 nmol of Anaxa. BILs were isolated and cultured during 6 h with matured BMDCs loaded or not with SIINFEKL peptide (SEQ ID NO: 35) in presence of BrefeldinA before intracellular staining for cytokines.

Figure 35:
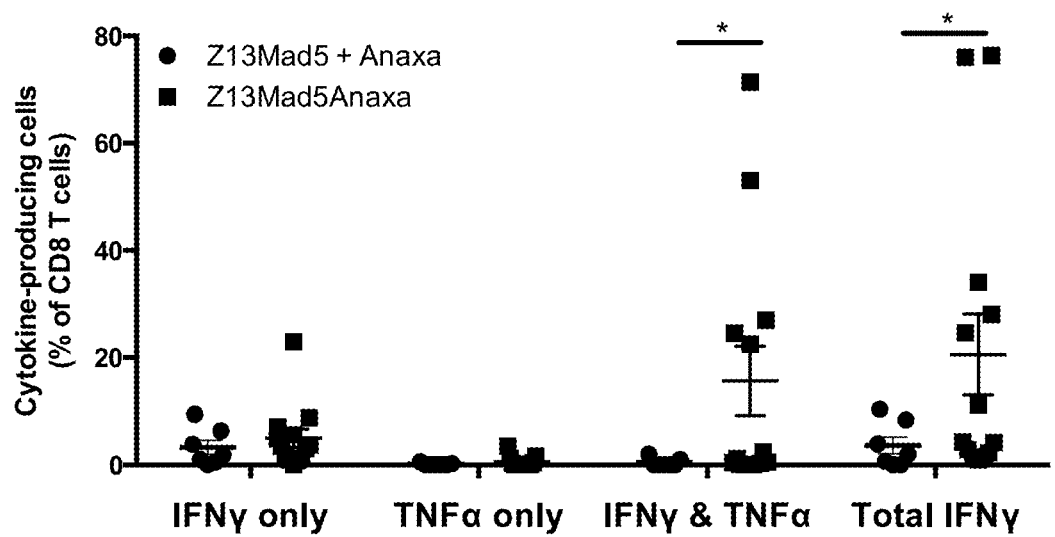
FIG. 35 shows for Example 20 the cytokine secretion. Briefly, C57BL/6 mice were implanted i.e. with 5×10$^5$ GI261-Quad tumor cells and vaccinated twice (d7 and 21) by s.c. injection of 2 nmol of Z13Mad5Anaxa or 2 nmol of Z13Mad5 and 2 nmol of Anaxa. BILs were isolated and cultured during 6 h with matured BMDCs loaded or not with SIINFEKL peptide in presence of BrefeldinA before intracellular staining for cytokines. % of CD8 T cells secreting cytokine (7-16 mice per group).

Results are shown in FIG. 35. In general, a high level of cytokine secretion was observed for brain-infiltrating CD8 T cells from mice vaccinated with Z13Mad5Anaxa. In particular, a significantly higher secretion of total IFN-γ and of IFN-γ and TNF-α together was observed for brain-infiltrating CD8 T cells from mice vaccinated with Z13Mad5Anaxa as compared to mice vaccinated with Z13Mad5 and Anaxa separately.

Taken together, these results demonstrate that Z13Mad5Anaxa vaccine (as compared to Z13Mad5 and Anaxa administered separately) was able to elicit a stronger SIINFEKL specific CD8 T cell immune response in the brain of tumor-bearing mice with potent effector function.

The results obtained are indicating that Z13Mad5Anaxa is efficacious for eliciting high brain infiltrating SIINFEKL-specific CD8 immune response. Z13Mad5Anaxa is able to promote the secretion of cytokine by antigen-specific CD8 T cells in the brain.

Example 21: Superior Efficacy of Z13Mad5Anaxa Fusion Construct Compared to Z13Mad5 and Anaxa in Naïve Mice Next, the efficacy of a complex according to the present invention was investigated in naïve mice. Namely, Z13Mad5Anaxa (SEQ ID NO: 28) was administered to one group of mice, whereas Z13Mad5 (SEQ ID NO: 46) and Anaxa (SEQ ID NO: 15) were administered (both together) to another group of mice.

C57BL/6 mice of the Z13Mad5Anaxa group and of the Z13Mad5+Anaxa group were vaccinated once (Week0) by s.c. injection of 2 nmol of Z13Mad5Anaxa (group 1) or 2 nmol of Z13Mad5 and 2 nmol of Anaxa (group 2). At day 14, the blood was analyzed, whereby SIINFEKL-specific CD8 T cells were quantified in blood by multimer staining (4-8 mice per group).

Figure 36:
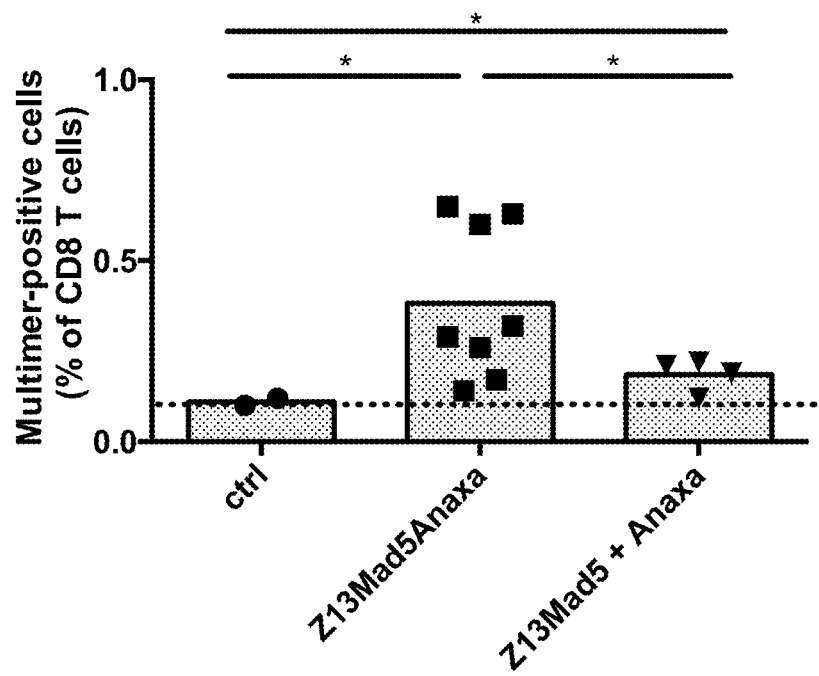
FIG. 36 shows for Example 21 the quantification of SIINFEKL-specific CD8 T cells in naïve mice. Briefly, C57BL/6 mice were vaccinated once (day 0) by s.c. injection of 2 nmol of Z13Mad5Anaxa (group "Z13Mad5Anaxa") or 2 nmol of Z13Mad5 and 2 nmol of Anaxa (group "Z13Mad5+Anaxa"). SIINFEKL-specific CD8 T cells were quantified in blood at d7 by multimer staining (4-8 mice per group).

Results are shown in FIG. 36. A significantly higher percentage of SIINFEKL-specific CD8 T cells was observed in the blood of Z13Mad5Anaxa-vaccinated mice as compared to mice vaccinated with Z13Mad5 and Anaxa separately (FIG. 36).

Taken together, these results demonstrate that Z13Mad5Anaxa vaccine (as compared to Z13Mad5 and Anaxa administered separately) was able to elicit a stronger SIINFEKL specific CD8 T cell immune response in the periphery.

Example 22: Effects of Combination of a PD1 Inhibitor and a Complex Comprising a Cell Penetrating Peptide, Different Antigens and a TLR Peptide Agonist on Tumor Growth and Survival Rate in a Colon Carcinoma Model In order to assess the effects of combination of a PD1 inhibitor and a complex comprising a cell penetrating peptide, different antigens and a TLR peptide agonist in treating colorectal cancer, the MC-38 tumor model was used. MC-38 is a colon carcinoma cell line.

To this end, "Z13Mad12Anaxa" was provided, which is a complex comprising a cell penetrating peptide "Z13", the antigenic cargo "MAD12" comprising three neoantigens as identified by Yadav et al. Nature. 2014 Nov. 27;515 (7528): 572-6 from MC-38 tumor cell line, and the TLR peptide agonist "Anaxa". In the following, the amino acid sequence of Z13Mad12Anaxa is shown:

```
                                         (SEQ ID NO: 45)
KRYKNRVASRKSRAKFKQLLQHYREVAAAKSSENDRLRLLLKLFRAAQLA

NDVVLQIMEHLELASMTNMELMSSIVVISASIIVFNLLELEGSTVHEILC

KLSLEGDHSTPPSAYGSVKPYTNFDAE
```

C57BL/6 mice (seven mice per group, female, 7 week old) were implanted s.c. with $2\times10^5$ MC-38 tumor cells in the left flank (day 0). After tumor implantation, mice of the groups "Z13Mad12Anaxa" and "Z13Mad12Anaxa+anti-PD1" were vaccinated at days 3, day10 and 17 subcutaneously with 2 nmol of Z13Mad12Anaxa at the tail base. 200 µg of anti-PD1 antibody RMP1-14 (BioXcell, West Lebanon, NH, USA) were administered i.p. on each of days 6, 10, 13, 17, 20, 24, 27 and 31 to mice of groups "anti-PD1" and "Z13Mad12Anaxa+anti-PD1". At days 10 and 17, when both, Z13Mad12Anaxa and anti-PD1 antibody, were administered to group "Z13Mad12Anaxa+anti-PD1", the antibody was administered i.p. just after s.c. administration of Z13Mad12Anaxa. Tumor size was measured with a caliper.

Figure 37:
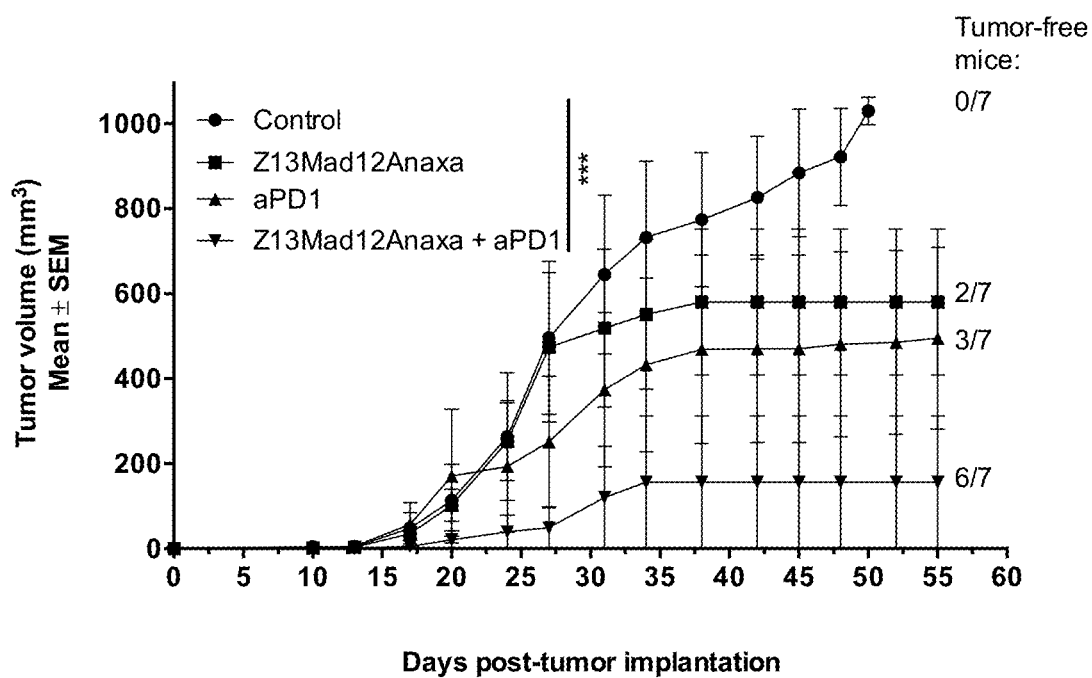
FIG. 37 shows for Example 22 the tumor growth (A) and the survival rate (B) of 7 mice per group (mean±SEM). C57BL/6 mice were implanted s.c. with 2×10$^5$ MC-38 tumor cells in the left flank. Mice of the groups "Z13Mad12Anaxa" and "Z13Mad12Anaxa+anti-PD1" were vaccinated 3 times (d3, d10 and d17) by subcutaneous injection of 2 nmol of Z13Mad12Anaxa at the tail base. 200 µg of anti-PD1 antibody were administered i.p. on each of days 6, 10, 13, 17, 20, 24, 27 and 31 to mice of groups "anti-PD1" and "Z13Mad12Anaxa+anti-PD1". Tumor size was measured with a caliper. The number of tumor-free mice of each group is indicated for each tumor growth curve. *, $p<0.05$; , $p<0.01$; *, $p<0.001$.
Figure 37:
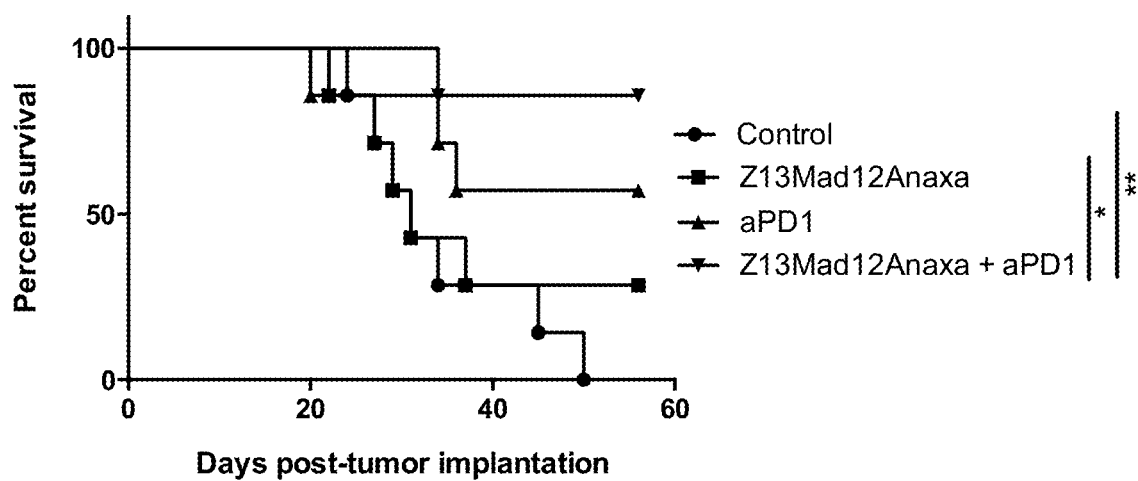
Figure 38:
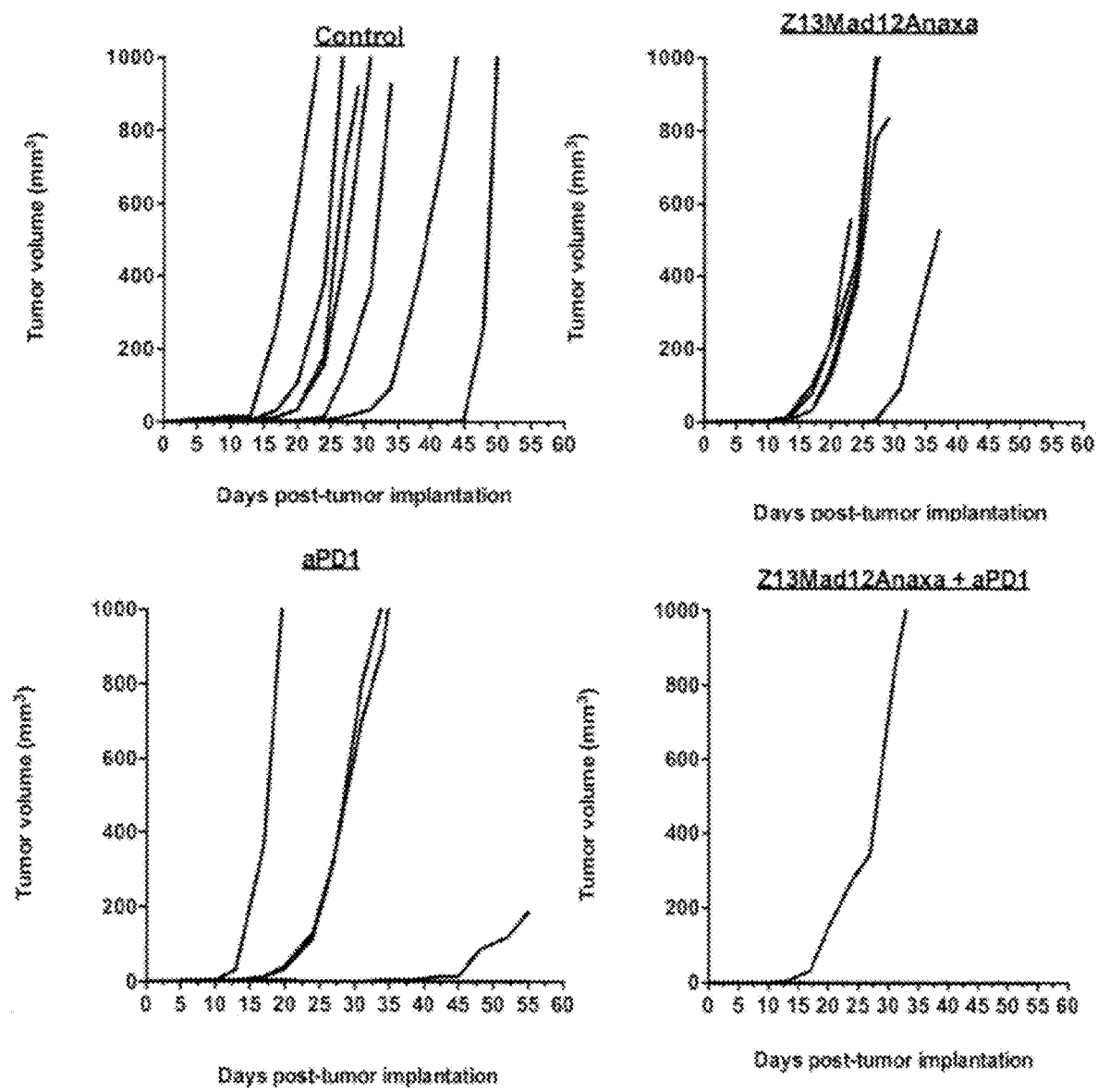
FIG. 38 shows for Example 22 individual tumor growth curves of 7 mice per group. C57BL/6 mice were implanted s.c. with 2×10$^5$ MC-38 tumor cells in the left flank. Mice of the groups "Z13Mad12Anaxa" and "Z13Mad12Anaxa+ anti-PD1" were vaccinated 3 times (d3, d10 and d17) by subcutaneous injection of 2 nmol of Z13Mad12Anaxa at the tail base. 200 µg of anti-PD1 antibody were administered i.p. on each of days 6, 10, 13, 17, 20, 24, 27 and 31 to mice of groups "anti-PD1" and "Z13Mad12Anaxa+anti-PD1". Tumor size was measured with a caliper.

As shown in FIGS. 37 and 38, treatment with the PD1 inhibitor alone or with Z13Mad12Anaxa alone resulted in significantly reduced tumor volume (FIG. 37A) and increased survival (FIG. 37B), as compared to the control group. However, the combination of both, the PD1 inhibitor and Z13Mad12Anaxa, resulted in the most pronounced improvement, namely in strongly decreased tumor volume and strongly increased survival rates. These data show that a combination of both, anti-PD1 therapy and Z13Mad12Anaxa vaccination, is more efficient than anti-PD1 therapy alone or Z13Mad12Anaxa vaccination alone. Moreover, in the control group all mice showed tumors (0/7 tumor free mice), whereas in Z13Mad12Anaxa group 2/7 mice were tumor free and in the anti-PD1 group 3/7 mice were tumor free. Interestingly, in the "Z13Mad12Anaxa+anti-PD1" only one mouse showed tumors, i.e. 6/7 mice were tumor free. This is more than the sum of tumor-free mice in the Z13Mad12Anaxa group (2/7) and in the anti-PD1 group (3/7). Taken together, these results indicate a strong synergistic effect of a combination of anti-PD1 therapy and Z13Mad12Anaxa vaccination.

Example 23: Effects of Combination of a PD1 Inhibitor and a Complex Comprising a Cell Penetrating Peptide, Different Antigens and a TLR Peptide Agonist on Tumor Growth and Survival Rate in Colon Carcinoma Model In Example 23, further animals were subdued to the experimental test of Example 22 in order to enlarge the group sizes of the different experimental groups of Example 22. Therefore, the experimental results "include" the results of the animals of Example 22 and those of additional animals.

Briefly, the effects of combination of a PD1 inhibitor and a complex comprising a cell penetrating peptide, different antigens and a TLR peptide agonist in treating cancer, the MC-38 tumor model was used. MC-38 is a colon carcinoma cell line.

"Z13Mad12Anaxa" was provided, which is a complex comprising a cell penetrating peptide "Z13", the antigenic cargo "MAD12" comprising three neoantigens as identified by Yadav et al. Nature. 2014 Nov. 27;515 (7528): 572-6 from MC-38 tumor cell line, and the TLR peptide agonist "Anaxa". In the following, the amino acid sequence of Z13Mad12Anaxa is shown:

(SEQ ID NO: 45)
KRYKNRVASRKSRAKFKQLLQHYREVAAAKSSENDRLRLLLKLFRAAQLA

NDVVLQIMEHLELASMTNMELMSSIVVISASIIVFNLLELEGSTVHEILC

KLSLEGDHSTPPSAYGSVKPYTNFDAE

C57BL/6 mice (thirteen to fourteen mice per group, female, 7 week old) were implanted s.c. with $2\times10^5$ MC-38 tumor cells in the left flank (day 0). After tumor implantation, mice of the groups "Z13Mad12Anaxa" and "Z13Mad12Anaxa+anti-PD1" were vaccinated at days 3, 10 and 17 subcutaneously with 2 nmol of Z13Mad12Anaxa at the tail base. 200 μg of anti-PD1 antibody RMP1-14 (BioXcell, West Lebanon, NH, USA) were administered i.p. on each of days 6, 10, 13, 17, 20, 24 and 27 to mice of groups "anti-PD1" and "Z13Mad12Anaxa+anti-PD1". At days 10 and 17, when both, Z13Mad12Anaxa and antibody, were administered, the antibody was administered i.p. just after s.c. administration of Z13Mad12Anaxa. Tumor size was measured with a caliper.

Figure 39:
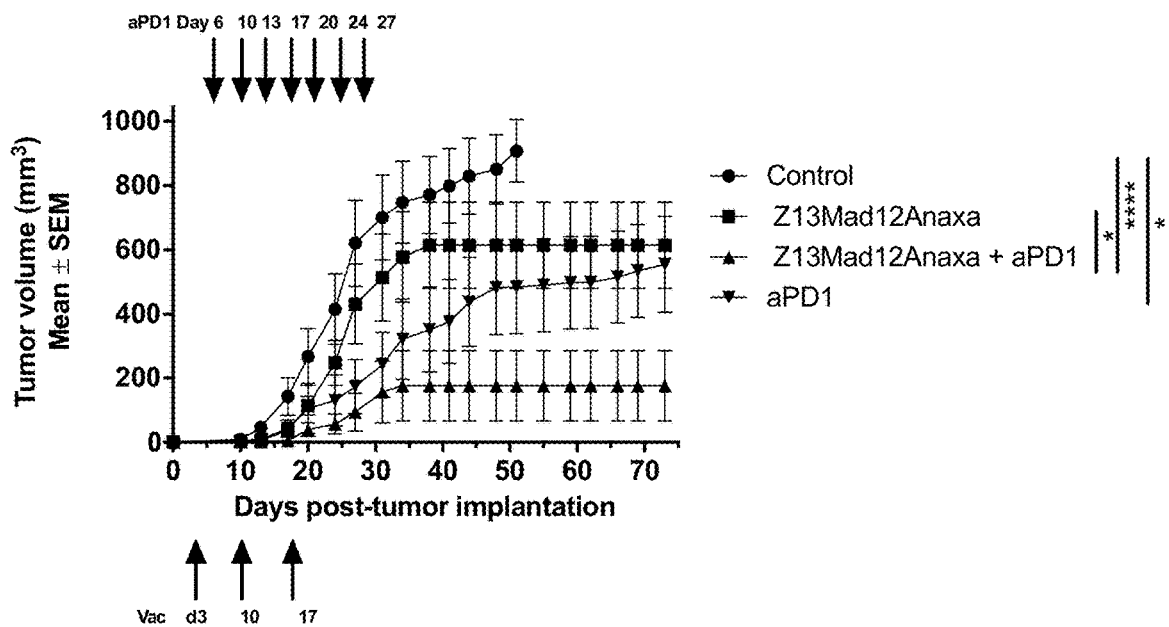
FIG. 39 shows for Example 23 the tumor growth (A) and the survival rate (B) of 13 to 14 mice per group (mean±SEM). C57BL/6 mice were implanted s.c. with 2×10⁵ MC-38 tumor cells on the back. Mice of the groups "Z13Mad12Anaxa" and "Z13Mad12Anaxa+anti-PD1" were vaccinated 3 times (d3, d10 and d17) by subcutaneous injection of 2 nmol of Z13Mad12Anaxa at the tail base. 200 µg of anti-PD1 antibody were administered i.p. on each of days 6, 10, 13, 17, 20, 24 and 27 to mice of groups "anti-PD1" and "Z13Mad12Anaxa+anti-PD1". Tumor size was measured with a caliper. The number of tumor-free mice of each group is indicated for each tumor growth curve. *, $p<0.05$; , $p<0.01$; *, $p<0.001$; ****, $p<0.0001$.
Figure 39:
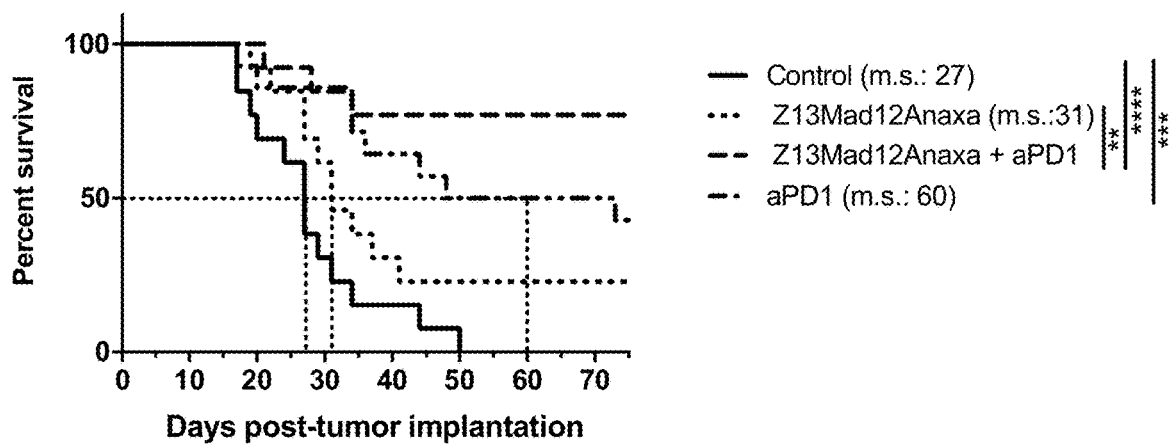
Figure 40:
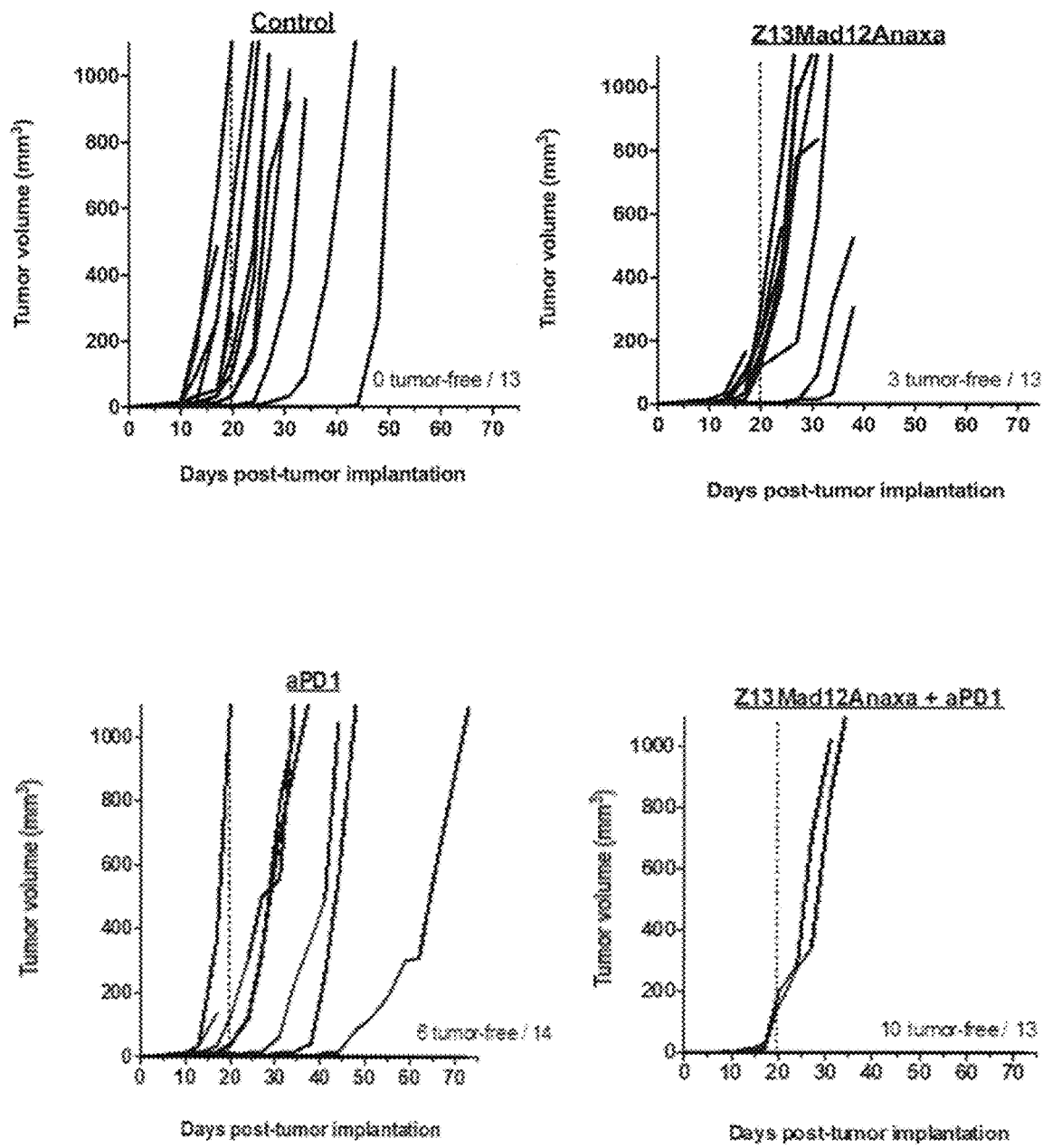
FIG. 40 shows for Example 23 individual tumor growth curves of 13 to 14 mice per group. C57BL/6 mice were implanted s.c. with 2×10⁵ MC-38 tumor cells on the back. Mice of the groups "Z13Mad12Anaxa" and "Z13Mad12Anaxa+anti-PD1" were vaccinated 3 times (d3, d10 and d17) by subcutaneous injection of 2 nmol of Z13Mad12Anaxa at the tail base. 200 µg of anti-PD1 antibody were administered i.p. on each of days 6, 10, 13, 17, 20, 24 and 27 to mice of groups "anti-PD1" and "Z13Mad12Anaxa+anti-PD1". Tumor size was measured with a caliper.

As shown in FIGS. 39 and 40, treatment with the PD1 inhibitor alone or with Z13Mad12Anaxa alone resulted in significantly reduced tumor volume (FIG. 39A) and increased survival (FIG. 39B), as compared to the control group. However, the combination of both, the PD1 inhibitor and Z13Mad12Anaxa, resulted in the most pronounced improvement, namely in strongly decreased tumor volume and strongly increased survival rates. Of note, in the "Z13Mad12Anaxa+aPD1" group only three mice developed tumors (whereas 10 mice remained tumor-free), whereas in the "aPD1" group and in the "Z13Mad12Anaxa" group eight and ten mice, respectively, developed tumors. In the control group all mice developed tumors.

These data show that a combination of both, anti-PD1 therapy and Z13Mad12Anaxa vaccination, is more efficient than anti-PD1 therapy alone or Z13Mad12Anaxa vaccination alone. These results thus indicate a synergistic effect of anti-PD1 therapy and Z13Mad12Anaxa vaccination.

| TABLE OF SEQUENCES AND SEQ ID NUMBERS (SEQUENCE LISTING): | | |
|---|---|---|
| SEQ ID NO | Sequence | Remarks |
| SEQ ID NO: 1 | RQIKIYFQNRRMKWKK | CPP: Penetratin |
| SEQ ID NO: 2 | YGRKKRRQRRR | CPP: TAT minimal |
| SEQ ID NO: 3 | MMDPNSTSEDVKFTPDPYQVPFVQAFDQATRV YQDLGGPSQAPLPCVLWPVLPEPLPQGQLTAY HVSTAPTGSWFSAPQPAPENAYQAYAAPQLFP VSDITQNQQTNQAGGEAPQPGDNSTVQTAA AVVFACPGANQGQQLADIGVPQPAPVAAPAR RTRKPQQPESLEECDSELEIKRYKNRVASRKCRAK FKQLLQHYREVAAAKSSENDRLRLLLKQMCPSL DVDSIIPRTPDVLHEDLLNF | ZEBRA amino acid sequence (natural sequence from Epstein - Barr virus (EBV)) (YP_401673) |
| SEQ ID NO: 4 | KRYKNRVASRKCRAKFKQLLQHYREVAAAKSSE NDRLRLLLKQMC | CPP1 (Z11) |
| SEQ ID NO: 5 | KRYKNRVASRKCRAKFKQLLQHYREVAAAKSSE NDRLRLLLK | CPP2 (Z12) |
| SEQ ID NO: 6 | KRYKNRVASRKSRAKFKQLLQHYREVAAAKSSE NDRLRLLLK | CPP3 (Z13) |
| SEQ ID NO: 7 | KRYKNRVASRKSRAKFKQLLQHYREVAAAK | CPP4 (Z14) |
| SEQ ID NO: 8 | KRYKNRVASRKSRAKFK | CPP5 (Z15) |
| SEQ ID NO: 9 | QHYREVAAAKSSEND | CPP6 (Z16) |
| SEQ ID NO: 10 | QLLQHYREVAAAK | CPP7 (Z17) |
| SEQ ID NO: 11 | REVAAAKSSENDRLRLLLK | CPP8 (Z18) |
| SEQ ID NO: 12 | KRYKNRVA | CPP9 (Z19) |
| SEQ ID NO: 13 | VASRKSRAKFK | CPP10 (Z20) |
| SEQ ID NO: 14 | ESLKISQAVHAAHAEINEAGREVVGVGAL KVPRNQDWLGVPRFAKFASFEAQGALA NIAVDKANLDVEQLESIINFEKLTEWTGS | MAD5 cargo |
| SEQ ID NO: 15 | STVHEILCKLSLEGDHSTPPSAYGSVKPYTNFDAE | TLR2 peptide agonist Anaxa |
| SEQ ID NO: 16 | DDDK | enterokinase target |

-continued

| SEQ ID NO | Sequence | Remarks |
|---|---|---|
| SEQ ID NO: 17 | IEDGR | factor Xa target site |
| SEQ ID NO: 18 | LVPRGS | thrombin target site |
| SEQ ID NO: 19 | ENLYFQG | protease TEV target |
| SEQ ID NO: 20 | LEVLFQGP | PreScission protease target |
| SEQ ID NO: 21 | RX(R/K)R | furin target site |
| SEQ ID NO: 22 | GGGGG | peptidic linker |
| SEQ ID NO: 23 | GGGG | peptidic linker |
| SEQ ID NO: 24 | EQLE | peptidic linker |
| SEQ ID NO: 25 | TEWT | peptidic linker |
| SEQ ID NO: 26 | MHHHHHHNIDRPKGLAFTDVDVDSIKIA WESPQGQVSRYRVTYSSPEDGIRELFPAP DGEDDTAELQGLRPGSEYTVSVVALHDD MESQPLIGIQSTKRYKNRVASRKSRAKFKQ LLQHYREVAAAKSSENDRLRLLLKESLKISQ AVHAAHAEINEAGREVVGVGALKVPRN QDWLGVPRFAKFASFEAQGALANIAVDK ANLDVEQLESIINFEKLTEWTGS | EDAZ13Mad5 |
| SEQ ID NO: 27 | MHHHHHHSTVHEILCKLSLEGDHSTPPSA YGSVKPYTNFDAEKRYKNRVASRKSRAKF KQLLQHYREVAAAKSSENDRLRLLLKESLKI SQAVHAAHAEINEAGREVVGVGALKVPR NQDWLGVPRFAKFASFEAQGALANIAVD KANLDVEQLESIINFEKLTEWTGS | AnaxaZ13Mad5 |
| SEQ ID NO: 28 | MHHHHHHKRYKNRVASRKSRAKFKQLL QHYREVAAAKSSENDRLRLLLKESLKISQA VHAAHAEINEAGREVVGVGALKVPRNQD WLGVPRFAKFASFEAQGALANIAVDKANL DVEQLESIINFEKLTEWTGSSTVHEILCKLSL EGDHSTPPSAYGSVKPYTNFDAE | Z13Mad5Anaxa |
| SEQ ID NO: 29 | MHHHHHHKRYKNRVASRKSRAKFKQLL QHYREVAAAKESLKISQAVHAAHAEINE AGREVVGVGALKVPRNQDWLGVPRFA KFASFEAQGALANIAVDKANLDVEQLESI INFEKLTEWTGSSTVHEILCKLSLEGDHST PPSAYGSVKPYTNFDAE | Z14Mad5Anaxa |
| SEQ ID NO: 30 | MHHHHHHREVAAAKSSENDRLRLLLKES LKISQAVHAAHAEINEAGREVVGVGALKV PRNQDWLGVPRFAKFASFEAQGALANIA VDKANLDVEQLESIINFEKLTEWTGSSTVH EILCKLSLEGDHSTPPSAYGSVKPYTNFDA E | Z18Mad5Anaxa |
| SEQ ID NO: 31 | MHHHHHHNIDRPKGLAFTDVDVDSIKIA WESPQGQVSRYRVTYSSPEDGIRELFPAP DGEDDTAELQGLRPGSEYTVSVVALHDD MESQPLIGIQSTKRYKNRVASRKSRAKFKQ LLQHYREVAAAKESLKISQAVHAAHAEIN EAGREVVGVGALKVPRNQDWLGVPRFA KFASFEAQGALANIAVDKANLDVEQLESII NFEKLTEWTGS | EDAZ14Mad5 |
| SEQ ID NO: 32 | MHHHHHHNIDRPKGLAFTDVDVDSIKIA WESPQGQVSRYRVTYSSPEDGIRELFPAP DGEDDTAELQGLRPGSEYTVSVVALHDD MESQPLIGIQSTREVAAAKSSENDRLRLLL KESLKISQAVHAAHAEINEAGREVVGVGA LKVPRNQDWLGVPRFAKFASFEAQGALA NIAVDKANLDVEQLESIINFEKLTEWTGS | EDAZ18Mad5 |

| TABLE OF SEQUENCES AND SEQ ID NUMBERS (SEQUENCE LISTING): | | |
|---|---|---|
| SEQ ID NO | Sequence | Remarks |
| SEQ ID NO: 33 | KRYKNRVASRKSRAKFKQLLQHYREVAAAKSSEN DRLRLLLKVTYHSPSYVYHQFERRAILNRLVQFIK DRISVVQALVLTSTVHEILCKLSLEGDHSTPPSAY GSVKPYTN FDAE | Z13Mad8Anaxa |
| SEQ ID NO: 34 | MHHHHHHNIDRPKGLAFTDVDVDSIKIAWESP QGQVSRYRVTYSSPEDGIRELFPAPDGEDDTAEL QGLRPGSEYTVSVVALHDDMESQPLIGIQSTESL KISQAVHAAHAEINEAGREVVGVGALKVPRNQ DWLGVPRFAKFASFEAQGALANIAVDKANLDVE QLE SIINFEKLTE WTGS | EDAMad5 |
| SEQ ID NO: 35 | SIINFEKL | SIINFEKL OVACD8 peptide |
| SEQ ID NO: 36 | VTYHSPSYAYHQFERRAILNRLVQFIKDRI | Mad8 |
| SEQ ID NO: 37 | NYRIATEKNWPFLEDCAMEELTVSEFLKLDRQR | Mad11 |
| SEQ ID NO: 38 | HLELASMTNMELMSSIV | Mad9 |
| SEQ ID NO: 39 | LFRAAQLANDVVLQIMEHLELASMTNMELMSSI VVISASIIVFNLLELEG | Mad12 |
| SEQ ID NO: 40 | NIDRPKGLAFTDVDVDSIKIAWESPQGQVSRYR VTYSSPEDGIRELFPAPDGEDDTAELQGLRPGSEY TVSVVALHDDMESQPLIGIQST | EDA |
| SEQ ID NO: 41 | KRYKNRVASRKSRAKFKQLLQHYREVAAAKSSEN DRLRLLLKVTYHSPSYAYHQFERRAILNRLVQFIK DRISVVQALVLTSTVHEILCKLSLEGDHSTPPSAY GSVKPYTN FDAE | Z13Mad8Anaxa |
| SEQ ID NO: 42 | KRYKNRVASRKSRAKFKQLLQHYREVAAAKSSEN DRLRLLLKNYRIATFKNWPFLEDCAMEELTVSEFL KLDRQRSTVHEILCKLSLEGDHSTPPSAYGSVKPY TNFDAE | Z13Mad11Anaxa |
| SEQ ID NO: 43 | KRYKNRVASRKSRAKFKQLLQHYREVAAAKSSEN DRLRLLLKHLELASMTNMELMSSIVSTVHEILCKLS LEGDHSTPPSAYGSVKPYTNFDAE | Z13Mad9Anaxa |
| SEQ ID NO: 44 | RKKRRQRRRRVKRISQAVHAAHAEINEAGRRVK RKVPRNQDWLRVKRASFEAQGALANIAVDKAR VKRSIINFEKLRVKRSTVHEILCKLSLEGDHSTPPSA YGSVKPYTNFDAE | TatFMad5Anaxa |
| SEQ ID NO: 45 | KRYKNRVASRKSRAKFKQLLQHYREVAAAKSSEN DRLRLLLKLFRAAQLANDVVLQIMEHLELASMTN MELMSSIVVISASIIVFNLLELEGSTVHEILCKLSLEG DHSTPPSAYGSVKPYTNFDAE | Z13Mad12Anaxa |
| SEQ ID NO: 46 | MHHHHHHKRYKNRVASRKSRAKFKQLLQHYRE VAAAKSSENDRLRLLLKESLKISQAVHAAHAEINE AGREVVGVGALKVPRNQDWLGVPRFAKFASFE AQGALANIAVDKANLDVEQLESIINFEKLTEWTG S | Z13Mad5 |
| SEQ ID NO: 47 | STVHEILSKLSLEGDHSTPPSAYGSVKPYTNFDAE | TLR peptide agonist: „Anaxa" sequence variant |

What is claimed is:

1. A combination comprising:
   (i) an immune checkpoint modulator, and
   (ii) a complex comprising:
      a) a cell penetrating peptide;
      b) at least one antigen or antigenic epitope; and
      c) at least one TLR peptide agonist, wherein the TLR peptide agonist is a TLR2 or TLR4 peptide agonist, and
   wherein components a)-c) are covalently linked.

2. The combination according to claim 1, wherein the complex is a recombinant polypeptide or a recombinant protein.

3. The combination according to claim 1, wherein the cell penetrating peptide:
   (i) has a length of 5 to 50 amino acids in total; and
   (ii) has an amino acid sequence comprising a fragment of the minimal domain of ZEBRA, said minimal domain extending from residue 170 to residue 220 of the ZEBRA amino acid sequence according to SEQ ID NO: 3, or a variant thereof wherein zero 1, 2, 3, 4, or 5 amino acids have been substituted, deleted, and/or added without abrogating said peptide's cell penetrating ability, or a variant thereof.

4. The combination according to claim 3, wherein the cell penetrating peptide has an amino acid sequence comprising the amino acid sequence according to SEQ ID NO: 6 (CPP3/Z13), SEQ ID NO: 7 (CPP4/Z14), SEQ ID NO: 8 (CPP5/Z15), or SEQ ID NO: 11 (CPP8/Z18), or a variant thereof sharing at least 90% sequence identity with at least one of SEQ ID NOs: 6, 7, 8, or 11.

5. The combination according to claim 4, wherein the cell penetrating peptide has an amino acid sequence comprising the amino acid sequence according to SEQ ID NO: 6 (CPP3/Z13), SEQ ID NO: 7 (CPP4/Z14), SEQ ID NO: 8 (CPP5/Z15), or SEQ ID NO: 11 (CPP8/Z18).

6. The combination according to claim 4, wherein the cell penetrating peptide has an amino acid sequence consisting of the amino acid sequence according to SEQ ID NO: 6 (CPP3/Z13), SEQ ID NO: 7 (CPP4/Z14), SEQ ID NO: 8 (CPP5/Z15), or SEQ ID NO: 11 (CPP8/Z18).

7. The combination according to claim 1, wherein the at least one antigen or antigenic epitope comprises at least one pathogen epitope, at least one tumor epitope, or a combination thereof.

8. The combination according to claim 1, wherein the complex comprises more than one antigen or antigenic epitope positioned consecutively in the complex.

9. The combination according to claim 1, wherein the at least one TLR peptide agonist comprises the amino acid sequence according to SEQ ID NO: 15 or 47 or a variant thereof sharing at least 90% sequence identity with SEQ ID NO: 15 or 47 without abrogating said peptide's TLR agonist ability.

10. The combination according to claim 9, wherein the at least one TLR peptide agonist comprises the amino acid sequence according to SEQ ID NO: 15 or 47.

11. The combination according to claim 1, wherein the immune checkpoint modulator is an activator or an inhibitor of one or more immune checkpoint point molecule(s) selected from the group consisting of CD27, CD28, CD40, CD122, CD137, OX40, GITR, ICOS, A2AR, B7-H3, B7-H4, BTLA, CTLA-4, IDO, KIR, LAG3, PD-1, TIM-3, VISTA, CEACAM1, GARP, PS, CSF1R, CD94/NKG2A, TDO, GITR, TNFR and FasR/DcR3; or an activator or an inhibitor of one or more ligands thereof.

12. The combination according to claim 11, wherein the immune checkpoint modulator is an inhibitor of an inhibitory checkpoint molecule.

13. The combination according to claim 11, wherein the immune checkpoint modulator is an activator of a stimulatory or costimulatory checkpoint molecule.

14. The combination according to claim 11, wherein the immune checkpoint modulator is a modulator of CD40, CTLA-4, PD-L1, PD-L2, PD-1 and/or IDO.

15. The combination according to claim 11 comprising more than one immune checkpoint modulator.

16. The combination according to claim 11, wherein the complex is a recombinant polypeptide or a recombinant protein wherein:
  a) the cell penetrating peptide has an amino acid sequence comprising the amino acid sequence according to SEQ ID NO: 6 (CPP3/Z13), SEQ ID NO: 7 (CPP4/Z14), SEQ ID NO: 8 (CPP5/Z15), or SEQ ID NO: 11 (CPP8/Z18), or a variant thereof sharing at least 90% sequence identity with at least one of SEQ ID NOs: 6, 7, 8, or 11 without abrogating said peptide's cell penetrating ability; and
  b) the at least one antigen or antigenic epitope is a peptide, polypeptide or protein.

17. The combination according to claim 11, wherein the complex is a recombinant polypeptide or a recombinant protein wherein:
  a) the cell penetrating peptide has an amino acid sequence consisting of the amino acid sequence according to SEQ ID NO: 6 (CPP3/Z13), SEQ ID NO: 7 (CPP4/Z14), SEQ ID NO: 8 (CPP5/Z15), or SEQ ID NO: 11 (CPP8/Z18), or a variant thereof sharing at least 90% sequence identity with at least one of SEQ ID NOs: 6, 7, 8, or 11 without abrogating said peptide's cell penetrating ability; and
  b) the at least one antigen or antigenic epitope is a peptide, polypeptide or protein.

18. The combination according to claim 1, wherein the at least one TLR peptide agonist consists of the amino acid sequence according to SEQ ID NO: 15 or 47 or a variant thereof sharing at least 90% sequence identity with SEQ ID NO:15 or 47 without abrogating said peptide's TLR agonist ability.

19. The combination according to claim 18, wherein the at least one TLR peptide agonist consists of the amino acid sequence according to SEQ ID NO: 15 or 47.

20. A kit comprising:
  (i) an immune checkpoint modulator; and
  (ii) a complex comprising:
    a) a cell penetrating peptide;
    b) at least one antigen or antigenic epitope; and
    c) at least one TLR peptide agonist, wherein the TLR peptide agonist is a TLR2 or TLR4 peptide agonist; and
    wherein components a)-c) are covalently linked; and
  (iii) a package insert or label having directions to treat cancer.

21. A pharmaceutical composition comprising:
  (i) an immune checkpoint modulator; and
  (ii) a complex comprising:
    a) a cell penetrating peptide;
    b) at least one antigen or antigenic epitope; and
    c) at least one TLR peptide agonist, wherein the TLR peptide agonist is a TLR2 or TLR4 peptide agonist; and
    wherein components a)-c) are covalently linked.

22. A combination comprising:
  (i) an immune checkpoint modulator; and
  (ii) a complex comprising:
    a) a cell penetrating peptide;
    b) at least one antigen or antigenic epitope; and
    c) at least one TLR peptide agonist, wherein the TLR peptide agonist is a TLR2 or TLR4 peptide agonist;
    wherein components a)-c) are covalently linked, and
    wherein the complex is a recombinant polypeptide or a recombinant protein.

23. The combination according to claim 22, wherein the cell penetrating peptide has an amino acid sequence comprising the amino acid sequence according to SEQ ID NO: 6 (CPP3/Z13), SEQ ID NO: 7 (CPP4/Z14), SEQ ID NO: 8 (CPP5/Z15), or SEQ ID NO: 11 (CPP8/Z18), or a variant thereof sharing at least 90% sequence identity with at least one of SEQ ID NOs: 6, 7, 8, or 11.

24. The combination according to claim 23, wherein the cell penetrating peptide has an amino acid sequence consisting of the amino acid sequence according to SEQ ID NO: 6 (CPP3/Z13), SEQ ID NO: 7 (CPP4/Z14), SEQ ID NO: 8 (CPP5/Z15), or SEQ ID NO: 11 (CPP8/Z18).

25. The combination according to claim 22, wherein the at least one antigen or antigenic epitope comprises at least one pathogen epitope, at least one tumor epitope, or a combination thereof.

26. The combination according to claim 22, wherein the complex comprises more than one antigen or antigenic epitope positioned consecutively in the complex.

27. The combination according to claim 22, wherein the at least one TLR peptide agonist comprises the amino acid sequence according to SEQ ID NO: 15 or 47 or a variant thereof sharing at least 90% sequence identity with SEQ ID NO:15 or 47 without abrogating said peptide's TLR agonist ability.

28. The combination according to claim 27, wherein the at least one TLR peptide agonist consists of the amino acid sequence according to SEQ ID NO: 15 or 47.

29. The combination according to claim 22, wherein the immune checkpoint modulator is an activator or an inhibitor of one or more immune checkpoint point molecule(s) selected from the group consisting of CD27, CD28, CD40, CD122, CD137, OX40, GITR, ICOS, A2AR, B7-H3, B7-H4, BTLA, CTLA-4, IDO, KIR, LAG3, PD-1, TIM-3, VISTA, CEACAM1, GARP, PS, CSF1R, CD94/NKG2A, TDO, GITR, TNFR and FasR/DcR3; or an activator or an inhibitor of one or more ligands thereof.

30. The combination according to claim 29, wherein the immune checkpoint modulator is a modulator of CD40, CTLA-4, PD-L1, PD-L2, PD-1 and/or IDO.

31. The combination according to claim 29 comprising more than one immune checkpoint modulator.

32. The combination according to claim 30, wherein:
  a) the cell penetrating peptide has an amino acid sequence consisting of the amino acid sequence according to SEQ ID NO: 6 (CPP3/Z13), SEQ ID NO: 7 (CPP4/Z14), SEQ ID NO: 8 (CPP5/Z15), or SEQ ID NO: 11 (CPP8/Z18);

b) the at least one TLR peptide agonist consists of the amino acid sequence according to SEQ ID NO: 15 or 47; and
c) the at least one antigen or antigenic epitope is a peptide, polypeptide or protein.

* * * * *

SEQUENCE LISTING

<160> NUMBER OF SEQ ID NOS: 47

<210> SEQ ID NO 1
<211> LENGTH: 16
<212> TYPE: PRT
<213> ORGANISM: Artificial Sequence

```
<220> FEATURE:
<223> OTHER INFORMATION: CPP: Penetratin

<400> SEQUENCE: 1

Arg Gln Ile Lys Ile Tyr Phe Gln Asn Arg Arg Met Lys Trp Lys Lys
1               5                   10                  15

<210> SEQ ID NO 2
<211> LENGTH: 11
<212> TYPE: PRT
<213> ORGANISM: Artificial Sequence
<220> FEATURE:
<223> OTHER INFORMATION: CPP: TAT minimal domain

<400> SEQUENCE: 2

Tyr Gly Arg Lys Lys Arg Arg Gln Arg Arg Arg
1               5                   10

<210> SEQ ID NO 3
<211> LENGTH: 245
<212> TYPE: PRT
<213> ORGANISM: Artificial Sequence
<220> FEATURE:
<223> OTHER INFORMATION: ZEBRA amino acid sequence (natural sequence
      from Epstein - Barr virus (EBV)) (YP_401673)

<400> SEQUENCE: 3

Met Met Asp Pro Asn Ser Thr Ser Glu Asp Val Lys Phe Thr Pro Asp
1               5                   10                  15

Pro Tyr Gln Val Pro Phe Val Gln Ala Phe Asp Gln Ala Thr Arg Val
                20                  25                  30

Tyr Gln Asp Leu Gly Gly Pro Ser Gln Ala Pro Leu Pro Cys Val Leu
            35                  40                  45

Trp Pro Val Leu Pro Glu Pro Leu Pro Gln Gly Gln Leu Thr Ala Tyr
50                  55                  60

His Val Ser Thr Ala Pro Thr Gly Ser Trp Phe Ser Ala Pro Gln Pro
65                  70                  75                  80

Ala Pro Glu Asn Ala Tyr Gln Ala Tyr Ala Ala Pro Gln Leu Phe Pro
                85                  90                  95

Val Ser Asp Ile Thr Gln Asn Gln Gln Thr Asn Gln Ala Gly Gly Glu
            100                 105                 110

Ala Pro Gln Pro Gly Asp Asn Ser Thr Val Gln Thr Ala Ala Ala Val
        115                 120                 125

Val Phe Ala Cys Pro Gly Ala Asn Gln Gly Gln Gln Leu Ala Asp Ile
    130                 135                 140

Gly Val Pro Gln Pro Ala Pro Val Ala Ala Pro Ala Arg Arg Thr Arg
145                 150                 155                 160

Lys Pro Gln Gln Pro Glu Ser Leu Glu Glu Cys Asp Ser Glu Leu Glu
                165                 170                 175

Ile Lys Arg Tyr Lys Asn Arg Val Ala Ser Arg Lys Cys Arg Ala Lys
            180                 185                 190

Phe Lys Gln Leu Leu Gln His Tyr Arg Glu Val Ala Ala Ala Lys Ser
        195                 200                 205

Ser Glu Asn Asp Arg Leu Arg Leu Leu Lys Gln Met Cys Pro Ser
    210                 215                 220

Leu Asp Val Asp Ser Ile Ile Pro Arg Thr Pro Asp Val Leu His Glu
225                 230                 235                 240

Asp Leu Leu Asn Phe
            245
```

<210> SEQ ID NO 4
<211> LENGTH: 45
<212> TYPE: PRT
<213> ORGANISM: Artificial Sequence
<220> FEATURE:
<223> OTHER INFORMATION: CPP1 (Z11)

<400> SEQUENCE: 4

Lys Arg Tyr Lys Asn Arg Val Ala Ser Arg Lys Cys Arg Ala Lys Phe
1               5                   10                  15

Lys Gln Leu Leu Gln His Tyr Arg Glu Val Ala Ala Ala Lys Ser Ser
            20                  25                  30

Glu Asn Asp Arg Leu Arg Leu Leu Leu Lys Gln Met Cys
        35                  40                  45

<210> SEQ ID NO 5
<211> LENGTH: 42
<212> TYPE: PRT
<213> ORGANISM: Artificial Sequence
<220> FEATURE:
<223> OTHER INFORMATION: CPP2 (Z12)

<400> SEQUENCE: 5

Lys Arg Tyr Lys Asn Arg Val Ala Ser Arg Lys Cys Arg Ala Lys Phe
1               5                   10                  15

Lys Gln Leu Leu Gln His Tyr Arg Glu Val Ala Ala Ala Lys Ser Ser
            20                  25                  30

Glu Asn Asp Arg Leu Arg Leu Leu Leu Lys
        35                  40

<210> SEQ ID NO 6
<211> LENGTH: 42
<212> TYPE: PRT
<213> ORGANISM: Artificial Sequence
<220> FEATURE:
<223> OTHER INFORMATION: CPP3 (Z13)

<400> SEQUENCE: 6

Lys Arg Tyr Lys Asn Arg Val Ala Ser Arg Lys Ser Arg Ala Lys Phe
1               5                   10                  15

Lys Gln Leu Leu Gln His Tyr Arg Glu Val Ala Ala Ala Lys Ser Ser
            20                  25                  30

Glu Asn Asp Arg Leu Arg Leu Leu Leu Lys
        35                  40

<210> SEQ ID NO 7
<211> LENGTH: 30
<212> TYPE: PRT
<213> ORGANISM: Artificial Sequence
<220> FEATURE:
<223> OTHER INFORMATION: CPP4 (Z14)

<400> SEQUENCE: 7

Lys Arg Tyr Lys Asn Arg Val Ala Ser Arg Lys Ser Arg Ala Lys Phe
1               5                   10                  15

Lys Gln Leu Leu Gln His Tyr Arg Glu Val Ala Ala Ala Lys
            20                  25                  30

<210> SEQ ID NO 8
<211> LENGTH: 17
<212> TYPE: PRT
<213> ORGANISM: Artificial Sequence

```
<220> FEATURE:
<223> OTHER INFORMATION: CPP5 (Z15)

<400> SEQUENCE: 8

Lys Arg Tyr Lys Asn Arg Val Ala Ser Arg Lys Ser Arg Ala Lys Phe
1               5                   10                  15
Lys

<210> SEQ ID NO 9
<211> LENGTH: 15
<212> TYPE: PRT
<213> ORGANISM: Artificial Sequence
<220> FEATURE:
<223> OTHER INFORMATION: CPP6 (Z16)

<400> SEQUENCE: 9

Gln His Tyr Arg Glu Val Ala Ala Ala Lys Ser Ser Glu Asn Asp
1               5                   10                  15

<210> SEQ ID NO 10
<211> LENGTH: 13
<212> TYPE: PRT
<213> ORGANISM: Artificial Sequence
<220> FEATURE:
<223> OTHER INFORMATION: CPP7 (Z17)

<400> SEQUENCE: 10

Gln Leu Leu Gln His Tyr Arg Glu Val Ala Ala Ala Lys
1               5                   10

<210> SEQ ID NO 11
<211> LENGTH: 19
<212> TYPE: PRT
<213> ORGANISM: Artificial Sequence
<220> FEATURE:
<223> OTHER INFORMATION: CPP8 (Z18)

<400> SEQUENCE: 11

Arg Glu Val Ala Ala Ala Lys Ser Ser Glu Asn Asp Arg Leu Arg Leu
1               5                   10                  15
Leu Leu Lys

<210> SEQ ID NO 12
<211> LENGTH: 8
<212> TYPE: PRT
<213> ORGANISM: Artificial Sequence
<220> FEATURE:
<223> OTHER INFORMATION: CPP9 (Z19)

<400> SEQUENCE: 12

Lys Arg Tyr Lys Asn Arg Val Ala
1               5

<210> SEQ ID NO 13
<211> LENGTH: 11
<212> TYPE: PRT
<213> ORGANISM: Artificial Sequence
<220> FEATURE:
<223> OTHER INFORMATION: CPP10 (Z20)

<400> SEQUENCE: 13

Val Ala Ser Arg Lys Ser Arg Ala Lys Phe Lys
1               5                   10

<210> SEQ ID NO 14
```

```
<211> LENGTH: 85
<212> TYPE: PRT
<213> ORGANISM: Artificial Sequence
<220> FEATURE:
<223> OTHER INFORMATION: MAD5 cargo

<400> SEQUENCE: 14

Glu Ser Leu Lys Ile Ser Gln Ala Val His Ala Ala His Ala Glu Ile
1               5                   10                  15

Asn Glu Ala Gly Arg Glu Val Val Gly Val Gly Ala Leu Lys Val Pro
            20                  25                  30

Arg Asn Gln Asp Trp Leu Gly Val Pro Arg Phe Ala Lys Phe Ala Ser
        35                  40                  45

Phe Glu Ala Gln Gly Ala Leu Ala Asn Ile Ala Val Asp Lys Ala Asn
    50                  55                  60

Leu Asp Val Glu Gln Leu Glu Ser Ile Ile Asn Phe Glu Lys Leu Thr
65                  70                  75                  80

Glu Trp Thr Gly Ser
                85

<210> SEQ ID NO 15
<211> LENGTH: 35
<212> TYPE: PRT
<213> ORGANISM: Artificial Sequence
<220> FEATURE:
<223> OTHER INFORMATION: TLR2 peptide agonist Anaxa

<400> SEQUENCE: 15

Ser Thr Val His Glu Ile Leu Cys Lys Leu Ser Leu Glu Gly Asp His
1               5                   10                  15

Ser Thr Pro Pro Ser Ala Tyr Gly Ser Val Lys Pro Tyr Thr Asn Phe
            20                  25                  30

Asp Ala Glu
        35

<210> SEQ ID NO 16
<211> LENGTH: 4
<212> TYPE: PRT
<213> ORGANISM: Artificial Sequence
<220> FEATURE:
<223> OTHER INFORMATION: enterokinase target site

<400> SEQUENCE: 16

Asp Asp Asp Lys
1

<210> SEQ ID NO 17
<211> LENGTH: 5
<212> TYPE: PRT
<213> ORGANISM: Artificial Sequence
<220> FEATURE:
<223> OTHER INFORMATION: factor Xa target site

<400> SEQUENCE: 17

Ile Glu Asp Gly Arg
1               5

<210> SEQ ID NO 18
<211> LENGTH: 6
<212> TYPE: PRT
<213> ORGANISM: Artificial Sequence
<220> FEATURE:
<223> OTHER INFORMATION: thrombin target site
```

```
<400> SEQUENCE: 18

Leu Val Pro Arg Gly Ser
1               5

<210> SEQ ID NO 19
<211> LENGTH: 7
<212> TYPE: PRT
<213> ORGANISM: Artificial Sequence
<220> FEATURE:
<223> OTHER INFORMATION: protease TEV target site

<400> SEQUENCE: 19

Glu Asn Leu Tyr Phe Gln Gly
1               5

<210> SEQ ID NO 20
<211> LENGTH: 8
<212> TYPE: PRT
<213> ORGANISM: Artificial Sequence
<220> FEATURE:
<223> OTHER INFORMATION: PreScission protease target site

<400> SEQUENCE: 20

Leu Glu Val Leu Phe Gln Gly Pro
1               5

<210> SEQ ID NO 21
<211> LENGTH: 4
<212> TYPE: PRT
<213> ORGANISM: Artificial Sequence
<220> FEATURE:
<223> OTHER INFORMATION: furin target site
<220> FEATURE:
<221> NAME/KEY: MISC_FEATURE
<222> LOCATION: (2)..(2)
<223> OTHER INFORMATION: X may be any amino acid
<220> FEATURE:
<221> NAME/KEY: MISC_FEATURE
<222> LOCATION: (3)..(3)
<223> OTHER INFORMATION: X is R or K

<400> SEQUENCE: 21

Arg Xaa Xaa Arg
1

<210> SEQ ID NO 22
<211> LENGTH: 5
<212> TYPE: PRT
<213> ORGANISM: Artificial Sequence
<220> FEATURE:
<223> OTHER INFORMATION: peptidic linker

<400> SEQUENCE: 22

Gly Gly Gly Gly Gly
1               5

<210> SEQ ID NO 23
<211> LENGTH: 4
<212> TYPE: PRT
<213> ORGANISM: Artificial Sequence
<220> FEATURE:
<223> OTHER INFORMATION: peptidic linker

<400> SEQUENCE: 23

Gly Gly Gly Gly
1
```

```
<210> SEQ ID NO 24
<211> LENGTH: 4
<212> TYPE: PRT
<213> ORGANISM: Artificial Sequence
<220> FEATURE:
<223> OTHER INFORMATION: peptidic linker

<400> SEQUENCE: 24

Glu Gln Leu Glu
1

<210> SEQ ID NO 25
<211> LENGTH: 4
<212> TYPE: PRT
<213> ORGANISM: Artificial Sequence
<220> FEATURE:
<223> OTHER INFORMATION: peptidic linker

<400> SEQUENCE: 25

Thr Glu Trp Thr
1

<210> SEQ ID NO 26
<211> LENGTH: 224
<212> TYPE: PRT
<213> ORGANISM: Artificial Sequence
<220> FEATURE:
<223> OTHER INFORMATION: EDAZ13Mad5

<400> SEQUENCE: 26

Met His His His His His Asn Ile Asp Arg Pro Lys Gly Leu Ala
1               5                   10                  15

Phe Thr Asp Val Asp Val Asp Ser Ile Lys Ile Ala Trp Glu Ser Pro
                20                  25                  30

Gln Gly Gln Val Ser Arg Tyr Arg Val Thr Tyr Ser Ser Pro Glu Asp
            35                  40                  45

Gly Ile Arg Glu Leu Phe Pro Ala Pro Asp Gly Glu Asp Asp Thr Ala
        50                  55                  60

Glu Leu Gln Gly Leu Arg Pro Gly Ser Glu Tyr Thr Val Ser Val Val
65                  70                  75                  80

Ala Leu His Asp Asp Met Glu Ser Gln Pro Leu Ile Gly Ile Gln Ser
                    85                  90                  95

Thr Lys Arg Tyr Lys Asn Arg Val Ala Ser Arg Ser Arg Ala Lys
                100                 105                 110

Phe Lys Gln Leu Leu Gln His Tyr Arg Glu Val Ala Ala Ala Lys Ser
            115                 120                 125

Ser Glu Asn Asp Arg Leu Arg Leu Leu Leu Lys Glu Ser Leu Lys Ile
        130                 135                 140

Ser Gln Ala Val His Ala His Ala Glu Ile Asn Glu Ala Gly Arg
145                 150                 155                 160

Glu Val Val Gly Val Gly Ala Leu Lys Val Pro Arg Asn Gln Asp Trp
                165                 170                 175

Leu Gly Val Pro Arg Phe Ala Lys Phe Ala Ser Phe Glu Ala Gln Gly
            180                 185                 190

Ala Leu Ala Asn Ile Ala Val Asp Lys Ala Asn Leu Asp Val Glu Gln
        195                 200                 205

Leu Glu Ser Ile Ile Asn Phe Glu Lys Leu Thr Glu Trp Thr Gly Ser
    210                 215                 220

<210> SEQ ID NO 27
```

```
<211> LENGTH: 169
<212> TYPE: PRT
<213> ORGANISM: Artificial Sequence
<220> FEATURE:
<223> OTHER INFORMATION: AnaxaZ13Mad5

<400> SEQUENCE: 27

Met His His His His His Ser Thr Val His Glu Ile Leu Cys Lys
1               5                   10                  15

Leu Ser Leu Glu Gly Asp His Ser Thr Pro Pro Ser Ala Tyr Gly Ser
            20                  25                  30

Val Lys Pro Tyr Thr Asn Phe Asp Ala Glu Lys Arg Tyr Lys Asn Arg
            35                  40                  45

Val Ala Ser Arg Lys Ser Arg Ala Lys Phe Lys Gln Leu Leu Gln His
        50                  55                  60

Tyr Arg Glu Val Ala Ala Ala Lys Ser Ser Glu Asn Asp Arg Leu Arg
65                  70                  75                  80

Leu Leu Leu Lys Glu Ser Leu Lys Ile Ser Gln Ala Val His Ala Ala
                85                  90                  95

His Ala Glu Ile Asn Glu Ala Gly Arg Glu Val Val Gly Val Gly Ala
            100                 105                 110

Leu Lys Val Pro Arg Asn Gln Asp Trp Leu Gly Val Pro Arg Phe Ala
        115                 120                 125

Lys Phe Ala Ser Phe Glu Ala Gln Gly Ala Leu Ala Asn Ile Ala Val
130                 135                 140

Asp Lys Ala Asn Leu Asp Val Glu Gln Leu Glu Ser Ile Ile Asn Phe
145                 150                 155                 160

Glu Lys Leu Thr Glu Trp Thr Gly Ser
                165

<210> SEQ ID NO 28
<211> LENGTH: 169
<212> TYPE: PRT
<213> ORGANISM: Artificial Sequence
<220> FEATURE:
<223> OTHER INFORMATION: Z13Mad5Anaxa

<400> SEQUENCE: 28

Met His His His His His Lys Arg Tyr Lys Asn Arg Val Ala Ser
1               5                   10                  15

Arg Lys Ser Arg Ala Lys Phe Lys Gln Leu Leu Gln His Tyr Arg Glu
            20                  25                  30

Val Ala Ala Ala Lys Ser Ser Glu Asn Asp Arg Leu Arg Leu Leu Leu
            35                  40                  45

Lys Glu Ser Leu Lys Ile Ser Gln Ala Val His Ala Ala His Ala Glu
        50                  55                  60

Ile Asn Glu Ala Gly Arg Glu Val Val Gly Val Gly Ala Leu Lys Val
65                  70                  75                  80

Pro Arg Asn Gln Asp Trp Leu Gly Val Pro Arg Phe Ala Lys Phe Ala
                85                  90                  95

Ser Phe Glu Ala Gln Gly Ala Leu Ala Asn Ile Ala Val Asp Lys Ala
            100                 105                 110

Asn Leu Asp Val Glu Gln Leu Glu Ser Ile Ile Asn Phe Glu Lys Leu
        115                 120                 125

Thr Glu Trp Thr Gly Ser Ser Thr Val His Glu Ile Leu Cys Lys Leu
        130                 135                 140

Ser Leu Glu Gly Asp His Ser Thr Pro Pro Ser Ala Tyr Gly Ser Val
```

```
                145                 150                 155                 160
Lys Pro Tyr Thr Asn Phe Asp Ala Glu
                165
```

<210> SEQ ID NO 29
<211> LENGTH: 157
<212> TYPE: PRT
<213> ORGANISM: Artificial Sequence
<220> FEATURE:
<223> OTHER INFORMATION: Z14Mad5Anaxa

<400> SEQUENCE: 29

```
Met His His His His His Lys Arg Tyr Lys Asn Arg Val Ala Ser
1               5                   10                  15

Arg Lys Ser Arg Ala Lys Phe Lys Gln Leu Leu Gln His Tyr Arg Glu
                20                  25                  30

Val Ala Ala Ala Lys Glu Ser Leu Lys Ile Ser Gln Ala Val His Ala
                35                  40                  45

Ala His Ala Glu Ile Asn Glu Ala Gly Arg Glu Val Val Gly Val Gly
        50                  55                  60

Ala Leu Lys Val Pro Arg Asn Gln Asp Trp Leu Gly Val Pro Arg Phe
65                  70                  75                  80

Ala Lys Phe Ala Ser Phe Glu Ala Gln Gly Ala Leu Ala Asn Ile Ala
                85                  90                  95

Val Asp Lys Ala Asn Leu Asp Val Glu Gln Leu Glu Ser Ile Ile Asn
                100                 105                 110

Phe Glu Lys Leu Thr Glu Trp Thr Gly Ser Ser Thr Val His Glu Ile
            115                 120                 125

Leu Cys Lys Leu Ser Leu Glu Gly Asp His Ser Thr Pro Pro Ser Ala
    130                 135                 140

Tyr Gly Ser Val Lys Pro Tyr Thr Asn Phe Asp Ala Glu
145                 150                 155
```

<210> SEQ ID NO 30
<211> LENGTH: 146
<212> TYPE: PRT
<213> ORGANISM: Artificial Sequence
<220> FEATURE:
<223> OTHER INFORMATION: Z18Mad5Anaxa

<400> SEQUENCE: 30

```
Met His His His His His Arg Glu Val Ala Ala Ala Lys Ser Ser
1               5                   10                  15

Glu Asn Asp Arg Leu Arg Leu Leu Lys Glu Ser Leu Lys Ile Ser
                20                  25                  30

Gln Ala Val His Ala Ala His Ala Glu Ile Asn Glu Ala Gly Arg Glu
            35                  40                  45

Val Val Gly Val Gly Ala Leu Lys Val Pro Arg Asn Gln Asp Trp Leu
    50                  55                  60

Gly Val Pro Arg Phe Ala Lys Phe Ala Ser Phe Glu Ala Gln Gly Ala
65                  70                  75                  80

Leu Ala Asn Ile Ala Val Asp Lys Ala Asn Leu Asp Val Glu Gln Leu
                85                  90                  95

Glu Ser Ile Ile Asn Phe Glu Lys Leu Thr Glu Trp Thr Gly Ser Ser
            100                 105                 110

Thr Val His Glu Ile Leu Cys Lys Leu Ser Leu Glu Gly Asp His Ser
        115                 120                 125
```

```
Thr Pro Pro Ser Ala Tyr Gly Ser Val Lys Pro Tyr Thr Asn Phe Asp
    130                 135                 140

Ala Glu
145

<210> SEQ ID NO 31
<211> LENGTH: 212
<212> TYPE: PRT
<213> ORGANISM: Artificial Sequence
<220> FEATURE:
<223> OTHER INFORMATION: EDAZ14Mad5

<400> SEQUENCE: 31

Met His His His His His Asn Ile Asp Arg Pro Lys Gly Leu Ala
1               5                   10                  15

Phe Thr Asp Val Asp Val Asp Ser Ile Lys Ile Ala Trp Glu Ser Pro
            20                  25                  30

Gln Gly Gln Val Ser Arg Tyr Arg Val Thr Tyr Ser Ser Pro Glu Asp
        35                  40                  45

Gly Ile Arg Glu Leu Phe Pro Ala Pro Asp Gly Glu Asp Asp Thr Ala
    50                  55                  60

Glu Leu Gln Gly Leu Arg Pro Gly Ser Glu Tyr Thr Val Ser Val Val
65                  70                  75                  80

Ala Leu His Asp Asp Met Glu Ser Gln Pro Leu Ile Gly Ile Gln Ser
                85                  90                  95

Thr Lys Arg Tyr Lys Asn Arg Val Ala Ser Arg Lys Ser Arg Ala Lys
            100                 105                 110

Phe Lys Gln Leu Leu Gln His Tyr Arg Glu Val Ala Ala Ala Lys Glu
        115                 120                 125

Ser Leu Lys Ile Ser Gln Ala Val His Ala Ala His Ala Glu Ile Asn
    130                 135                 140

Glu Ala Gly Arg Glu Val Val Gly Val Gly Ala Leu Lys Val Pro Arg
145                 150                 155                 160

Asn Gln Asp Trp Leu Gly Val Pro Arg Phe Ala Lys Phe Ala Ser Phe
                165                 170                 175

Glu Ala Gln Gly Ala Leu Ala Asn Ile Ala Val Asp Lys Ala Asn Leu
            180                 185                 190

Asp Val Glu Gln Leu Glu Ser Ile Ile Asn Phe Glu Lys Leu Thr Glu
        195                 200                 205

Trp Thr Gly Ser
    210

<210> SEQ ID NO 32
<211> LENGTH: 201
<212> TYPE: PRT
<213> ORGANISM: Artificial Sequence
<220> FEATURE:
<223> OTHER INFORMATION: EDAZ18Mad5

<400> SEQUENCE: 32

Met His His His His His Asn Ile Asp Arg Pro Lys Gly Leu Ala
1               5                   10                  15

Phe Thr Asp Val Asp Val Asp Ser Ile Lys Ile Ala Trp Glu Ser Pro
            20                  25                  30

Gln Gly Gln Val Ser Arg Tyr Arg Val Thr Tyr Ser Ser Pro Glu Asp
        35                  40                  45

Gly Ile Arg Glu Leu Phe Pro Ala Pro Asp Gly Glu Asp Asp Thr Ala
    50                  55                  60
```

```
Glu Leu Gln Gly Leu Arg Pro Gly Ser Glu Tyr Thr Val Ser Val Val
 65                  70                  75                  80

Ala Leu His Asp Asp Met Glu Ser Gln Pro Leu Ile Gly Ile Gln Ser
                 85                  90                  95

Thr Arg Glu Val Ala Ala Lys Ser Ser Glu Asn Asp Arg Leu Arg
            100                 105                 110

Leu Leu Leu Lys Glu Ser Leu Lys Ile Ser Gln Ala Val His Ala Ala
            115                 120                 125

His Ala Glu Ile Asn Glu Ala Gly Arg Glu Val Val Gly Val Gly Ala
        130                 135                 140

Leu Lys Val Pro Arg Asn Gln Asp Trp Leu Gly Val Pro Arg Phe Ala
145                 150                 155                 160

Lys Phe Ala Ser Phe Glu Ala Gln Gly Ala Leu Ala Asn Ile Ala Val
                165                 170                 175

Asp Lys Ala Asn Leu Asp Val Glu Gln Leu Glu Ser Ile Ile Asn Phe
            180                 185                 190

Glu Lys Leu Thr Glu Trp Thr Gly Ser
        195                 200

<210> SEQ ID NO 33
<211> LENGTH: 116
<212> TYPE: PRT
<213> ORGANISM: Artificial Sequence
<220> FEATURE:
<223> OTHER INFORMATION: Z13Mad8Anaxa

<400> SEQUENCE: 33

Lys Arg Tyr Lys Asn Arg Val Ala Ser Arg Lys Ser Arg Ala Lys Phe
1               5                   10                  15

Lys Gln Leu Leu Gln His Tyr Arg Glu Val Ala Ala Ala Lys Ser Ser
            20                  25                  30

Glu Asn Asp Arg Leu Arg Leu Leu Leu Lys Val Thr Tyr His Ser Pro
        35                  40                  45

Ser Tyr Val Tyr His Gln Phe Glu Arg Arg Ala Ile Leu Asn Arg Leu
    50                  55                  60

Val Gln Phe Ile Lys Asp Arg Ile Ser Val Val Gln Ala Leu Val Leu
65                  70                  75                  80

Thr Ser Thr Val His Glu Ile Leu Cys Lys Leu Ser Leu Glu Gly Asp
                85                  90                  95

His Ser Thr Pro Pro Ser Ala Tyr Gly Ser Val Lys Pro Tyr Thr Asn
            100                 105                 110

Phe Asp Ala Glu
        115

<210> SEQ ID NO 34
<211> LENGTH: 182
<212> TYPE: PRT
<213> ORGANISM: Artificial Sequence
<220> FEATURE:
<223> OTHER INFORMATION: EDAMad5

<400> SEQUENCE: 34

Met His His His His His Asn Ile Asp Arg Pro Lys Gly Leu Ala
1               5                   10                  15

Phe Thr Asp Val Asp Val Asp Ser Ile Lys Ile Ala Trp Glu Ser Pro
            20                  25                  30

Gln Gly Gln Val Ser Arg Tyr Arg Val Thr Tyr Ser Ser Pro Glu Asp
```

```
                35                  40                  45
Gly Ile Arg Glu Leu Phe Pro Ala Pro Asp Gly Glu Asp Thr Ala
 50                  55                  60
Glu Leu Gln Gly Leu Arg Pro Gly Ser Glu Tyr Thr Val Ser Val
 65                  70                  75                  80
Ala Leu His Asp Asp Met Glu Ser Gln Pro Leu Ile Gly Ile Gln Ser
                 85                  90                  95
Thr Glu Ser Leu Lys Ile Ser Gln Ala Val His Ala His Ala Glu
                100                 105                 110
Ile Asn Glu Ala Gly Arg Glu Val Val Gly Val Gly Ala Leu Lys Val
                115                 120                 125
Pro Arg Asn Gln Asp Trp Leu Gly Val Pro Arg Phe Ala Lys Phe Ala
                130                 135                 140
Ser Phe Glu Ala Gln Gly Ala Leu Ala Asn Ile Ala Val Asp Lys Ala
145                 150                 155                 160
Asn Leu Asp Val Glu Gln Leu Glu Ser Ile Ile Asn Phe Glu Lys Leu
                165                 170                 175
Thr Glu Trp Thr Gly Ser
                180
```

<210> SEQ ID NO 35
<211> LENGTH: 8
<212> TYPE: PRT
<213> ORGANISM: Artificial Sequence
<220> FEATURE:
<223> OTHER INFORMATION: SIINFEKL OVACD8 peptide

<400> SEQUENCE: 35

```
Ser Ile Ile Asn Phe Glu Lys Leu
1               5
```

<210> SEQ ID NO 36
<211> LENGTH: 30
<212> TYPE: PRT
<213> ORGANISM: Artificial Sequence
<220> FEATURE:
<223> OTHER INFORMATION: Mad8

<400> SEQUENCE: 36

```
Val Thr Tyr His Ser Pro Ser Tyr Ala Tyr His Gln Phe Glu Arg Arg
1               5                   10                  15
Ala Ile Leu Asn Arg Leu Val Gln Phe Ile Lys Asp Arg Ile
                20                  25                  30
```

<210> SEQ ID NO 37
<211> LENGTH: 33
<212> TYPE: PRT
<213> ORGANISM: Artificial Sequence
<220> FEATURE:
<223> OTHER INFORMATION: Mad11

<400> SEQUENCE: 37

```
Asn Tyr Arg Ile Ala Thr Phe Lys Asn Trp Pro Phe Leu Glu Asp Cys
1               5                   10                  15
Ala Met Glu Glu Leu Thr Val Ser Glu Phe Leu Lys Leu Asp Arg Gln
                20                  25                  30
Arg
```

<210> SEQ ID NO 38
<211> LENGTH: 17

```
<212> TYPE: PRT
<213> ORGANISM: Artificial Sequence
<220> FEATURE:
<223> OTHER INFORMATION: Mad9

<400> SEQUENCE: 38

His Leu Glu Leu Ala Ser Met Thr Asn Met Glu Leu Met Ser Ser Ile
1               5                   10                  15

Val

<210> SEQ ID NO 39
<211> LENGTH: 50
<212> TYPE: PRT
<213> ORGANISM: Artificial Sequence
<220> FEATURE:
<223> OTHER INFORMATION: Mad12

<400> SEQUENCE: 39

Leu Phe Arg Ala Ala Gln Leu Ala Asn Asp Val Val Leu Gln Ile Met
1               5                   10                  15

Glu His Leu Glu Leu Ala Ser Met Thr Asn Met Glu Leu Met Ser Ser
                20                  25                  30

Ile Val Val Ile Ser Ala Ser Ile Ile Val Phe Asn Leu Leu Glu Leu
            35                  40                  45

Glu Gly
    50

<210> SEQ ID NO 40
<211> LENGTH: 90
<212> TYPE: PRT
<213> ORGANISM: Artificial Sequence
<220> FEATURE:
<223> OTHER INFORMATION: EDA

<400> SEQUENCE: 40

Asn Ile Asp Arg Pro Lys Gly Leu Ala Phe Thr Asp Val Asp Val Asp
1               5                   10                  15

Ser Ile Lys Ile Ala Trp Glu Ser Pro Gln Gly Gln Val Ser Arg Tyr
                20                  25                  30

Arg Val Thr Tyr Ser Ser Pro Glu Asp Gly Ile Arg Glu Leu Phe Pro
            35                  40                  45

Ala Pro Asp Gly Glu Asp Asp Thr Ala Glu Leu Gln Gly Leu Arg Pro
        50                  55                  60

Gly Ser Glu Tyr Thr Val Ser Val Val Ala Leu His Asp Asp Met Glu
65                  70                  75                  80

Ser Gln Pro Leu Ile Gly Ile Gln Ser Thr
                85                  90

<210> SEQ ID NO 41
<211> LENGTH: 116
<212> TYPE: PRT
<213> ORGANISM: Artificial Sequence
<220> FEATURE:
<223> OTHER INFORMATION: Z13Mad8Anaxa

<400> SEQUENCE: 41

Lys Arg Tyr Lys Asn Arg Val Ala Ser Arg Lys Ser Arg Ala Lys Phe
1               5                   10                  15

Lys Gln Leu Leu Gln His Tyr Arg Glu Val Ala Ala Ala Lys Ser Ser
                20                  25                  30

Glu Asn Asp Arg Leu Arg Leu Leu Leu Lys Val Thr Tyr His Ser Pro
```

```
                35                  40                  45

Ser Tyr Ala Tyr His Gln Phe Glu Arg Arg Ala Ile Leu Asn Arg Leu
 50                  55                  60

Val Gln Phe Ile Lys Asp Arg Ile Ser Val Val Gln Ala Leu Val Leu
 65                  70                  75                  80

Thr Ser Thr Val His Glu Ile Leu Cys Lys Leu Ser Leu Glu Gly Asp
                 85                  90                  95

His Ser Thr Pro Pro Ser Ala Tyr Gly Ser Val Lys Pro Tyr Thr Asn
                100                 105                 110

Phe Asp Ala Glu
            115

<210> SEQ ID NO 42
<211> LENGTH: 110
<212> TYPE: PRT
<213> ORGANISM: Artificial Sequence
<220> FEATURE:
<223> OTHER INFORMATION: Z13Mad11Anaxa

<400> SEQUENCE: 42

Lys Arg Tyr Lys Asn Arg Val Ala Ser Arg Lys Ser Arg Ala Lys Phe
 1                   5                  10                  15

Lys Gln Leu Leu Gln His Tyr Arg Glu Val Ala Ala Ala Lys Ser Ser
                 20                  25                  30

Glu Asn Asp Arg Leu Arg Leu Leu Lys Asn Tyr Arg Ile Ala Thr
             35                  40                  45

Phe Lys Asn Trp Pro Phe Leu Glu Asp Cys Ala Met Glu Glu Leu Thr
 50                  55                  60

Val Ser Glu Phe Leu Lys Leu Asp Arg Gln Arg Ser Thr Val His Glu
 65                  70                  75                  80

Ile Leu Cys Lys Leu Ser Leu Glu Gly Asp His Ser Thr Pro Pro Ser
                 85                  90                  95

Ala Tyr Gly Ser Val Lys Pro Tyr Thr Asn Phe Asp Ala Glu
                100                 105                 110

<210> SEQ ID NO 43
<211> LENGTH: 94
<212> TYPE: PRT
<213> ORGANISM: Artificial Sequence
<220> FEATURE:
<223> OTHER INFORMATION: Z13Mad9Anaxa

<400> SEQUENCE: 43

Lys Arg Tyr Lys Asn Arg Val Ala Ser Arg Lys Ser Arg Ala Lys Phe
 1                   5                  10                  15

Lys Gln Leu Leu Gln His Tyr Arg Glu Val Ala Ala Ala Lys Ser Ser
                 20                  25                  30

Glu Asn Asp Arg Leu Arg Leu Leu Lys His Leu Glu Leu Ala Ser
             35                  40                  45

Met Thr Asn Met Glu Leu Met Ser Ser Ile Val Ser Thr Val His Glu
 50                  55                  60

Ile Leu Cys Lys Leu Ser Leu Glu Gly Asp His Ser Thr Pro Pro Ser
 65                  70                  75                  80

Ala Tyr Gly Ser Val Lys Pro Tyr Thr Asn Phe Asp Ala Glu
                 85                  90

<210> SEQ ID NO 44
<211> LENGTH: 115
```

<212> TYPE: PRT
<213> ORGANISM: Artificial Sequence
<220> FEATURE:
<223> OTHER INFORMATION: TatFMad5Anaxa

<400> SEQUENCE: 44

```
Arg Lys Lys Arg Arg Gln Arg Arg Arg Val Lys Arg Ile Ser Gln
1               5                   10                  15

Ala Val His Ala Ala His Ala Glu Ile Asn Glu Ala Gly Arg Arg Val
                20                  25                  30

Lys Arg Lys Val Pro Arg Asn Gln Asp Trp Leu Arg Val Lys Arg Ala
            35                  40                  45

Ser Phe Glu Ala Gln Gly Ala Leu Ala Asn Ile Ala Val Asp Lys Ala
    50                  55                  60

Arg Val Lys Arg Ser Ile Ile Asn Phe Glu Lys Leu Arg Val Lys Arg
65                  70                  75                  80

Ser Thr Val His Glu Ile Leu Cys Lys Leu Ser Leu Glu Gly Asp His
                85                  90                  95

Ser Thr Pro Pro Ser Ala Tyr Gly Ser Val Lys Pro Tyr Thr Asn Phe
            100                 105                 110

Asp Ala Glu
        115
```

<210> SEQ ID NO 45
<211> LENGTH: 127
<212> TYPE: PRT
<213> ORGANISM: Artificial Sequence
<220> FEATURE:
<223> OTHER INFORMATION: Z13Mad12Anaxa

<400> SEQUENCE: 45

```
Lys Arg Tyr Lys Asn Arg Val Ala Ser Arg Lys Ser Arg Ala Lys Phe
1               5                   10                  15

Lys Gln Leu Leu Gln His Tyr Arg Glu Val Ala Ala Ala Lys Ser Ser
                20                  25                  30

Glu Asn Asp Arg Leu Arg Leu Leu Lys Leu Phe Arg Ala Ala Gln
            35                  40                  45

Leu Ala Asn Asp Val Val Leu Gln Ile Met Glu His Leu Glu Leu Ala
    50                  55                  60

Ser Met Thr Asn Met Glu Leu Met Ser Ser Ile Val Val Ile Ser Ala
65                  70                  75                  80

Ser Ile Ile Val Phe Asn Leu Leu Glu Leu Glu Gly Ser Thr Val His
                85                  90                  95

Glu Ile Leu Cys Lys Leu Ser Leu Glu Gly Asp His Ser Thr Pro Pro
            100                 105                 110

Ser Ala Tyr Gly Ser Val Lys Pro Tyr Thr Asn Phe Asp Ala Glu
        115                 120                 125
```

<210> SEQ ID NO 46
<211> LENGTH: 134
<212> TYPE: PRT
<213> ORGANISM: Artificial Sequence
<220> FEATURE:
<223> OTHER INFORMATION: Z13Mad5

<400> SEQUENCE: 46

```
Met His His His His His His Lys Arg Tyr Lys Asn Arg Val Ala Ser
1               5                   10                  15

Arg Lys Ser Arg Ala Lys Phe Lys Gln Leu Leu Gln His Tyr Arg Glu
```

```
                    20                  25                  30
Val Ala Ala Ala Lys Ser Ser Glu Asn Asp Arg Leu Arg Leu Leu Leu
                35                  40                  45

Lys Glu Ser Leu Lys Ile Ser Gln Ala Val His Ala Ala His Ala Glu
        50                  55                  60

Ile Asn Glu Ala Gly Arg Glu Val Val Gly Val Gly Ala Leu Lys Val
 65                  70                  75                  80

Pro Arg Asn Gln Asp Trp Leu Gly Val Pro Arg Phe Ala Lys Phe Ala
                85                  90                  95

Ser Phe Glu Ala Gln Gly Ala Leu Ala Asn Ile Ala Val Asp Lys Ala
                100                 105                 110

Asn Leu Asp Val Glu Gln Leu Glu Ser Ile Ile Asn Phe Glu Lys Leu
            115                 120                 125

Thr Glu Trp Thr Gly Ser
            130

<210> SEQ ID NO 47
<211> LENGTH: 35
<212> TYPE: PRT
<213> ORGANISM: Artificial Sequence
<220> FEATURE:
<223> OTHER INFORMATION: TLR peptide agonist: "Anaxa" sequence variant

<400> SEQUENCE: 47

Ser Thr Val His Glu Ile Leu Ser Lys Leu Ser Leu Glu Gly Asp His
 1               5                  10                  15

Ser Thr Pro Pro Ser Ala Tyr Gly Ser Val Lys Pro Tyr Thr Asn Phe
                20                  25                  30

Asp Ala Glu
        35
```